United States Patent
Metcalf et al.

(10) Patent No.: US 11,014,884 B2
(45) Date of Patent: May 25, 2021

(54) MODULATORS OF HEMOGLOBIN

(71) Applicant: Global Blood Therapeutics, Inc., South San Francisco, CA (US)

(72) Inventors: Brian W. Metcalf, South San Francisco, CA (US); Zhe Li, San Diego, CA (US); Qing Xu, South San Francisco, CA (US); Kobina N. Dufu, San Mateo, CA (US); James Partridge, South San Francisco, CA (US); Hing Sham, South San Francisco, CA (US); Ming Yu, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/588,753

(22) Filed: Sep. 30, 2019

(65) Prior Publication Data

US 2020/0140384 A1    May 7, 2020

Related U.S. Application Data

(60) Provisional application No. 62/821,311, filed on Mar. 20, 2019, provisional application No. 62/739,757, filed on Oct. 1, 2018.

(51) Int. Cl.

| | | |
|---|---|---|
| A61K 31/444 | (2006.01) | |
| A61K 31/443 | (2006.01) | |
| A61K 31/4436 | (2006.01) | |
| A61K 31/4439 | (2006.01) | |
| A61K 31/55 | (2006.01) | |
| A61K 31/5375 | (2006.01) | |
| A61K 31/54 | (2006.01) | |
| A61K 31/44 | (2006.01) | |
| C07D 211/32 | (2006.01) | |
| A61P 7/00 | (2006.01) | |
| C07D 207/12 | (2006.01) | |
| C07D 213/50 | (2006.01) | |
| C07D 223/04 | (2006.01) | |
| C07D 295/104 | (2006.01) | |
| C07D 307/48 | (2006.01) | |
| C07D 401/04 | (2006.01) | |
| C07D 405/04 | (2006.01) | |
| C07D 417/04 | (2006.01) | |

(52) U.S. Cl.
CPC .............. C07D 211/32 (2013.01); A61P 7/00 (2018.01); C07D 207/12 (2013.01); C07D 213/50 (2013.01); C07D 223/04 (2013.01); C07D 295/104 (2013.01); C07D 307/48 (2013.01); C07D 401/04 (2013.01); C07D 405/04 (2013.01); C07D 417/04 (2013.01)

(58) Field of Classification Search
None
See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,266,582 A | 11/1993 | De Nanteuil et al. |
| 5,290,941 A | 3/1994 | Volante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 11/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greenwald et al. |
| 6,627,646 B2 | 9/2003 | Bakale |

(Continued)

FOREIGN PATENT DOCUMENTS

| | | |
|---|---|---|
| CA | 2720096 | 10/2009 |
| CN | 101113148 | 1/2008 |

(Continued)

OTHER PUBLICATIONS

U.S. Appl. No. 61/581,053, filed Dec. 28, 2011, Metcalf et al.
U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.
Abdulmalik et al., Sickle cell disease: current therapeutic approaches, Expert Opinion Ther. Patents, 2005, vol. 15(11), pp. 1497-1506.
Abraham et al., Vanillin, a Potential Agent for the Treatment of Sickle Cell Anemia, Blood, Mar. 1991, vol. 77 (6), pp. 1334-1341.

(Continued)

Primary Examiner — Samantha L Shterengarts
(74) Attorney, Agent, or Firm — Sheppard Mullin Richter & Hampton LLP

(57) ABSTRACT

The present disclosure relates generally to compounds and pharmaceutical compositions suitable as modulators of hemoglobin, and methods for their use in treating disorders mediated by hemoglobin.

60 Claims, 2 Drawing Sheets

(56) References Cited

U.S. PATENT DOCUMENTS

| | | | |
|---|---|---|---|
| 6,630,496 B1 | 10/2003 | Seehra et al. |
| 7,160,910 B2 | 1/2007 | Safo et al. |
| 7,411,083 B2 | 8/2008 | Gopalsamy et al. |
| 7,994,367 B2 | 8/2011 | Nakazawa |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,150,569 B2 | 10/2015 | Fukuda et al. |
| 9,248,199 B2 | 2/2016 | Metcalf et al. |
| 9,422,279 B2 | 8/2016 | Metcalf et al. |
| 9,447,071 B2 | 9/2016 | Li et al. |
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |
| 9,957,250 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,137,118 B2 | 11/2018 | Li et al. |
| 10,450,269 B1 | 10/2019 | Xu et al. |
| 10,683,285 B2 | 6/2020 | Li |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0015752 A1 | 1/2007 | Hangauer |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann |
| 2009/0163512 A1 | 6/2009 | Chen et al. |
| 2009/0312315 A1 | 12/2009 | Yamaguchi et al. |
| 2010/0048901 A1 | 2/2010 | Takahashi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2013/0273157 A1 | 10/2013 | Ishii et al. |
| 2014/0004184 A1 | 1/2014 | Ashraf et al. |
| 2014/0142149 A1 | 5/2014 | Zhang et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0225366 A1 | 8/2015 | Li |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0355713 A1 | 12/2017 | Harris et al. |
| 2018/0125789 A1 | 5/2018 | Dalziel et al. |
| 2018/0186807 A1 | 7/2018 | Yee et al. |
| 2018/0201577 A1 | 7/2018 | Xu et al. |
| 2018/0354929 A1 | 12/2018 | Metcalf et al. |
| 2019/0010121 A1 | 1/2019 | Xu et al. |
| 2019/0010176 A1 | 1/2019 | Harris |
| 2019/0106404 A1 | 4/2019 | Li et al. |
| 2019/0111037 A1 | 4/2019 | Li et al. |
| 2019/0112287 A1 | 4/2019 | Metcalf et al. |
| 2019/0160060 A1 | 5/2019 | Metcalf et al. |
| 2019/0202782 A1 | 7/2019 | Xu et al. |
| 2019/0255031 A1 | 8/2019 | Li et al. |
| 2020/0048280 A1 | 2/2020 | Li et al. |
| 2020/0079732 A1 | 3/2020 | Xu et al. |
| 2020/0190058 A1 | 6/2020 | Metcalf et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2217016 | 1/1900 |
| FR | 2909379 | 6/2008 |

(56) References Cited

FOREIGN PATENT DOCUMENTS

| | | |
|---|---|---|
| GB | 1409865 | 10/1975 |
| GB | 1593417 | 7/1981 |
| IL | 64573 | 4/1985 |
| JP | 57-145844 | 9/1982 |
| JP | 59029667 | 2/1984 |
| JP | 61-040236 | 2/1986 |
| JP | 63230687 | 9/1988 |
| JP | S-63258463 | 10/1988 |
| JP | 01190688 | 7/1989 |
| JP | 06-041118 | 2/1994 |
| JP | 07-025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006-342115 | 12/2006 |
| JP | 2009-203230 | 9/2009 |
| WO | WO-91/19697 | 12/1991 |
| WO | WO-92/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/41120 | 11/1997 |
| WO | WO-97/44306 | 11/1997 |
| WO | WO-98/08818 | 3/1998 |
| WO | WO 98/09967 | 3/1998 |
| WO | WO-98/21199 | 5/1998 |
| WO | WO-99/29694 | 6/1999 |
| WO | WO-99/43672 | 9/1999 |
| WO | WO-99/47529 | 9/1999 |
| WO | WO-99/48490 | 9/1999 |
| WO | WO-99/59978 | 11/1999 |
| WO | WO-99/62908 | 12/1999 |
| WO | WO-00/12121 | 3/2000 |
| WO | WO-00/26202 | 5/2000 |
| WO | WO-00/35858 | 6/2000 |
| WO | WO-00/40564 | 7/2000 |
| WO | WO-00/71123 A1 | 11/2000 |
| WO | WO-00/75145 | 12/2000 |
| WO | WO-00/78746 | 12/2000 |
| WO | WO-01/00612 | 1/2001 |
| WO | WO-01/19823 | 3/2001 |
| WO | WO-01/23383 | 4/2001 |
| WO | WO-01/32596 | 5/2001 |
| WO | WO-01/36375 | 5/2001 |
| WO | WO 01/51919 | 7/2001 |
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO 02/40456 | 5/2002 |
| WO | WO-02/051849 | 7/2002 |
| WO | WO-02/053547 | 7/2002 |
| WO | WO-03/051366 | 6/2003 |
| WO | WO-03/053368 | 7/2003 |
| WO | WO-03/101959 | 12/2003 |
| WO | WO-2004/014899 | 2/2004 |
| WO | WO-2004/018430 | 3/2004 |
| WO | WO-2004/024705 | 3/2004 |
| WO | WO-2004/050030 | 6/2004 |
| WO | WO-2004/056727 | 7/2004 |
| WO | WO-2004/058790 | 7/2004 |
| WO | WO 2004/073675 | 9/2004 |
| WO | WO-2004/087075 | 10/2004 |
| WO | WO-2004/111031 | 12/2004 |
| WO | WO-2005/047249 | 5/2005 |
| WO | WO-2005/074513 | 8/2005 |
| WO | WO-2005/077932 | 8/2005 |
| WO | WO-2005/086951 | 9/2005 |
| WO | WO-2005/087766 | 9/2005 |
| WO | WO-2005/096337 | 10/2005 |
| WO | WO-2006/011469 | 2/2006 |
| WO | WO-2006/065204 | 6/2006 |
| WO | WO-2006/088173 | 8/2006 |
| WO | WO 2006/101318 | 9/2006 |
| WO | WO 2006/101321 | 9/2006 |
| WO | WO-2006/103463 | 10/2006 |
| WO | WO-2006/106711 | 10/2006 |
| WO | WO-2006/116764 | 11/2006 |
| WO | WO-2006/003923 | 12/2006 |
| WO | WO-2007/003962 | 1/2007 |
| WO | WO-2007/009389 | 1/2007 |
| WO | WO-2007/017267 | 2/2007 |
| WO | WO-2007/047204 | 4/2007 |
| WO | WO-2007/049675 | 5/2007 |
| WO | WO-2007/061923 | 5/2007 |
| WO | WO-2007/084914 | 7/2007 |
| WO | WO 2007/095495 | 8/2007 |
| WO | WO-2007/117180 | 10/2007 |
| WO | WO 2008/012495 | 1/2008 |
| WO | WO-2008/013414 | 1/2008 |
| WO | WO-2008/016132 | 2/2008 |
| WO | WO-2008/029200 | 3/2008 |
| WO | WO-2008/041118 | 4/2008 |
| WO | WO-2008/051532 | 5/2008 |
| WO | WO-2008/060391 | 5/2008 |
| WO | WO-2008/066145 | 6/2008 |
| WO | WO-2008/081096 | 7/2008 |
| WO | WO-2008/101682 | 8/2008 |
| WO | WO-2008/116620 | 10/2008 |
| WO | WO-2009/001214 | 12/2008 |
| WO | WO-2009/011850 | 1/2009 |
| WO | WO-2009/050183 | 4/2009 |
| WO | WO-2009/125606 | 10/2009 |
| WO | WO-2009/128537 | 10/2009 |
| WO | WO-2009/130560 | 10/2009 |
| WO | WO-2009/136889 | 11/2009 |
| WO | WO-2009/146555 | 12/2009 |
| WO | WO 2009/153191 | 12/2009 |
| WO | WO-2010/031589 | 3/2010 |
| WO | WO-2010/056631 | 5/2010 |
| WO | WO-2010/129055 | 11/2010 |
| WO | WO-2011/033045 | 3/2011 |
| WO | WO-2011/088201 | 7/2011 |
| WO | WO-2011/136459 | 11/2011 |
| WO | WO-2012/020060 | 2/2012 |
| WO | WO-2012/138981 | 10/2012 |
| WO | WO-2012/141228 | 10/2012 |
| WO | WO-2013/052803 | 4/2013 |
| WO | WO-2013/102142 | 7/2013 |
| WO | WO-2013/102145 | 7/2013 |
| WO | WO-2014/104384 | 7/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |
| WO | WO-2015/120133 | 8/2015 |
| WO | WO 2016/043849 | 3/2016 |
| WO | WO-2016/160755 | 10/2016 |
| WO | WO-2017/096230 | 6/2017 |

OTHER PUBLICATIONS

Adhikary, P.K., et al., "A new antisickling agent: In vitro studies of its effect on S/S erythrocytes and on hemoglobin S", Experientia. 1978, vol. 34, No. 6, pp. 804-806.

Appendix A provided with Israel office action dated Aug. 11, 2016 for IL 233329.

Arya R, et al. "Tucaresol increases oxygen affinity and reduces haemolysis in subjects with sickle cell anaemia," Br. J. Haematol., 93(4):817-21 (1996).

Ashizawa et al., Polymorphism and crystallization of the pharmaceutical drugs (Iyakuhin No Takeigensho To Shoseki No Kagaku)

(56) References Cited

OTHER PUBLICATIONS

Maruzen Planet Co., Ltd., Sep. 20, 2002, pp. 3-16 and pp. 273-278. (in Japanese with partial English translation).
Australian Examination Report dated Nov. 7, 2016 for AU 2016203755.
Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.
Bacsa et al., "Novel products from Baylis-Hillman reactions of salicylaldehydes", South African Journal of Chemistry (1998), 51(1), 47-54 CODEN: SAJCDG; ISSN: 0379-4350.
Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.
Ballet et al., Novel selective human melanocortin-3 receptor ligands: Use of the 4-amino-1,2,4,5-tetrahydro-2-benzazepin-3-one (Aba) scaffold, Bioorganic & Medicinal Chemistry Letters (2007), 17(9), 2492-2498 CODEN: BMCLES; ISSN: 0960-894X.
Barnes, et al., "Prospects for new drugs for chronic obstructive pulmonary disease." The Lancet, 2004, 364, 985-996.
Barnes. "COPD: is there light at the end of the tunnel?" Current Opinion in Pharmacology, 2004, 4:263-272.
Baxter et al., "Reductive aminations of carbonyl compounds with borohydride and borane reducing agents", Organic Reactions (Hoboken, NJ, United States) (2002), 59, No pp. given bin/mrwhome/107610747/HOME.
Beaumont et al., Design of ester prodrugs to enhance oral absorption of poorly permeable compounds: challenges to the discovery scientist. Curr. Drug Metab. 2003, 4:461-85.
Beddell, Substituted benzaldehydes designed to increase the oxygen affinity of human haemoglobin and inhibit the sickling of sickle erythrocycles, Br. J. Pharmac., 82:397-407, 1984.
Beena et al., "Synthesis and antibacterial activity evaluation of metronidazole-triazole conjugates", Bioorganic & Medicinal Chemistry Letters, 2009, 19(5):1396-1398.
Behanna. Equity Research—Global Blood Therapeutics. Sep. 8, 2015. Retrieved from the Internet: URL:http://www.fintechsecurities.com/Websites/fintechsecurities/images/Research_Blog/Zacks/Sep2015/GBT150908.pdf.
Berge et al., "Pharmaceutical Salts", Journal of Pharmaceutical Science, 1977, 66:1-19.
Beringer et al., Remington's Pharmaceutical Sciences, Mack Pub., 21st Edition, 2005, pp. 1072-1076.
Bernstein. Crystals in Supramolecular Chemistry. ACA Transactions. 2004; 39:1-14.
Bernstein. Polymorphism in Molecular Crystals. Clarendon Press, Oxford. 2002. 115-118, 272.
Bode et al.,"Novel synthesis and x-ray crystal structure of a coumarin derivative", South African Journal of Chemistry (1992), 45(1), 25-7 CODEN: SAJCDG; ISSN:0379-4350.
Bonaventura, et al., "Molecular Controls of the Oxygenation and Redox Reactions of Hemoglobin." Antioxidants & Redox Signaling, 18(17), 2013, 2298-2313.
Bottino, et al. Study on the scope of tert-amino effect: new extensions of type 2 reactions to bridged biaryls. J. Phys. Org. Chem. 2012; 25(11):1033-1041.
Bradbury et al., "New nonpeptide angiotensin II receptor antagonists", Journal of Medicinal Chemistry, 1993, vol. 36, pp. 1245-1254.
Braga, et al. Making crystals from crystals: a green route to crystal engineering and polymorphism. Chem Commun (Camb). Aug. 7, 2005;(29):3635-45. Epub Jun. 15, 2005.
Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.
Brown et al., "1,2-Dihydroisoquinollnes. III, Dimerization", Tetrahedron (1966), 22(8), 2437-43 CODEN: TETRAB; ISSN;0040-4020.
Byrn, et al. Pharmaceutical solids: a strategic approach to regulatory considerations. Pharmaceutical Research. 1995; 12(7):945-954.
Caira. Crystalline Polymorphism of Organic Compounds. Topics in Current Chemistry, Springer, Berlin, DE. 1998; 198:163-208.
"Can Voxelotor Offer New HOPE for Sickle Cell Disease?," Dec. 3, 2018, available at: https://www.ashclinicalnews.org/on-location/voxelotor-offers-new-hope-sickle-cell-disease/. 4 pages.
CAS Reg. No. 921186-17-6, entered into STN on Feb. 15, 2007.
CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 329222-79-9; STN Entry Date Mar. 28, 2001; Benzaldehyde, 2-[(4-chloro-3-methylphenoxy)methyl]-4-methoxy-.
CAS Registry No. 631858-40-7; entry dated Dec. 29, 2003.
CAS Registry No. 733030-49-4; STN Entry Date Aug. 26, 2004; Benzaldehyde, 5-bromo-2-(phenoxymethyl)-.
CAS Registry No. 886362-88-5; STN Entry Date Jun. 1, 2006; Benzaldehyde, 2,4-dichloro-6-[(4-fluorophenoxy)methyl]-.
Chemical Abstract Registry No. 1142191-55-6, indexed in the Registry File on STN CA ONLINE May 4, 2009.
Cheng, et al. Vilsmeier formylation of tert-anilines: dibenzo[b,f][1,5]diazocines and quinazolinium salts via the 't-amino effect'. J. Chem. Soc., Perkin Trans 1. 1998; 1257-1262.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-b][1,3]oxazin-6-yl)-(4-trifluoromethoxybenzyl)amine (6-Amino PA-824).," J. Med. Chem., Aug. 2011, vol. 54(16), pp. 5639-5659.
Ciganek, "The catalyzed a-hydroxyalkylation and a-aminoalkylation of activated olefins (the Morita-Baylis-Hillman reaction)", Organic Reactions (Hoboken, NJ, United States) (1997), 51, No pp given CODEN:ORHNBA URL:http://www3.Interscience.wiley.com/cgi-bin/mnwhome/107610747/HOME.
CMU Pharmaceutical polymorphism, internet p. 1-3 (2002) printout Apr. 3, 2008.
Concise Encyclopedia Chemistry, NY: Walter de Gruyter, 1993, 872-873.
Congreve et al. Application of Fragment Screening by X-ray Crystallography to the Discovery of Aminopyridines as Inhibitors of Beta-Secretase. J. Med. Chem. 50:1124-1132 (2007).
Cos et al., "Structure-Activity Relationship and Classification of Flavonoids as Inhibitors of Xanthine Oxidase and Superoxide Scavengers," J. Nat. Prod., (1998), 61:71-76.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN:1427163-92-5 & CN 102 952 062 A, Mar. 6, 2013, 2 pages.
Database Pubchem Compound Dec. 4, 2011 XP 003033770 (11 pages).
Database Registry RN 1184773-12-3. Retrieved from STN, Sep. 15, 2009.
Database Registry, 2011, RN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Davidovich, et al. Detection of polymorphism by powder x-ray diffraction: interference by preferred orientation. Am. Pharm. Rev. 2004; 10, 12, 14, 16, 100.
Dean. Analytical Chemistry Handbook. University of Tennesse, Knoxville. McGraw-Hill, Inc. 1995; 10.24-10.26.
Deem. "Red Blood Cells and Hemoglobin in Hypoxic Pulmonary Vasoconstriction" Advances in experimental medicine and biology, (2006) 588, 217-231.
Desai et al. Preparation of N-[ro-(4-aryl-1-piperazinyl)ethyl/propyl]-3-hydroxyphthalimidines. Indian Journal of Chemistry. 39:455-457 (2000).

(56) References Cited

OTHER PUBLICATIONS

Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.

Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).

Ding et al., "Crystal structure of bis[µ2-2-(2-formylphenoxy)acetato-O,O]-bis[2-2-2-formylphynoxy)acetato-O,O]-octakis(n-butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.

Doelker, English translation of S.T.P, Pratiques (1999), 9(5), 399-409.

Doelker. English translation of Ann. Pharm. Fr., 2002, 60: 161-176.

Einfalt, et al. Methods of amorphization and investigation of the amorphous state. Acta Pharm. 2013; 63:305-334.

Elwahy, "Synthesis of new benzo-substituted macrocyclic containing quinoxaline subunits" Tetrahedron (2000), 56(6), 897-907 CODEN:TETRAB; ISSN:0040-4020.

Epsztajn et al., "Application of organolithium", Tetrahedron, Elsevier Science Publishers, Amsterdam, NL, 1991, vol. 47, No. 9, pp. 1697-1706.

European Search Report and Search Opinion dated Aug. 4, 2015 for EP Application No. 12862525.8. 9 pages.

European Search Report and Search Opinion dated Jul. 21, 2016 for EP Application No. 14769616.5. 8 pages.

European Search Report and Search Opinion dated May 28, 2015 for EP Application No. 12862096.0. 13 pages.

European Search Report and Search Opinion dated Nov. 16, 2016 for EP Application No. 16194019.2. 13 pages.

European Search Report and Search Opinion dated Sep. 26, 2016 for EP Application No. 14768759.4. 6 pages.

Experimental Chemistry (vol. 2)(Jikken Kagaku Koza, Zoku), Separation and refining, Maruzen Co.Ltd. Jan. 25, 1967, pp. 159-178 and pp. 186-187. (in Japanese with partial English translation).

Extended European Search Report and opinion dated Jul. 20, 2016 for EP Application No. 14768414.6. 10 pages.

Extended European Search Report and opinion dated Nov. 11, 2019 for EP Application No. 17796828.6. 7 pages.

Extended European Search Report and Search Opinion dated Jul. 18, 2016 for EP Application No. 14770695.6. 13 pages.

Extended European Search Report and Search Opinion dated Jul. 7, 2016 for EP Application No. 14768317.1. 7 pages.

Extended European Search Report and Search Opinion dated May 17, 2017 for EP Application No. 15746995.8. 8 pages.

Extended European Search Report and Search Opinion dated Nov. 23, 2015 for EP Application No. 12862525.8. 16 pages.

Extended European Search Report and Search Opinion dated Sep. 22, 2020 for EP Application No. 20167746.5. 8 pages.

FDA approves voxelotor for sickle cell disease. dated Nov. 25, 2019. https://www.fda.gov/drugs/resources-information-approved-drugs/fda-approves-voxelotor-sickle-cell-disease. 2 pages.

Gadaginamath, et al., "Synthesis and antibacterial activity of novel 1-butyl-2-phenoxyl2-phenylthlol2-aminomethyl-5-methoxyindole derivatives", Polish Journal of Chemistry (1997), 71(7), 923-928 CODEN: PJCHDQ; ISSN:0137-5083.

Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.

GBT Announces Positive Top-line Data from Part A of the Phase 3 HOPE Study of Voxelotor in Sickle Cell Disease, Press Release dated Jun. 27, 2018. Available at http://ir.gbt.com/phoenix.zhtml?c=254105&p=irol-newsArticle&ID=2356168.

Ghate et al., "Synthesis of vanillin ethers from 4-(bromomethyl) coumarins as anti-inflammatory agents,"European Journal of Medicinal Chemistry (2003), 38(3), 297-302 CODEN: EJMCAS; ISSN: 0223-5234.

Gibson et al., "Novel small molecule bradykinin B2 receptor antagonists", Journal of Medicinal Chemistry, 2009, vol. 52, pp. 4370-4379.

Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).

Goodman and Gilman's The Pharmacological Basis of Therapeutics (Tenth Edition 2001), McGraw Hill. Chapter I, pp. 3-29.

Grashey, "The nitro group as a 1,3-dipole in cycloadditions"Angewandte Chemie (1962), 74, 155 CODEN: ANCEAD; ISSN: 0044-8249.

Gu, et al. Grouping solvents by statistical analysis of solvent property parameters: implication to polymorph screening. Int J Pharm. Sep. 28, 2004;283(1-2):117-25.

Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.

Guillory (in Brittain ed.) Polymorphism in Pharmaceutical Solids. NY, Marcel Dekker, Inc. 1999; 1-2:183-226.

Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.

"Handbook of Pharmaceutical Excipients"; Fifth Ed. Edited by Raymond C Rowe et al., ISBN 978-0-85369-618-6, p. 132-134, 211-213, 346-347, 389-394, 430-433—Dec. 31, 2006.

Hang, Song. "Pharmaceutical Separation Engineering" East China University of Technology Press. Aug. 31, 2011; 270-272. (in Chinese with English abstract).

Hanmantgad et al., "Synthesis and pharmacological properties of some r-(2-benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.

He et al., "Prodrugs of Phosphonates, Phosphinates, and Phosphates", Prodrugs: Challenges and rewards Part 2, edited by Stella et al., 2007, pp. 223-264.

Hebbel et al., "Sickle hemoglobin oxygen affinity-shifting strategies have unequal cerebrovascular risks," Am. J. Hematol., 93(3), 321-325 (2018).

Heimbach et al., "Enzyme-mediated precipitation of patent drugs from their phosphate prodrugs", International Journal of Pharmaceutics, 261, p. 81-92, 2003.

Heimbach et al., "Prodrugs: Challenges and Rewards Part I," New York, NY, Singer:AAPS Press, (2007), 5(Chapter 2.2.1):157-215 Overcoming Poor Aqueous Solubility of Drugs for Oral Delivery.

Heimgartner et al., "Stereoselective synthesis of swainsonines from pyridines", Tetrahedron, Elsevier Science Publishers, Amsterdam, NL, 2005, vol. 61, No. 3, pp. 643-655.

Hoffman, et al. 3-Hydroxy-3-methylglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).

Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.

Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.

International Preliminary Report on Patentability dated Jun. 5, 2018 for PCT/US2016/064723. (10 pages).

International Preliminary Report on Patentability for PCT/US2014/022846 dated Sep. 15, 2015. 7 pages.

International Preliminary Report on Patentability for PCT/US2014/022742 dated Sep. 15, 2015. 7 pages.

International Preliminary Report on Patentability for PCT/US2014/022733 dated Sep. 15, 2015. 11 pages.

International Preliminary Report on Patentability for PCT/US2014/022769 dated Sep. 15, 2015. 8 pages.

(56) References Cited

OTHER PUBLICATIONS

International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Aug. 4, 2017 for PCT Application No. PCT/US2017/032104. 10 pages.
International Search Report and Written Opinion dated Dec. 8, 2014 for PCT Application No. PCT/US2014/052575. 10 pages.
International Search Report and Written Opinion dated Jan. 2, 2020 for PCT Application No. PCT/US2019/053862. 13 pages.
International Search Report and Written Opinion dated Jan. 22, 2018 for PCT Application No. PCT/US2017/056352. 12 pages.
International Search Report and Written Opinion dated Jul. 22, 2014 for PCT Application No. PCT/US2014/022846. 11 pages.
International Search Report and Written Opinion dated Jul. 30, 2014 for PCT Application No. PCT/US2014/029682. 16 pages.
International Search Report and Written Opinion dated Jul. 31, 2014 for PCT Application No. PCT/US2014/022789. 13 pages.
International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 11, 2015 for PCT Application No. PCT/US2015/014589. 5 pages.
International Search Report and Written Opinion dated May 20, 2013 for PCT Application No. PCT/US2012/072183. 11 pages.
International Search Report and Written Opinion dated May 3, 2017 for PCT Application No. PCT/US2016/064723. 15 pages.
International Search Report and Written Opinion dated Nov. 28, 2014 for PCT Application No. PCT/US2014/052576. 10 pages.
International Search Report and Written Opinion dated Oct. 31, 2014 for PCT Application No. PCT/US2014/013575. 10 pages.
Israel office action dated Aug. 11, 2016 for Israeli Patent Application No. 233329.
Ito et al., A medium-term rat liver bioassay for rapid in vivo detection of carcinogenic potential of chemicals,01D Cancer Science, Jan. 2003, 94, pp. 3-8.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Jarvest et al., "Discovery and optimisation of potent, selective, ethanolamine Inhibitors of bacterial phenylalanyl tRNA synthetase", Bioorganic & Medicinal Chemistry Letter (2005), 15(9), 2305-2309 CODEN: BMCLES; ISSN: 0960-894X.
Karche et al., "Electronic Effects in Migratory Groups [1,4]-versus [1,2]-Rearrangement in Rhodium Carbenoid Generated Bicyclic Oxonium Ylides", Journal of Organic Chemistry (2001), 66(19), 6323-6332 CODEN: JOCEAH; ISSN: 0022-3263.
Katritzky et al., "Syntheses of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journal/2003/Vargoglis/AV-622A/6ss.pdf.
Kawaguchi, et al. Drug and crystal polymorphism. Journal of Human Environmental Engineering, 2002, v.4, pp. 310-317. (in Japanese with partial English translation).
Kaye et al., "DABCO-catalyzed reactions of salicylaldehydes with acrylate derivatives", Synthetic Communications (1996), 26(11), 2085-97 CODEN: SYNCAV; ISSN: 0039-7911.
Kaye et al., "Does the Dabco-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Keidan, et al. Effect of BW12C on oxygen affinity of hemoglobin in sickle-cell disease. The Lancet. 1986; 327(8485):831-834.
Kessar et al., "Synthesis of Isoindolobenzazepines via photocyclisation of N-(2-formylphenethyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., An Interesting Application of Photocyclisation in Apophdeadane Alkaloid Synthesis. Tetrahedron Letters (1987), 28(44), 5323-5326. CODEN: TELEAY; ISSN: 0040-4039.
Kirk-Othmer Encyclopedia of Chemical Technology. 2002; 8:95-147.
Kise et al., "Electroreductive Intramolecular Coupling of Phthalimides with Aromatic Aldehydes: Application to the Synthesis of Lennoxamine". Journal of Organic Chemistry (2011), 76(23), 9856-9880 CODEN:JOCEAH; ISSN: 0022-3263.
Klis, et al. Halogen-lithium exchange versus deprotonation: synthesis of diboronic acids derived from aryl-benzyl ethers. Tetrahedron Letters, 48(7):1169-1173 (2007).
Kratochvil. Chapter 8 Solid Forms of Pharmaceutical Molecules. J. Sestak et al. (eds.), Glassy, Amorphous and Nano-Crystalline Materials. Hot Topics in Thermal Analysis and Calorimetry 8, 2011, pp. 129-140.
Kraus, et al. Michael additions in anhydrous media. A novel synthesis of oxygenated coumarins. J. Org. Chem., 1979, 44 (14), pp. 2480-2482.
Krow,"The Baeyer-Villiger oxidation of ketones and aldehydes", Organic Reactions (Hoboken, NJ, United States) (1993), 43, No pp given CODEN: ORHNBA URL: http://www3.interscience.wiley.com/cgi- bin/mrwhome/107610747/HOME.
Kucera, et al. Evaluation of Ceolus(TM) microcrystalline cellulose grades for the direct compression of enteric-coated pellets. Drug Development and Industrial Pharmacy. Mar. 1, 2012; 38(3):341-350.
Lakkannavar et al., "4-[2'-benzylideneanlino aryloxymethyl] coumarins E and Z isomers". Indian Journal of Heterocyclic Chemistry (1995), 4(4), 303-4 CODEN: IJCHEI; ISSN: 0971-1627.
Lehrer, et al. GBT440, a novel anti-polymerization agent, for the treatment of sickle cell disease. Global Blood Therapeutics. Apr. 1, 2016. (50 pages) Retrieved from the Internet: http://casicklecell.org/img/PresentationSlidesWebinar3.pdf.
Li, et al. Iron-Catalyzed Cascase Arene-Aldehyde/Cyclizations for the Highly Efficient Synthesis of Xanthenes and Its Analogous: Observation of a C—C Bond Cleavage in Indole-Based Triarylmethanes. J. Org. Chem., 2009, 74, 6797-6801.
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Liu et al., "Synthesis of Double-Armed Benzo- 15-crown-5 and Their Complexation Thermodynamics with Alkali Cations", Journal of Inclusion Phenomena and Macrocyclic Chemistry (2005), 52(3-4), 229-235 CODEN: JIPCF5; ISSN: 1388-3127.
Luan, et al. Tops-Mode model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.
Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.
Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL FARMACO, 1996, vol . 51, No. 8, 9, pp. 579-587.
Mantyla et al., Synthesis, in vitro evaluation, and antileishmanial activity of water-soluble prodrugs of buparvaquone. J. Med. Chem. 2004, 47:188-195.

(56) References Cited

OTHER PUBLICATIONS

Marchetti et al., "Synthesis and biological evaluation of 5-substituted 04-alkylpyrimidines as CDK2 inhibitors," Org. Biomol. Chem, 2010, vol. 8, pp. 2397-2407.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
Mathur. "Microcrystalline Cellulose" In: "Handbook of Pharmaceutical Excipients, Second Edition", Jan. 1, 1994, The Pharmaceutical Press, London, pp. 84-87.
McKay et al., 7,11,15,28—Tetrakis[(2-formylphenoxy)methyl]-1,21,23,25-tetramethylresorcin[4]arene cavitand ethyl acetate clathrate at 173 K, Acta Crystallographica, Section E: Structure Reports Online (2009), E65(4), 692-693 CODEN: ACSEBH; ISSN: 1600-5368 URL: http://journals.lucr.org/e/issues/2009/04/00fl22 33/fl2233.pdf.
McKay et al., "Microwave-assisted synthesis of a new series of resorcin[4]arene cavitand-capped porphyrin capsules", Organic & Biomolecular Chemistry (2009), 7(19), 3958-3968 CODEN: OBCRAK; ISSN: 1477-0520.
Merlino et al., "Development of second generation amidinohydrazones, thio- and semicarbazones as Trypanosoma cruzi-inhibitors bearing benzofuroxan and benzimidazole 1,3-dioxide core scaffolds", MedChemComm (2010), 1(3), 216-228 CODEN: MCCEAY; ISSN: 2040-2503.
Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.
Metcalf, et al., "Discovery of GBT440, an Orally Bioavailable R-State Stabilizer of Sickle Cell Hemoglobin," ACS Med. Chem. Lett., 2017, 8, 321-326.
Mitra et al., "Synthesis and biological evaluation of dibenz[b,f][1,5]oxazocine derivatives for agonist activity at x-opioid receptor", European Journal of Medicinal Chemistry (2011), 46(5), 1713-1720 CODEN: EJMCA5; ISSN: 0223-5234.
Mulwad et al., "Synthesis and antimicrobial activity of [6'-methyl-4'-methoxy-2-oxo-2H-[1]-benzopyran)-2",4" dihydro-[1",2",4"{-triazol-3'-one and 3'phenylthiazolidin-4'-one-phenoxymethyl derivatives of dipyranoquinoline", Pharmaceutical Chemistry Journal Ahead of Print CODEN: PCJOAU; ISSN: 0091-150, 2011; pp. 427-432.
Muzaffar, et al., "Polymorphism and Drug Availability: a Review" J of Pharm. (Lahore), 1979, 1(1), 59-66.
Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.
Neelima et al., "A novel annelation reaction: synthesis of 6H-[1]benzopyrano[4,3-b]quinolines" Chemistry & Industry (London, United Kingdom) (1986), (4), 141-2 CODEN: CHINAG; ISSN: 0009-3068.
New Introduction of Pharmacology (Sin Yakuzaigaku Soron)(revised 3rd Edition),Apr. 10,1987, Nankodo Co., Ltd p. 111. (in Japanese with partial English translation).
New Pharmaceutical Preparation (Shin Seizaigaku), Nanzando Co.,Ltd., Apirl 25, 1984, p. 102-103 and pp. 232-233. (in Japanese with partial English translation).
Nnamani, et al., "Pyridyl derivatives of benzaldehyde as potential antisickling agents," Chem. Biodivers., (2008), 5(9):1762-1769.
Nogrady, Medicinal Chemistry A Biochemical Approach, Oxford University Press, New York, pp. 388-393 (1985).
Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.
Notice of Allowance dated Dec. 19, 2014 for U.S. Appl. No. 13/730,730. 11 pages.

Nozaki, et al. 5.2.2 Bioisosterism. Drug Discovery Chemistry, Kagaku Dojin, 1995, 1st Ed., p. 98-99. (in Japanese with English translation).
Nyerges et al, "Synthesis of Indazole N-oxides via the 1,7-electrocyclization of azomethine ylides", Tetrahedron Letters (2001), 42(30), 5081-5083 CODEN: TELEAY; ISSN:0040-4039.
Nyerges et al, "Synthesis of Indazole N-oxides via the 1,7-electrocyclization of azomethine ylides", Tetrahedron Letters (2004), 60(44), 9937-9944 CODEN: TETRAB; ISSN:0040-4020.
OECD SIDS "SIDS Initial Assessment Report for 13th SIAM," Nov. 2001, pp. 1-95.
Office Action dated Aug. 29, 2014 for U.S. Appl. No. 13/730,730. 17 pages.
Office Action dated Dec. 3, 2013 for U.S. Appl. No. 13/730,674. 8 pages.
Office Action dated Jul. 6, 2015 for U.S. Appl. No. 13/815,874. 14 pages.
Office Action dated Jun. 12, 2015 for CN Application No. 201280070743.5. 13 pages.
Office Action dated Jun. 29, 2015 for U.S. Appl. No. 13/815,810. 19 pages.
Office Action dated Jun. 30, 2014 for U.S. Appl. No. 13/730,674. 9 pages.
Office Action dated Sep. 18, 2013 for U.S. Appl. No. 13/730,674. 10 pages.
Oh, et al. Solid-phase synthesis of 1,3-oxazolidine derivatives. Tetrahedron Letters. 2000; 41:5069-5072.
Ooshima, Hiroshi. Crystallization of Polymorphs and Pseudopolymorphs and its Control. PHARM STAGE, 2007, 6(10), pp. 48-53. (in Japanese with partial English translation).
O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.
Otsuka, et al., "Effect of Polymorphic Forms of Bulk Powders on Pharmaceutical Properties of Carbamazepine Granules." Chem. Pharm. Bull., 47(6) 852-856 (1999).
Patani, et al. Bioisosterism: A Rational Approach in Drug Design. J. Chem Rev. 1996, 96(8), pp. 3147-3176.
Paul, et al. Hydroxyl directed C-arylation: synthesis of 3-hydroxyflavones and 2-phenyl-3-hydroxy pyran-4-ones under transition-metal free conditions. Org. Biomol. Chem., 2018, 16:444-451.
Pearson, et al. Experimental and Computational Studies into an ATPH-Promoted exo-Selective IMDA Reaction: A Short Total Synthesis of Δ9-THC*. Chem. Eur. J. 2010, 16, 8280-8284.
Perez et al., "Preparation of new 1,2-disubstituted ferrocenyl ammonium salt", Polyhedron (2009), 28(14), 3115-3119 CODEN: PLYHE; ISSN:0277-5387.
Perkins et al., "Manganese(II), Iron(II), cobalt(II), and cooper(II)complexes of an extended inherently chiral tris-bipyridyl cage", Proceedings of the National Academy of Sciences of the United States of America (2006), 103(3), 532-537 CODEN: PNASA6; ISSN: 0027-8424.
Pharmaceutical Affairs Bureau Notification. Ministry of Health, Labour and Welfare. 2001, vol. 568. 46 pages. (in Japanese with partial English translation).
Pharmacy—Foundation and Application—(Chozaigaku, Kiso to Ouyou), Nanzando Co.,Ltd., Sep. 20, 1977 p. 142-145. (in Japanese with partial English translation).
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Prohens, et al. Polymorphism in pharmaceutical industry. The Pharmacist. Apr. 1, 2007; 373:58-68. (in Spanish with English abstract).
Pubchem CID 54009805 Create Date: Dec. 4, 2011 p. 1.
Pubchem CID 54883281 Create Date: Aug. 19, 2012 p. 1.
Reagan-Shaw, et al. Dose translation from animal to human studies revisited. The FASEB Journal. Mar. 2007; 22:659-661.

(56) References Cited

OTHER PUBLICATIONS

Remington's Pharmaceutical Sciences, 17th Edition, A. Gennaro editor, Easton Pennsylvania. Table of Contents. (1985).
Rodriguez-Spong, et al. General principles of pharmaceutical solid polymorphism: a supramolecular perspective. Adv Drug Deliv Rev. Feb. 23, 2004;56(3):241-74.
Rolan et al., "The pharmacokinetics, tolerability and pharmacodynamics of tucaresol (589C80); 4[2-formyl-3-hydroxyphenoxymethyl] benzoic acid), a potential anti-sickling agent, following oral administration to healthy subjects", British Journal of Clinical Pharmacology, 1993, 35(4):419-425.
Rooseboom et al., Enzyme-catalyzed activation of anticancer prodrugs. Pharmacol. Rev. 2004, 56:53-102.
Ruchirawat et al., "A novel synthesis of aporhoeadanes", Tetrahedron Letters (1984), 25(32), 3485-8 CODEN: TELEAY; ISSN: 0040-4039.
Safo, et al. Structural basis for the potent antisickling effect of a novel class of five-membered heterocyclic aldehydic compounds. J Med Chem. Sep. 9, 2004;47(19):4665-76.
Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.
Sahm et al., "Synthesis of 2-arylbenzofurans" Justus Liebigs Annalen der Chemie (1974), (4), 523-38 CODEN: JLACBF; ISSN: 0075-4617.
Sainsbury et al., "1,2-Dihydroisoquinolines, IV. Acylation" Tetrahedron (1966), 22(8), 2445-52 CODEN: TETRAB; ISSN: 0040-4020.
Sarodnick et al., "Quinoxalines XV, Convenient Synthesis and Structural Study of Pyrazolo[1,5-a]quinoxalines", Journal of Organic Chemistry (2009), 74(3), 1282-1287 CODEN: JOCEAH; ISSN: 0022-3263.
Schudel, et al. Uber die Chemie des Vitamins E. Helvetica Chimica Acta. 1963; 66:636-649.
Seddon. Pseudopolymorph: A Polemic. The QUILL Centre, The Queen's University of Belfast, United Kingdom. Jul. 26, 2004. 2 pages.
Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Shin, et al. Interpretation of Animal Dose and Human Equivalent Dose for Drug Development. The Journal of Korean Oriental Medicine. 2010; 31(3):1-7.
Siddiqui et al., "The Presence of Substitutents on the Aryl Moiety of the Aryl Phosphoramidate Derivative of d4T Enhances Anti-HIV Efficacy in Cell Culture-Activity Relationship," J. Med. Chem., (1999), 42:393-399.
Silva et al., "Advances in prodrug design," Mini Rev. Med. Chem., (2005), 5(10):893-914.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Singhal, et al., "Drug Polymorphism and Dosage Form Design: a Practical Perspective" Advanced Drug Delivery reviews 56, p. 335-347 (2004).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Srivastava et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Synthesis and mass spectrometric study of aryloxymethylquinoxalines and benzo[b]furylquinoxalines" Tetrahedron (2004), 60(29), 6063-6078 CODEN: TETRAB; ISSN:0040-4020.

Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley. Solubilizing excipients in oral and injectable formulations. Pharm Res. Feb. 2004;21(2):201-30.
Swann et al., "Rates of reductive elimination of substituted nitrophenols from the (indol-3-yl)methyl position of indolequinones", Journal of the Chemical Society, Perkin Transactions 2 (2001), (8), 1340-1345.
Table of Compounds, each of which can be found either in Table 1 of U.S. Pat. No. 9,018,210 issued Apr. 28, 2015 or Table 1 of U.S. Pat. No. 9,012,450 issued Apr. 21, 2015.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
Takata, Noriyuki. API form screening and selection in drug discovery stage. Pharm Stage, 2007, 6(10), pp. 20-25. (in Japanese with partial English translation).
Testa et al., Hydrolysis in Drug and Prodrug Metabolism, Jun. 2003, Wiley-VCH, Zurich, 419-534.
The Pharmacopoeia of Japan the Sixteen edition, 2011 pp. 64-68 2.58 X-ray powder diffraction measuring method p. 2070 (in Japanese with partial English translation).
Tome et al., "Product class 13: 1,2,3-triazoles", Science of Synthesis (2004), 13, 415-601 CODEN: SSCYJ9.
Tsuge, et al. Suppressive Effect of Vitamin B6-Sugar Derivatives on The Proliferation of Feline Mammary Tumor Cell, FRM. Vitamins (Japan), 2006; 80(11):537-542. (in Japanese with English Abstract).
U.S. Pharmacopia #23, National Formulary #18, 1995, 1843-1844.
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
VanRompaey et al., "A versatile synthesis of 2-substituted 4-amino-1,2,4,5-tetrahydro-2-benzazepine-3-ones", Tetrahedron (2003), 59(24), 4421-4432 CODEN: TETRAB; ISSN:0040-4020.
VanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes" Organometallics (2010), 29(2), 409-416.
Vichinsky et al., "A Phase 3 Randomized Trial of Voxelotor in Sickle Cell Disease," N. Engl. J. Med, 2019; 381(6), 509-519.
Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Wang et al., "Studies of Benzothiophene Template as Potent Factor IXa (FIXa) Inhibitors in Thrombosis", Journal of Medicinal Chemistry (2010), 53, 1465-1472.
Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.
Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Wermuth, Camille G., "Molecular Variations Based on Isosteric Replacements", The Practice of Medicinal Chemistry, 1996, pp. 203-232.
Yamano, Mitsuhisa. Approach to Crystal Polymorphs in Process Research of New Drug. Journal of Synthetic Organic Chemistry, Japan, 2007, 65(9), pp. 907-913. (in Japanese with partial English translation).

(56) References Cited

OTHER PUBLICATIONS

Yan et al., "Synthesis, crystal structure and antibacterial activity of dibutylitin carboxylate", Huaxue Tongbao (2007), 70(4), 313-316 CODEN: HHTPAU; ISSN: 0441-3776.

Yan et al., "Synthesis, crystal structure and antibacterial activity of di-n-butyltin di-2(2-formylphenoxy)acetic ester", Yingyong Huaxue (2007), 24(6), 660-664.

Yang, et al. Structural requirement of chalcones for the inhibitory activity of interleukin-5. Bioorg Med Chem. Jan. 1, 2007;15(1):104-11. Epub Oct. 10, 2006.

Yoon et al., The Chirality Conversion Reagent for Amino Acids Based on Salicyl Aldehyde. Bull. Korean Chem. Soc., (2012), 33:1715-1718.

Zhang et al., "DFT study on Rull-catalyzed cyclization of terminal alkynals to cycloalkenes", International Journal of Quantum Chemistry (2009), 109(4), 679-687 CODEN: IJQCB2; ISSN:0020-7608.

Zhang, et al. A selective fluorescent chemosensor with 1, 2, 4-triazole as subunit for Cu (II) and its application in imaging Cu (II) in living cells. Dyes and Pigments. 2012; 92(3):1370-1375.

Zhang, et al. Current prodrug strategies for improving oral absorption of nucleoside analogues. Asian Journal of Pharmaceutical Sciences. Apr. 2014; 9(2):65-74.

Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.

Zwaagstra et al., "Synthesis and Structure-Activity Relationships of Carboxylated Chalcones: A Novel Series of Cys-LT1 (LTD4) Receptor Antagonists", Journal of Medicinal Chemistry (1997), 40(7), 1075-1089 CODEN: JMCMAR; ISSN: 0022-2623.

MODULATORS OF HEMOGLOBIN

CROSS-REFERENCE TO RELATED APPLICATIONS

This application claims the benefit under 35 U.S.C. § 119(e) of U.S. Provisional Application 62/739,757, filed Oct. 1, 2018, and U.S. Provisional Application 62/821,311, filed Mar. 20, 2019, which are hereby incorporated by reference in their entireties.

FIELD

Provided herein are compounds and pharmaceutical compositions suitable as modulators of hemoglobin, and methods for their use in treating disorders mediated by hemoglobin.

BACKGROUND

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin A (HbA).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels. A need exists for compounds that can treat disorders that are mediated by abnormal Hb such as HbS and methods of treating such disorders.

SUMMARY

Provided herein are compounds of formula (I):

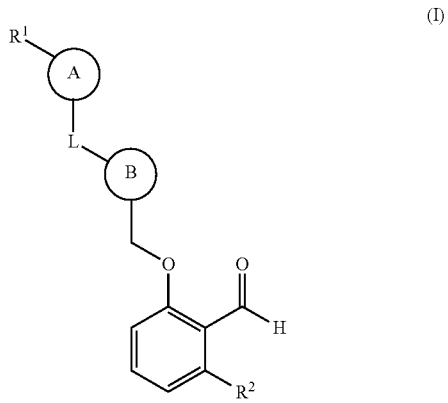

(I)

or a pharmaceutically acceptable salt thereof,
or an isotopically enriched analog, stereoisomer, mixture of stereoisomers or prodrug thereof or
a pharmaceutically acceptable salt of each thereof,
wherein:
ring A is aryl or heteroaryl, wherein ring A is optionally substituted with 1-3 $R^3$;
ring B is aryl, nitrogen-containing heteroaryl, or nitrogen-containing heterocyclyl,
wherein ring B is optionally substituted with 1-3 $R^4$;
L is absent, —C(O)—, —C(O)O—, or —CH$_2$—;
$R^1$ is —C(O)H;
$R^2$ is H or OH;
each $R^3$ is independently halo, hydroxy, $C_{1-3}$ alkyl, $C_{2-3}$ alkenyl, $C_{1-3}$ alkoxy, $C_{1-3}$ haloalkyl, or $C_{1-3}$ haloalkoxy; and
each $R^4$ is independently oxo, $C_{1-3}$ alkyl, $C_{1-3}$ alkoxy, $C_{1-3}$ haloalkyl, $C_{1-3}$ haloalkoxy, or $C_{3-5}$ cycloalkyl.

Some embodiments provide for pharmaceutical compositions comprising a compound as described herein or a pharmaceutically acceptable salt thereof, or an isotopically enriched analog, stereoisomer, mixture of stereoisomers or prodrug thereof or a pharmaceutically acceptable salt of each thereof, and a pharmaceutically acceptable excipient.

Also provided herein are methods for increasing oxygen affinity of hemoglobin S in a subject in need thereof, comprising administering to the subject a compound as described herein or a pharmaceutical composition as described herein.

Also provided herein are methods for treating a disorder mediated by hemoglobin in a subject in need thereof, comprising administering to the subject a compound as described herein or a pharmaceutical composition as described herein.

Also provided herein are methods for treating sickle cell disease in a subject in need thereof, comprising administering to the subject a compound as described herein or a pharmaceutical composition as described herein.

DETAILED DESCRIPTION

Definitions

Figure 1:
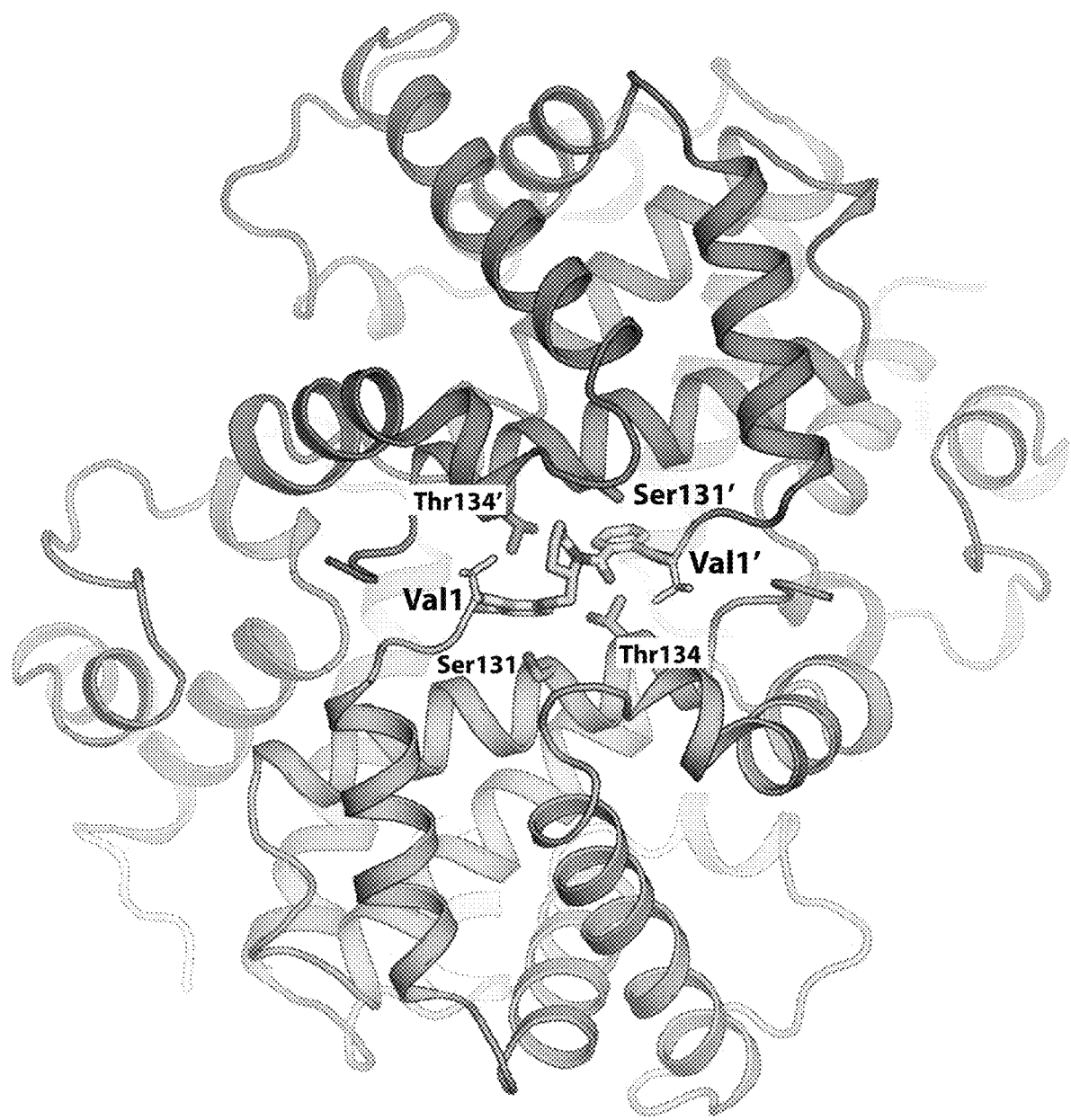
FIG. 1 illustrates binding of Compound 2 to two distinct areas of hemoglobin. The crystallographic studies and image shown in FIG. 1 were performed according to methods described in Example 21.
Figure 2:
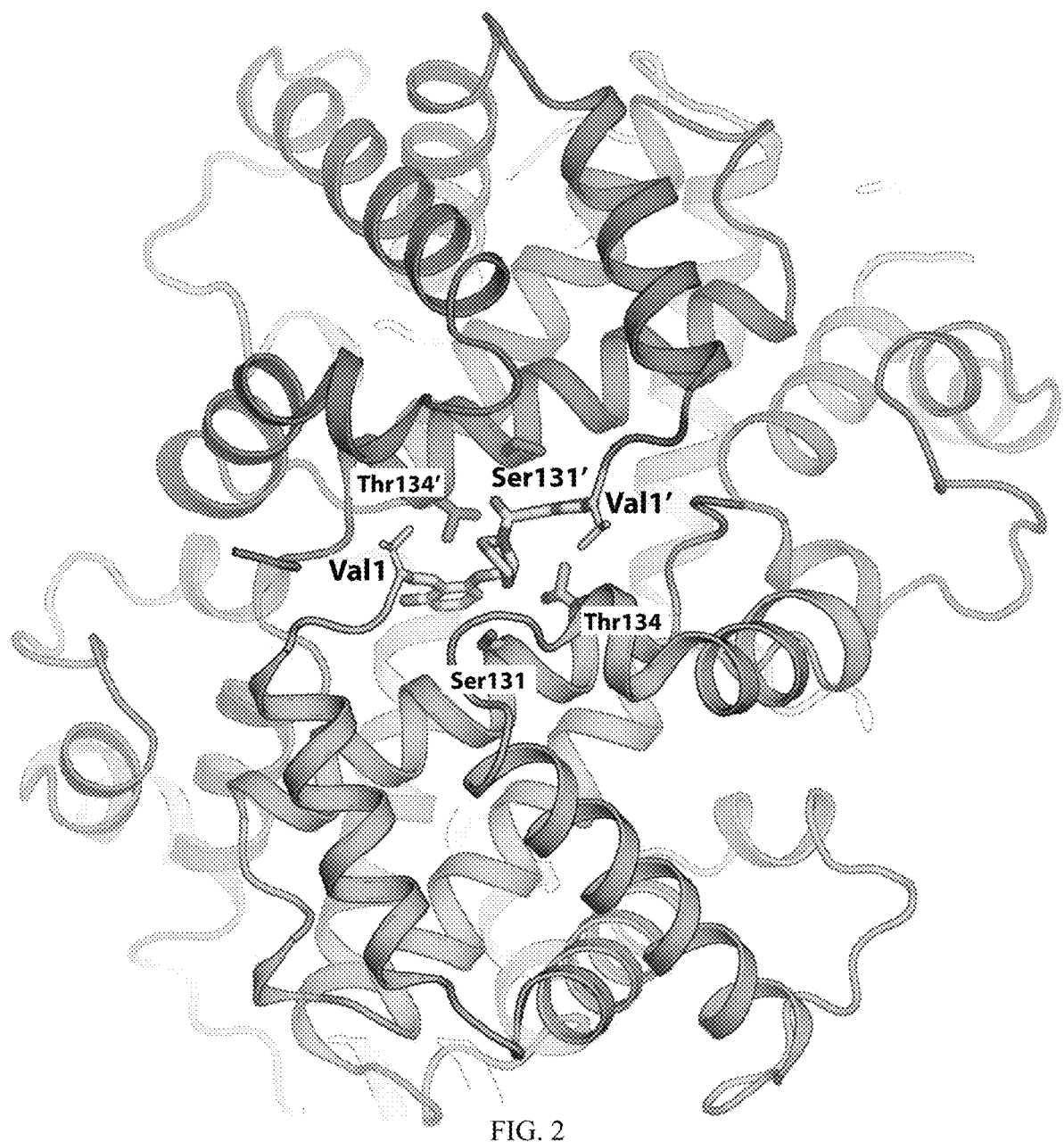
FIG. 2 illustrates binding of Compound 1 to two distinct areas of hemoglobin. The crystallographic studies and image shown in FIG. 2 were performed according to methods described in Example 21.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-henoxy and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-S(O)$_2$—". "Alkylsulfonylalkyl" refers to -alkyl-S(O)$_2$-alkyl.

"Acyl" refers to a group —C(O)$R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to the group —C(O)$NR^yR^z$ and an "N-amido" group which refers to the group —$NR^yC(O)R^z$, wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to the group —$NR^yR^z$ wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C($NR^y$)($NR^z_2$), wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)$NR^yR^z$ and an "N-carbamoyl" group which refers to the group —$NR^yC(O)OR^z$, wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)$R^x$ and —C(O)$OR^x$, wherein $R^x$ is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-".

"Guanidino" refers to —NR$^y$C(=NR$^z$)(NR$^y$R$^z$), wherein each R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Hydrazino" refers to —NHNH$_2$.

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6 or 1 to 3) hydrogen atoms are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indolizinyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

"Oxime" refers to the group —$CR^y$(=NOH) wherein $R^y$ is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —$S(O)_2R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —$S(O)R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5 or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5 or 1 to 3) hydrogen atom is replaced by a bond to a non-hydrogen atom such as, but not limited to: alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —$NHNH_2$, =$NNH_2$, imino, imido, hydroxy, oxo, oxime, nitro, sulfonyl, sulfinyl, alkylsulfonyl, alkylsulfinyl, thiocyanate, —$S(O)OH$, —$S(O)_2OH$, sulfonamido, thiol, thioxo, N-oxide or —$Si(R^y)_3$, wherein each $R^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5 or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, —$OC(=O)NR^gR^h$, —$OR^g$, —$SR^g$, —$S(=O)R^g$, —$S(=O)_2R^g$, —$OS(=O)_{1-2}R^g$, —$S(=O)_{1-2}OR^g$, —$NR^gS(=O)_{1-2}NR^gR^h$, =$NSO_2R^g$, =$NOR^g$, —$S(=O)_{1-2}NR^gR^h$, —$SF_5$, —$SCF_3$ or —$OCF_3$. In certain embodiments, "substituted" also means any of the above groups in which one or more (e.g., 1 to 5 or 1 to 3) hydrogen atoms are replaced with —$C(=O)R^g$, —$C(=O)OR_9$, —$C(=O)NR^gR^h$, —$CH_2SO_2R^g$, or —$CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5 or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN$(alkyl)$_2$), trialkyl amines (i.e., $N$(alkyl)$_3$), substituted alkyl amines (i.e., $NH_2$(substituted alkyl)), di(substituted alkyl) amines (i.e., $HN$(substituted alkyl)$_2$), tri(substituted alkyl) amines (i.e., $N$(substituted alkyl)$_3$), alkenyl amines (i.e., $NH_2$(alkenyl)), dialkenyl amines (i.e., $HN$(alkenyl)$_2$), trialkenyl amines (i.e., $N$(alkenyl)$_3$), substituted alkenyl amines (i.e., $NH_2$(substituted alkenyl)), di(substituted alkenyl) amines (i.e., $HN$(substituted alkenyl)$_2$), tri(substituted alkenyl) amines (i.e., $N$(substituted alkenyl)$_3$, mono-, di- or tri-cycloalkyl amines (i.e., $NH_2$(cycloalkyl), $HN$(cycloalkyl)$_2$, $N$(cycloalkyl)$_3$), mono-, di- or tri-arylamines (i.e., $NH_2$(aryl), $HN$(aryl)$_2$, $N$(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like. In some embodiments, a pharmaceutically acceptable salt does not include a salt of a primary amine.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) of the compounds of the invention may be reduced in vivo to a —CH$_2$OH moiety.

Compounds

Provided herein are compounds that are useful as modulators of hemoglobin. Unlike previously known modulators of hemoglobin, it is contemplated that compounds disclosed herein interact at two distinct areas of hemoglobin (e.g., at Val1 of one alpha chain and Val1' of the second, neighboring alpha chain; or at Val1 of one alpha chain and Ser131' and/or Thr134' of the second, neighboring alpha chain).

Provided herein are compounds of formula (I):

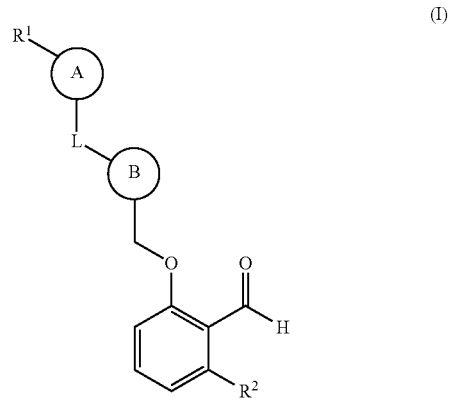

or a pharmaceutically acceptable salt thereof, or an isotopically enriched analog, stereoisomer, mixture of stereoisomers or prodrug thereof or a pharmaceutically acceptable salt of each thereof, wherein:

ring A is aryl or heteroaryl, wherein ring A is optionally substituted with 1-3 $R^3$;

ring B is aryl, nitrogen-containing heteroaryl, or nitrogen-containing heterocyclyl, wherein ring B is optionally substituted with 1-3 $R^4$;

L is absent, —C(O)—, —C(O)O—, or —CH$_2$—;

$R^1$ is —C(O)H;

$R^2$ is H or OH;

each $R^3$ is independently halo, hydroxy, $C_{1-3}$ alkyl, $C_{2-3}$ alkenyl, $C_{1-3}$ alkoxy, $C_{1-3}$ haloalkyl, or $C_{1-3}$ haloalkoxy; and each $R^4$ is independently oxo, $C_{1-3}$ alkyl, $C_{1-3}$ alkoxy, $C_{1-3}$ haloalkyl, $C_{1-3}$ haloalkoxy, or $C_{3-5}$ cycloalkyl.

Provided herein is a compound of formula (Ia):

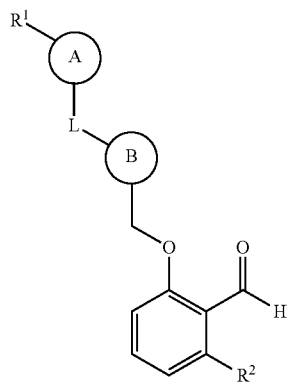
(Ia)

or a pharmaceutically acceptable salt thereof,
or an isotopically enriched analog, stereoisomer, mixture of stereoisomers or prodrug thereof or a pharmaceutically acceptable salt of each thereof,
wherein:
ring A is aryl or heteroaryl, wherein ring A is optionally substituted with 1-3 $R^3$;
ring B is aryl, nitrogen-containing heteroaryl, or nitrogen-containing heterocyclyl,
wherein ring B is optionally substituted with 1-3 $R^4$;
L is absent or —C(O)—;
$R^1$ is —C(O)H;
$R^2$ is H or OH;
each $R^3$ is independently halo, hydroxy, $C_{1-3}$ alkyl, $C_{2-3}$ alkenyl, $C_{1-3}$ alkoxy, $C_{1-3}$ haloalkyl, or $C_{1-3}$ haloalkoxy; and
each $R^4$ is independently oxo, $C_{1-3}$ alkyl, $C_{1-3}$ alkoxy, $C_{1-3}$ haloalkyl, $C_{1-3}$ haloalkoxy, or $C_{3-5}$ cycloalkyl.

In some embodiments, L is absent, and ring B is aryl or nitrogen-containing heteroaryl, wherein ring B is optionally substituted with 1-3 $R^4$.

In some embodiments, L is absent, and ring B is $C_{6-10}$ aryl optionally substituted with 1-3 $R^4$.

In some embodiments, L is absent, and ring B is $C_6$ or $C_{10}$ aryl optionally substituted with 1-3 $R^4$.

In some embodiments, ring A is monocyclic. In some embodiments, ring B is monocyclic. In some embodiments, ring A and ring B are monocyclic.

In some embodiments, ring B is phenyl optionally substituted with 1-3 $R^4$.

In some embodiments, ring B is phenyl.

In some embodiments, L is absent, and ring B is a 5-membered or 6-membered nitrogen-containing heteroaryl optionally substituted with 1-3 $R^4$.

In some embodiments, ring B is a pyridyl ring or pyrazinyl ring, each of which is optionally substituted with 1-3 $R^4$.

In some embodiments, ring B is a pyridyl ring optionally substituted with 1-3 $R^4$.

In some embodiments, ring B is a pyrazinyl ring optionally substituted with 1-3 $R^4$.

In some embodiments,

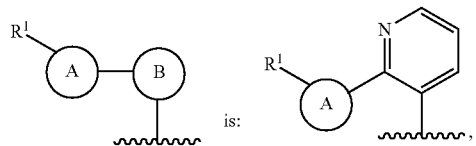

is:

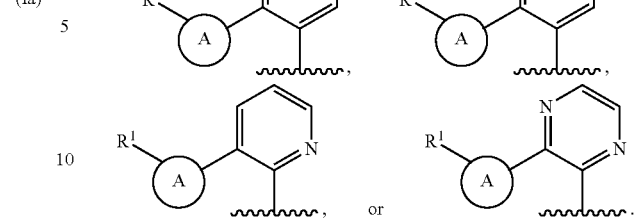

In some embodiments,

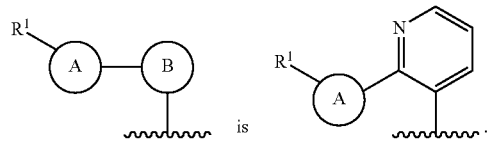

In some embodiments,

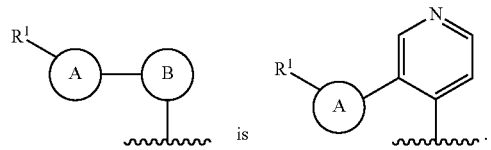

In some embodiments,

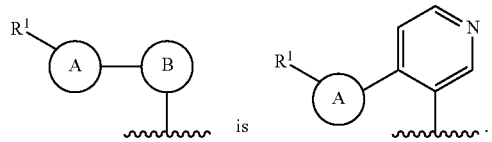

In some embodiments,

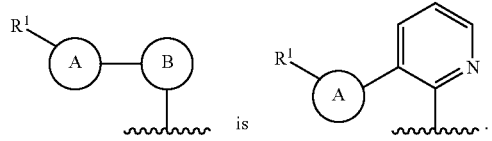

In some embodiments,

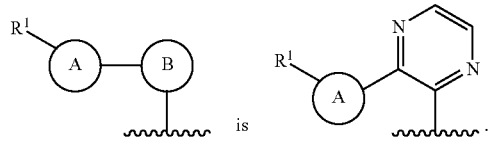

In some embodiments, L is —C(O)—, —C(O)O—, or —CH$_2$—, and ring B is a nitrogen-containing heterocyclyl optionally substituted with 1-3 $R^4$.

In some embodiments, L is —C(O)—, and ring B is a nitrogen-containing heterocyclyl optionally substituted with 1-3 R⁴.

In some embodiments, ring B is a 5-membered or 6-membered nitrogen-containing heterocyclyl optionally substituted with 1-3 R⁴.

In some embodiments, ring B is a 5-membered or 6-membered nitrogen-containing heterocyclyl.

In some embodiments, ring B is

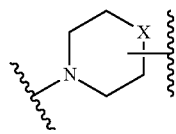

optionally substituted with 1-3 R⁴, and X is absent, —CH₂—, —N(R⁵)—, —O—, —S—, —S(O)₁₋₂—, —CH₂CH₂—, —CH₂—O—, or —O—CH₂—; wherein R⁵ is H, $C_{1-3}$ alkyl, or $C_{3-5}$ cycloalkyl.

In some embodiments, ring B is

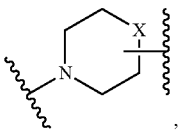

, and X is absent, —CH₂—, —N(R⁵)—, —O—, —S(O)₀₋₂—, —CH₂CH₂—, —CH₂—O—, or —O—CH₂—; wherein R⁵ is H, $C_{1-3}$ alkyl, or $C_{3-5}$ cycloalkyl.

In some embodiments, ring B is

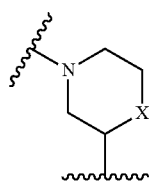

optionally substituted with 1-3 R⁴, and X is absent, —CH₂—, —N(R⁵)—, —O—, —S—, —S(O)₁₋₂—, —CH₂CH₂—, —CH₂—O—, or —O—CH₂—; wherein R⁵ is H, $C_{1-3}$ alkyl, or $C_{3-5}$ cycloalkyl.

In some embodiments, ring B is

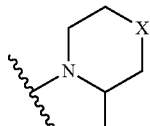

optionally substituted with 1-3 R⁴, and X is absent, —CH₂—, —N(R⁵)—, —O—, —S—, —S(O)₁₋₂—, —CH₂CH₂—, —CH₂—O—, or —O—CH₂—; wherein R⁵ is H, $C_{1-3}$ alkyl, or $C_{3-5}$ cycloalkyl.

In some embodiments, ring B is

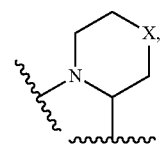

and X is absent, —CH₂—, —N(R⁵)—, —O—, —S(O)₀₋₂—, —CH₂CH₂—, —CH₂—O—, or —O—CH₂—; wherein R⁵ is H.

In some embodiments, ring B is

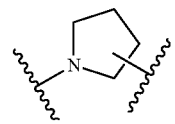

In some embodiments, ring B is

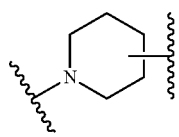

In some embodiments, ring B is

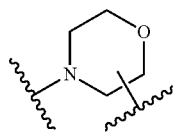

In some embodiments, ring B is

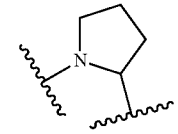 [SMILES: *C1CCCN1*]

optionally substituted with 1-3 R⁴, and each R⁴ is independently oxo or $C_{1-3}$ alkyl.

In some embodiments, ring B is

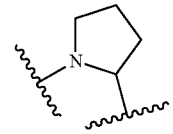

.

In some embodiments, ring B is

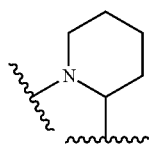

optionally substituted with 1-3 R⁴, and each R⁴ is independently oxo or $C_{1-3}$ alkyl. In some embodiments, ring B is

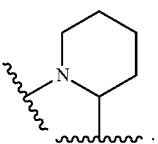 [SMILES: *C1CCCCN1*]

In some embodiments, ring B is

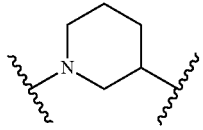

In some embodiments, ring B is

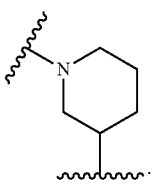 [SMILES: *C1CCCN(*)C1]

In some embodiments, ring B is

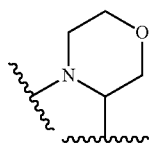 [SMILES: *C1COCCN1*]

optionally substituted with 1-3 R⁴, and each R⁴ is independently oxo or $C_{1-3}$ alkyl. In some embodiments, ring B is

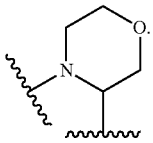 [SMILES: *C1COCCN1*]

In some embodiments, ring B is

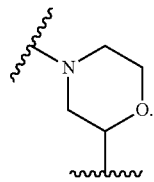 [SMILES: *C1CN(*)CCO1]

In some embodiments, ring B is

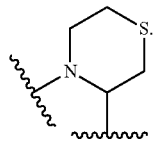 [SMILES: *C1CSCCN1*]

In some embodiments,

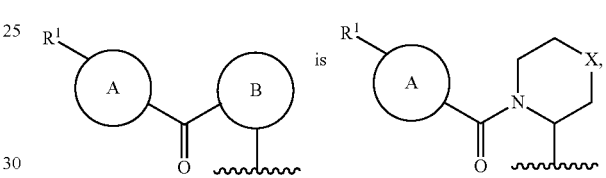

wherein X is as defined herein. In some embodiments, X is CH₂. In some embodiments, X is —O—. In some embodiments, X is —S—.

In some embodiments,

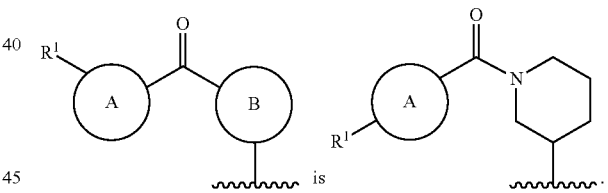

In some embodiments, ring B is a 5-membered or 6-membered nitrogen-containing heterocyclyl substituted with one R⁴, wherein R⁴ is $C_{1-3}$ alkyl. In some embodiments, ring B is a 5-membered or 6-membered nitrogen-containing heterocyclyl substituted with one R⁴, wherein R⁴ is methyl.

In some embodiments, ring B is

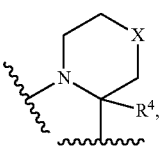

wherein X and R⁴ are as defined herein. In some embodiments, X is absent, —CH₂—, —N(R⁵)—, —O—, —S(O)₀₋₂—, —CH₂CH₂—, —CH₂—O—, or —O—CH₂—; wherein R⁵ is H, $C_{1-3}$ alkyl, or $C_{3-5}$ cycloalkyl. In some embodiments, ring B is

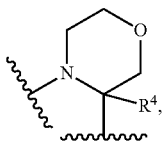

wherein $R^4$ is $C_{1-3}$ alkyl. In some embodiments, ring B is

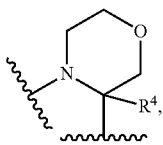

wherein $R^4$ is methyl.

In some embodiments,

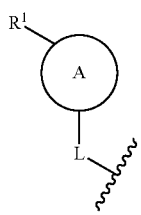 and 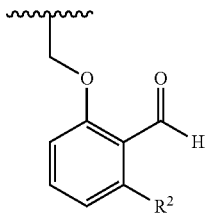

and $R^2$ are attached in a 1,4-position relative to each other (i.e., their attachment points are separated by two ring atoms; corresponding to para for benzene derivatives) on ring B.

In some embodiments,

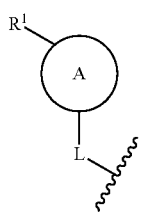 and 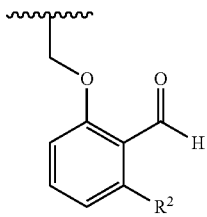

and $R^2$ are attached in a 1,3-position relative to each other (i.e., their attachment points are separated by one ring atom; corresponding to meta for benzene derivatives) on ring B.

In some embodiments,

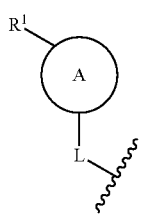 and 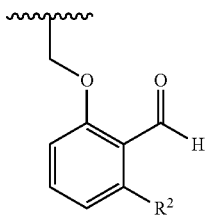

and $R^2$ are attached in a 1,2-position relative to each other (i.e., they are attached to adjacent ring atoms; corresponding to ortho for benzene derivatives) on ring B.

In some embodiments, ring A is a $C_{6-10}$ aryl optionally substituted with 1-3 $R^3$.

In some embodiments, ring A is a $C_6$ or $C_{10}$ aryl optionally substituted with 1-3 $R^3$.

In some embodiments, ring A is a phenyl optionally substituted with 1-3 $R^3$.

In some embodiments, ring A is a phenyl substituted with 1-3 $R^3$.

In some embodiments, ring A is a phenyl substituted with one $R^3$.

In some embodiments, ring A is a 5-membered or 6-membered heteroaryl optionally substituted with 1-3 $R^3$.

In some embodiments, ring A is a 5-membered heteroaryl substituted with 1-3 $R^3$.

In some embodiments, ring A is a 6-membered heteroaryl substituted with 1-3 $R^3$.

In some embodiments, ring A is a pyridinyl, pyrimidinyl, pyrazolyl, furanyl, oxazolyl, or thiazolyl, each of which is substituted with 1-3 $R^3$.

In some embodiments, $R^1$ and L are attached in a 1,3-position relative to each other (i.e., their attachment points are separated by one ring atom; corresponding to meta for benzene derivatives) on ring A.

In some embodiments, $R^1$ and L are attached in a 1,2-position relative to each other (i.e., they are attached to adjacent ring atoms; corresponding to ortho for benzene derivatives) on ring A.

In some embodiments, $R^1$ and L are attached in a 1,4-position relative to each other (i.e., their attachment points are separated by two ring atoms; corresponding to para for benzene derivatives) on ring A.

In some embodiments, each $R^3$ is independently halo, hydroxy, $C_{1-3}$ alkyl, or $C_{1-3}$ alkoxy.

Some embodiments provide for a compound of formula (IIa):

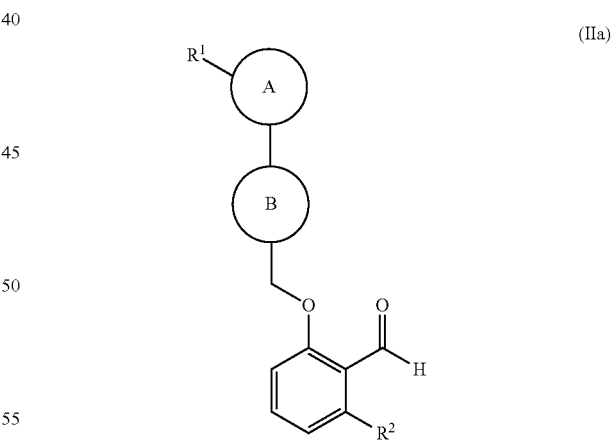

(IIa)

or a pharmaceutically acceptable salt thereof, or an isotopically enriched analog, stereoisomer, mixture of stereoisomers or prodrug thereof or a pharmaceutically acceptable salt of each thereof, wherein:

ring B is aryl or nitrogen-containing heteroaryl, wherein ring B is optionally substituted with 1-3 $R^4$; and $R^1$ and ring B are attached in a 1,3-position relative to each other on ring A.

Some embodiments provide for a compound of formula (IIb):

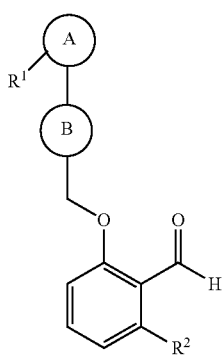

(IIb)

or a pharmaceutically acceptable salt thereof, or an isotopically enriched analog, stereoisomer, mixture of stereoisomers or prodrug thereof or a pharmaceutically acceptable salt of each thereof, wherein:

ring B is aryl or nitrogen-containing heteroaryl, wherein ring B is optionally substituted with 1-3 $R^4$; and $R^1$ and ring B are attached in a 1,2-position relative to each other on ring A.

Some embodiments provide for a compound of formula (IIc):

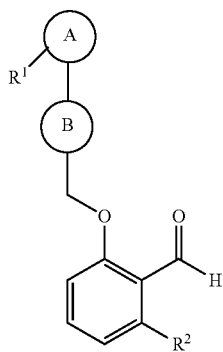

(IIc)

or a pharmaceutically acceptable salt thereof, or an isotopically enriched analog, stereoisomer, mixture of stereoisomers or prodrug thereof or a pharmaceutically acceptable salt of each thereof, wherein:

ring B is aryl or nitrogen-containing heteroaryl, wherein ring B is optionally substituted with 1-3 $R^4$; and $R^1$ and ring B are attached in a 1,4-position relative to each other on ring A.

In some embodiments, if ring B is a pyridinyl ring, then ring A is not a heteroaryl.

In some embodiments, if ring B is a pyridinyl ring, then ring A is not pyrazolyl.

Some embodiments provide for a compound of formula (IIIa):

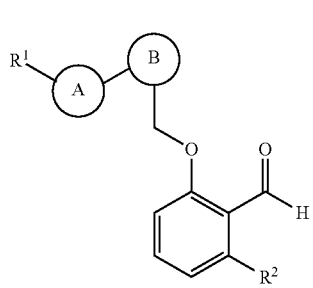

(IIIa)

or a pharmaceutically acceptable salt thereof, or an isotopically enriched analog, stereoisomer, mixture of stereoisomers or prodrug thereof or a pharmaceutically acceptable salt of each thereof, wherein:

ring B is phenyl or 6-membered nitrogen-containing heteroaryl; and ring A and

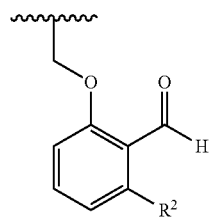

are attached on adjacent ring carbon atoms of ring B.

Some embodiments provide for a compound of formula (IIIa(i)):

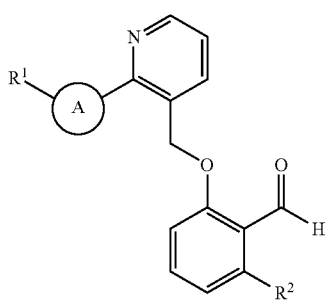

(IIIa(i))

or a pharmaceutically acceptable salt thereof, or an isotopically enriched analog, stereoisomer, mixture of stereoisomers or prodrug thereof or a pharmaceutically acceptable salt of each thereof.

In some embodiments, $R^1$ and

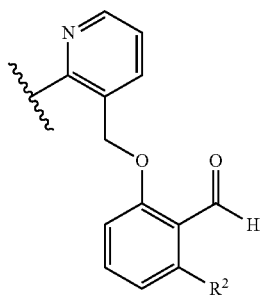

are attached in a 1,3-position relative to each other on ring A.

In some embodiments, ring A is phenyl, 5-membered heteroaryl, or 6-membered heteroaryl, each of which is optionally substituted with 1-3 $R^3$; wherein each $R^3$ is independently halo, hydroxy, $C_{1-3}$ alkyl, or $C_{1-3}$ alkoxy.

Some embodiments provide for a compound of formula (IVa):

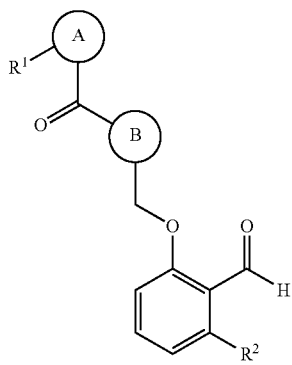

(IVa)

or a pharmaceutically acceptable salt thereof, or an isotopically enriched analog, stereoisomer, mixture of stereoisomers or prodrug thereof or a pharmaceutically acceptable salt of each thereof, wherein:

ring B is a nitrogen-containing heterocyclyl optionally substituted with 1-3 $R^4$; and $R^1$ and —C(O)— of the moiety

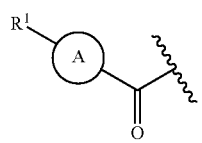

are attached on adjacent ring atoms of ring A.

Some embodiments provide for a compound of formula (IVb):

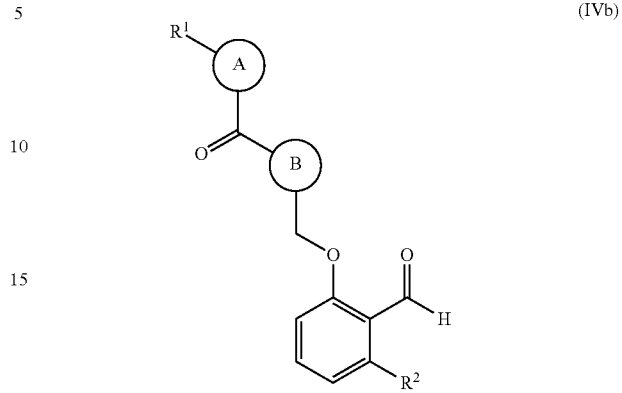

(IVb)

or a pharmaceutically acceptable salt thereof, or an isotopically enriched analog, stereoisomer, mixture of stereoisomers or prodrug thereof or a pharmaceutically acceptable salt of each thereof, wherein ring B is a nitrogen-containing heterocyclyl optionally substituted with 1-3 $R^4$; and $R^1$ and —C(O)— of the moiety

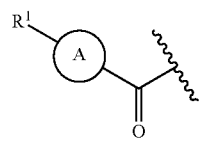

are attached in a 1,3-position relative to each other on ring A.

Some embodiments provide for a compound of formula (IVc):

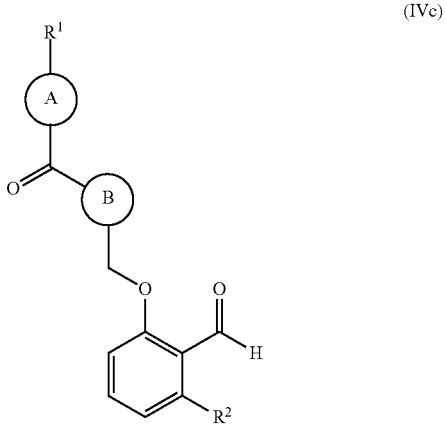

(IVc)

or a pharmaceutically acceptable salt thereof, or an isotopically enriched analog, stereoisomer, mixture of stereoisomers or prodrug thereof or a pharmaceutically acceptable salt of each thereof, wherein ring B is a nitrogen-containing heterocyclyl optionally substituted with 1-3 $R^4$; and $R^1$ and —C(O)— of the moiety

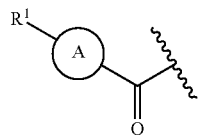

are attached in a 1,4-position relative to each other on ring A.

Some embodiments provide for a compound of formula (Va(1)):

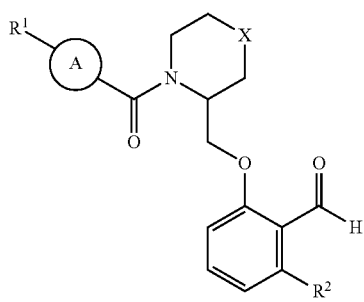

(Va(1))

or a pharmaceutically acceptable salt thereof, or an isotopically enriched analog, stereoisomer, mixture of stereoisomers or prodrug thereof or a pharmaceutically acceptable salt of each thereof, wherein X is absent, —$CH_2$—, —$CH_2CH_2$—, —O—, or —S—.

Some embodiments provide for a compound of formula (Va(2)):

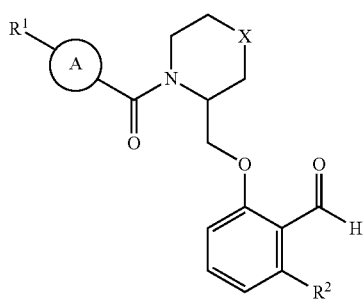

(Va(2))

or a pharmaceutically acceptable salt thereof, or an isotopically enriched analog, stereoisomer, mixture of stereoisomers or prodrug thereof or a pharmaceutically acceptable salt of each thereof, wherein X is absent, —$CH_2$—, —$CH_2CH_2$—, or —O—.

Some embodiments provide for a compound of formula (Va(1)(i)):

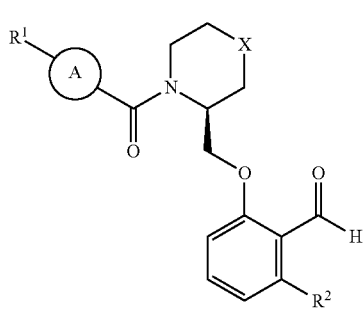

(Va(1)(i))

or a pharmaceutically acceptable salt thereof, or an isotopically enriched analog or prodrug thereof or a pharmaceutically acceptable salt of each thereof, wherein X is absent, —$CH_2$—, —$CH_2CH_2$—, —O—, or —S—.

Some embodiments provide for a compound of formula (Va(2)(i)):

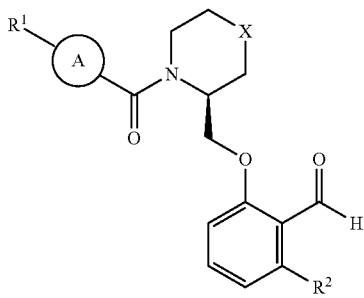

(Va(2)(i))

or a pharmaceutically acceptable salt thereof, or an isotopically enriched analog or prodrug thereof or a pharmaceutically acceptable salt of each thereof, wherein X is absent, —$CH_2$—, —$CH_2CH_2$—, or —O—.

Some embodiments provide for a compound of formula (Vb):

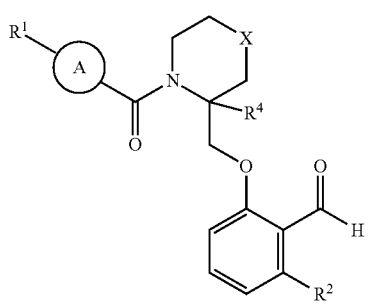

(Vb)

or a pharmaceutically acceptable salt thereof, or an isotopically enriched analog, stereoisomer, mixture of stereoisomers or prodrug thereof or a pharmaceutically acceptable salt of each thereof, wherein ring A, X, $R^1$, $R^2$, and $R^4$ are as defined herein.

Some embodiments provide for a compound of formula (Vb(i)):

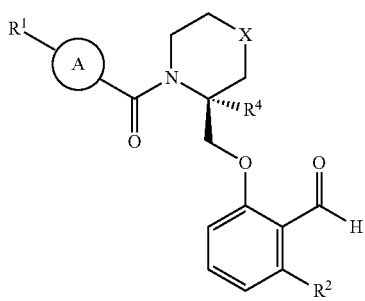

or a pharmaceutically acceptable salt thereof, or an isotopically enriched analog or prodrug thereof or a pharmaceutically acceptable salt of each thereof, wherein ring A, X, $R^1$, $R^2$, and $R^4$ are as defined herein.

In some embodiments, $R^1$ and —C(O)— of the moiety

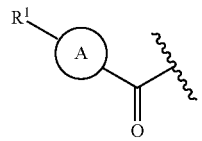

are attached on adjacent ring atoms of ring A.

In some embodiments, ring A is phenyl or pyridinyl, each of which is optionally substituted with 1-3 $R^3$; wherein each $R^3$ is independently halo, hydroxy, $C_{1-3}$ alkyl, or $C_{1-3}$ alkoxy.

In some embodiments, ring A is phenyl optionally substituted with 1-3 $R^3$; wherein each $R^3$ is independently halo, hydroxy, $C_{1-3}$ alkyl, or $C_{1-3}$ alkoxy.

Some embodiments provide for a compound of formula (VIa):

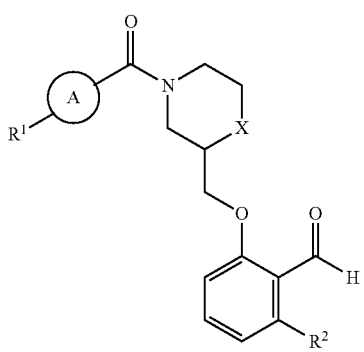

or a pharmaceutically acceptable salt thereof,
or an isotopically enriched analog, stereoisomer, mixture of stereoisomers or prodrug thereof or a pharmaceutically acceptable salt of each thereof, wherein X is absent, —CH$_2$—, —CH$_2$CH$_2$—, —O—, or —S—.

Some embodiments provide for a compound of formula (VIa(1)):

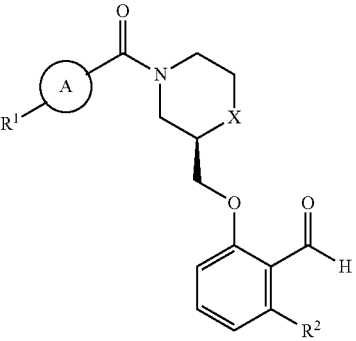

or a pharmaceutically acceptable salt thereof,
or an isotopically enriched analog, stereoisomer, mixture of stereoisomers or prodrug thereof or a pharmaceutically acceptable salt of each thereof, wherein X is absent, —CH$_2$—, —CH$_2$CH$_2$—, —O—, or —S—.

Some embodiments provide for a compound of formula (VIb):

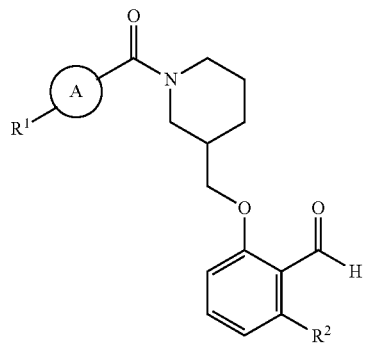

or a pharmaceutically acceptable salt thereof,
or an isotopically enriched analog, stereoisomer, mixture of stereoisomers or prodrug thereof or a pharmaceutically acceptable salt of each thereof.

Some embodiments provide for a compound of formula (VIb(1)):

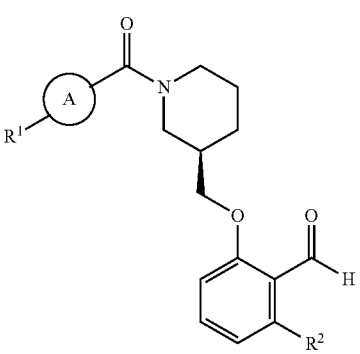

or a pharmaceutically acceptable salt thereof,
or an isotopically enriched analog or prodrug thereof or a pharmaceutically acceptable salt of each thereof.

In some embodiments, $R^1$ and —C(O)— of the moiety

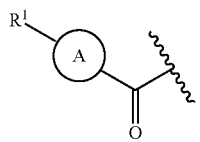

are in a 1,2-position or 1,3-position relative to each other on ring A.

In some embodiments, ring A is phenyl optionally substituted with 1-3 $R^3$; wherein each $R^3$ is independently halo, hydroxy, $C_{1-3}$ alkyl, or $C_{1-3}$ alkoxy.

In some embodiments, each $R^3$ is independently halo, hydroxy, $C_{1-3}$ alkyl, $C_{2-3}$ alkenyl, $C_{1-3}$ alkoxy, $C_{1-3}$ haloalkyl, or $C_{1-3}$ haloalkoxy.

In some embodiments, each $R^3$ is independently halo, hydroxy, $C_{1-3}$ alkyl, $C_{1-3}$ alkoxy, $C_{1-3}$ haloalkyl, or $C_{1-3}$ haloalkoxy.

In some embodiments, each $R^3$ is independently halo, hydroxy, $C_{1-3}$ alkyl, or $C_{1-3}$ alkoxy.

In some embodiments, each $R^4$ is independently oxo, $C_{1-3}$ alkyl, $C_{1-3}$ alkoxy, $C_{1-3}$ haloalkyl, $C_{1-3}$ haloalkoxy, or $C_{3-5}$ cycloalkyl.

In some embodiments, each $R^4$ is independently oxo, $C_{1-3}$ alkyl, $C_{1-3}$ alkoxy, $C_{1-3}$ haloalkyl, or $C_{1-3}$ haloalkoxy.

In some embodiments, each $R^4$ is independently oxo. In some embodiments, each $R^4$ is independently $C_{1-3}$ alkyl. In some embodiments, each $R^4$ is methyl.

In some embodiments, $R^2$ is OH.

In some embodiments, $R^2$ is H.

In some embodiments, provided is a compound selected from Table 1:

TABLE 1

| Compound Number | Structure | IUPAC name |
|---|---|---|
| 1 | 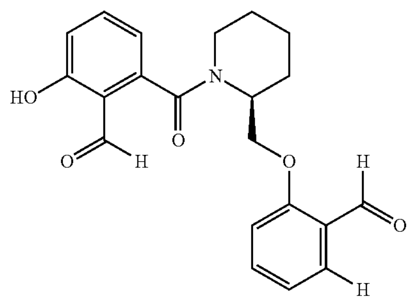 [SMILES: O=Cc1ccccc1OC[C@@H]1CCCCN1C(=O)c1cccc(O)c1C=O] | 2-[(2S)-2-[(2-formyl-3-hydroxyphenoxy)methyl]piperidine-1-carbonyl]-6-hydroxybenzaldehyde |
| 2 | 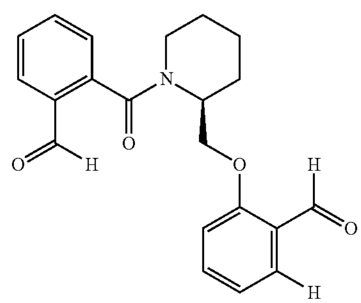 [SMILES: O=Cc1ccccc1OC[C@@H]1CCCCN1C(=O)c1ccccc1C=O] | 2-{[(2S)-1-(2-formylbenzoyl)piperidin-2-yl]methoxy}-6-hydroxybenzaldehyde |
| 3 | 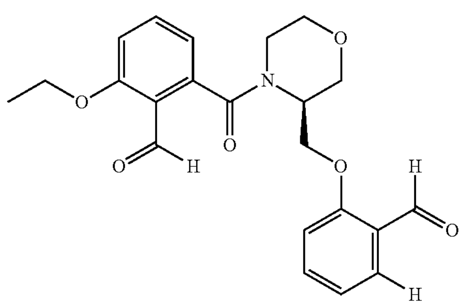 [SMILES: CCOc1cccc(C(=O)N2CCOC[C@H]2COc2ccccc2C=O)c1C=O] | 2-ethoxy-6-[(3S)-3-[(2-formyl-3-hydroxyphenoxy)methyl]morpholine-4-carbonyl]benzaldehyde |

TABLE 1-continued

| Compound Number | Structure | IUPAC name |
|---|---|---|
| 4 | 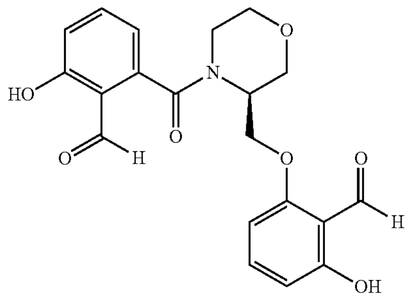 [SMILES: O=Cc1c(O)cccc1OC[C@@H]1COCCN1C(=O)c1cccc(O)c1C=O] | (S)-2-((4-(2-formyl-3-hydroxybenzoyl)morpholin-3-yl)methoxy)-6-hydroxybenzaldehyde |
| 5 | 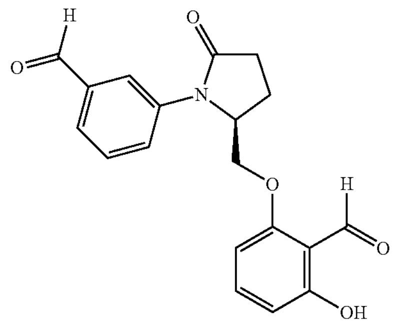 [SMILES: O=Cc1cccc(N2C(=O)CC[C@H]2COc2cccc(O)c2C=O)c1] | 2-{[(2S)-1-(3-formylphenyl)-5-oxopyrrolidin-2-yl]methoxy}-6-hydroxybenzaldehyde |
| 6 | 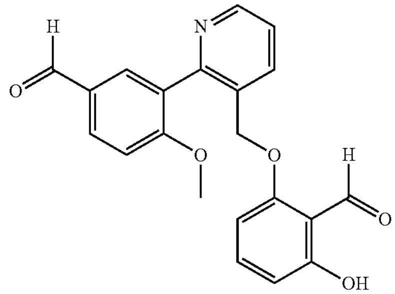 [SMILES: COc1ccc(C=O)cc1-c1ncccc1COc1cccc(O)c1C=O] | 3-{3-[(2-formyl-3-hydroxyphenoxy)methyl]pyridin-2-yl}-4-methoxybenzaldehyde |
| 7 | 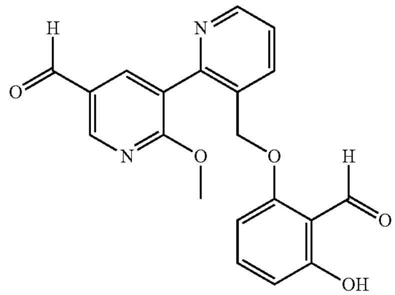 [SMILES: COc1ncc(C=O)cc1-c1ncccc1COc1cccc(O)c1C=O] | 3-[(2-formyl-3-hydroxyphenoxy)methyl]-2'-methoxy-[2,3'-bipyridine]-5'-carbaldehyde |
| 8 | 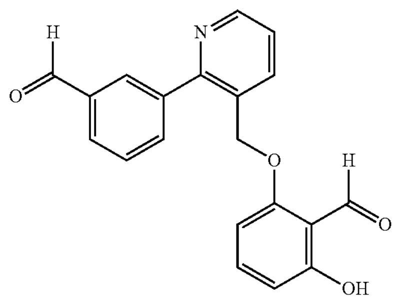 | 3-{3-[(2-formyl-3-hydroxyphenoxy)methyl]pyridin-2-yl}benzaldehyde |

TABLE 1-continued

| Compound Number | Structure | IUPAC name |
|---|---|---|
| 9 | 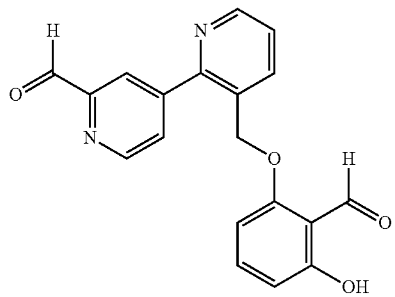 | 3-[(2-formyl-3-hydroxyphenoxy)methyl]-[2,4'-bipyridine]-2'-carbaldehyde |
| 10 | 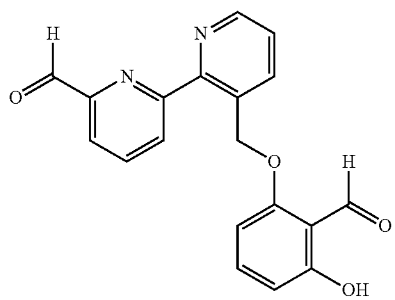 | 3'-[(2-formyl-3-hydroxyphenoxy)methyl]-[2,2'-bipyridine]-6-carbaldehyde |
| 11 | 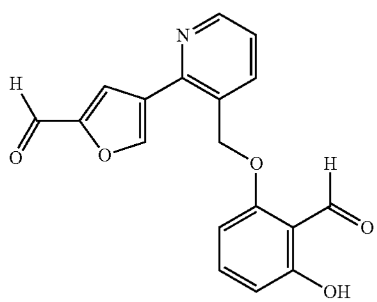 [SMILES: O=Cc1cc(-c2ncccc2COc2cccc(O)c2C=O)co1] | 4-{3-[(2-formyl-3-hydroxyphenoxy)methyl]pyridin-2-yl}furan-2-carbaldehyde |
| 12 | 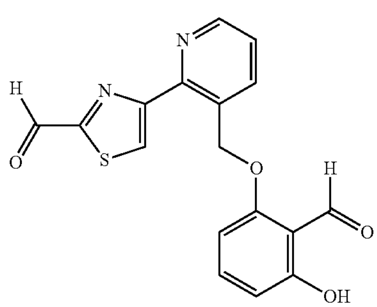 [SMILES: O=Cc1nc(-c2ncccc2COc2cccc(O)c2C=O)cs1] | 4-{3-[(2-formyl-3-hydroxyphenoxy)methyl]pyridin-2-yl}-1,3-thiazole-2-carbaldehyde |

TABLE 1-continued

| Compound Number | Structure | IUPAC name |
|---|---|---|
| 13 | 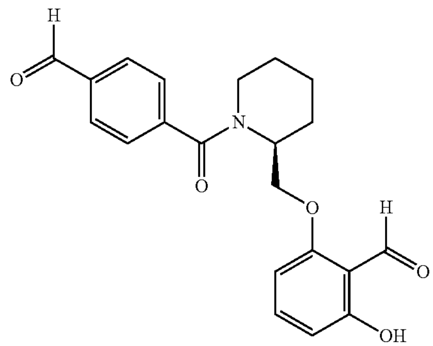 [SMILES: O=Cc1ccc(C(=O)N2CCCC[C@H]2COc2cccc(O)c2C=O)cc1] | 2-{[(2S)-1-(4-formylbenzoyl)piperidin-2-yl]methoxy}-6-hydroxybenzaldehyde |
| 14 | 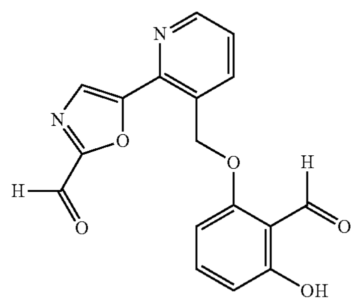 [SMILES: O=Cc1ncc(-c2ncccc2COc2cccc(O)c2C=O)o1] | 5-(3-((2-formyl-3-hydroxyphenoxy)methyl)pyridin-2-yl)oxazole-2-carbaldehyde |
| 15 | 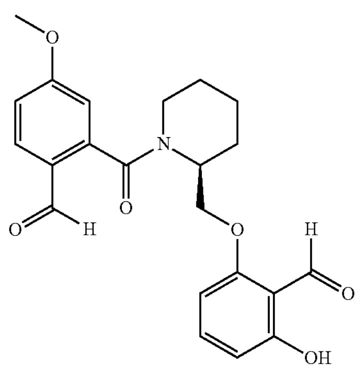 [SMILES: COc1ccc(C=O)c(C(=O)N2CCCC[C@H]2COc2cccc(O)c2C=O)c1] | 2-[(2S)-2-[(2-formyl-3-hydroxyphenoxy)methyl]piperidine-1-carbonyl]-4-methoxybenzaldehyde |
| 16 | 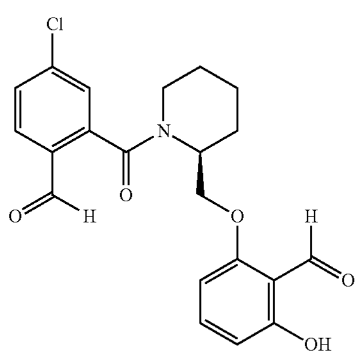 [SMILES: O=Cc1ccc(Cl)cc1C(=O)N1CCCC[C@H]1COc1cccc(O)c1C=O] | 4-chloro-2-[(2S)-2-[(2-formyl-3-hydroxyphenoxy)methyl]piperidine-1-carbonyl]benzaldehyde |

TABLE 1-continued

| Compound Number | Structure | IUPAC name |
|---|---|---|
| 17 | 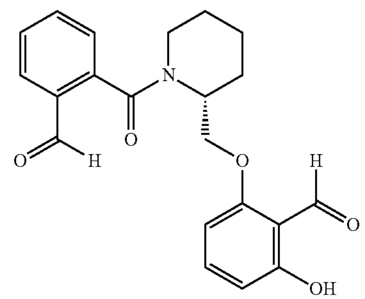 [SMILES: O=Cc1ccccc1C(=O)N1CCCC[C@@H]1COc1cccc(O)c1C=O] | 2-{[(2R)-1-(2-formylbenzoyl)piperidin-2-yl]methoxy}-6-hydroxybenzaldehyde |
| 18 | 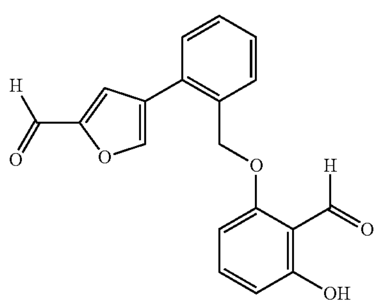 [SMILES: O=Cc1cc(-c2ccccc2COc2cccc(O)c2C=O)co1] | 4-{2-[(2-formyl-3-hydroxyphenoxy)methyl]phenyl}furan-2-carbaldehyde |
| 19 | 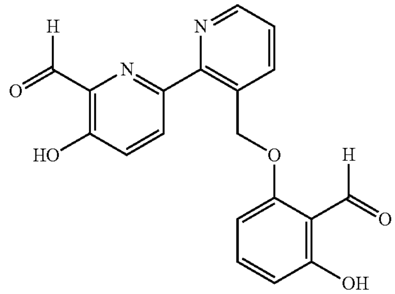 [SMILES: O=Cc1nc(-c2ncccc2COc2cccc(O)c2C=O)ccc1O] | 3'-[(2-formyl-3-hydroxyphenoxy)methyl]-5-hydroxy-[2,2'-bipyridine]-6-carbaldehyde |
| 20 | 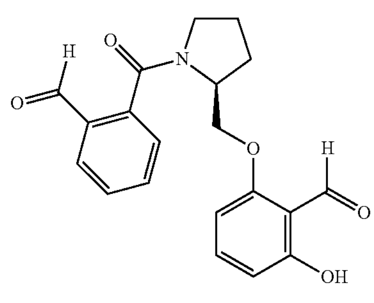 [SMILES: O=Cc1ccccc1C(=O)N1CCC[C@H]1COc1cccc(O)c1C=O] | 2-{[(2S)-1-(2-formylbenzoyl)pyrrolidin-2-yl]methoxy}-6-hydroxybenzaldehyde |
| 21 | 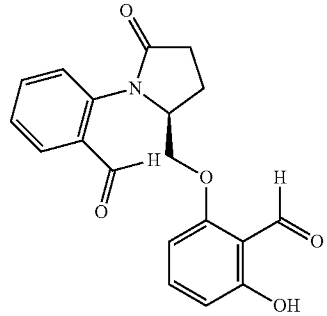 [SMILES: O=Cc1ccccc1N1C(=O)CC[C@H]1COc1cccc(O)c1C=O] | 2-{[(2S)-1-(2-formylphenyl)-5-oxopyrrolidin-2-yl]methoxy}-6-hydroxybenzaldehyde |

TABLE 1-continued

| Compound Number | Structure | IUPAC name |
|---|---|---|
| 22 | 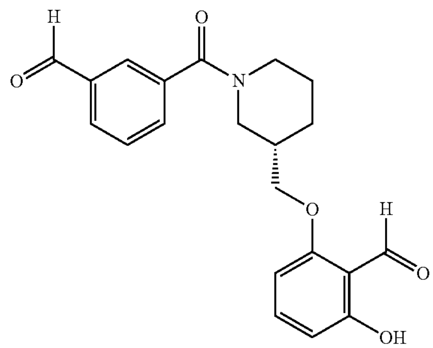 [SMILES: O=Cc1cccc(C(=O)N2CCC[C@H](COc3cccc(O)c3C=O)C2)c1] | 2-{[(3S)-1-(3-formylbenzoyl)piperidin-3-yl]methoxy}-6-hydroxybenzaldehyde |
| 23 | 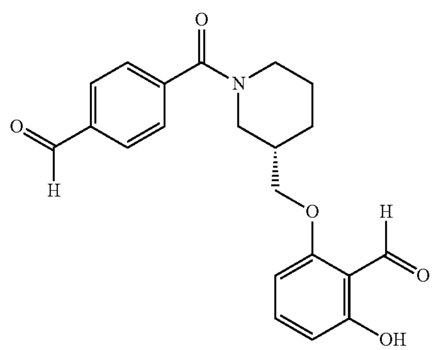 [SMILES: O=Cc1ccc(C(=O)N2CCC[C@H](COc3cccc(O)c3C=O)C2)cc1] | 2-{[(3S)-1-(4-formylbenzoyl)piperidin-3-yl]methoxy}-6-hydroxybenzaldehyde |
| 24 | 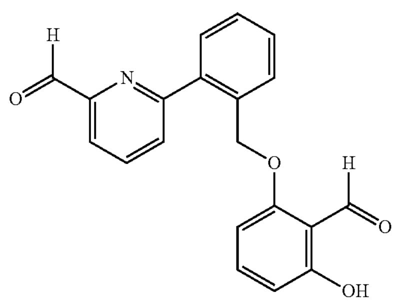 | 6-{2-[(2-formyl-3-hydroxyphenoxy)methyl]phenyl}pyridine-2-carbaldehyde |
| 25 | 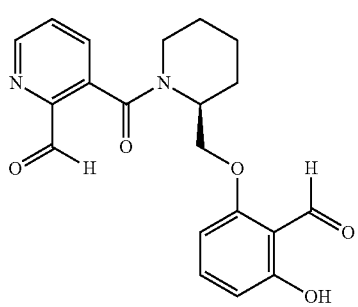 [SMILES: O=Cc1ncccc1C(=O)N1CCCC[C@H]1COc1cccc(O)c1C=O] | 3-[(2S)-2-[(2-formyl-3-hydroxyphenoxy)methyl]piperidine-1-carbonyl]pyridine-2-carbaldehyde |

TABLE 1-continued

| Compound Number | Structure | IUPAC name |
|---|---|---|
| 26 | 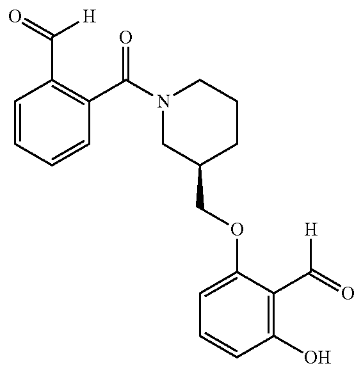 [SMILES: O=Cc1ccccc1C(=O)N1CCC[C@@H](COc2cccc(O)c2C=O)C1] | 2-{[(3R)-1-(2-formylbenzoyl)piperidin-3-yl]methoxy}-6-hydroxybenzaldehyde |
| 27 | 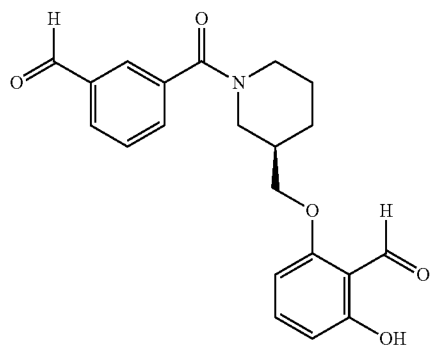 [SMILES: O=Cc1cccc(C(=O)N2CCC[C@@H](COc3cccc(O)c3C=O)C2)c1] | 2-{[(3R)-1-(3-formylbenzoyl)piperidin-3-yl]methoxy}-6-hydroxybenzaldehyde |
| 28 | 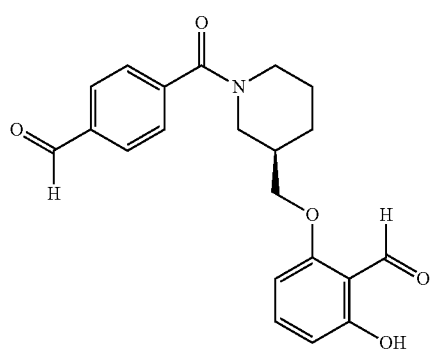 [SMILES: O=Cc1ccc(C(=O)N2CCC[C@@H](COc3cccc(O)c3C=O)C2)cc1] | 2-{[(3R)-1-(4-formylbenzoyl)piperidin-3-yl]methoxy}-6-hydroxybenzaldehyde |
| 29 | 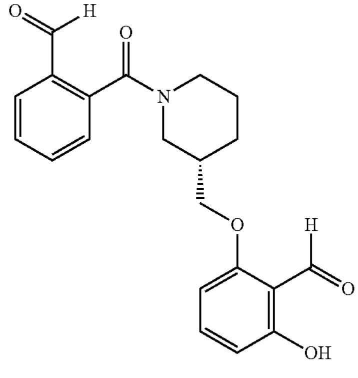 [SMILES: O=Cc1ccccc1C(=O)N1CCC[C@H](COc2cccc(O)c2C=O)C1] | 2-{[(3S)-1-(2-formylbenzoyl)piperidin-3-yl]methoxy}-6-hydroxybenzaldehyde |

TABLE 1-continued

| Compound Number | Structure | IUPAC name |
|---|---|---|
| 30 | 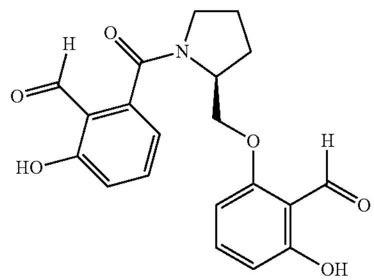 [SMILES: O=Cc1c(O)cccc1OC[C@@H]1CCCN1C(=O)c1cccc(O)c1C=O] | 2-[(2S)-2-[(2-formyl-3-hydroxyphenoxy)methyl]pyrrolidine-1-carbonyl]-6-hydroxybenzaldehyde |
| 31 | 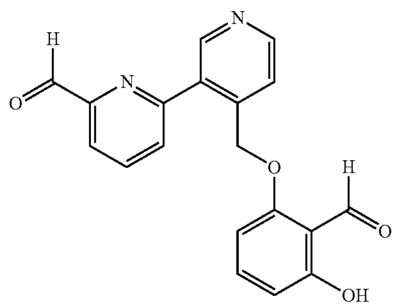 [SMILES: O=Cc1cccc(-c2cnccc2COc2cccc(O)c2C=O)n1] | 4'-[(2-formyl-3-hydroxyphenoxy)methyl]-[2,3'-bipyridine]-6-carbaldehyde |
| 32 | 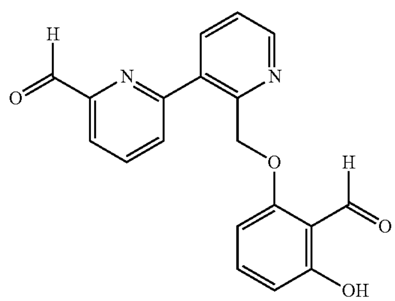 [SMILES: O=Cc1cccc(-c2cccnc2COc2cccc(O)c2C=O)n1] | 2'-[(2-formyl-3-hydroxyphenoxy)methyl]-[2,3'-bipyridine]-6-carbaldehyde |
| 33 | 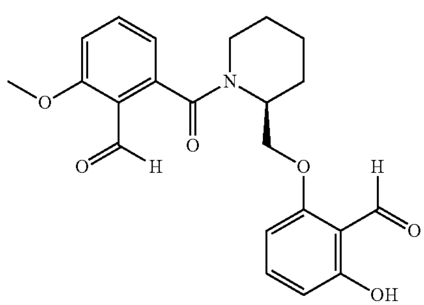 [SMILES: COc1cccc(C(=O)N2CCCC[C@H]2COc2cccc(O)c2C=O)c1C=O] | 2-[(2S)-2-[(2-formyl-3-hydroxyphenoxy)methyl]piperidine-1-carbonyl]-6-methoxybenzaldehyde |
| 34 | 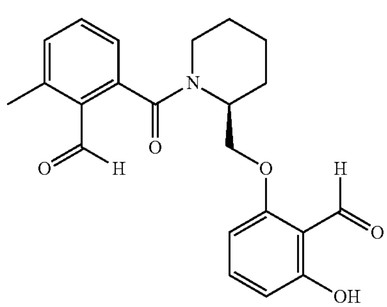 [SMILES: Cc1cccc(C(=O)N2CCCC[C@H]2COc2cccc(O)c2C=O)c1C=O] | 2-[(2S)-2-[(2-formyl-3-hydroxyphenoxy)methyl]piperidine-1-carbonyl]-6-methylbenzaldehyde |

TABLE 1-continued

| Compound Number | Structure | IUPAC name |
|---|---|---|
| 35 | 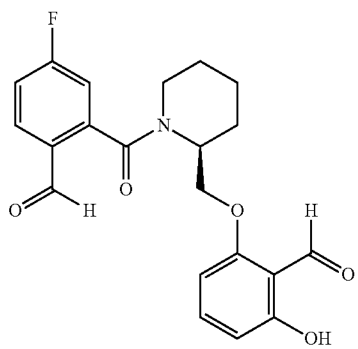 [SMILES: O=Cc1ccc(F)cc1C(=O)N1CCCC[C@H]1COc1cccc(O)c1C=O] | 4-fluoro-2-[(2S)-2-[(2-formyl-3-hydroxyphenoxy)methyl]piperidine-1-carbonyl]benzaldehyde |
| 36 | 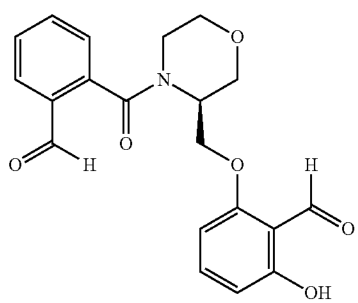 | 2-{[(3S)-4-(2-formylbenzoyl)morpholin-3-yl]methoxy}-6-hydroxybenzaldehyde |
| 37 | 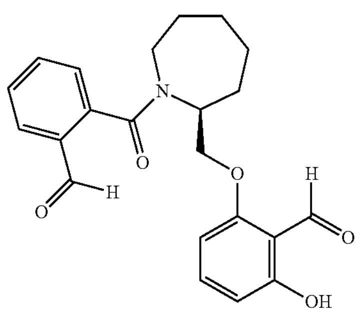 [SMILES: O=Cc1ccccc1C(=O)N1CCCCC[C@H]1COc1cccc(O)c1C=O] | 2-{[1-(2-formylbenzyl)azepan-2-yl]methoxy}-6-hydroxybenzaldehyde |
| 38 | 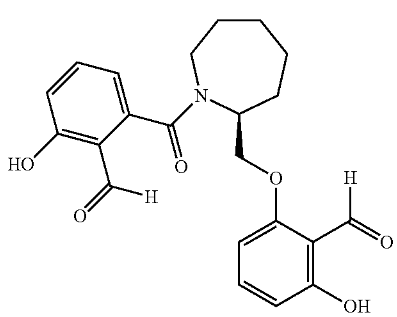 [SMILES: O=Cc1c(O)cccc1OC[C@@H]1CCCCCN1C(=O)c1cccc(O)c1C=O] | 2-{2-[(2-formyl-3-hydroxyphenoxy)methyl]azepane-1-carbonyl}-6-hydroxybenzaldehyde |

TABLE 1-continued

| Compound Number | Structure | IUPAC name |
|---|---|---|
| 39 | 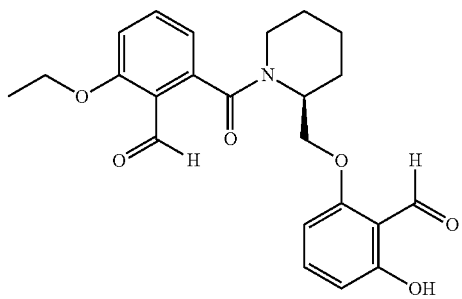 [SMILES: CCOc1cccc(C(=O)N2CCCC[C@H]2COc2cccc(O)c2C=O)c1C=O] | 2-ethoxy-6-[(2S)-2-[(2-formyl-3-hydroxyphenoxy)methyl]piperidine-1-carbonyl]benzaldehyde |
| 40 | 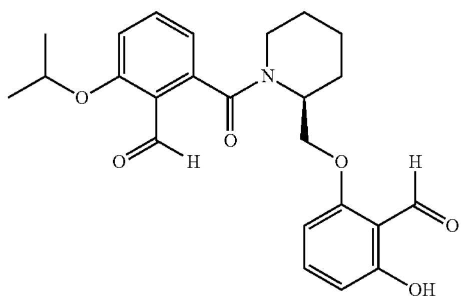 [SMILES: CC(C)Oc1cccc(C(=O)N2CCCC[C@H]2COc2cccc(O)c2C=O)c1C=O] | 2-[(2S)-2-[(2-formyl-3-hydroxyphenoxy)methyl]piperidine-1-carbonyl]-6-(propan-2-yloxy)benzaldehyde |
| 41 | 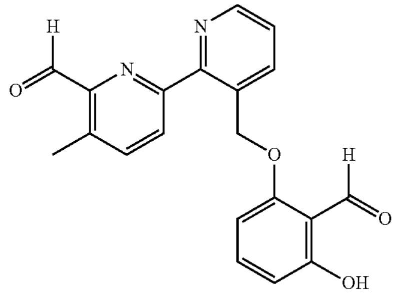 [SMILES: Cc1ccc(-c2ncccc2COc2cccc(O)c2C=O)nc1C=O] | 3'-[(2-formyl-3-hydroxyphenoxy)methyl]-5-methyl-[2,2'-bipyridine]-6-carbaldehyde |
| 42 | 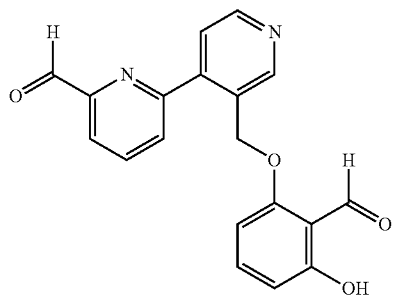 [SMILES: O=Cc1cccc(-c2ccncc2COc2cccc(O)c2C=O)n1] | 3'-[(2-formyl-3-hydroxyphenoxy)methyl]-[2,4'-bipyridine]-6-carbaldehyde |
| 43 | 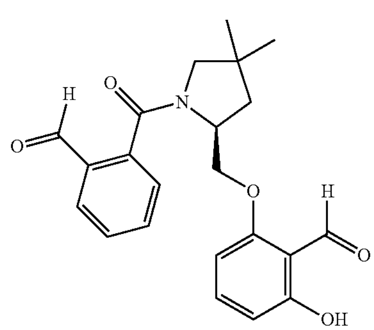 [SMILES: CC1(C)C[C@@H](COc2cccc(O)c2C=O)N(C(=O)c2ccccc2C=O)C1] | 2-{[(2S)-1-(2-formylbenzoyl)-4,4-dimethylpyrrolidin-2-yl]methoxy}-6-hydroxybenzaldehyde |

TABLE 1-continued

| Compound Number | Structure | IUPAC name |
|---|---|---|
| 44 | 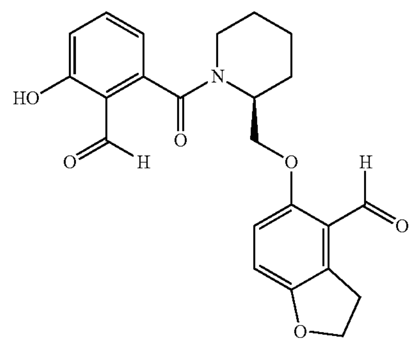 [SMILES: O=Cc1c(O)cccc1C(=O)N1CCCC[C@H]1COc1ccc2c(c1C=O)CCO2] | 5-{[(2S)-1-(2-formyl-3-hydroxybenzoyl)piperidin-2-yl]methoxy}-2,3-dihydro-1-benzofuran-4-carbaldehyde |
| 45 | 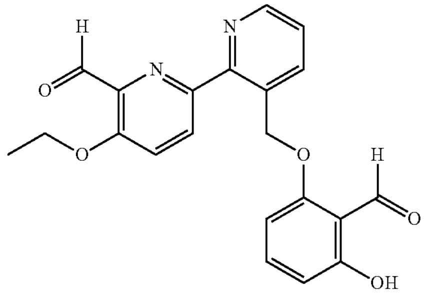 [SMILES: CCOc1ccc(-c2ncccc2COc2cccc(O)c2C=O)nc1C=O] | 5-ethoxy-3'-[(2-formyl-3-hydroxyphenoxy)methyl]-[2,2'-bipyridine]-6-carbaldehyde |
| 46 | 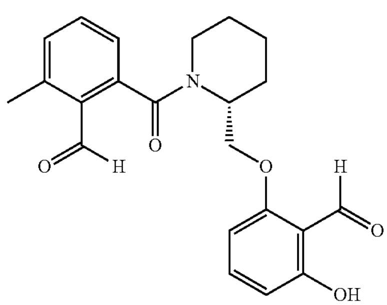 [SMILES: Cc1cccc(C(=O)N2CCCC[C@@H]2COc2cccc(O)c2C=O)c1C=O] | 2-[(2R)-2-[(2-formyl-3-hydroxyphenoxy)methyl]piperidine-1-carbonyl]-6-methylbenzaldehyde |
| 47 | 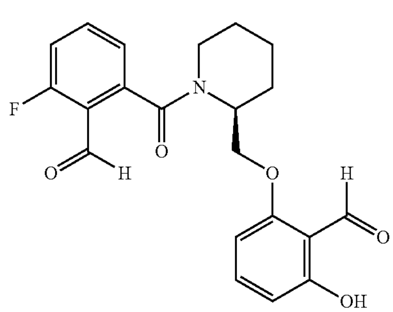 [SMILES: O=Cc1c(O)cccc1OC[C@@H]1CCCCN1C(=O)c1cccc(F)c1C=O] | 2-fluoro-6-[(2S)-2-[(2-formyl-3-hydroxyphenoxy)methyl]piperidine-1-carbonyl]benzaldehyde |

TABLE 1-continued

| Compound Number | Structure | IUPAC name |
|---|---|---|
| 48 | 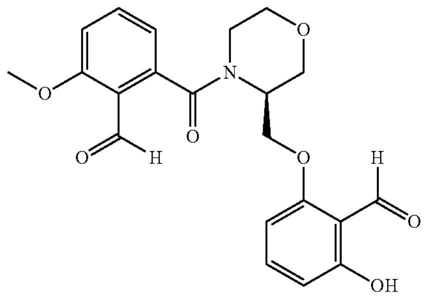 | 2-[(3S)-3-[(2-formyl-3-hydroxyphenoxy)methyl]morpholine-4-carbonyl]-6-methoxybenzaldehyde |
| 49 | 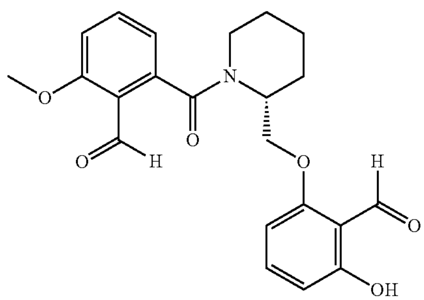 [SMILES: COc1cccc(C(=O)N2CCCC[C@@H]2COc2cccc(O)c2C=O)c1C=O] | 2-[(2R)-2-[(2-formyl-3-hydroxyphenoxy)methyl]piperidine-1-carbonyl]-6-methoxybenzaldehyde |
| 50 | 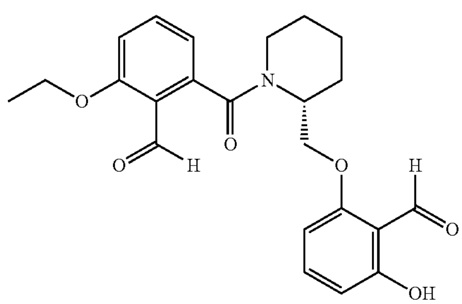 [SMILES: CCOc1cccc(C(=O)N2CCCC[C@@H]2COc2cccc(O)c2C=O)c1C=O] | 2-ethoxy-6-[(2R)-2-[(2-formyl-3-hydroxyphenoxy)methyl]piperidine-1-carbonyl]benzaldehyde |
| 51 | 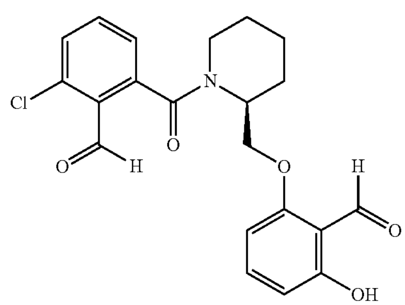 [SMILES: O=Cc1c(O)cccc1OC[C@@H]1CCCCN1C(=O)c1cccc(Cl)c1C=O] | 2-chloro-6-[(2S)-2-[(2-formyl-3-hydroxyphenoxy)methyl]piperidine-1-carbonyl]benzaldehyde |
| 52 | 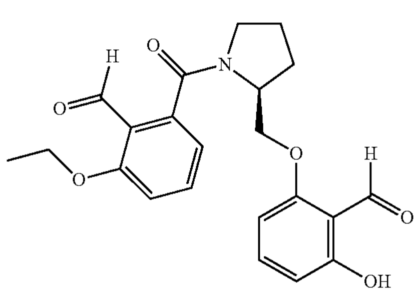 [SMILES: CCOc1cccc(C(=O)N2CCC[C@H]2COc2cccc(O)c2C=O)c1C=O] | 2-ethoxy-6-[(2S)-2-[(2-formyl-3-hydroxyphenoxy)methyl]pyrrolidine-1-carbonyl]benzaldehyde |

TABLE 1-continued

| Compound Number | Structure | IUPAC name |
|---|---|---|
| 53 | 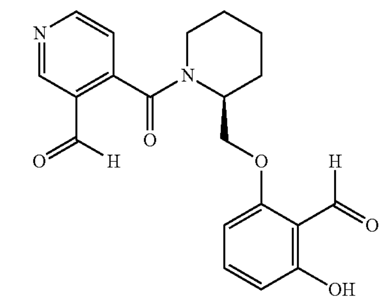 [SMILES: O=Cc1cnccc1C(=O)N1CCCC[C@H]1COc1cccc(O)c1C=O] | 4-[(2S)-2-[(2-formyl-3-hydroxyphenoxy)methyl]piperidine-1-carbonyl]pyridine-3-carbaldehyde |
| 54 | 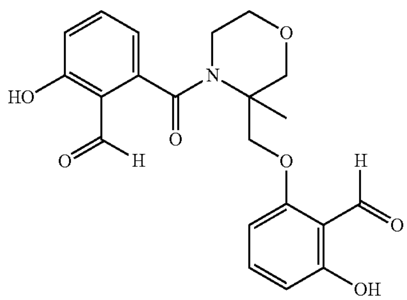 [SMILES: CC1(COc2cccc(O)c2C=O)COCCN1C(=O)c1cccc(O)c1C=O] | 2-((4-(2-formyl-3-hydroxybenzoyl)-3-methylmorpholin-3-yl)methoxy)-6-hydroxybenzaldehyde |
| 55 | 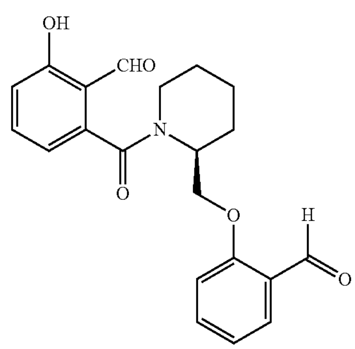 [SMILES: O=Cc1ccccc1OC[C@@H]1CCCCN1C(=O)c1cccc(O)c1C=O] | (S)-2-(2-((2-formylphenoxy)methyl)piperidine-1-carbonyl)-6-hydroxybenzaldehyde |
| 56 | 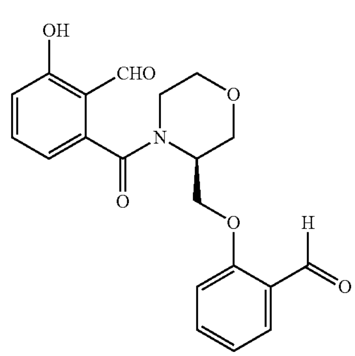 [SMILES: O=Cc1ccccc1OC[C@@H]1COCCN1C(=O)c1cccc(O)c1C=O] | (S)-2-(3-((2-formylphenoxy)methyl)morpholine-4-carbonyl)-6-hydroxybenzaldehyde |

TABLE 1-continued

| Compound Number | Structure | IUPAC name |
|---|---|---|
| 57 | 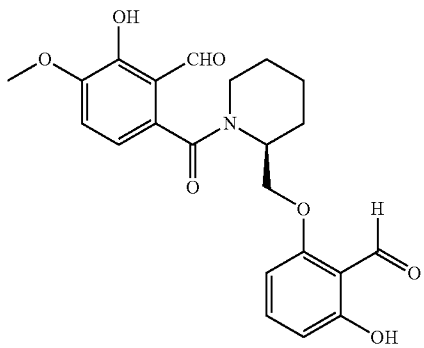 [SMILES: COc1ccc(C(=O)N2CCCC[C@H]2COc2cccc(O)c2C=O)c(C=O)c1O] | (S)-6-(2-((2-formyl-3-hydroxyphenoxy)methyl)piperidine-1-carbonyl)-2-hydroxy-3-methoxybenzaldehyde |
| 58 | 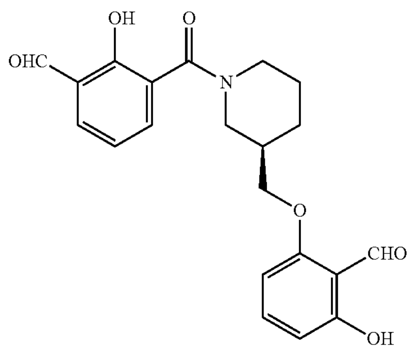 [SMILES: O=Cc1cccc(C(=O)N2CCC[C@@H](COc3cccc(O)c3C=O)C2)c1O] | 2-[[(3R)-1-(3-formyl-2-hydroxybenzoyl)piperidin-1-yl]methoxy]-6-hydroxybenzaldehyde |
| 59 | 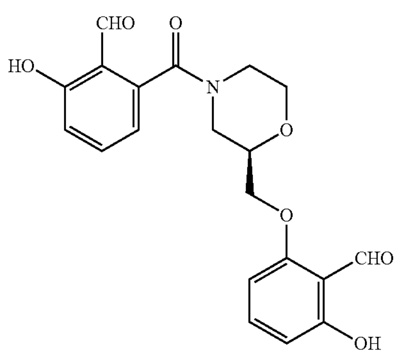 [SMILES: O=Cc1c(O)cccc1OC[C@H]1CN(C(=O)c2cccc(O)c2C=O)CCO1] | 2-[[(2R)-4-(2-formyl-3-hydroxybenzoyl)morpholin-2-yl]methoxy]-6-hydroxybenzaldehyde |
| 60 | 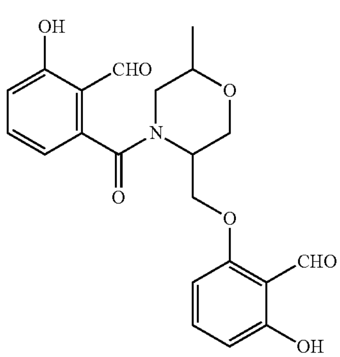 [SMILES: CC1CN(C(=O)c2cccc(O)c2C=O)C(COc2cccc(O)c2C=O)CO1] | 2-((4-(2-formyl-3-hydroxybenzoyl)-6-methylmorpholin-3-yl)methoxy)-6-hydroxybenzaldehyde |

TABLE 1-continued

| Compound Number | Structure | IUPAC name |
|---|---|---|
| 61 | 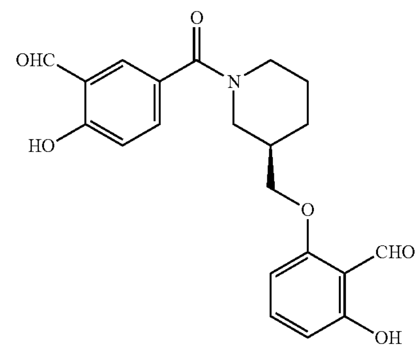 [SMILES: O=Cc1cc(C(=O)N2CCC[C@@H](COc3cccc(O)c3C=O)C2)ccc1O] | 2-[[(3R)-1-(3-formyl-4-hydroxybenzoyl)piperidin-3-yl]methoxy]-6-hydroxybenzaldehyde |
| 62 | 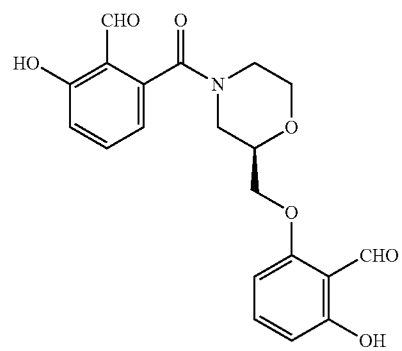 [SMILES: O=Cc1c(O)cccc1OC[C@H]1CN(C(=O)c2cccc(O)c2C=O)CCO1] | 2-[[(2R)-4-(2-formyl-3-hydroxybenzoyl)morpholin-2-yl]methoxy]-6-hydroxybenzaldehyde |
| 63 | 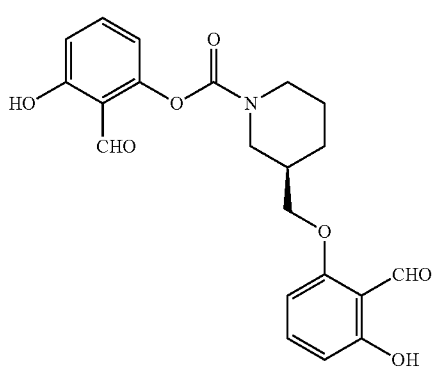 [SMILES: O=Cc1c(O)cccc1OC[C@@H]1CCCN(C(=O)Oc2cccc(O)c2C=O)C1] | 2-formyl-3-hydroxyphenyl (3R)-3-(2-formyl-3-hydroxyphenoxymethyl)piperidine-1-carboxylate |
| 64 | 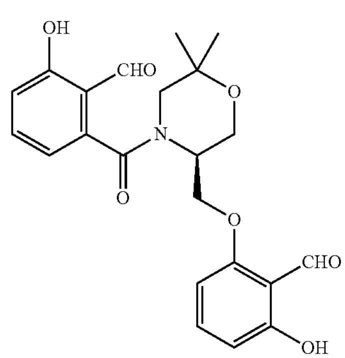 [SMILES: CC1(C)CN(C(=O)c2cccc(O)c2C=O)[C@H](COc2cccc(O)c2C=O)CO1] | 2-[[(3S)-4-(2-fomryl-3-hydroxybenzoyl)-3-methylmorpholin-3-yl]methoxy]-6-hydroxybenzaldehyde |

TABLE 1-continued

| Compound Number | Structure | IUPAC name |
|---|---|---|
| 65 | 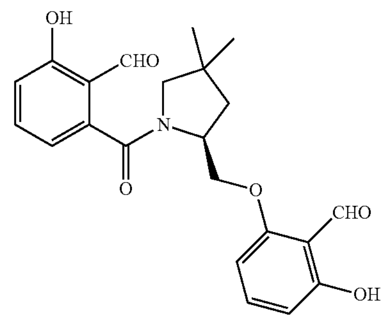 [SMILES: CC1(C)C[C@@H](COc2cccc(O)c2C=O)N(C(=O)c2cccc(O)c2C=O)C1] | 2-[[(2S)-1-(2-formyl-3-hydroxybenzoyl)-4,4-dimethylpyrrolidin-2-yl]methoxy]-6-hydroxybenzaldehyde |
| 66 | 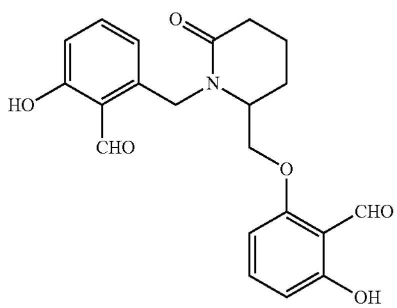 [SMILES: O=Cc1c(O)cccc1CN1C(=O)CCCC1COc1cccc(O)c1C=O] | 2-((1-(2-formyl-3-hydroxybenzyl)-6-oxopiperidin-2-yl)methoxy)-6-hydroxybenzaldehyde |
| 67 (Enantiomer 1) | 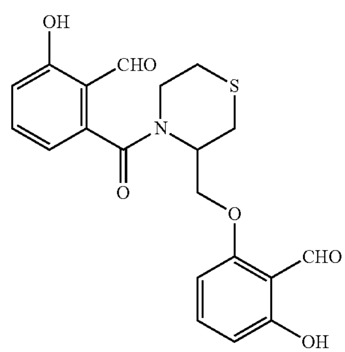 [SMILES: O=Cc1c(O)cccc1OCC1CSCCN1C(=O)c1cccc(O)c1C=O] | 2-((4-(2-formyl-3-hydroxybenozyl)thiomorpholin-3-yl)methoxy)-6-hydroxybenzaldehyde |
| 67 (Enantiomer 2) | | 2-((4-(2-formyl-3-hydroxybenzoyl)thiomorpholin-3-yl)methoxy)-6-hydroxybenzaldehyde | or a pharmaceutically acceptable salt thereof, or an isotopically enriched analog, stereoisomer, mixture of stereoisomers or prodrug thereof or a pharmaceutically acceptable salt of each thereof.

In some embodiments, provided is a compound selected from Table 2:

TABLE 2

| Structure | IUPAC name |
|---|---|
| (structure) | (R)-2-((4-(2-formyl-3-hydroxybenzoyl)thiomorpholin-3-yl)methoxy)-6-hydroxybenzaldehyde |
| (structure) | (S)-2-((4-(2-formyl-3-hydroxybenzoyl)thiomorpholin-3-yl)methoxy)-6-hydroxybenzaldehyde | or a pharmaceutically acceptable salt thereof, or an isotopically enriched analog or prodrug thereof or a pharmaceutically acceptable salt of each thereof.

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art.

The selected compounds may be further characterized to examine the safety or tolerance dosage in human or non-human subjects. Such properties may be examined using commonly known methods to those skilled in the art.

The term "hemoglobin" as used herein refers to any hemoglobin protein, including normal hemoglobin (HbA) and abnormal hemoglobin, such as sickle hemoglobin (HbS).

The term "sickle cell disease" refers to diseases mediated by sickle hemoglobin (HbS) that results from a single point mutation in the hemoglobin (Hb). Sickle cell diseases include sickle cell anemia (HbSS), hemoglobin SC disease (HbSC), hemoglobin S beta-plus-thalassemia (HbS/β+) and hemoglobin S beta-zero-thalassemia (HbS/β0).

Provided herein are methods for treating sickle cell disease (SCD). Sickle hemoglobin (HbS) contains a point mutation where glutamic acid is replaced with valine, making HbS susceptible to polymerization under hypoxic conditions to give the HbS containing red blood cells their characteristic sickle shape. The sickled cells are also more rigid than normal red blood cells, and their lack of flexibility can lead to blockage of blood vessels. It is contemplated that an approach to therapy would be to maintain the HbS in the oxygenated state, as polymerization occurs only in the deoxygenated state under hypoxic conditions.

In some embodiments, provided herein is a method for increasing oxygen affinity of hemoglobin S in a subject in need thereof, comprising administering to the subject a compound as described herein or a pharmaceutical composition as described herein.

In some embodiments, provided herein is a method for treating a disorder mediated by hemoglobin in a subject in need thereof, comprising administering to the subject a compound as described herein or a pharmaceutical composition as described herein. In some embodiments, the disorder is a hemoglobinopathy.

In some embodiments, the hemoglobin is sickle hemoglobin.

In some embodiments, provided herein is a method for treating sickle cell disease in a subject in need thereof, comprising administering to the subject a compound as described herein or a pharmaceutical composition as described herein.

Pharmaceutical Compositions and Modes of Administration

Compounds provided herein are usually administered in the form of pharmaceutical compositions. Thus, provided herein are also pharmaceutical compositions that comprise one or more of the compounds described herein or a pharmaceutically acceptable salt, a stereoisomer, or a mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, a stereoisomer, or a mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, a stereoisomer, or a mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, a stereoisomer, or a mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

General Synthetic Approaches to a Compound of Formula (I):

A compound of formula (I) can be synthesized by two synthetic pathways as shown in Schemes 1 and 2.

In some embodiments of Scheme 1, Y is a leaving group (including but not limited to halo, triflate, and the like), R is H, X is halo, and $R^1$, ring A, ring B, L, and $R^2$ are as described herein. As shown in Scheme 1, compound 1-2 and compound 1-3 are coupled first to give a compound 1-4a, which can be then assembled onto 2-hydroxybenzaldehyde analog 1-5 to produce compound of formula (I).

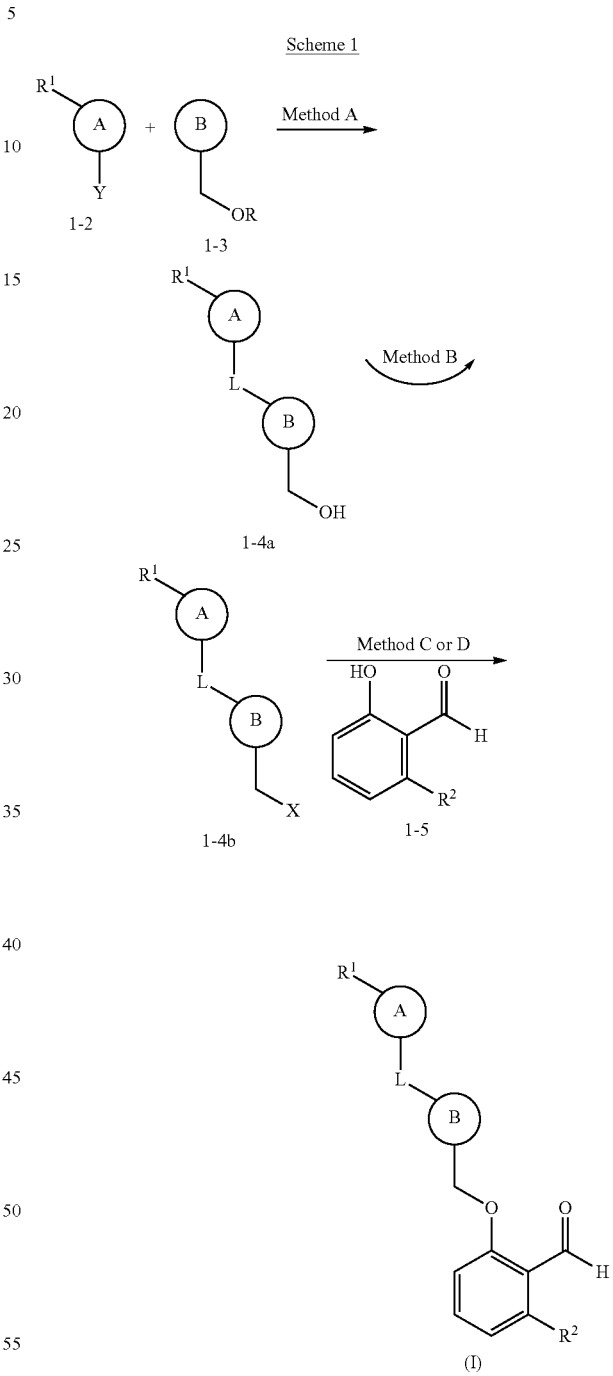

Scheme 1

In some embodiments of Scheme 2, Y is a $CO_2H$ or a leaving group (including but not limited to halo, triflate, and the like), X is halo, and $R^1$, ring A, ring B, L, and $R^2$ are as described herein. In some embodiments, ring B may be substituted with a boronic acid or boronic ester. As shown in Scheme 2, compound 2-3a or compound 2-3b is added on to aldehyde 2-5 first to form intermediate 2-6, which is then capped with ring A by combining a compound 1-2 to give a compound of formula (I).

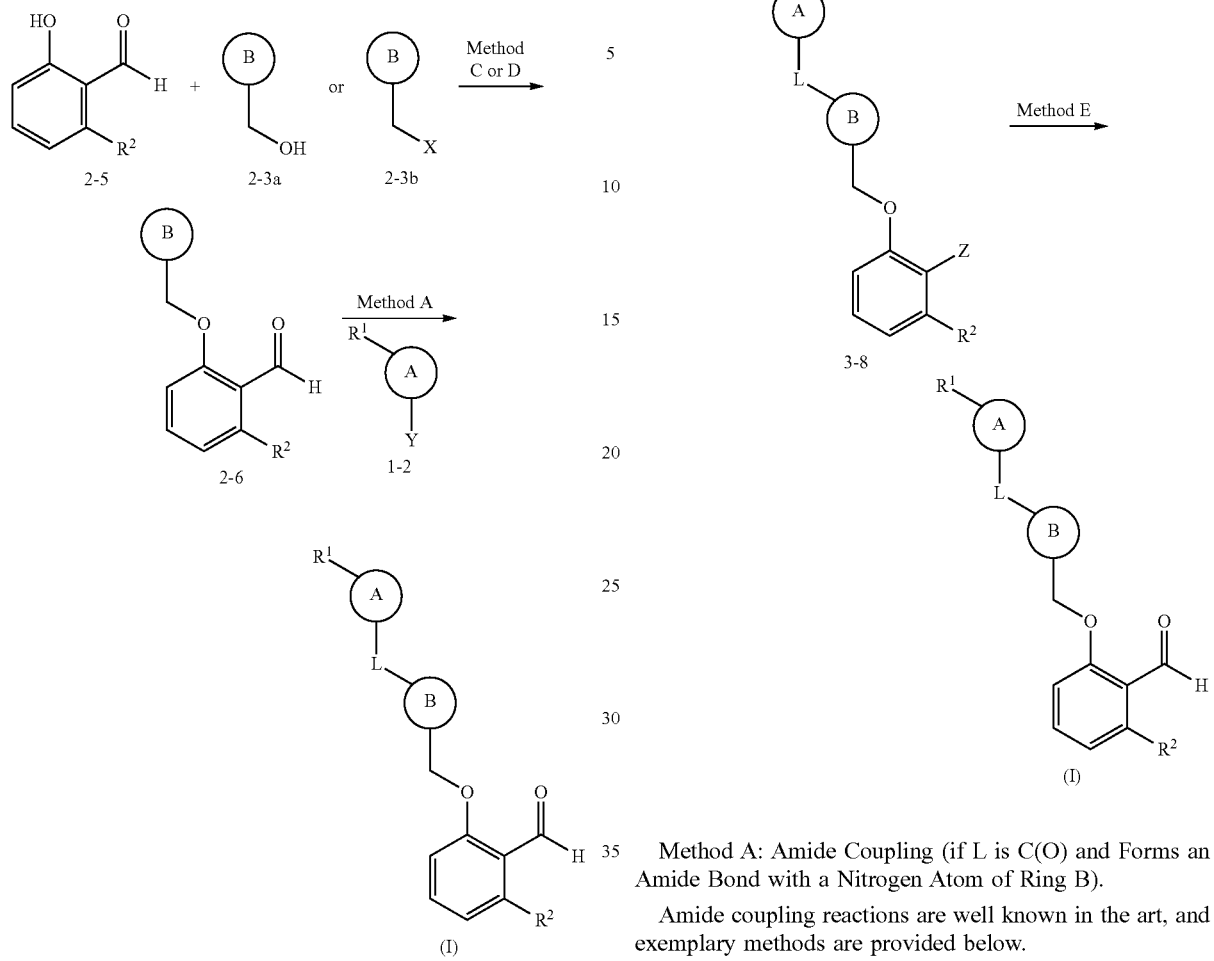

Scheme 3 depicts an alternative method of synthesizing a compound of formula (I) from intermediate 1-4b, which may be prepared as described above. In some embodiments of Scheme 3, X is halo, Z is H or halo, and $R^1$, ring A, ring B, L, and $R^2$ are as described herein. In some embodiments, if an aldehyde-precursor such as a phenol or 2-bromophenol analog (e.g., compound 3-7 of Scheme 3, wherein Z is H or halo) is used instead of aldehyde 1-5 of Scheme 1, the aldehyde functionality can be introduced to intermediate 3-8 according to Method E described herein.

Scheme 3

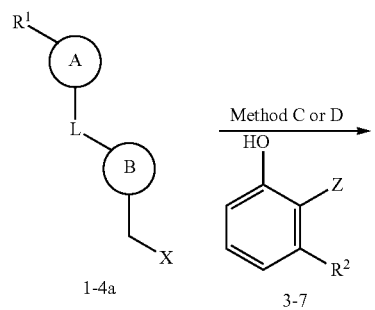

Method A: Amide Coupling (if L is C(O) and Forms an Amide Bond with a Nitrogen Atom of Ring B).

Amide coupling reactions are well known in the art, and exemplary methods are provided below.

Amide Formation Procedure 1:

DMF (10 mL) was added to a mixture of acid (e.g., intermediate 1-2 wherein Y is $CO_2H$, 1 mmol), amine (e.g., intermediate 1-3 wherein ring B is a nitrogen-containing heterocycle, 1 mmol) and HATU (1.2 mmol) at 0° C. The resulting mixture is stirred for 5 mins at 0° C., NMP (5 mmol) was then added slowly. The reaction mixture is continued stirred at RT for 1 to 24 hrs. 25 mL brine is then added, the layers are separated, and the aqueous layer is extracted with three 30-mL portions of EtOAc. The combined organic layers are washed with two 25-mL portions of saturated sodium chloride and dried over anhydrous magnesium sulfate or sodium sulfate. Evaporation of the solvent gives the crude product that is purified by chromatography on silica gel column or preparative HPLC.

Amide Formation Procedure 2:

To a solution of the acid (e.g., intermediate 1-2 wherein Y is $CO_2H$, 1 mmol), amine (e.g., intermediate 1-3 wherein ring B is a nitrogen-containing heterocycle, 1.2 mmol), HOBt (1.25 mmol) and Hunig's base (2 mmol) in 4 mL DMF 0° C. was added EDCI (1.25 mmol). Ice bath was removed and the reaction was continued for 0.5 hr to 3 days at RT. The solution was then diluted with DCM (100 mL) and washed with 2N HCl (50 mL). The organic phase was separated and dried over $Na_2SO_4$, and was concentrated to give crude product which that is purified by chromatography on silica gel column or preparative HPLC.

Method A: Suzuki Coupling (if L is a Bond Between Two Aryl and/or Heteroaryl Rings)

Suzuki Coupling Procedure 1:

Into a 20 mL microwave vial was added halide (e.g., intermediate 1-2 wherein Y is halo, 1 mmol) and boronic acid or ester (e.g., intermediate 1-3 wherein ring B is substituted with a boronic acid or boronic ester, 1.5 mmol). Dioxane (5 mL) and saturated sodium bicarbonate (3 mL) was added and the mixture was degassed by bubbling $N_2$ through the solution for 10 minutes. After degassing, 1,1'-bis-diphenyl phosphinoferrocene dichloro palladium (II) (Pd (dppf)$Cl_2$) (5% mol) was added and the reaction was capped. The reaction was microwaved at 60 to 150° C. for 10 to 120 minutes, and the reaction was transferred to a round bottom flask and the solvent was removed under vacuum. Saturated ammonium chloride (25 mL) and ethyl acetate (25 mL) was added to the residue and transferred to a separatory funnel. The organic layer was separated, and the aqueous layer was further extracted with ethyl acetate (2×25 mL). The organic layers were combined and dried over sodium sulfate. Solution was filtered, and the solvent was removed under vacuum. The residue was purified by chromatography on silica gel column or preparative HPLC.

Suzuki Coupling Procedure 2:

To a mixture of the triflates (intermediate 1-2 wherein Y is triflate, 1 mmol), boronic acid (e.g., intermediate 1-3 wherein ring B is substituted with a boronic acid or boronic ester, 1.1 to 2 mmol) and potassium phosphate (2 to 3 mmol) in 8 mL dioxane was added palladium(0) tetrakistriphenylphosphine (3% mol). The mixture was de-oxygenated for 5 cycles (vacuo/flash with nitrogen) and was then heated at 60 to 150° C. for 10 to 120 minutes in a microwave reactor. The mixture was filtered through a pad of $SiO_2$ and celite, washed with EtOAc, and was concentrated to give crude product, which can be purified by chromatography on silica gel column or HPLC.

Method A (if L is a Bond Between Ring A (which is an Aryl or Heteroaryl) and Nitrogen Atom of Lactam Ring as Ring B, Scheme 4)

Buchwald-Hartwig Coupling Procedure (Scheme 4):

In some embodiments of Scheme 4, X is a halide, R is H, and ring A and $R^1$ are as described herein. Into a 250-mL round-bottom flask purged and maintained with an inert atmosphere of nitrogen, was placed lactam 4-2 (34 mmol, 1.3 eq), halide 4-1 (26 mmol, 1 eq), DMF (60 mL), $Cs_2CO_3$ (12.80 g, 39.289 mmol, 1.5 equiv), $N^1$,$N^2$-dimethylcyclohexane-1,2-diamine (26 mmol, 1 equiv), CuI (13.1 mmol, 0.5 equiv). The resulting solution was stirred for 30 min to 24 h at 60 to 125° C. in an oil bath. The reaction mixture was cooled to room temperature with a water/ice bath. The solid was filtered out. The filtrate was concentrated under vacuum, the residue was purified by flash column with THF/PE (36%). The residue was purified by chromatography on silica gel column. Other heterocyclic analogs with C—N linkage are synthesized by applying this Buchwald/Hartwig amination conditions.

Scheme 4

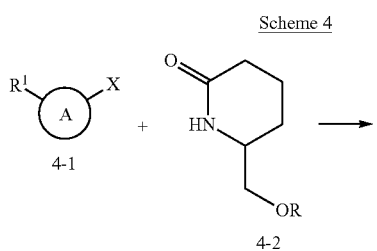

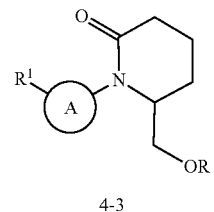

4-3

Method B: General method for preparing substituted methylene chloride from Substituted Methylene Alcohol.

To a Solution of Substituted Methylene Alcohol (e.g., intermediate 1-4a, 0.1 to 2 mmol) in DCM (1-10 mL) was added $SOCl_2$ dropwise (2 eq to 5 eq) at 0° C. or rt. The reaction mixture was stirred at rt for 10 min to 6 h, or until reaction is judged complete (LC/MS). The reaction mixture is concentrated to dryness over a rotavap. The crude chloride residue was suspended in toluene, sonicated and concentrated to dryness. The process was repeated three times and dried under vacuum to give the substituted methylene chloride, which is used for next step without further purification. Alternatively, a solution of aqueous 1 N $Na_2CO_3$ is then added to produce a solution of pH~8. the mixture was extracted with DCM (3×10-50 mL), dried over sodium sulfate, and concentrated to the crude substituted methylene chloride, which is then purified by chromatography on silica gel column or HPLC.

Method B: General Method for Preparing Substituted Methylene Bromide.

To a solution of substituted methylene alcohol (e.g., intermediate 1-4a, 0.1 to 2 mmol) in DCM (1-10 mL) was added $Ph_3P$ and $Br_2$ dropwise (2 eq to 5 eq) at 0° C. or rt. The reaction mixture was stirred at rt for 10 min to 2 h, or until reaction is judged complete (LC/MS). The reaction mixture is concentrated to dryness under vacuum. The residue was purified by chromatography on silica gel column or HPLC.

Method C: Preparation of Aryloxy/Heteroarylether Analogs (Compounds of Formula (I) or 2-6) from Substituted Methylene Alcohol and Hydroxyl (Hetero)Aryl Aldehyde Derivatives (Compounds 1-3a, 1-4a, 2-3b, or 1-4b) Via Mitsunobu Reaction.

Mitsunobu reactions are well known in the art, and exemplary methods are provided below.

Mitsunobu Reaction Procedure 1:

A hydroxyl (hetero)arylaldehyde derivatives (intermediate 1-5) (0.1-2 mmol) mixture with substituted methylene alcohol (intermediate 2-3a or 1-4b) (0.8 to 1.2 eq) and $PPh_3$ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 20 min period. The ice cooling bath was allowed to expire over 90 min and the mixture was stirred at RT for 2- to 48 hours. The mixture was stirred for 10 min, then filtered through a pad of silica. The silica was washed with ethyl acetate 2-20 mL. The combined filtrates were evaporated, and the residue was dried under vacuum. The residue was purified by preparative HPLC or flash silica gel chromatography.

Mitsunobu Reaction Procedure 2:

A solution of hydroxymethylene analog (intermediate 2-3a or 1-4a) (47.63 mmol; 1.00 eq.), phenol 3-7 (50.01 mmol; 1.05 eq.) and (tributylphosphoranylidene)acetonitrile (70 mmol; 1.40 eq.) in toluene (51 mL; 3.50 V) under $N_2$ was stirred at 100° C. in an oil bath for 20 to 120 min. After being cooled to rt, the reaction mixture was treated with saturated aq. NH₄Cl solution (60 mL), diluted with water (200 mL), and extracted with EtOAc thrice. The combined organic layers were washed with water (100 mL) thrice and brine. After removal of the organic solvents under reduced pressure, the residue was purified by flash chromatography on silica gel column.

Method D: Preparation of Aryloxy/Heteroarylether Analogs (Compounds of Formula (I) or 2-6) from Substituted Methylene Halide (2-3b or 1-4b) and Hydroxyl (Hetero)Aryl Aldehyde Derivatives Via Alkylation Reaction.

A mixture of hydroxyl (hetero)arylaldehyde derivatives (intermediate 1-5 or 3-7) (0.1-2 mmol, 1-4 eq.), substituted methylene chloride or bromide (intermediate 2-3b or 1-4b) (1 eq), and K₂CO₃ (2-5 eq.) (catalytic amount of NaI or Bu₄NI may also be added) in DMF or acetonitrile (1 to 10 mL) was stirred at RT or heating up to 120° C. for 0.5-8 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous NH₄Cl was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography.

Method E: Preparation of Aryloxy/Heteroarylether Analogs from Aryl or Intermediate 3-8 Via Lithiation and or Halide-Lithium Exchange Reaction:

To a −78° C. solution of intermediate 3-8 (4152.00 mg; 7.38 mmol; 1.00 eq) and N,N,N',N'-tetramethyl-1,2-ethanediamine (4.87 mL; 32.48 mmol; 4.40 eq.) (pre-dried over excess activated sieves overnight) in THF (24.91 mL; 6.00 V) under N₂ was added sec-butyllithium (23.20 mL; 1.40 mol/L; 32.48 mmol; 4.40 eq.) dropwise over 8 min. After stirring at −78° C. for 25 min, the reaction flask was placed into a −65° C. ice bath and allowed to stir for additional 15 min at −65° C. to −55° C. The reaction flask was placed back to the −78° C. and to this solution was added solution A over 2 to 30 mins [Solution A was made as such: To 2.0 mL of THF at rt was added 1.3 mL iPrMgBr (2.9 N in methyl-THF). To this was added N,N-dimethylformamide that was pre-dried over activated MS for 3 hr (4.57 mL; 59.05 mmol; 8.00 eq.), the resulting mixture or solution A]. The reaction mixture was allowed to stir at −78° C. for additional 10 to 120 min, quenched with a mixture of AcOH (4.5 mL, 78.75 mL, 10.6 eq.) and saturated aq. NH₄Cl (15 mL), warmed to rt and extracted with EtOAc thrice. After removal of the organic solvents under reduced pressure, the remaining residue was dissolved and purified by flash chromatography on silica gel column.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

SYNTHETIC EXAMPLES

Example 1a. Synthesis of 2-[(2S)-2-[(2-formyl-3-hydroxyphenoxy)methyl]piperidine-1-carbonyl]-6-hydroxybenzaldehyde (Compound 1), Procedure 1

Compound 1 was made according to scheme below.

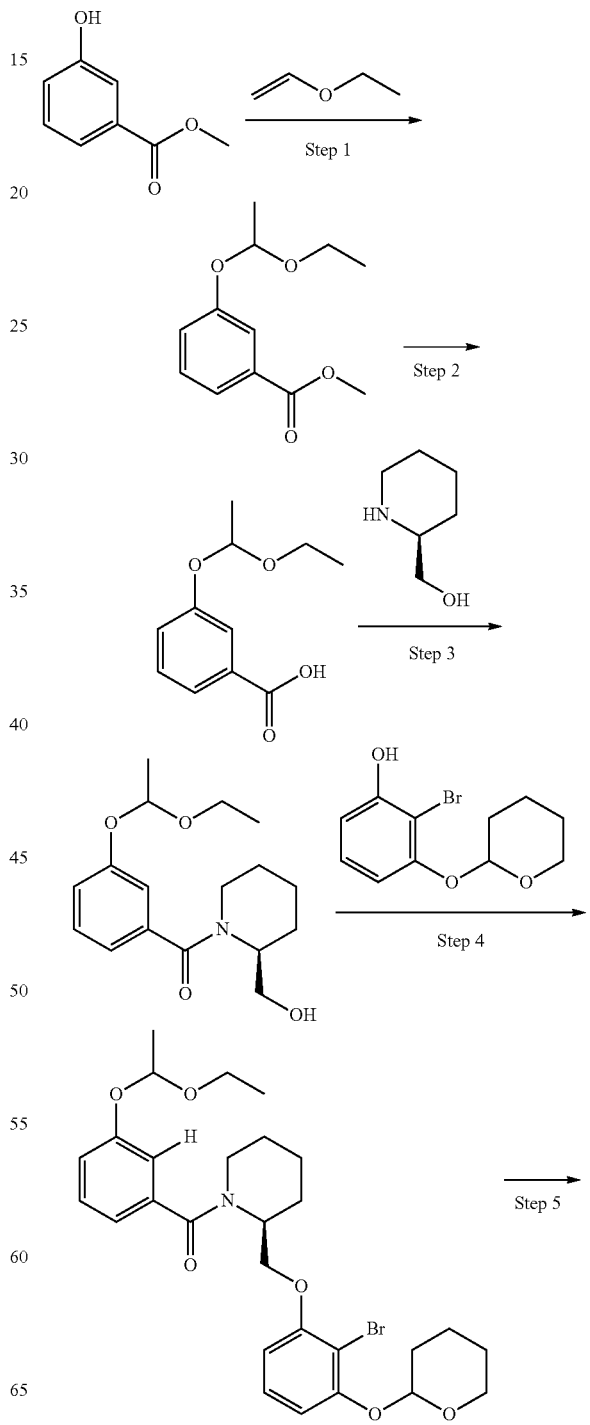

-continued

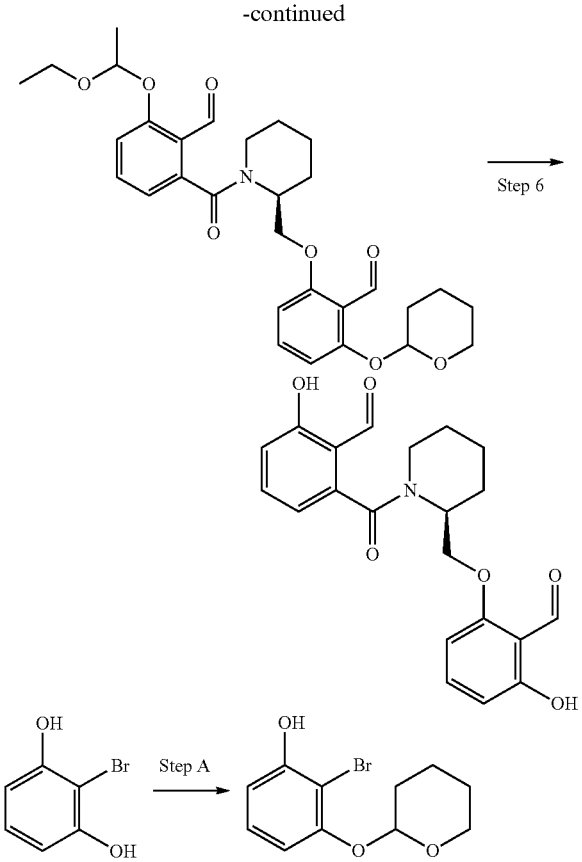

Step A:

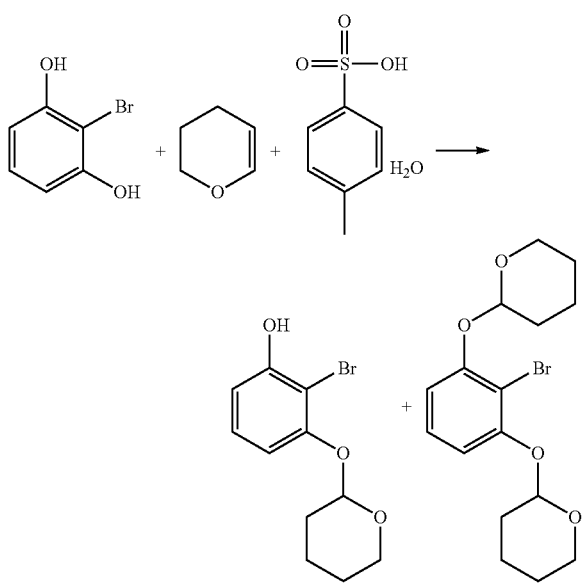

A room temperature mixture of 2-bromo-1,3-benzenediol (20.00 g; 105.82 mmol; 1.00 eq.) and 4-methylbenzenesulfonic acid hydrate (2.01 g; 10.58 mmol; 0.10 eq.) in THF (120 m L) was purged with running $N_2$ line through the solution for 5 min. To the resulting mixture was added 3,4-dihydro-2H-pyran (11.58 mL; 126.98 mmol; 1.20 eq.). This mixture was allowed to stir at rt under $N_2$ atmosphere for 25-40 min. During this period, TLC (20% EtOAc/Hexanes) was used to closely monitor the reaction progress. When TLC suggested a significant conversion but no further progression of 2-bromo-1,3-benzenediol to 2-bromo-3-(oxan-2-yloxy)phenol, the reaction mixture was added saturated aqueous $NaHCO_3$(20 mL) and water (120 mL). The mixture was extracted with EtOAc thrice and the organic layers were combined. After removal of the organic solvents under reduced pressure, the remaining residue was purified by flash chromatography on 220 g silica gel column using 0-15% EtOAc/Hexanes and to provide the desired 2-bromo-3-(oxan-2-yloxy)phenol.

Step 1:

To a rt solution of methyl 3-hydroxybenzoate (50.00 g; 328.63 mmol; 1.00 eq.) in anhydrous THF (200 mL) was added ethyl vinyl ether (157.34 mL; 1 643.14 mmol; 5.00 eq.) (Aldrich) and pyridin-1-ium 4-methylbenzene-1-sulfonate (3.30 g; 13.15 mmol; 0.04 eq.). The resulting reaction mixture was allowed to stir at rt (~24 h) until 95% conversion of methyl 3-hydroxybenzoate to the desired methyl 3-(1-ethoxyethoxy)benzoate was achieved (LC/MS UV).

The volatiles were evaporated under reduced pressure, and the residue was re-dissolved in ethyl acetate (500 mL) and washed with aq. $NaHCO_3$(100 mL). The aqueous layer was back extracted with EtOAc (200 mL) and the organic solutions were combined. After removal of the organic solvents under reduced pressure, the remaining residue was purified by flash chromatography on 220 g silica gel column using 0-50% EtOAc/Hexanes to provide methyl 3-(1-ethoxyethoxy)benzoate; $^1$H NMR (400 MHz, Chloroform-d) δ 7.70-7.63 (m, 2H), 7.37-7.31 (m, 1H), 7.20 (ddd, J=8.2, 2.5, 1.1 Hz, 1H), 5.43 (q, J=5.3 Hz, 1H), 3.91 (s, 3H), 3.83-3.74 (m, 1H), 3.60-3.50 (m, 1H), 1.53-1.49 (m, 3H), 1.21 (t, J=7.1 Hz, 3H).

Step 2:

To a solution of methyl 3-(1-ethoxyethoxy)benzoate (70.00 g; 312.15 mmol; 1.00 eq.) in THF (320 mL) and methanol (80 mL) in ice bath was added aqueous NaOH (156.07 mL; 4.00 mol/L; 624.29 mmol; 2.00 eq.). The resulting mixture was allowed to stir at rt for 4.5 h and most of the solvents were evaporated under reduced pressure. To the resulting mixture was added toluene (125 mL) and the mixture was evaporated under reduced pressure until no obvious solvents present. The residue was dissolved in THF (100 mL). The solution was cooled in an ice bath for 10 min, and aq. $NH_4Cl$ solution (5 N, 125 mL) was added dropwise. Some additional water was added to help solubilize the mixture and the aqueous phases were separated. The aqueous phase was extracted with THF (3×100 mL) and ethyl acetate (100 mL). All the organic fractions were combined, washed with brine and then dried over magnesium sulfate to provide solution A.

Ethyl acetate (100 mL) was added to the above combined aqueous phases and then cooled in an ice bath. To the solution was added aq. HCl (6.0 N) slowly to reach pH~5 (~10 mL). The phases were separated, and the aqueous phase was back extracted with ethyl acetate (2×100 mL) and dried over magnesium sulfate separately. All the organic layers/extracts collected from these operations were combined with solution A from above to provide a solution of 3-(1-ethoxyethoxy)benzoic acid that stored at -10° C. LCMS (ES-) [M-1]$^-$ m/z [209].

Step 3:

To the above solution of 3-(1-ethoxyethoxy)benzoic acid (equals to ~30.00 g based on solution volume; 0.14 mol; 1.10 eq.) in THF/EtOAc at rt was added py (30 mL) and DMF (200 mL). The resulting mixture was allowed to evaporate off most of the low boiling point volatiles under reduced pressure on rotovap. To the solution was added additional DMF (120 mL) and Et₃N (30 mL). The resulting mixture was placed into a 0° C. ice bath, and under N₂ atmosphere was added a solution of (S)-piperidin-2-yl-methanol (17.93 g; 0.16 mol; 1.20 eq., azeotroped with toluene under reduced pressure at 50° C. twice) in toluene (40 mL). The resulting reaction mixture was allowed to warm with the ice bath to rt and allowed to stir at rt for 24 hr. The reaction mixture was quenched with saturated aq. NH₄Cl solution (60 mL), diluted with water (200 mL), and extracted with EtOAc twice. The combined organic layers were washed with water (150 mL) thrice and brine. After removal of the organic solvents under reduced pressure, the remaining residue was dissolved in CH₂Cl₂ (40 mL) and purified by flash chromatography on 340 g silica gel column equilibrated with using 10% EtOAc/CH₂Cl₂, eluted with 10%-50% EtOAc/CH₂Cl₂ (5 V) and 50%-75% EtOAc/CH₂Cl₂ (7 V) to provide 3-(1-ethoxyethoxy)phenyl)((S)-2-(hydroxymethyl)piperidin-1-yl)methanone, together with a less pure fraction of 3-(1-ethoxyethoxy)phenyl)((S)-2-(hydroxymethyl)piperidin-1-yl)methanone.

This less pure fraction was re-purified as above using 10%-75% EtOAc/CH₂Cl₂ (4 V) and then 40%-75% EtOAc/CH₂Cl₂ (5 V) to provide additional pure fraction of 3-(1-ethoxyethoxy)phenyl)((S)-2-(hydroxymethyl)piperidin-1-yl)methanone. Combined the pure fractions from above provided the desired product. ¹H NMR (400 MHz, Chloroform-d) δ 7.22-7.12 (m, 2H), 6.86-6.80 (m, 2H), 3.96 (t, J=10.6 Hz, 1H), 3.82-3.35 (m, 8H), 1.77-1.44 (m, 6H), 1.23-1.11 (m, 6H). LCMS (ES) [M+1]⁺ m/z [308.2].

Step 4:

A solution of (3-(1-ethoxyethoxy)phenyl)((S)-2-(hydroxymethyl)piperidin-1-yl)methanone (14.64 g; 47.63 mmol; 1.00 eq.), 2-bromo-3-(oxan-2-yloxy)phenol (13 658.61 mg; 50.01 mmol; 1.05 eq.) and (tributylphosphoranylidene)acetonitrile (16 093.07 mg; 0.07 mol; 1.40 eq.) in toluene (51.24 mL; 3.50 V) under N₂ was allowed to stir at 104° C. bath for 25 min.

After being cooled to rt, the reaction mixture was treated with saturated aq. NH₄Cl solution (60 mL), diluted with water (200 mL), and extracted with EtOAc thrice. The combined organic layers were washed with water (100 mL) thrice and brine. After removal of the organic solvents under reduced pressure, the remaining residue was dissolved in 30 mL of CH₂Cl₂ and purified by flash chromatography on 220 g silica gel column using 0-0% EtOAc/Hexanes for 5 V, and 20-25% EtOAc/Hexanes to provide (2S)-2-[2-bromo-3-(oxan-2-yloxy)phenoxymethyl]-1-[3-(1-ethoxyethoxy)benzoyl]piperidine. LCMS (ES) [M+1]⁺ m/z [562.2] and [564.2].

Step 5:

To a -78° C. solution of (2S)-2-[2-bromo-3-(oxan-2-yloxy)phenoxymethyl]-1-[3-(1-ethoxyethoxy)benzoyl]piperidine (4152.00 mg; 7.38 mmol; 1.00 eq., this material was azeotroped with toluene trice right before being used) and N,N,N',N'-tetramethyl-1,2-ethanediamine (4.87 mL; 32.48 mmol; 4.40 eq.) (pre-dried over excess activated sieves overnight) in THF (24.91 mL; 6.00 V) under N₂ was added sec-butyllithium (23.20 mL; 1.40 mol/L; 32.48 mmol; 4.40 eq.) dropwise over 8 min. After stirring at -78° C. for 25 min, the reaction flask was placed into a -65° C. ice bath and allowed to stir for additional 15 min at -65° C. to -55° C. The reaction flask was placed back to the -78° C. and to this solution was added solution A (Solution A was made as such: To 2.0 mL of THF at rt was added 1.3 mL iPrMgBr (2.9 N in methyl-THF). To this mixture was added N,N-dimethylformamide that pre-dried over activated MS for 3 hr (4.57 mL; 59.05 mmol; 8.00 eq.), After being mixed for 20 seconds, the whole warm mixture, called solution A, was taken and added to the reaction solution over 2 min). The reaction mixture was allowed to stir at -78° C. for 10 min, quenched with a mixture of AcOH (4.5 mL, 78.75 mL, 10.6 eq.) and saturated aq. NH₄Cl (15 mL), warmed to rt and extracted with EtOAc thrice. After removal of the organic solvents under reduced pressure, the remaining residue was dissolved purified by flash chromatography on 50 g silica gel column using 0% EtOAc/Hexanes for 3 V, 20%-20% EtOAc/Hexanes for 3 V, and then 20%-55% EtOAc/Hexanes to provide 2-(1-ethoxyethoxy)-6-[(2S)-2-[2-formyl-3-(oxan-2-yloxy)phenoxymethyl]piperidine-1-carbonyl]benzaldehyde. LCMS (ES) [M+23]⁺ m/z [562.3].

Step 6:

To a rt solution of 2-(1-ethoxyethoxy)-6-[(2S)-2-[2-formyl-3-(oxan-2-yloxy)phenoxymethyl]piperidine-1-carbonyl]benzaldehyde (1040.00 mg; 1.93 mmol; 1.00 eq.) in tetrahydrofuran (20.0 mL) was added aq. hydrogen chloride (1.28 mL; 6.00 mol/L; 7.71 mmol; 4.00 eq.). This mixture was allowed to stir at rt for 60, quenched with water, and was adjusted to pH=7.0 with saturated aq. NaHCO₃ solution and extracted with EtOAc thrice. The organic layers were combined. After removal of the organic solvents under reduced pressure, the remaining residue was purified by flash chromatography on 10 g silica gel column using 0% EtOAc/Hexanes for 5V, 20%-75% EtOAc/Hexanes to provide 2-[(2S)-2-[(2-formyl-3-hydroxyphenoxy)methyl]piperidine-1-carbonyl]-6-hydroxybenzaldehyde. ¹H NMR (400 MHz, DMSO-d₆) δ 11.70 (d, J=35.9 Hz, 2H), 10.35-9.97 (m, 2H), 7.67-7.28 (m, 2H), 6.99 (t, J=7.9 Hz, 1H), 6.72 (d, J=8.3 Hz, 1H), 6.50 (dd, J=12.7, 8.4 Hz, 2H), 5.08 (b, 1H), 4.48 (dd, J=10.0, 7.8 Hz, 1H), 4.41-4.01 (m, 2H), 3.07 (s, 2H), 1.93 (d, J=28.7 Hz, 1H), 1.78-1.36 (m, 3H), 1.36-1.09 (m, 1H); LCMS (ES) [M+1]⁺ m/z [384.2]

Example 1b. Synthesis of 2-[(2S)-2-[(2-formyl-3-hydroxyphenoxy)methyl]piperidine-1-carbonyl]-6-hydroxybenzaldehyde (Compound 1), Procedure 2

Compound 1 was also made according to scheme below.

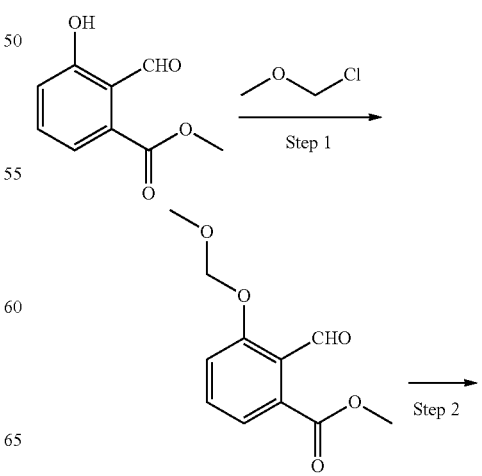

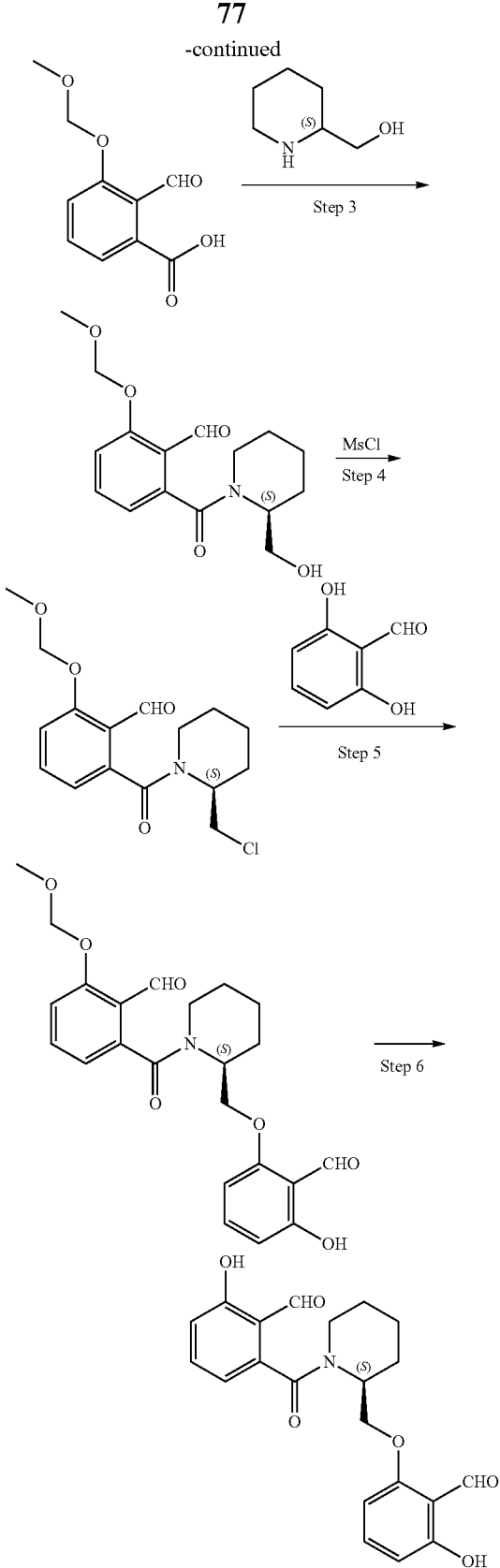

of methyl 2-formyl-3-hydroxybenzoate (5.0 g, 27.8 mmol, 1.0 equiv), DCM (50 mL,), DIEA (14.35 g, 111 mmol, 4.0 equiv), to which was added chloro(methoxy)methane (5.59 g, 69.4 mmol, 2.5 equiv) dropwise at 0° C. The resulting solution was stirred for 20 hours at room temperature. Saturated aqueous NH$_4$Cl aq (50 mL) was added, and the organic layer was separated. The aqueous layer was further extracted with CH$_2$Cl$_2$ (3×50 mL), the combined organic extracts were dried over Na$_2$SO$_4$, and the solvent was removed in vacuum. The residue was applied onto a silica gel column with ethyl acetate/petroleum ether (1/9). The collected fractions were combined and concentrated. This resulted in methyl 2-formyl-3-(methoxymethoxy)benzoate. LCMS (ES) [M+1]+m/z: 225.1.

Step 2:

Into a 250-mL round-bottom flask, was placed a mixture of methyl 2-formyl-3-(methoxymethoxy)benzoate (5.0 g, 22.3 mmol, 1.0 equiv), MeOH (50 mL), H$_2$O (10 mL) and NaOH (1.78 g, 44.6 mmol, 2.0 equiv). The resulting solution was stirred for 2 hours at room temperature. The resulting mixture was concentrated. The resulting solution was diluted with 100 mL of H$_2$O. The reaction mixture was cooled with an EtOH/ice bath. The pH value of the solution was adjusted to 5 with Citric acid aqueous solution at 0° C., and the precipitations were collected and dried. This resulted in 2-formyl-3-(methoxymethoxy)benzoic acid. LCMS (ES) [M+1]+m/z: 211.1.

Step 3:

Into a 50-mL round-bottom flask, was placed a mixture of 2-formyl-3-(methoxymethoxy)benzoic acid (2.0 g, 9.52 mmol, 1.0 equiv), DCM (20 mL), [(2S)-piperidin-2-yl]methanol (1.32 g, 11.4 mmol, 1.2 equiv), DIEA (3.69 g, 28.5 mmol, 3.0 equiv), to which was added HATU (5.43 g, 14.3 mmol, 1.5 equiv) in portions at 0° C. The resulting solution was stirred for 2 hours at room temperature. The resulting mixture was washed with 30 ml of H$_2$O and 2×30 mL of saturated aqueous NaHCO$_3$. The resulting mixture was concentrated. The residue was applied onto a silica gel column with ethyl acetate/petroleum ether (9/1). This resulted in 2-[(2S)-2-(hydroxymethyl)piperidine-1-carbonyl]-6-(methoxymethoxy)benzaldehyde. LCMS (ES) [M+1]+m/z: 308.2.

Step 4:

Into a 40-mL vial, was placed a solution of 2-[(2S)-2-(hydroxymethyl)piperidine-1-carbonyl]-6-(methoxymethoxy)benzaldehyde (500 mg, 1.63 mmol, 1.0 equiv), DCE (10 mL), DIEA (631 mg, 4.88 mmol, 3.0 equiv), to which was added MsCl (373 mg, 3.25 mmol, 2.0 equiv) dropwise at 0° C. The resulting solution was stirred for 2 hours at 0° C. The resulting mixture was used directly for the next step without any purification. LCMS (ES) [M+1]+m/z: 326.1.

Step 5:

Into a 40-mL vial, was placed a previous reaction mixture contained 2-[(2S)-2-(chloromethyl)piperidine-1-carbonyl]-6-(methoxymethoxy)benzaldehyde (~400 mg, 1.23 mmol, 1.0 equiv) in DCE (10 mL), to which were added DIEA (317 mg, 2.46 mmol, 2.0 equiv) and 2,6-dihydroxybenzaldehyde (254 mg, 1.84 mmol, 1.5 equiv). The resulting solution was stirred for 2 hours at 80° C. The resulting mixture was concentrated. The residue was applied onto a silica gel column with ethyl acetate/petroleum ether (1/3). This resulted in 2-[(2S)-2-[(2-formyl-3-hydroxyphenoxy)methyl]piperidine-1-carbonyl]-6-(methoxymethoxy)benzaldehyde. LCMS (ES) [M+1]$^+$ m/z: 428.2.

Step 6:

Into a 20-mL vial, was placed a solution of 2-[(2S)-2-[(2-formyl-3-hydroxyphenoxy)methyl]piperidine-1-carbonyl]-6-(methoxymethoxy)benzaldehyde (130 mg, 0.304 mmol, 1 equiv) and 4N HCl/dioxane (3 mL). The resulting solution was stirred for 30 min at room temperature. The resulting mixture was concentrated. The crude product was purified by Prep-HPLC with the following conditions: Column, SunFire Prep C18 OBD Column 9*150 mm, 5 um; mobile phase, Water (0.1% FA) and ACN (41% Phase B up to 57% in 7 min); Detector, UV 254 nm. This resulted in 2-[(2S)-2-[(2-formyl-3-hydroxyphenoxy)methyl]piperidine-1-carbonyl]-6-hydroxybenzaldehyde. $^1$H NMR (300 MHz, DMSO-$d_6$) δ 11.82 (br, 1H), 10.28-10.11 (m, 1H), 8.43 (s, 1H), 7.58-7.40 (m, 2H), 6.99-6.93 (m, 1H), 6.76-6.49 (m, 3H), 5.09 (br, 1H), 4.55-4.47 (m, 1H), 4.33-4.25 (m, 1H), 3.32-3.07 (m, 2H), 1.92-1.24 (m, 6H). LCMS (ES) [M+1]+ m/z: 384.2.

Example 2. Synthesis of 2-{[(2S)-1-(2-formylbenzoyl)piperidin-2-yl]methoxy}-6-hydroxybenzaldehyde (Compound 2)

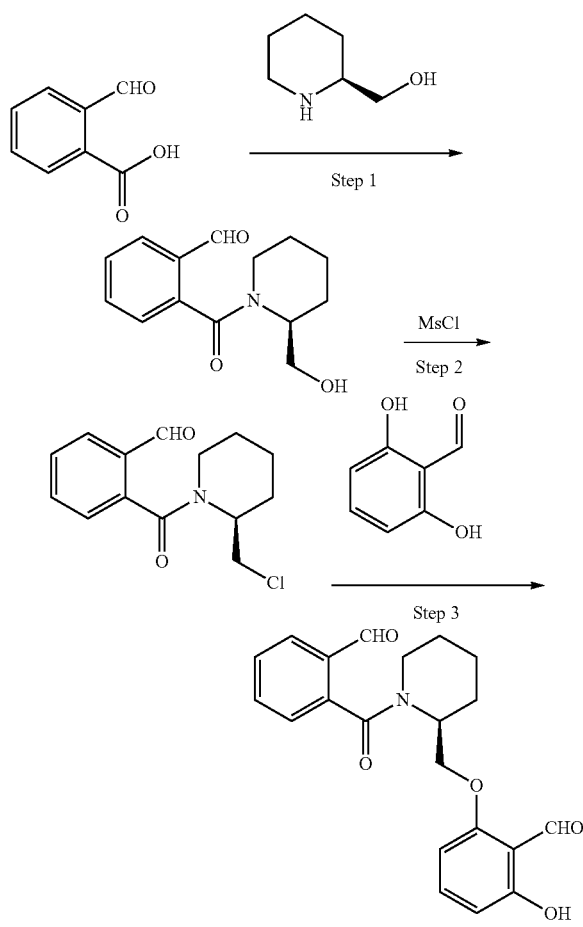

Step 1:

Into a 1-L round-bottom flask, was placed a mixture of 2-formylbenzoic acid (20 g, 133 mmol, 1 equiv), DCM (300 mL), [(2S)-piperidin-2-yl]methanol (16.9 g, 147 mmol, 1.1 equiv), DIEA (51.7 g, 400 mmol, 3.0 equiv) and HATU (60.8 g, 160 mmol, 1.2 equiv) at 0° C. The resulting solution was stirred for 2 hours at room temperature. The resulting mixture was washed with 1×300 mL of H$_2$O, 2×300 mL of NaHCO$_3$ and concentrated. The residue was applied onto a silica gel column with ethyl acetate/petroleum ether (9/1). This resulted in 2-[(2S)-2-(hydroxymethyl)piperidine-1-carbonyl]benzaldehyde. LCMS (ES) [M+1]$^+$ m/z: 248.2.

Step 2:

Into a 250-mL round-bottom flask, was placed a solution of 2-[(2S)-2-(hydroxymethyl)piperidine-1-carbonyl]benzaldehyde (12.0 g, 48.5 mmol, 1.0 equiv), DCE (150 mL) and DIEA (18.8 g, 146 mmol, 3.0 equiv), to which was added MsCl (11.1 g, 97.1 mmol, 2.0 equiv) dropwise at 0° C. The resulting solution was stirred for 2 hours at 0° C. The resulting solution was used directly for the next step without any workup. LCMS (ES) [M+1]$^+$ m/z: 266.1.

Step 3:

Into a 250-mL round-bottom flask, was placed a previous reaction mixture contained 2-[(2S)-2-(chloromethyl)piperidine-1-carbonyl]benzaldehyde (equals to 11.0 g, 41.4 mmol, 1.0 equiv) in DCE (150 mL), to which were added DIEA (10.7 g, 82.8 mmol, 2.0 equiv) and 2,6-dihydroxybenzaldehyde (11.4 g, 82.8 mmol, 2.0 equiv). The resulting solution was stirred for 30 minutes at 80° C. The resulting mixture was concentrated. The crude product was purified by Flash-Prep-HPLC with the following conditions: welch, Ultimate XB-C18 50×250 mm, Column 10-Micron; mobile phase, Water (0.2% FA) and ACN (30% Phase B up to 75% in 15 min); Detector, UV 254 nm. This resulted in 2-[[(2S)-1-(2-formylbenzoyl)piperidin-2-yl]methoxy]-6-hydroxybenzaldehyde. $^1$H NMR (300 MHz, DMSO-$d_6$) δ 11.67 (br, 1H), 10.26 (br, 1H), 10.21 (s, 1H), 7.99-7.93 (m, 1H), 7.74-7.71 (m, 1H), 7.69-7.65 (m, 1H), 7.63-7.60 (m, 1H), 7.50-7.40 (m, 1H), 6.66-6.60 (m, 1H), 6.55-6.52 (m, 1H), 5.19-5.17 (br, 1H), 4.58-4.53 (m, 1H), 4.37-4.25 (m, 1H), 3.25-3.06 (m, 2H), 1.91-1.44 (m, 6H). LCMS (ES) [M+1]+m/z: 368.2.

Example 3. Synthesis of 2-ethoxy-6-[(3S)-3-[(2-formyl-3-hydroxyphenoxy)methyl]morpholine-4-carbonyl]benzaldehyde (Compound 3)

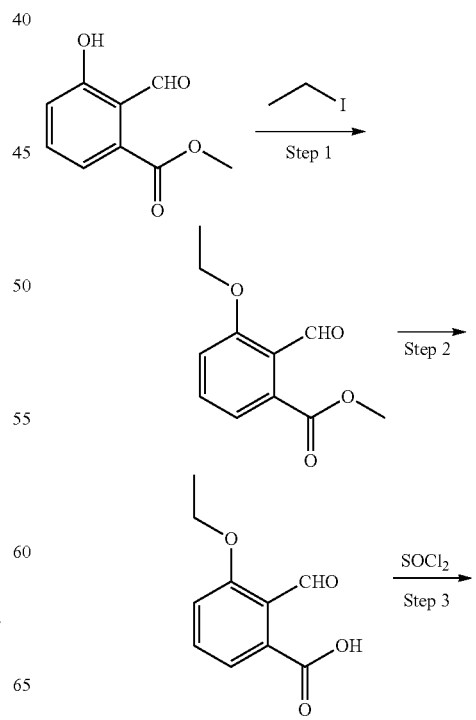

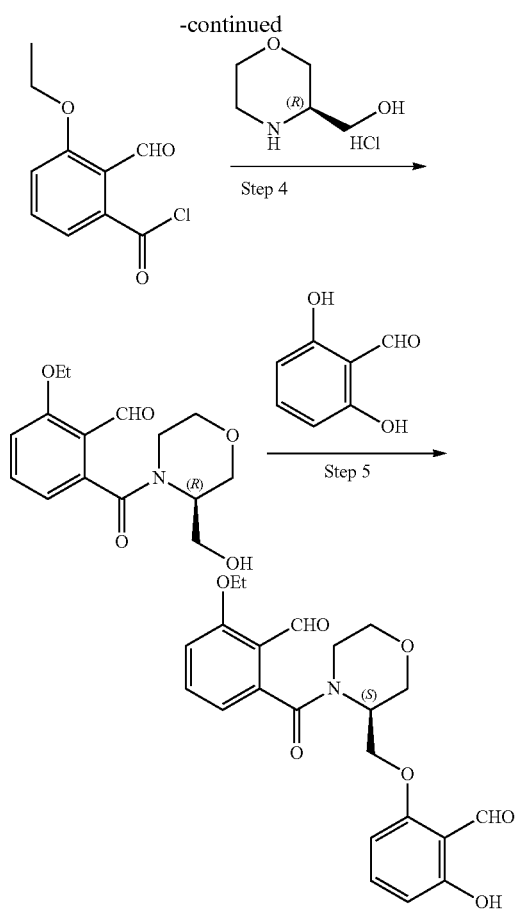

Step 1:

Into a 100-mL 3-necked round-bottom flask, was placed methyl 2-formyl-3-hydroxybenzoate (4 g, 22.2 mmol, 1.0 equiv) in DMF (40 mL), followed by iodoethane (10.4 g, 66.6 mmol, 3.0 equiv) and K$_2$CO$_3$ (9.2 g, 66.6 mmol, 3.0 equiv) were added. The mixture was stirred overnight at room temperature. The reaction was then quenched by the addition of 10 mL of cold water and extracted with 3×40 mL of ethyl acetate, combined the organic phase and washed with 3×20 ml of brine. The organic phase was dried over anhydrous sodium sulfate, filtered and concentrated under vacuum. Methyl 3-ethoxy-2-formylbenzoate was obtained and used to the next step directly without further purification. LCMS (ES) [M+1]$^+$ m/z: 209.

Step 2:

Into a 100-mL round-bottom flask, was placed methyl 3-ethoxy-2-formylbenzoate (2.7 g, 13.0 mmol, 1.0 equiv) in THF (28 mL), followed by the addition of a solution of LiOH (0.62 g, 26.0 mmol, 2.0 equiv) in H$_2$O (12 mL). The mixture was stirred for at room temperature. The resulting mixture was concentrated under vacuum to remove the THF. The pH value of the residue was adjusted to 3-4 with HCl (3N). The solids were collected by filtration and dried under infrared lamp. 3-ethoxy-2-formylbenzoic acid was obtained. LCMS (ES) [M+1]$^+$ m/z: 195.

Step 3:

Into a 50-mL round-bottom flask, was placed 3-ethoxy-2-formylbenzoic acid (2 g, 10.3 mmol, 1.0 equiv), toluene (20 mL), SOCl$_2$ (12.2 g, 103.0 mmol, 10.0 equiv). The mixture was stirred for 2 hr at 80° C. After cooled to room temperature, the clear solution was concentrated under vacuum to remove the solvent. 3-ethoxy-2-formylbenzoyl chloride was obtained. LCMS (ES) [M+1]$^+$ m/z: 213.

Step 4:

Into a 50-mL 3-necked round-bottom flask purged and maintained with an inert atmosphere of nitrogen, was placed [(3R)-morpholin-3-yl]methanol hydrochloride (0.8 g, 5.2 mmol, 1.1 equiv), DCM (10 mL), TEA (1.9 g, 18.8 mmol, 4.0 equiv), and cooled to 0° C. This was followed by addition of 3-ethoxy-2-formylbenzoyl chloride (1 g, 4.7 mmol, 1.0 equiv) in DCM (5 mL). The mixture was stirred for 1 h at room temperature. The reaction solution was diluted with 10 mL of H$_2$O and extracted with 3×20 mL of dichloromethane, dried over anhydrous sodium sulfate and concentrated under vacuum. The residue was purified by silica gel column with ethyl acetate/petroleum (from 10% to 100%). 2-ethoxy-6-[(3R)-3-(hydroxymethyl)morpholine-4-carbonyl]benzaldehyde was obtained. LCMS (ES) [M+1]+ m/z: 294.

Step 5:

Into a 100-mL 3-necked round-bottom flask purged and maintained with an inert atmosphere of nitrogen, was placed 2-ethoxy-6-[(3R)-3-(hydroxymethyl)morpholine-4-carbonyl]benzaldehyde (600 mg, 2.0 mmol, 1.0 equiv), 2,6-dihydroxybenzaldehyde (339 mg, 2.4 mmol, 1.2 equiv), THF (30 mL), PPh$_3$ (1.1 g, 4.0 mmol, 2.0 equiv). The mixture was cooled to 0° C. and stirred for 15 min, followed by the addition of DBAD (942. mg, 4.0 mmol, 2.0 equiv). The resulting solution was allowed to stir overnight at room temperature. After concentrated under vacuum, the residue was purified by Flash-Prep-HPLC with the following conditions (IntelFlash-1): C18 column-180 g, mobile phase, CH$_3$CN/H$_2$O (0.05% FA)=5% increasing to 60% within 15 min, Detector, UV 254 nm. 2-[[(3S)-4-(3-ethoxy-2-formylbenzoyl)morpholin-3-yl]methoxy]-6-hydroxybenzaldehyde was obtained. LCMS (ES, m/z): [M+H]$^+$: 414. H-NMR (300 MHz, DMSO-d$_6$, ppm): δ 11.78 (br, 1H), 10.39-10.12 (m, 2H), 7.71-7.24 (m, 3H), 6.60-6.49 (m, 3H), 4.80 (s, 1H), 4.47-4.09 (m, 5H), 4.30-4.05 (m, 3H), 3.39-3.17 (m, 1H), 2.91 (d, J=12.0 Hz, 1H), 1.40 (td, J=6.9, 3.0 Hz, 3H).

Example 4. Synthesis of (S)-2-((4-(2-formyl-3-hydroxybenzoyl)morpholin-3-yl)methoxy)-6-hydroxybenzaldehyde (Compound 4)

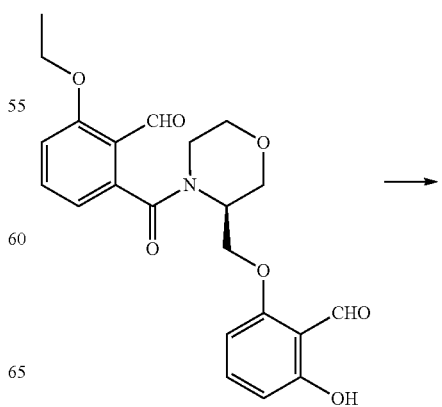

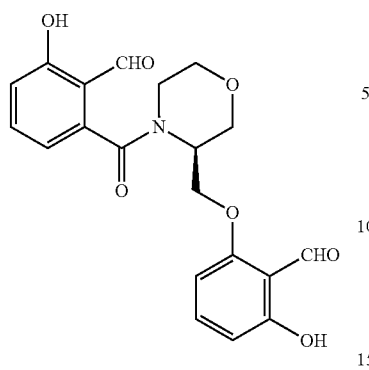

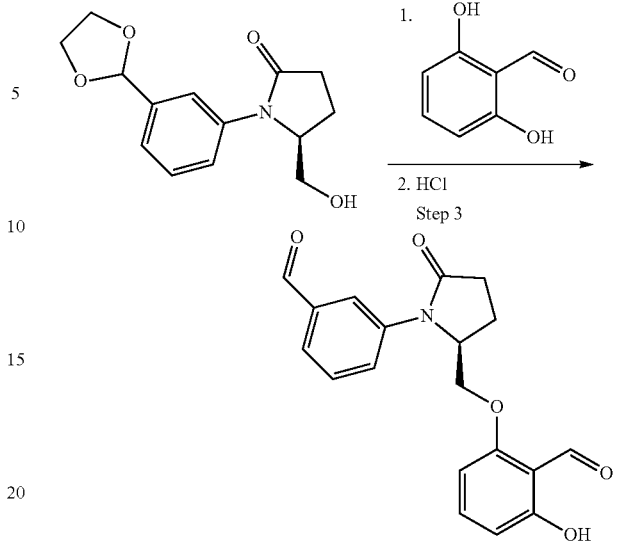

Into a 50-mL 3-necked round-bottom flask, was placed a solution of (S)-2-ethoxy-6-(3-((2-formyl-3-hydroxyphenoxy)methyl)morpholine-4-carbonyl)benzaldehyde (200 mg, 0.48 mmol, 1.00 equiv) in DCM (8 mL). The reaction was stirred under an atmosphere of nitrogen, BBr$_3$ (4.8 mL, 4.8 mmol, 10.00 equiv, 1.0 M in DCM) was added into the reaction mixture dropwise at −78° C. Then the temperature warmed to 0° C. naturally and stirred for 6 hours. The resulting solution was quenched with saturated aqueous NaHCO$_3$(20 mL), extracted with DCM (50 mL×3), the combined organic layers were dried over anhydrous sodium sulfate, dried over anhydrous sodium sulfate, filtered and concentrated. The crude reaction mixture was subjected to reverse preparative HPLC (Prep-C18, 5 mM XBridge column, 19×150 mm, waters; gradient elution of 5% MeCN in water to 5% MeCN in water over a 2 min period, 5% MeCN in water to 40% MeCN in water over another 12 min period, where both solvents contain 0.1% FA). This resulted in (S)-2-((4-(2-formyl-3-hydroxybenzoyl)morpholin-3-yl)methoxy)-6-hydroxybenzaldehyde. $^1$H NMR (300 MHz, DMSO-d$_6$) δ 11.78 (brs, 1H), 11.15 (brs, 1H), 10.30-10.13 (m, 2H), 7.60-7.41 (m, 2H), 7.05-7.00 (m, 1H), 6.79-6.74 (m, 1H), 6.66 (brs, 1H), 6.56-6.49 (m, 1H), 4.89-4.75 (m, 1H), 4.47-4.08 (m, 3H), 3.88-3.53 (m, 3H), 3.49-2.95 (m, 2H).

LCMS (ES) [M+1]$^+$ m/z: 386.1.

Example 5. Synthesis of 2-{[(2S)-1-(3-formylphenyl)-5-oxopyrrolidin-2-yl]methoxy}-6-hydroxybenzaldehyde (Compound 5)

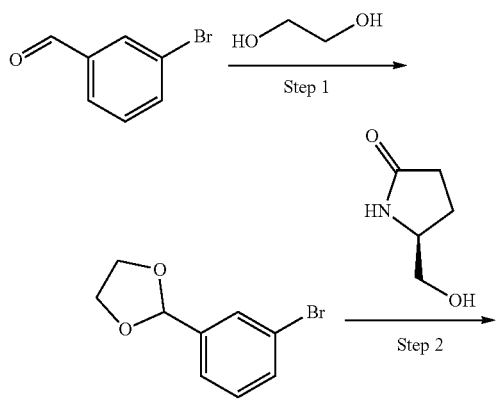

Step 1:
Into a 500-mL round-bottom flask, was placed 3-bromobenzaldehyde (10 g, 54.048 mmol, 1 equiv), ethane-1,2-diol (26.837 g, 432.386 mmol, 8.00 equiv), toluene (300 mL), p-TSA (930.72 mg, 5.405 mmol, 0.1 equiv). The reaction was heated for 8 h under reflux and water separation, cooled to room temperature. The resulting mixture was concentrated, and diluted with 300 mL of water, extracted with 2×300 mL of ethyl acetate dried over anhydrous sodium sulfate and concentrated. The residue was purified by flash column with ethyl acetate/petroleum ether (20%). This resulted in 2-(3-bromophenyl)-1,3-dioxolane.

Step 2:
Into a 250-mL round-bottom flask purged and maintained with an inert atmosphere of nitrogen, was placed 5-(hydroxymethyl)pyrrolidin-2-ol (3.99 g, 34.050 mmol, 1.30 equiv), 2-(3-bromophenyl)-1,3-dioxolane (6 g, 26.193 mmol, 1 equiv), DMF (60 mL), Cs$_2$CO$_3$ (12.80 g, 39.289 mmol, 1.5 equiv), N$^1$,N$^2$-dimethylcyclohexane-1,2-diamine (3.73 g, 26.193 mmol, 1 equiv), CuI (2.49 g, 13.096 mmol, 0.5 equiv). The resulting solution was stirred for 4 h at 90° C. in an oil bath. The reaction mixture was cooled to room temperature with a water/ice bath. The solid was filtered out. The residue was purified by flash column with THF/PE (36%). This resulted in (5S)-1-[3-(1,3-dioxolan-2-yl)phenyl]-5-(hydroxymethyl)pyrrolidin-2-one.

Step 3:
Into a 50-mL 3-necked round-bottom flask purged and maintained with an inert atmosphere of nitrogen, was placed 2,6-dihydroxybenzaldehyde (157.38 mg, 1.139 mmol, 1.2 equiv), (5S)-1-[3-(1,3-dioxolan-2-yl)phenyl]-5-(hydroxymethyl)pyrrolidin-2-one (250 mg, 0.950 mmol, 1 equiv), THF (5 mL), PPh$_3$ (298.85 mg, 1.139 mmol, 1.2 equiv). This was followed by the addition of DIAD (230.40 mg, 1.139 mmol, 1.2 equiv) dropwise with stirring at 0° C. The resulting solution was stirred for 16 h at 25° C. To this was added HCl (5.00 mL, 1 mol/L) dropwise with stirring at 0° C. The resulting solution was stirred for 1 h at 25° C. The pH value of the solution was adjusted to 7 with Sat.NaHCO$_3$. The resulting solution was extracted with 3×50 mL of ethyl acetate and the organic layers combined and dried over anhydrous sodium sulfate. The crude product was purified by Prep-HPLC with the following conditions: Column, XBridge Prep C18 OBD Column, 19 cm, 150 mm, 5 um;

mobile phase, Water (0.1% HCOOH) and ACN; Detector, 254 nm. This resulted in 2-{[(2S)-1-(3-formylphenyl)-5-oxopyrrolidin-2-yl]methoxy}-6-hydroxybenzaldehyde.
LCMS (ES, m/z): [M+H]$^+$:340; H-NMR: (300 MHz, DMSO-d$_6$, ppm): δ 11.60 (s, 1H), 9.97 (s, 1H), 9.71 (s, 1H), 8.03 (t, J=1.8 Hz, 1H), 7.88-7.68 (m, 2H), 7.60 (t, J=7.8 Hz, 1H), 7.44 (t, J=8.4 Hz, 1H), 6.55-6.43 (m, 2H), 5.00-4.86 (m, 1H), 4.28-4.12 (m, 2H), 2.84-2.63 (m, 1H), 2.50-2.32 (m, 2H), 2.14-2.02 (m, 1H).

Example 6. Synthesis of (S)-2-(2-((2-formylphenoxy)methyl)piperidine-1-carbonyl)-6-hydroxybenzaldehyde (Compound 55)

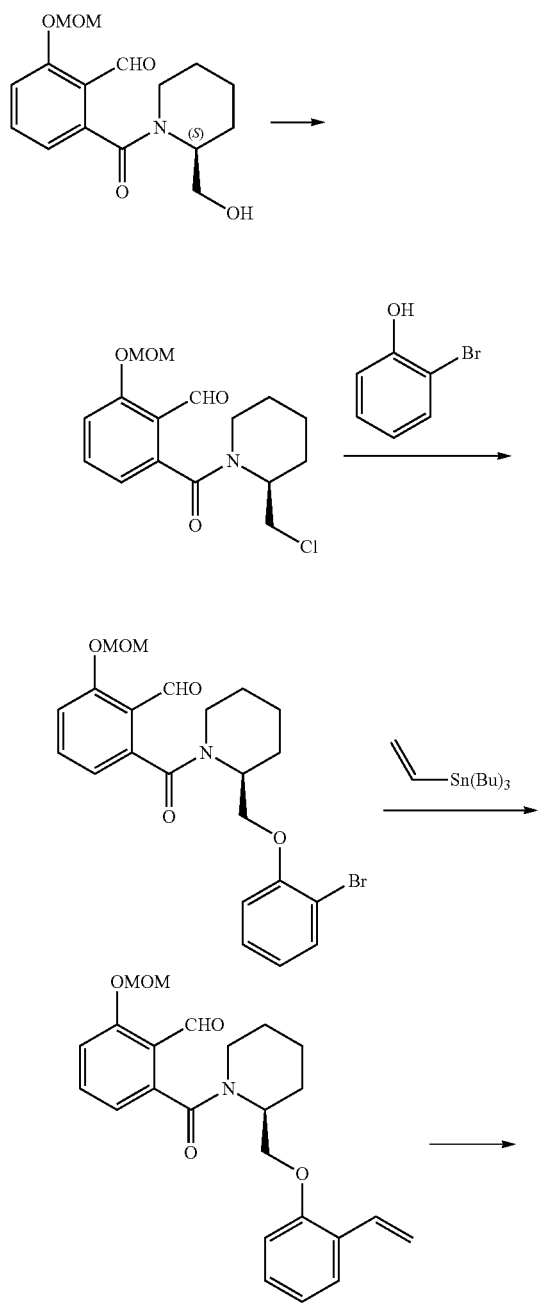

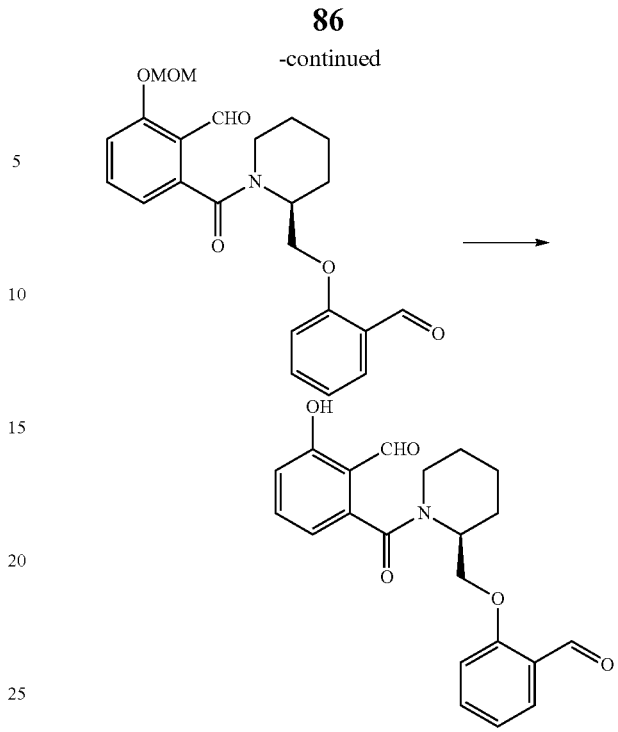

Step 1:
Into a 100-mL round-bottom flask, was placed 2-[(2S)-2-(hydroxymethyl)piperidine-1-carbonyl]-6-(methoxymethoxy)benzaldehyde (3.00 g, 9.761 mmol, 1.00 equiv), DCE (50.00 mL, 631.575 mmol, 64.70 equiv), DIEA (3.78 g, 29.283 mmol, 3 equiv), and MsCl (2.24 g, 19.555 mmol, 2.00 equiv). The resulting solution was stirred for 0 min at 20° C. The resulting solution was allowed to react, with stirring, for an additional 4 hr at room temperature. The mixture was used to next step directly.

Step 2:
Into a 100-mL round-bottom flask, was placed 2-[(2S)-2-(chloromethyl)piperidine-1-carbonyl]-6-(methoxymethoxy)benzaldehyde (3.11 g, 9.546 mmol, 0.50 equiv), DCE (50 mL) DIEA (2.47 g, 19.074 mmol, 1.00 equiv), and 2-bromophenol (3.30 g, 19.074 mmol, 1.00 equiv). The resulting solution was stirred for 16 hr at 80° C. The reaction mixture was cooled to room temperature with a water/ice bath. The resulting mixture was concentrated under vacuum. The resulting solution was extracted with 3×50 mL of ethyl acetate, and the organic layers were combined and dried over anhydrous sodium sulfate. The residue was applied onto a silica gel column with ethyl acetate/petroleum ether (1:2.5). This resulted in (S)-2-(2-((2-bromophenoxy)methyl)piperidine-1-carbonyl)-6-(methoxymethoxy)benzaldehyde. LCMS (ES) [M+1]$^+$ m/z: 462.1.

Step 3:
Into a 100-mL round-bottom flask purged and maintained with an inert atmosphere of nitrogen, was placed (S)-2-(2-((2-bromophenoxy)methyl)piperidine-1-carbonyl)-6-(methoxymethoxy)benzaldehyde (1.10 g, 2.379 mmol, 1.00 equiv), tributyl(ethenyl)stannane (1.51 g, 4.762 mmol, 2.00 equiv), toluene (20.00 mL), and Pd(PPh$_3$)$_4$ (0.27 g, 0.238 mmol, 0.1 equiv). The resulting solution was stirred for 16 hr at 110° C. The reaction mixture was cooled to room temperature with a water/ice bath. The resulting mixture was concentrated under vacuum. The mixture was dried over anhydrous sodium sulfate. The residue was applied onto a silica gel column with ethyl acetate/petroleum ether (1:4). This resulted in (S)-2-(methoxymethoxy)-6-(2-((2-vinylphenoxy)methyl)piperidine-1-carbonyl)benzaldehyde. LCMS (ES) [M+1]+ m/z: 410.2.

Step 4:

Into a 50-mL round-bottom flask, was placed (S)-2-(methoxymethoxy)-6-(2-((2-vinylphenoxy)methyl)piperidine-1-carbonyl)benzaldehyde (600.00 mg, 1.465 mmol, 1.00 equiv), tetraoxodipotassioosmium (24.35 mg, 0.073 mmol, 0.05 equiv), NaIO₄ (940.23 mg, 4.396 mmol, 3.00 equiv), and H₂O (2.00 mL). The resulting solution was stirred for 6 hr at room temperature. The resulting mixture was concentrated under vacuum. The resulting solution was extracted with 3×30 mL of dichloromethane, and the organic layers were combined and dried over anhydrous sodium sulfate. The residue was applied onto a silica gel column with ethyl acetate/petroleum ether (1:3). This resulted in (S)-2-(2-((2-formylphenoxy)methyl)piperidine-1-carbonyl)-6-(methoxymethoxy)benzaldehyde.

Step 5:

Into a 50-mL round-bottom flask, was placed (S)-2-(2-((2-formylphenoxy)methyl)piperidine-1-carbonyl)-6-(methoxymethoxy)benzaldehyde (580 mg, 1.410 mmol, 1.00 equiv) and HCl(gas) in 1,4-dioxane (5.00 mL, 20.000 mmol, 14.19 equiv). The resulting solution was stirred for 2 hr at room temperature. The resulting mixture was concentrated under vacuum. The pH value of the solution was adjusted to 6 with NaHCO₃. The resulting solution was extracted with 3×30 mL of dichloromethane and the organic layers combined and dried over anhydrous sodium sulfate. The crude reaction mixture was subjected to reverse preparative HPLC (Prep-C18, 5 mM XBridge column, 19×150 mm, waters; gradient elution of 5% MeCN in water to 5% MeCN in water over a 2 min period, 5% MeCN in water to 40% MeCN in water over another 12 min period, where both solvents contain 0.1% FA). This resulted in (S)-2-(2-((2-formylphenoxy)methyl)piperidine-1-carbonyl)-6-hydroxybenzaldehyde.

LCMS (ES) [M+1]+ m/z: 368.2. ¹H NMR (300 MHz, DMSO-d₆) δ 11.00 (br, 1H), 10.39 (s, 1H), 10.24 (s, 1H), 7.82-7.63 (m, 2H), 7.62-7.41 (m, 1H), 7.37 (d, J=8.3 Hz, 1H), 7.22-7.07 (m, 1H), 7.06-6.74 (m, 2H), 5.21-5.12 (m, 1H), 4.54-4.21 (m, 2H), 3.19-2.78 (m, 2H), 2.04-1.17 (m, 6H).

Example 7. Synthesis of (S)-2-(3-((2-formylphenoxy)methyl)morpholine-4-carbonyl)-6-hydroxybenzaldehyde (Compound 56)

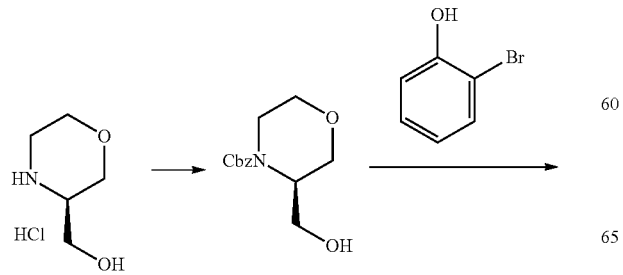

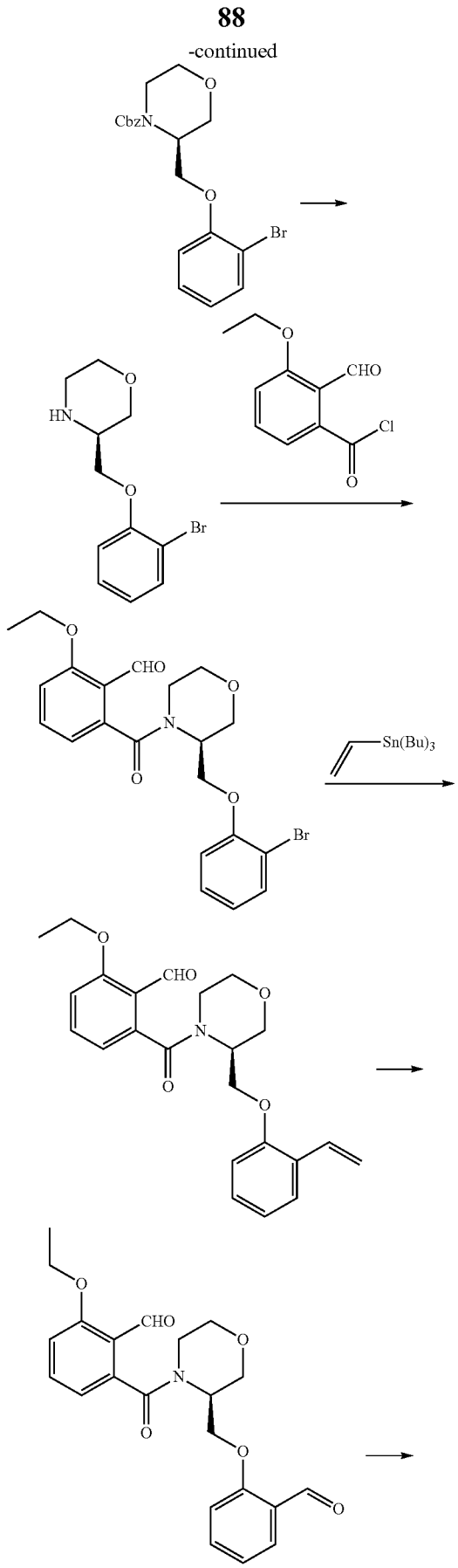

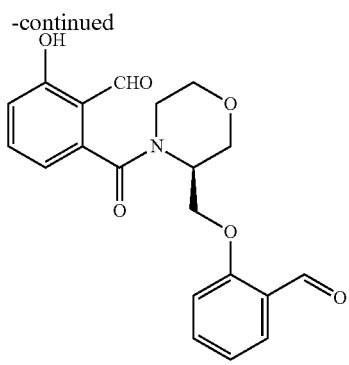

Step 1:

Into a 250-mL round-bottom flask, was placed (3R)-morpholin-3-ylmethanol hydrochloride (5.00 g, 32.550 mmol, 1.00 equiv), benzyl chloroformate (8.33 g, 48.831 mmol, 1.50 equiv), TEA (6.59 g, 65.100 mmol, 2 equiv), and DCM (100.00 mL). The resulting solution was stirred for 15 min at 0° C. The resulting solution was allowed to react, with stirring, for an additional 3 hr at room temperature. The reaction was then quenched by the addition of water/ice. The resulting solution was extracted with 3×100 mL of dichloromethane, and the organic layers were combined and dried over anhydrous sodium sulfate and concentrated under vacuum. The residue was applied onto a silica gel column with THF/PE (1:3). This resulted in benzyl (R)-3-(hydroxymethyl)morpholine-4-carboxylate. LCMS (ES) $[M+1]^+$ m/z: 252.1.

Step 2:

Into a 250-mL round-bottom flask purged and maintained with an inert atmosphere of nitrogen, was placed benzyl (R)-3-(hydroxymethyl)morpholine-4-carboxylate (3.00 g, 11.939 mmol, 1.00 equiv), 2-bromophenol (4.13 g, 23.878 mmol, 2.00 equiv), triphenylphosphine (6.26 g, 23.878 mmol, 2 equiv), THF (30.00 mL), and DBAD (5.50 g, 23.878 mmol, 2 equiv). The resulting solution was stirred for 15 min at 0° C. The resulting solution was allowed to react, with stirring, for an additional 16 hr at room temperature. The resulting solution was extracted with 3×200 mL of ethyl acetate, and the organic layers were combined and dried over anhydrous sodium sulfate and concentrated under vacuum. The residue was applied onto a silica gel column with THF/PE (1:5). This resulted in benzyl (S)-3-((2-bromophenoxy)methyl)morpholine-4-carboxylate. LCMS (ES) $[M+1]^+$ m/z: 406.1.

Step 3:

Into a 100-mL round-bottom flask, was placed benzyl (S)-3-((2-bromophenoxy)methyl)morpholine-4-carboxylate (2.00 g, 1.00 equiv), and HBr in AcOH (50.00 mL). The resulting solution was stirred for 8 hr at room temperature. The resulting mixture was concentrated under vacuum. This resulted in (S)-3-((2-bromophenoxy)methyl)morpholine.
LCMS (ES) $[M+1]^+$ m/z: 272.

Step 4:

Into a 50-mL round-bottom flask, was placed (S)-3-((2-bromophenoxy)methyl)morpholine (800.00 mg, 2.940 mmol, 1.00 equiv), 3-ethoxy-2-formylbenzoyl chloride (937.58 mg, 4.409 mmol, 1.5 equiv), DIEA (1139.79 mg, 8.819 mmol, 3 equiv), and DCM (30.00 mL, 471.901 mmol, 160.53 equiv). The resulting solution was stirred for 4 hr at room temperature. The resulting solution was extracted with 3×20 mL of dichloromethane, and the organic layers were combined and dried over anhydrous sodium sulfate and concentrated under vacuum. This resulted in (S)-2-(3-((2-bromophenoxy)methyl)morpholine-4-carbonyl)-6-ethoxybenzaldehyde. LCMS (ES) $[M+1]^+$ m/z: 448.1.

Step 5:

Into a 50-mL round-bottom flask, was placed (S)-2-(3-((2-bromophenoxy)methyl)morpholine-4-carbonyl)-6-ethoxybenzaldehyde (300.00 mg, 0.669 mmol, 1.00 equiv), tributyl(ethenyl)stannane (424.40 mg, 1.338 mmol, 2 equiv), tetrakis(triphenylphosphine)palladium(0) (77.33 mg, 0.067 mmol, 0.1 equiv), and toluene (10.00 mL). The resulting solution was stirred for 16 hr at 110° C. The reaction mixture was cooled to room temperature. The resulting solution was extracted with 3×30 mL of ethyl acetate, and the organic layers were combined and dried over anhydrous sodium sulfate and concentrated under vacuum. The residue was applied onto a silica gel column with THF/PE (1:5). This resulted in (S)-2-ethoxy-6-(3-((2-vinylphenoxy)methyl)morpholine-4-carbonyl)benzaldehyde. LCMS (ES) $[M+1]^+$ m/z: 396.2.

Step 6:

Into a 50-mL round-bottom flask, was placed (S)-2-ethoxy-6-(3-((2-vinylphenoxy)methyl)morpholine-4-carbonyl)benzaldehyde (180.00 mg, 0.455 mmol, 1.00 equiv), tetraoxodipotassioosmium (7.57 mg, 0.023 mmol, 0.05 equiv), sodium periodate (292.07 mg, 1.366 mmol, 3 equiv), and acetone (6.00 mL), $H_2O$ (1.00 mL). The resulting solution was stirred for 4 hr at room temperature. The resulting solution was extracted with 3×20 mL of dichloromethane, and the organic layers were combined and dried over anhydrous sodium sulfate and concentrated under vacuum. The residue was applied onto a silica gel column with THF/PE (1:3). This resulted in (S)-2-ethoxy-6-(3-((2-formylphenoxy)methyl)morpholine-4-carbonyl)benzaldehyde. LCMS (ES) $[M+1]^+$ m/z: 398.2.

Step 7:

Into a 50-mL round-bottom flask, was placed (S)-2-ethoxy-6-(3-((2-formylphenoxy)methyl)morpholine-4-carbonyl)benzaldehyde (120.00 mg, 0.302 mmol, 1.00 equiv), boron tribromide (756.43 mg, 3.019 mmol, 10.00 equiv), and DCM (10.00 mL, 157.300 mmol, 520.96 equiv). The resulting solution was stirred for 1 hr at −78° C. The resulting solution was allowed to react, with stirring, for an additional 3 hr at 0° C. The reaction was then quenched by the addition of water. The resulting solution was extracted with 3×20 mL of dichloromethane, and the organic layers combined and dried over anhydrous sodium sulfate and concentrated under vacuum. The crude reaction mixture was subjected to reverse preparative HPLC (Prep-C18, 5 mM XBridge column, 19×150 mm, waters; gradient elution of 5% MeCN in water to 5% MeCN in water over a 2 min period, 5% MeCN in water to 40% MeCN in water over another 12 min period, where both solvents contain 0.1% FA). This resulted in (S)-2-(3-((2-formylphenoxy)methyl)morpholine-4-carbonyl)-6-hydroxybenzaldehyde. LCMS (ES) $[M+1]^+$ m/z: 370.1. $^1$H NMR (300 MHz, DMSO-$d_6$) δ 11.11 (br, 1H), 10.41 (s, 1H), 10.28 (s, 1H), 7.81-7.61 (m, 2H), 7.62-7.46 (m, 1H), 7.38 (d, J=8.3 Hz, 1H), 7.14-6.96 (m, 2H), 6.79-6.61 (m, 1H), 4.89-4.73 (m, 1H), 4.67-4.21 (m, 2H), 4.11 (d, J=12.1 Hz, 1H), 3.86 (d, J=12.1 Hz, 1H), 3.80-3.55 (m, 2H), 3.22-3.00 (m, 1H), 2.98 (d, J=11.9 Hz, 1H).

Example 8. Synthesis of (S)-6-(2-((2-formyl-3-hydroxyphenoxy)methyl)piperidine-1-carbonyl)-2-hydroxy-3-methoxybenzaldehyde (Compound 57)

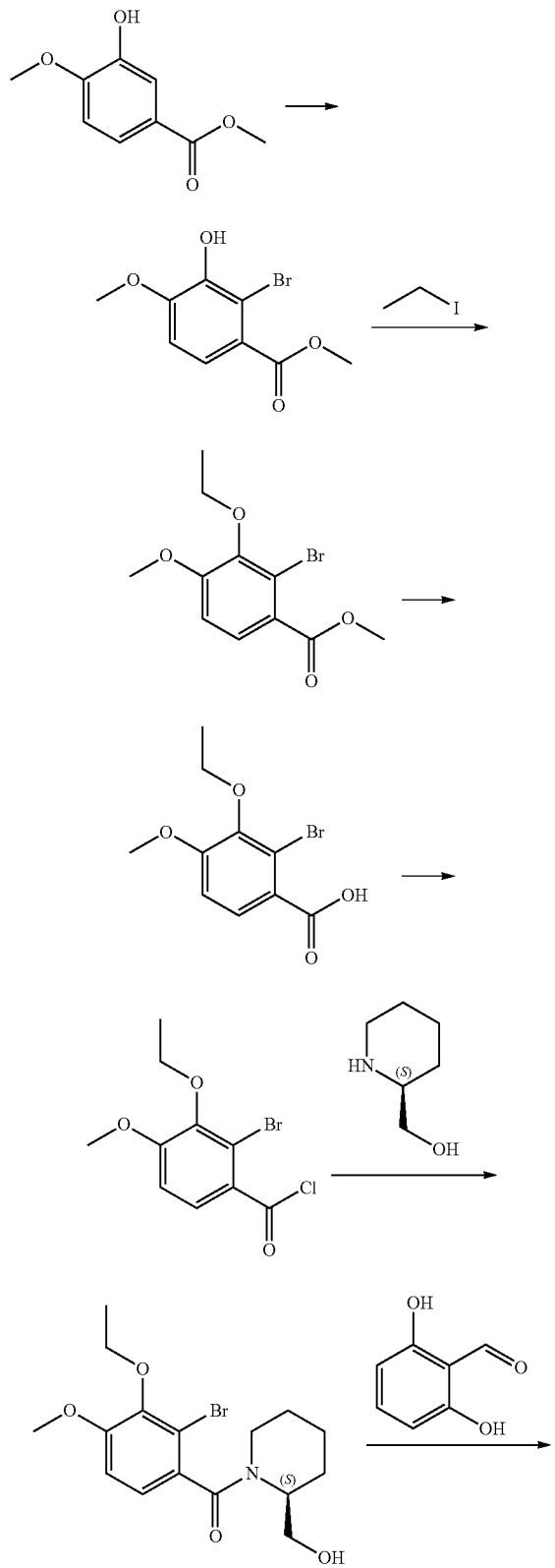

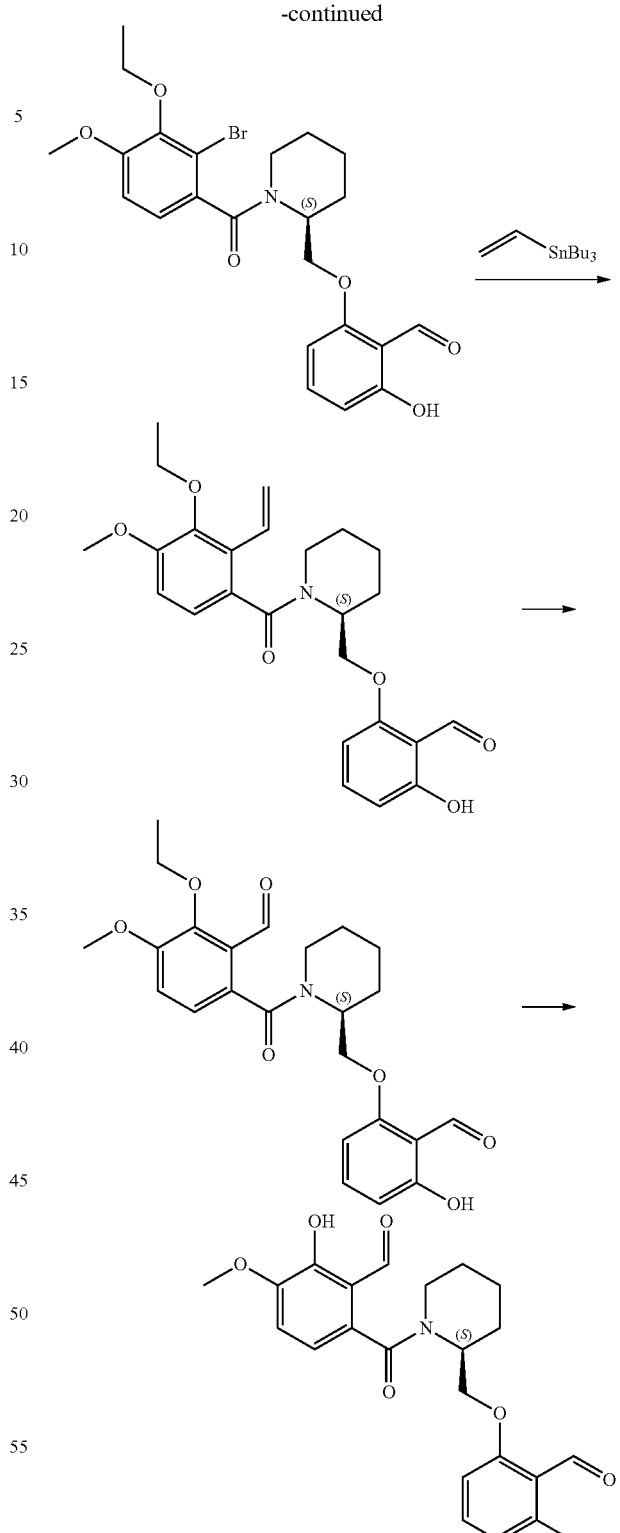

Step 1:
Into a 250-mL round-bottom flask, was placed methyl 3-hydroxy-4-methoxybenzoate (10.00 g, 54.892 mmol, 1.00 equiv), acetic acid (80.00 mL), and dibromine (6.14 g, 38.425 mmol, 0.70 equiv). The resulting solution was stirred for 16 hr at 25° C. The reaction was then quenched by the addition of 100 mL of 10% $Na_2S_2O_3$ and extracted with 200 mL of ethyl acetate; the organic layer was washed with 3×100 mL of water. The organic layer was dried over $Na_2SO_4$ and concentrated under vacuum. The residue was applied onto a silica gel column with ethyl acetate/petroleum ether (10:1). This resulted in methyl 2-bromo-3-hydroxy-4-methoxybenzoate. LCMS (ES) [M+1]$^+$ m/z 261.

Step 2:

Into a 100-mL round-bottom flask, was placed methyl 2-bromo-3-hydroxy-4-methoxybenzoate (2.00 g, 7.661 mmol, 1.00 equiv), acetonitrile (40 mL), potassium methaneperoxoate potassium (2.13 g, 15.322 mmol, 2.00 equiv), and iodoethane (2.39 g, 15.322 mmol, 2.00 equiv). The resulting solution was stirred for 16 hr at 60° C. The resulting mixture was concentrated. The residue was applied onto a silica gel column with ethyl acetate/petroleum ether (1:2). This resulted in methyl 2-bromo-3-ethoxy-4-methoxybenzoate. LCMS (ES) [M+1]$^+$ m/z 289.

Step 3:

Into a 50-mL round-bottom flask, was placed methyl 2-bromo-3-ethoxy-4-methoxybenzoate (1.80 g, 6.226 mmol, 1.00 equiv), water (20 mL), and lithium hydroxide (0.30 g, 12.451 mmol, 2.00 equiv). The resulting solution was stirred for 3 hr at 25° C. The pH value of the solution was adjusted to 5 with HCl (1 mol/L). The solids were collected by filtration. This resulted in 2-bromo-3-ethoxy-4-methoxybenzoic acid. LCMS (ES) [M−1]$^-$ m/z 273.

Step 4:

Into a 100-mL round-bottom flask, was placed 2-bromo-3-ethoxy-4-methoxybenzoic acid (1.60 g, 5.816 mmol, 1.00 equiv), toluene (20.00 mL), and thionyl chloride (2.08 g, 17.448 mmol, 3.00 equiv). The resulting solution was stirred for 3 hr at 80° C. The resulting mixture was concentrated. This resulted in 2-bromo-3-ethoxy-4-methoxybenzoyl chloride.

Step 5:

Into a 100-mL round-bottom flask, was placed (S)-piperidin-2-ylmethanol (0.63 g, 5.451 mmol, 1.00 equiv), DCM (40.00 mL, 629.202 mmol, 115.43 equiv), triethylamine (1.65 g, 16.352 mmol, 3.00 equiv), and 2-bromo-3-ethoxy-4-methoxybenzoyl chloride (1.60 g, 5.451 mmol, 1.00 equiv). The resulting solution was stirred for 16 hr at 25° C. The resulting mixture was concentrated. The residue was applied onto a silica gel column with ethyl acetate/petroleum ether (1:2). The collected fractions were combined and concentrated. This resulted in (S)-(2-bromo-3-ethoxy-4-methoxyphenyl)(2-(hydroxymethyl)piperidin-1-yl)methanone. LCMS (ES) [M+1]$^+$ m/z 372.1.

Step 6:

Into a 100-mL round-bottom flask, was placed (S)-(2-bromo-3-ethoxy-4-methoxyphenyl)(2-(hydroxymethyl)piperidin-1-yl)methanone (1.50 g, 4.029 mmol, 1.00 equiv), oxolane (40 mL), 2,6-dihydroxybenzaldehyde (0.56 g, 4.029 mmol, 1.00 equiv), PPh$_3$ (1.27 g, 4.842 mmol, 1.20 equiv), and DIAD (0.98 g, 4.846 mmol, 1.20 equiv). The resulting solution was stirred for 16 hr at 25° C. The resulting mixture was concentrated. The residue was applied onto a silica gel column with ethyl acetate/petroleum ether (1:3). The collected fractions were combined and concentrated. This resulted in (S)-2-((1-(2-bromo-3-ethoxy-4-methoxybenzoyl)piperidin-2-yl)methoxy)-6-hydroxybenzaldehyde. LCMS (ES) [M+1]$^+$ m/z 492.1.

Step 7:

Into a 100-mL round-bottom flask, was placed (S)-2-((1-(2-bromo-3-ethoxy-4-methoxybenzoyl)piperidin-2-yl)methoxy)-6-hydroxybenzaldehyde (1.20 g, 2.437 mmol, 1.00 equiv), toluene (20.00 mL, 187.978 mmol, 77.13 equiv), tributyl(ethenyl)stannane (1.55 g, 4.874 mmol, 2.00 equiv), and tetrakis(triphenylphosphane) palladium (0.28 g, 0.244 mmol, 0.10 equiv). The resulting solution was stirred for 16 hr at 110° C. The resulting mixture was concentrated. The residue was applied onto a silica gel column with ethyl acetate/petroleum ether (1:3). The collected fractions were combined and concentrated. This resulted in (S)-2-((1-(3-ethoxy-4-methoxy-2-vinylbenzoyl)piperidin-2-yl)methoxy)-6-hydroxybenzaldehyde. LCMS (ES) [M+1]$^+$ m/z 440.2.

Step 8:

Into a 100-mL round-bottom flask, was placed (S)-2-((1-(3-ethoxy-4-methoxy-2-vinylbenzoyl)piperidin-2-yl)methoxy)-6-hydroxybenzaldehyde (600.00 mg, 1.365 mmol, 1.00 equiv), acetone (24.00 mL), water (4 mL), and NaIO$_4$ (876.00 mg, 4.096 mmol, 3.00 equiv), K$_2$OsO$_4$.2H$_2$O (10.00 mg, 0.027 mmol, 0.02 equiv). The resulting solution was stirred for 16 hr at 25° C. The resulting solution was diluted with 50 mL of EA and washed with 3×20 ml of water. The mixture was dried over anhydrous sodium sulfate and concentrated. The residue was applied onto a silica gel column with ethyl acetate/petroleum ether (1:3). The collected fractions were combined and concentrated. This resulted in (S)-2-ethoxy-6-(2-((2-formyl-3-hydroxyphenoxy)methyl)piperidine-1-carbonyl)-3-methoxybenzaldehyde. LCMS (ES) [M+1]+m/z 442.2.

Step 9:

Into a 100-mL round-bottom flask, was placed (S)-2-ethoxy-6-(2-((2-formyl-3-hydroxyphenoxy)methyl)piperidine-1-carbonyl)-3-methoxybenzaldehyde (200.00 mg, 0.453 mmol, 1.00 equiv), and DCM (20.00 mL). Then, tribromoborane (4.53 mL, 1M in DCM, 4.53 mmol, 10.00 eq) was added dropwise at −78° C. The resulting solution was stirred for 3 hr at −40° C. The reaction was then quenched by the addition of 20 mL of NaHCO$_3$ and extracted with 50 mL of ethyl acetate concentrated. The organic layer was dried over anhydrous sodium sulfate and concentrated under vacuum. The crude reaction mixture was filtered and subjected to reverse phase preparative HPLC (Prep-C18, 20-45 uM, 120 g, Tianjin Bonna-Agela Technologies; gradient elution of 40% MeCN in water to 50% MeCN in water over a 10 min period, where both solvents contain 0.1% FA) to provide the title compound. LCMS (ES) [M+1]$^+$ m/z 414.1. $^1$H NMR (300 MHz, DMSO-d$_6$) δ 11.77 (s, 1H), 10.64 (s, 1H), 10.27 (s, 2H), 10.22 (s, 1H), 7.56 (t, J=8.4 Hz, 1H), 7.23 (d, J=8.1 Hz, 1H), 6.75 (d, J=8.4 Hz, 1H), 6.65-6.48 (m, 2H), 5.17-5.04 (m, 1H), 4.50 (t, J=9.0 Hz, 1H), 4.36-4.21 (m, 1H), 3.86 (s, 3H), 3.21-2.85 (m, 2H), 2.10-1.21 (m, 6H).

Example 9. Synthesis of 2-[[(3R)-1-(3-formyl-2-hydroxybenzoyl)piperidin-3-yl]methoxy]-6-hydroxybenzaldehyde (Compound 58)

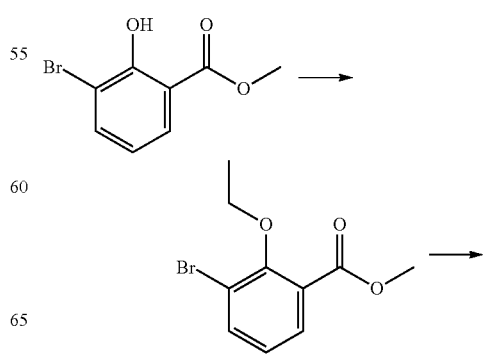

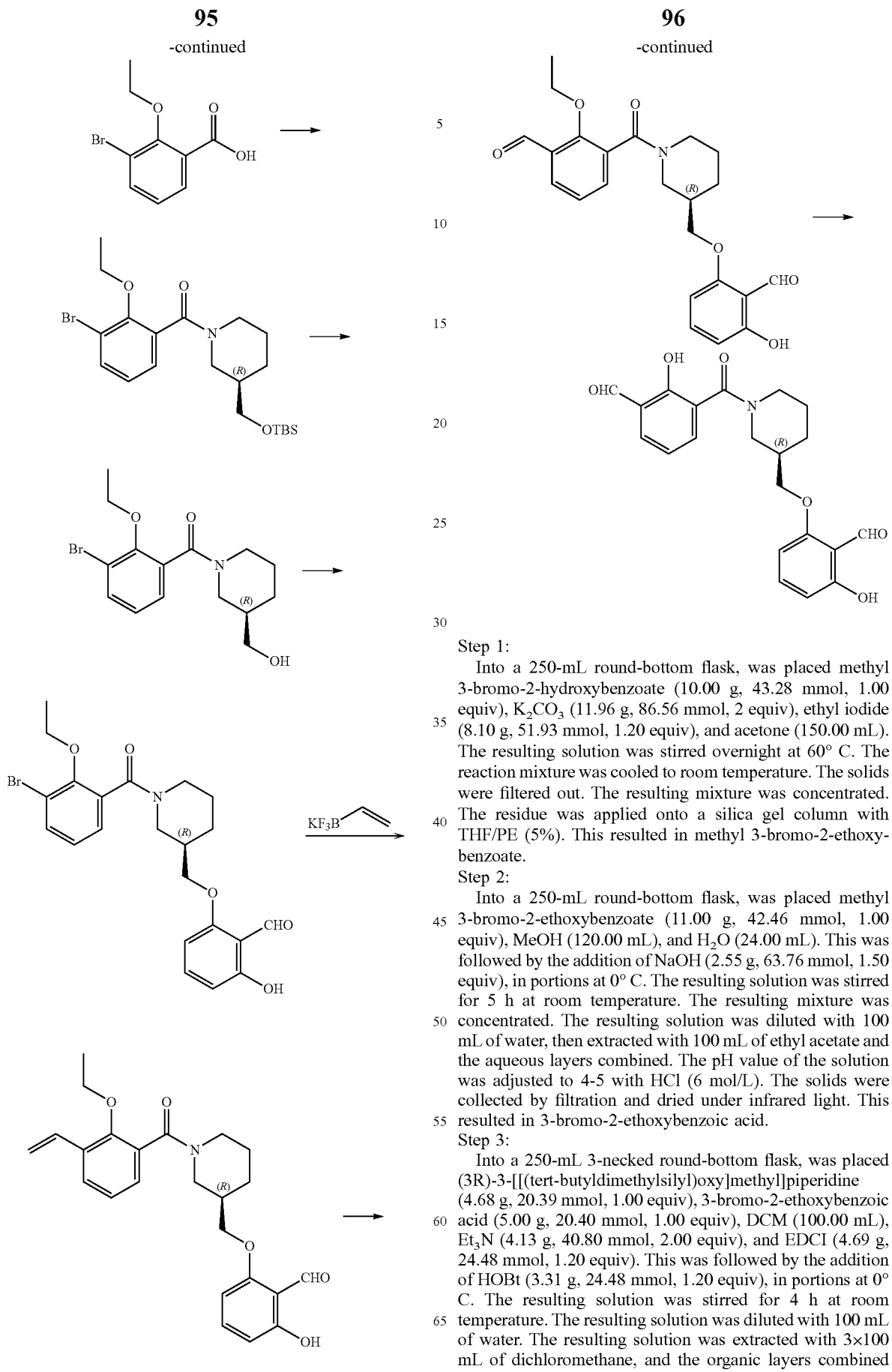

Step 1:
Into a 250-mL round-bottom flask, was placed methyl 3-bromo-2-hydroxybenzoate (10.00 g, 43.28 mmol, 1.00 equiv), $K_2CO_3$ (11.96 g, 86.56 mmol, 2 equiv), ethyl iodide (8.10 g, 51.93 mmol, 1.20 equiv), and acetone (150.00 mL). The resulting solution was stirred overnight at 60° C. The reaction mixture was cooled to room temperature. The solids were filtered out. The resulting mixture was concentrated. The residue was applied onto a silica gel column with THF/PE (5%). This resulted in methyl 3-bromo-2-ethoxybenzoate.

Step 2:
Into a 250-mL round-bottom flask, was placed methyl 3-bromo-2-ethoxybenzoate (11.00 g, 42.46 mmol, 1.00 equiv), MeOH (120.00 mL), and $H_2O$ (24.00 mL). This was followed by the addition of NaOH (2.55 g, 63.76 mmol, 1.50 equiv), in portions at 0° C. The resulting solution was stirred for 5 h at room temperature. The resulting mixture was concentrated. The resulting solution was diluted with 100 mL of water, then extracted with 100 mL of ethyl acetate and the aqueous layers combined. The pH value of the solution was adjusted to 4-5 with HCl (6 mol/L). The solids were collected by filtration and dried under infrared light. This resulted in 3-bromo-2-ethoxybenzoic acid.

Step 3:
Into a 250-mL 3-necked round-bottom flask, was placed (3R)-3-[[(tert-butyldimethylsilyl)oxy]methyl]piperidine (4.68 g, 20.39 mmol, 1.00 equiv), 3-bromo-2-ethoxybenzoic acid (5.00 g, 20.40 mmol, 1.00 equiv), DCM (100.00 mL), $Et_3N$ (4.13 g, 40.80 mmol, 2.00 equiv), and EDCI (4.69 g, 24.48 mmol, 1.20 equiv). This was followed by the addition of HOBt (3.31 g, 24.48 mmol, 1.20 equiv), in portions at 0° C. The resulting solution was stirred for 4 h at room temperature. The resulting solution was diluted with 100 mL of water. The resulting solution was extracted with 3×100 mL of dichloromethane, and the organic layers combined and dried over anhydrous sodium sulfate and concentrated. This resulted in (3R)-1-(3-bromo-2-ethoxybenzoyl)-3-[[(tert-butyldimethylsilyl)oxy]methyl]piperidine.

Step 4:

Into a 250-mL round-bottom flask, was placed (3R)-1-(3-bromo-2-ethoxybenzoyl)-3-[[(tert-butyldimethylsilyl)oxy]methyl]piperidine (9.00 g, 19.72 mmol, 1.00 equiv), and THF (40.00 mL). This was followed by the addition of TBAF/THF (39.43 mL, 39.43 mmol, 2.00 equiv) dropwise with stirring at 0° C. The resulting solution was stirred for 5 h at room temperature. The resulting mixture was concentrated. The residue was applied onto a silica gel column with THF/PE (40%). This resulted in [(3R)-1-(3-bromo-2-ethoxybenzoyl)piperidin-3-yl]methanol.

Step 5:

Into a 250-mL 3-necked round-bottom flask purged and maintained with an inert atmosphere of nitrogen, was placed 2,6-dihydroxybenzaldehyde (1.45 g, 10.49 mmol, 1.20 equiv), [(3R)-1-(3-bromo-2-ethoxybenzoyl)piperidin-3-yl]methanol (3.00 g, 8.77 mmol, 1.00 equiv), DCM (150.00 mL), and PPh$_3$ (2.76 g, 10.52 mmol, 1.20 equiv). This was followed by the addition of DIAD (2.13 g, 10.52 mmol, 1.20 equiv) dropwise with stirring at 0° C. The resulting solution was stirred for overnight at room temperature. The resulting mixture was concentrated. The residue was applied onto a silica gel column with THF/PE (22%). This resulted in 2-[[(3R)-1-(3-bromo-2-ethoxybenzoyl)piperidin-3-yl]methoxy]-6-hydroxybenzaldehyde.

Step 6:

Into a 100-mL round-bottom flask purged and maintained with an inert atmosphere of nitrogen, was placed ethenyltrifluoro-lambda4-borane potassium (1.16 g, 8.66 mmol, 2.00 equiv), 2-[[(3R)-1-(3-bromo-2-ethoxybenzoyl)piperidin-3-yl]methoxy]-6-hydroxybenzaldehyde (2.00 g, 4.33 mmol, 1.00 equiv), Et$_3$N (1.31 g, 12.98 mmol, 3.00 equiv), EtOH (50.00 mL), and Pd(dppf)Cl$_2$ (0.32 g, 0.43 mmol, 0.10 equiv). The resulting solution was stirred for 3 h at 80° C.

The resulting mixture was concentrated. The residue was applied onto a silica gel column with THF/PE (23%). This resulted in 2-[[(3R)-1-(3-ethenyl-2-ethoxybenzoyl)piperidin-3-yl]methoxy]-6-hydroxybenzaldehyde.

Step 7:

Into a 100-mL round-bottom flask, was placed 2-[[(3R)-1-(3-ethenyl-2-ethoxybenzoyl)piperidin-3-yl]methoxy]-6-hydroxybenzaldehyde (1.20 g, 2.93 mmol, 1.00 equiv), acetone (12.00 mL), H$_2$O (2.00 mL), sodium periodate (1.88 g, 8.79 mmol, 3.00 equiv), and K$_2$OsO$_4$·2H$_2$O (21.60 mg, 0.06 mmol, 0.02 equiv). The resulting solution was stirred overnight at room temperature. The resulting mixture was concentrated. The resulting solution was diluted with 50 mL of water. The resulting solution was extracted with 3×50 mL of dichloromethane, and the organic layers combined and dried over anhydrous sodium sulfate and concentrated. The residue was applied onto a silica gel column with THF/PE (23%). This resulted in 2-[[(3R)-1-(2-ethoxy-3-formylbenzoyl)piperidin-3-yl]methoxy]-6-hydroxybenzaldehyde.

Step 8:

Into a 100-mL 3-necked round-bottom flask purged and maintained with an inert atmosphere of nitrogen, was placed 2-[[(3R)-1-(2-ethoxy-3-formylbenzoyl)piperidin-3-yl]methoxy]-6-hydroxybenzaldehyde (500 mg, 1.22 mmol, 1.00 equiv), and DCM (20.00 mL). This was followed by the addition of BBr$_3$/DCM (12.15 mL, 12.15 mmol, 10.00 equiv) dropwise with stirring at −78° C. The resulting solution was stirred for 0.5 h at 0° C. The reaction was then quenched by the addition of 50 mL of water/ice. The resulting solution was extracted with 3×50 mL of dichloromethane and the organic layers combined and dried over anhydrous sodium sulfate and concentrated. The crude product (400 mg) was purified by Prep-HPLC with the following conditions: Column, XBridge Prep C18 OBD Column, 19 cm, 150 mm, 5 um; mobile phase, Water (0.1% HCOOH) and CAN (30% Phase B up to 60% in 11 min); Detector, 254. This resulted in 2-[[(3R)-1-(3-formyl-2-hydroxybenzoyl)piperidin-3-yl]methoxy]-6-hydroxybenzaldehyde.

$^1$H-NMR (300 MHz, DMSO-d$_6$): δ 11.62 (s, 1H), 11.09 (s, 1H), 10.07 (s, 1H), 9.63 (s, 1H), 7.80 (dd, J=7.6, 1.7 Hz, 1H), 7.50 (d, J=7.6 Hz, 2H), 7.05 (s, 1H), 6.51 (t, J=13.3 Hz, 2H), 4.46-3.83 (m, 3H), 3.54-3.37 (m, 1H), 3.13-2.99 (m, 2H), 2.13-2.05 (m, 1H), 1.88-1.84 (m, 1H), 1.74 (d, J=14.0 Hz, 1H), 1.53-1.40 (m, 2H). LCMS (ES, m/z): [M+H]$^+$: 384.0.

Example 9. Synthesis of 2-[[(2R)-4-(2-formyl-3-hydroxybenzoyl)morpholin-2-yl]methoxy]-6-hydroxybenzaldehyde (Compound 59)

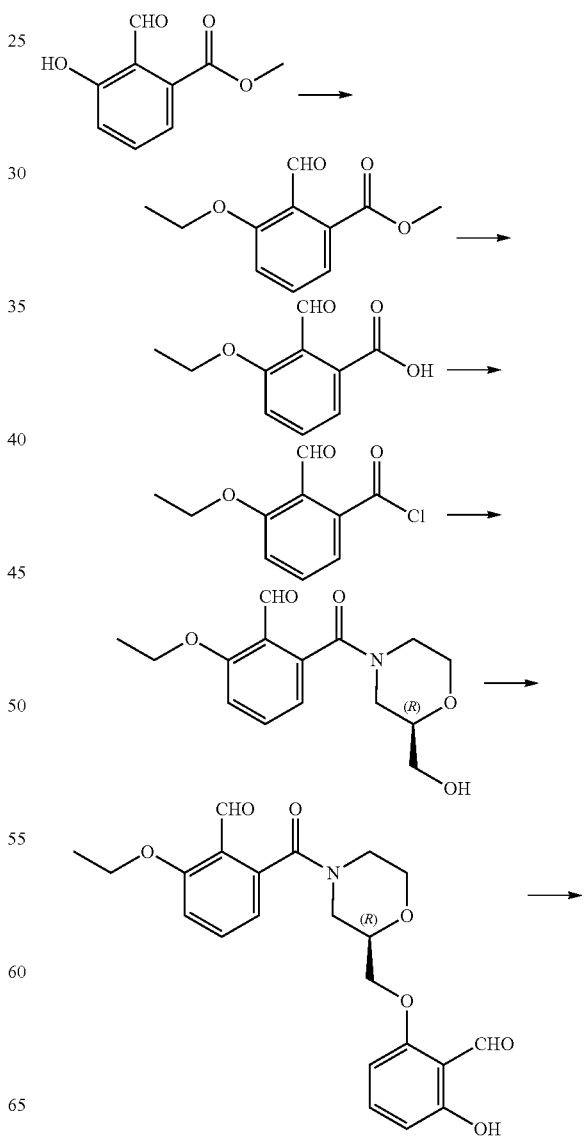

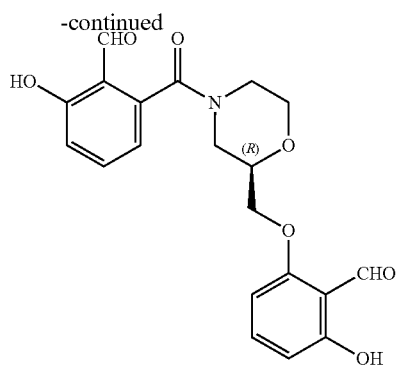

Step 1:

Into a 250-mL round-bottom flask, was placed methyl 2-formyl-3-hydroxybenzoate (8.20 g, 45.52 mmol, 1.00 equiv), DMF (200.00 mL), $K_2CO_3$ (12.58 g, 91.03 mmol, 2.00 equiv), and ethyl iodide (10.65 g, 68.28 mmol, 1.50 equiv). The resulting solution was stirred for overnight at room temperature. The solids were filtered out. The resulting solution was diluted with 200 mL of water, then extracted with 2×200 mL of ethyl acetate; the organic layers were combined and dried over anhydrous sodium sulfate and concentrated. This resulted in methyl 3-ethoxy-2-formylbenzoate.

Step 2:

Into a 250-mL round-bottom flask, was placed methyl 3-ethoxy-2-formylbenzoate (9.00 g, 43.23 mmol, 1.00 equiv), THF (50.00 mL), and $H_2O$ (50.00 mL). This was followed by the addition of $LiOH \cdot H_2O$ (3.63 g, 86.45 mmol, 2.00 equiv), in portions at 0° C. The resulting solution was stirred for 3 h at room temperature. The resulting mixture was concentrated. The resulting solution was extracted with 100 mL of ethyl acetate and the aqueous layers combined. The pH value of the solution was adjusted to 4-5 with HCl (6 mol/L). The solids were collected by filtration, and dried under infrared light. This resulted in 3-ethoxy-2-formylbenzoic acid.

Step 3:

Into a 100-mL round-bottom flask, was placed 3-ethoxy-2-formylbenzoic acid (1.00 g, 5.15 mmol, 1.00 equiv), toluene (30.00 mL), and $SOCl_2$ (3.06 g, 25.75 mmol, 5.00 equiv). The resulting solution was stirred for overnight at 50° C. The resulting mixture was concentrated. This resulted in 3-ethoxy-2-formylbenzoyl chloride.

Step 4:

Into a 100-mL 3-necked round-bottom flask, was placed (2R)-morpholin-2-ylmethanol hydrochloride (0.70 g, 4.56 mmol, 1.00 equiv), DCM (20.00 mL), and $Et_3N$ (1.84 g, 18.23 mmol, 4.00 equiv). This was followed by the addition of 3-ethoxy-2-formylbenzoyl chloride (1.07 g, 5.03 mmol, 1.10 equiv), in portions at 0° C. The resulting solution was stirred for 2 h at room temperature. The reaction was then quenched by the addition of 20 mL of water. The resulting solution was extracted with 3×20 mL of dichloromethane, and the organic layers were combined and dried over anhydrous sodium sulfate and concentrated. The residue was applied onto a silica gel column with THF/PE (50%). This resulted in 2-ethoxy-6-[(2R)-2-(hydroxymethyl)morpholine-4-carbonyl]benzaldehyde.

Step 5:

Into a 100-mL 3-necked round-bottom flask purged and maintained with an inert atmosphere of nitrogen, was placed 2,6-dihydroxybenzaldehyde (0.73 g, 5.29 mmol, 1.19 equiv), 2-ethoxy-6-[(2R)-2-(hydroxymethyl)morpholine-4-carbonyl]benzaldehyde (1.30 g, 4.43 mmol, 1.00 equiv), $PPh_3$ (1.39 g, 5.32 mmol, 1.20 equiv), and THF (50.00 mL). This was followed by the addition of DIAD (1.08 g, 5.32 mmol, 1.2 equiv) dropwise with stirring at 0° C. The resulting solution was stirred for overnight at room temperature. The resulting mixture was concentrated. The residue was applied onto a silica gel column with THF/PE (30%). This resulted in 2-[[(2R)-4-(3-ethoxy-2-formylbenzoyl)morpholin-2-yl]methoxy]-6-hydroxybenzaldehyde.

Step 6:

Into a 100-mL 3-necked round-bottom flask purged and maintained with an inert atmosphere of nitrogen, was placed 2-[[(2R)-4-(3-ethoxy-2-formylbenzoyl)morpholin-2-yl] methoxy]-6-hydroxybenzaldehyde (500 mg, 1.21 mmol, 1.00 equiv), and DCM (20.00 mL). This was followed by the addition of $BBr_3$/DCM (12.11 mL, 12.11 mmol, 10.01 equiv) dropwise with stirring at −78° C. The resulting solution was stirred for 0.5 h at 0° C. The reaction was then quenched by the addition of 20 mL of water/ice. The resulting solution was extracted with 3×20 mL of dichloromethane, and the organic layers were combined and dried over anhydrous sodium sulfate and concentrated. The crude product was purified by Prep-HPLC with the following conditions: Column, XBridge Prep C18 OBD Column, 19 cm, 150 mm, 5 um; mobile phase, Water (0.1% HCOOH) and CAN (30% Phase B up to 60% in 11 min); Detector, 254. This resulted in 2-[[(2R)-4-(2-formyl-3-hydroxybenzoyl)morpholin-2-yl]methoxy]-6-hydroxybenzaldehyde.

$^1$H-NMR (300 MHz, DMSO-$d_6$) δ 11.69 (s, 1H), 11.06 (s, 1H), 10.39-9.99 (m, 2H), 7.61-7.40 (m, 2H), 7.09-6.98 (m, 1H), 6.80-6.45 (m, 3H), 4.49-4.22 (m, 2H), 4.11-3.87 (m, 2H), 3.74-3.36 (m, 2H), 3.33-3.22 (m, 1H), 3.11-2.87 (m, 2H).

LCMS: (ES, m/z): [M+Na]$^+$: 408.0.

Example 10. Synthesis of 2-((4-(2-formyl-3-hydroxybenzoyl)-6-methylmorpholin-3-yl)methoxy)-6-hydroxybenzaldehyde (Compound 60)

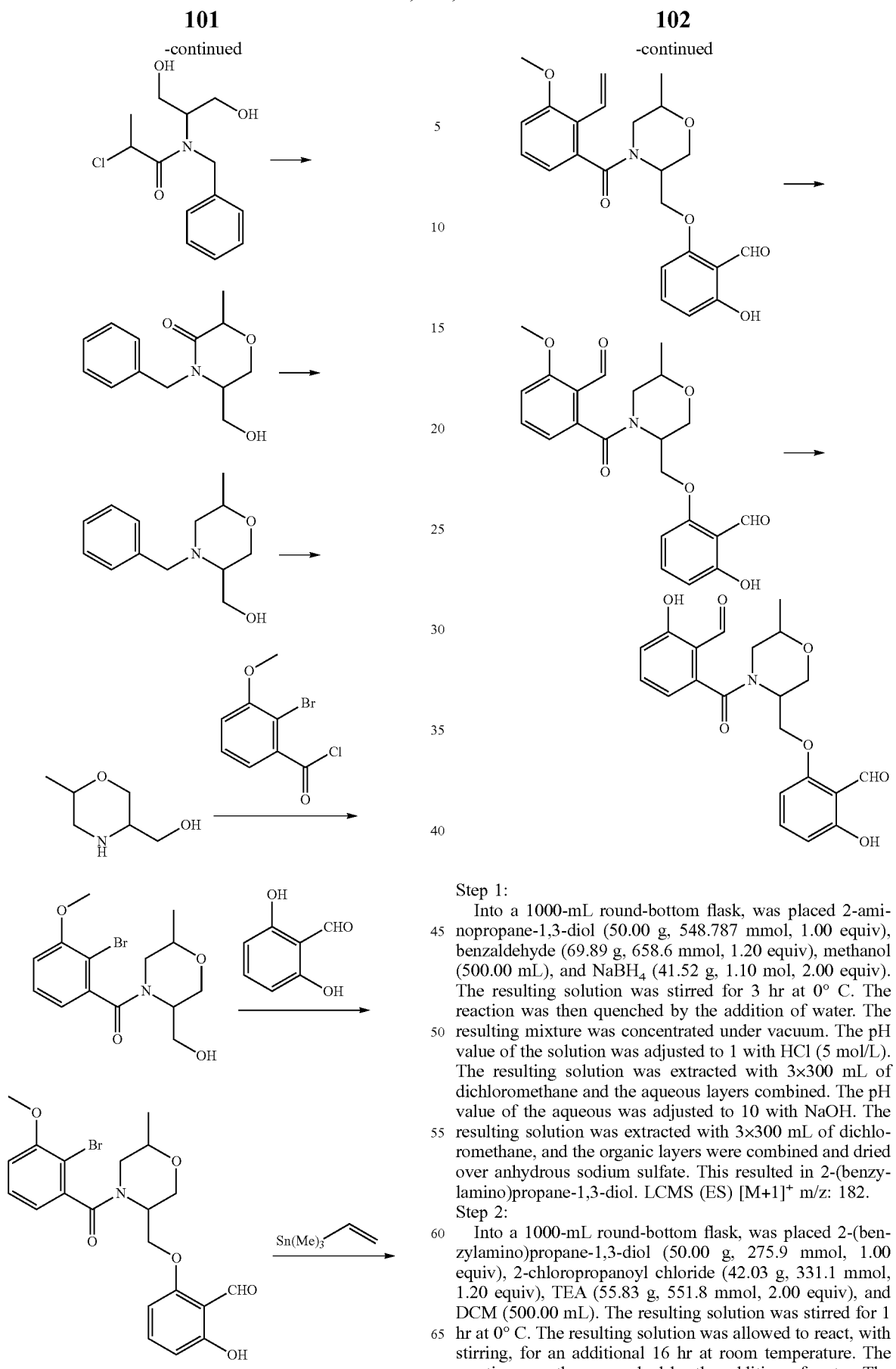

Step 1:
Into a 1000-mL round-bottom flask, was placed 2-aminopropane-1,3-diol (50.00 g, 548.787 mmol, 1.00 equiv), benzaldehyde (69.89 g, 658.6 mmol, 1.20 equiv), methanol (500.00 mL), and NaBH$_4$ (41.52 g, 1.10 mol, 2.00 equiv). The resulting solution was stirred for 3 hr at 0° C. The reaction was then quenched by the addition of water. The resulting mixture was concentrated under vacuum. The pH value of the solution was adjusted to 1 with HCl (5 mol/L). The resulting solution was extracted with 3×300 mL of dichloromethane and the aqueous layers combined. The pH value of the aqueous was adjusted to 10 with NaOH. The resulting solution was extracted with 3×300 mL of dichloromethane, and the organic layers were combined and dried over anhydrous sodium sulfate. This resulted in 2-(benzylamino)propane-1,3-diol. LCMS (ES) [M+1]$^+$ m/z: 182.

Step 2:
Into a 1000-mL round-bottom flask, was placed 2-(benzylamino)propane-1,3-diol (50.00 g, 275.9 mmol, 1.00 equiv), 2-chloropropanoyl chloride (42.03 g, 331.1 mmol, 1.20 equiv), TEA (55.83 g, 551.8 mmol, 2.00 equiv), and DCM (500.00 mL). The resulting solution was stirred for 1 hr at 0° C. The resulting solution was allowed to react, with stirring, for an additional 16 hr at room temperature. The reaction was then quenched by the addition of water. The resulting solution was extracted with 3×200 mL of dichloromethane, and the organic layers were combined and dried over anhydrous sodium sulfate and concentrated under vacuum. The residue was applied onto a silica gel column with THF/PE (1:4). This resulted in N-benzyl-2-chloro-N-(1,3-dihydroxypropan-2-yl)propanamide. LCMS (ES) [M+1]$^+$ m/z: 272.

Step 3:

Into a 1000-mL round-bottom flask, was placed N-benzyl-2-chloro-N-(1,3-dihydroxypropan-2-yl)propanamide (44.00 g, 162 mmol, 1.00 equiv), tert-butoxypotassium (54.51 g, 485.8 mmol, 3.00 equiv), and isopropyl alcohol (300.00 mL). The resulting solution was stirred for 20 min at 0° C. The resulting solution was allowed to react, with stirring, for an additional 16 hr at room temperature. The reaction was then quenched by the addition of water. The resulting solution was extracted with 3×300 mL of dichloromethane, and the organic layers were combined and dried over anhydrous sodium sulfate and concentrated under vacuum. The residue was applied onto a silica gel column with ethyl acetate/petroleum ether (2:1). This resulted in 4-benzyl-5-(hydroxymethyl)-2-methylmorpholin-3-one. LCMS (ES) [M+1]$^+$ m/z: 236.

Step 4:

Into a 500-mL round-bottom flask, was placed 4-benzyl-5-(hydroxymethyl)-2-methylmorpholin-3-one (15.00 g, 63.8 mmol, 1.00 equiv), and tetrahydrofuran (300.00 mL). BH$_3$-Me$_2$S (18.14 mL, 238.8 mmol, 3.00 equiv) was added at 0° C. The resulting solution was allowed to react, with stirring, for 80 hr at 4° C. The reaction mixture was cooled. MeOH (100.00 mL) was added at 0° C. The resulting solution was allowed to react, with stirring, for an additional 80 hr at 3° C. The resulting mixture was concentrated under vacuum. The residue was applied onto a silica gel column with THF/PE (1:1). This resulted in (4-benzyl-6-methylmorpholin-3-yl)methanol. LCMS (ES) [M+1]$^+$ m/z: 222.

Step 5:

Into a 250-mL round-bottom flask, was placed (4-benzyl-6-methylmorpholin-3-yl)methanol (5.00 g, 22.594 mmol, 1.00 equiv), hydrogen, methanol (2.00 g, 62.418 mmol, 2.76 equiv), and Pd(OH)$_2$/C (50 mL). The resulting solution was stirred for 5 hr at room temperature. The solids were filtered out. The resulting mixture was concentrated under vacuum. This resulted in (6-methylmorpholin-3-yl)methanol. LCMS (ES) [M+1]$^+$ m/z: 132.

Step 6:

Into a 100-mL round-bottom flask, was placed (6-methylmorpholin-3-yl)methanol (2.50 g, 19.059 mmol, 1.00 equiv), 2-bromo-3-methoxybenzoyl chloride (5.71 g, 22.9 mmol, 1.20 equiv), TEA (5.79 g, 57.2 mmol, 3.00 equiv), and DCM (50 mL). The resulting solution was stirred for 4 hr at room temperature. The reaction was then quenched by the addition of water. The resulting solution was extracted with 3×50 mL of dichloromethane, and the organic layers were combined and dried over anhydrous sodium sulfate and concentrated under vacuum. The residue was applied onto a silica gel column with ethyl acetate/petroleum ether (2:3). This resulted in [4-(2-bromo-3-methoxybenzoyl)-6-methylmorpholin-3-yl]methanol. LCMS (ES) [M+1]$^+$ m/z: 344.

Step 7:

Into a 100-mL round-bottom flask purged and maintained with an inert atmosphere of nitrogen, was placed [4-(2-bromo-3-methoxybenzoyl)-6-methylmorpholin-3-yl]methanol (1.50 g, 4.36 mmol, 1.00 equiv), 2,6-dihydroxybenzaldehyde (1.20 g, 8.69 mmol, 1.99 equiv), triphenylphosphine (2.29 g, 8.72 mmol, 2.00 equiv) and tetrahydrofuran (30.0 mL). Then, DIAD (1.76 g, 8.72 mmol, 2.00 equiv) was added at 0° C. for 15 min. The resulting solution was allowed to react, with stirring, for an additional 16 hr at room temperature. The resulting solution was extracted with 3×30 mL of ethyl acetate, and the organic layers were combined and dried over anhydrous sodium sulfate and concentrated under vacuum. The residue was applied onto a silica gel column with THF/PE (1:2). This resulted in 2-[[4-(2-bromo-3-methoxybenzoyl)-6-methylmorpholin-3-yl]methoxy]-6-hydroxybenzaldehyde. LCMS (ES) [M+1]$^+$ m/z: 464.

Step 8:

Into a 100-mL round-bottom flask purged and maintained with an inert atmosphere of nitrogen, was placed 2-[[4-(2-bromo-3-methoxybenzoyl)-6-methylmorpholin-3-yl]methoxy]-6-hydroxybenzaldehyde (700 mg, 1.51 mmol, 1.00 equiv), trimethyl(vinyl)stannane (872.4 mg, 4.52 mmol, 3.00 equiv), tetrakis(triphenylphosphine)palladium (0) (174 mg, 0.15 mmol, 0.10 equiv), and toluene (20.00 mL). The resulting solution was stirred for 16 hr at 100° C. The reaction mixture was cooled. The resulting solution was extracted with 3×30 mL of ethyl acetate, and the organic layers were combined and dried over anhydrous sodium sulfate and concentrated under vacuum. The residue was applied onto a silica gel column with ethyl acetate/petroleum ether (1:3). This resulted in 2-[[4-(2-ethenyl-3-methoxybenzoyl)-6-methylmorpholin-3-yl]methoxy]-6-hydroxybenzaldehyde. LCMS (ES) [M+1]$^+$ m/z: 412.

Step 9:

Into a 100-mL round-bottom flask, was placed 2-[[4-(2-ethenyl-3-methoxybenzoyl)-6-methylmorpholin-3-yl]methoxy]-6-hydroxybenzaldehyde (601 mg, 1.46 mmol, 1.00 equiv), sodium periodate (937.3 mg, 4.38 mmol, 3.00 equiv), K$_2$OsO$_4$.2H$_2$O (26.91 mg, 0.073 mmol, 0.05 equiv), and acetone (12.00 mL), H$_2$O (2.00 mL). The resulting solution was stirred for 16 hr at room temperature. The resulting solution was extracted with 3×30 mL of dichloromethane, and the organic layers were combined and dried over anhydrous sodium sulfate and concentrated under vacuum. The residue was applied onto a silica gel column with ethyl acetate/petroleum ether (3:2). This resulted in 2-[[4-(2-formyl-3-methoxybenzoyl)-6-methylmorpholin-3-yl]methoxy]-6-hydroxybenzaldehyde. LCMS (ES) [M+1]$^+$ m/z: 414.

Step 10

Into a 100-mL 3-necked round-bottom flask purged and maintained with an inert atmosphere of nitrogen, was placed 2-[[4-(2-formyl-3-methoxybenzoyl)-6-methylmorpholin-3-yl]methoxy]-6-hydroxybenzaldehyde (511 mg, 1.24 mmol, 1.00 equiv), DCM (10.00 mL), and BBr$_3$ (12.4 mL, 12.4 mmol, 10 equiv). The resulting solution was stirred for 4 hr at −78° C. The reaction was then quenched by the addition of water/ice. The resulting solution was extracted with 3×30 mL of dichloromethane, and the organic layers were combined and dried over anhydrous sodium sulfate and concentrated under vacuum. The crude product was purified by Prep-HPLC with the following conditions: (5% MeCN in water to 40% MeCN in water over another 12 min period, where both solvents contain 0.1% FA). This resulted in 2-((4-(2-formyl-3-hydroxybenzoyl)-6-methylmorpholin-3-yl)methoxy)-6-hydroxybenzaldehyde. $^1$H NMR (300 MHz, DMSO-d$_6$) δ 11.78 (s, 0.5H), 11.70 (s, 0.5H), 11.04 (s, 1H), 10.48-10.02 (m, 2H), 7.64-7.38 (m, 2H), 7.04 (dd, J=8.3, 1.0 Hz, 1H), 6.83-6.53 (m, 2H), 4.90-4.78 (m, 1H), 4.54-4.32 (m, 2H), 4.26-4.05 (m, 1H), 3.97-3.50 (m, 2H), 3.12-2.70

(m, 2H), 1.19 (d, J=6.2 Hz, 1H), 0.97 (d, J=6.1 Hz, 2H). LCMS (ES) [M+1]+ m/z: 400.

Example 11. Synthesis of 2-[[(3R)-1-(3-formyl-4-hydroxybenzoyl)piperidin-3-yl]methoxy]-6-hydroxybenzaldehyde (Compound 61)

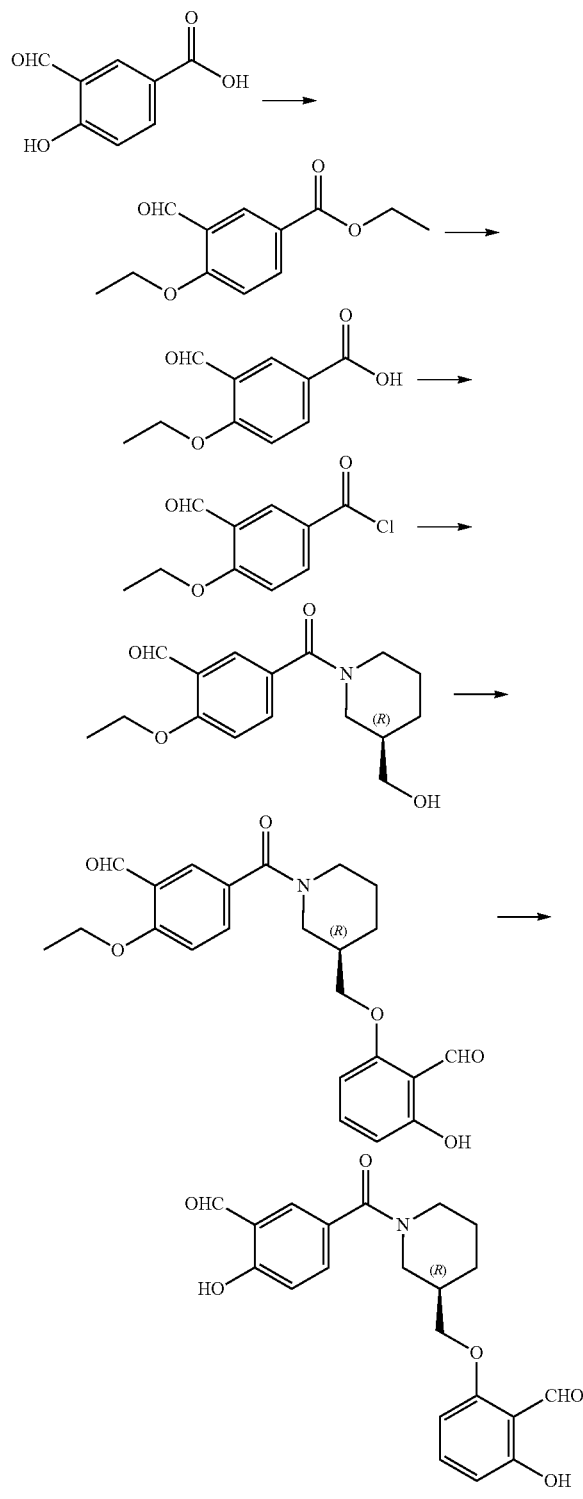

Step 1:
Into a 500-mL round-bottom flask, was placed 3-formyl-4-hydroxybenzoic acid (10.00 g, 60.19 mmol, 1.00 equiv), DMF (200.00 mL), K₂CO₃ (24.96 g, 180.58 mmol, 3.00 equiv), and ethyl iodide (28.16 g, 180.55 mmol, 3.00 equiv). The resulting solution was stirred for overnight at room temperature. The solids were filtered out. The resulting solution was diluted with 200 mL of water. The resulting solution was extracted with 2×200 mL of ethyl acetate, and the organic layers were combined and dried over anhydrous sodium sulfate and concentrated. This resulted in ethyl 4-ethoxy-3-formylbenzoate.

Step 2:
Into a 250-mL round-bottom flask, was placed ethyl 4-ethoxy-3-formylbenzoate (12.00 g, 53.99 mmol, 1.00 equiv), and THF (60.00 mL), H₂O (60.00 mL). This was followed by the addition of LiOH.H₂O (4.53 g, 107.95 mmol, 2.00 equiv), in portions at 0° C. The resulting solution was stirred for overnight at room temperature. The resulting mixture was concentrated.

The resulting solution was extracted with 100 mL of ethyl acetate, and the aqueous layers were combined. The pH value of the solution was adjusted to 4-5 with HCl (6 mol/L). The solids were collected by filtration and dried under infrared light. This resulted in 4-ethoxy-3-formylbenzoic acid.

Step 3:
Into a 100-mL round-bottom flask, was placed 4-ethoxy-3-formylbenzoic acid (2.00 g, 10.30 mmol, 1.00 equiv), toluene (30.00 mL), and SOCl₂ (6.13 g, 51.53 mmol, 5.00 equiv). The resulting solution was stirred for overnight at 50° C. The resulting mixture was concentrated. This resulted in 4-ethoxy-3-formylbenzoyl chloride.

Step 4:
Into a 100-mL 3-necked round-bottom flask, was placed (3R)-piperidin-3-ylmethanol (1.00 g, 8.68 mmol, 1.00 equiv), Et₃N (2.64 g, 26.05 mmol, 3.00 equiv), and DCM (30.00 mL). This was followed by the addition of 4-ethoxy-3-formylbenzoyl chloride (2.03 g, 9.55 mmol, 1.10 equiv), in portions at 0° C. The resulting solution was stirred for 2 h at room temperature. The resulting solution was diluted with 50 mL of water. The resulting solution was extracted with 3×50 mL of dichloromethane, and the organic layers were combined and dried over anhydrous sodium sulfate and concentrated. The residue was applied onto a silica gel column with THF/PE (40%). This resulted in 2-ethoxy-5-[(3R)-3-(hydroxymethyl)piperidine-1-carbonyl]benzaldehyde.

Step 5:
Into a 100-mL 3-necked round-bottom flask purged and maintained with an inert atmosphere of nitrogen, was placed 2,6-dihydroxybenzaldehyde (1.02 g, 7.41 mmol, 1.20 equiv), 2-ethoxy-5-[(3R)-3-(hydroxymethyl)piperidine-1-carbonyl]benzaldehyde (1.80 g, 6.18 mmol, 1.00 equiv), PPh₃ (1.94 g, 7.41 mmol, 1.20 equiv), and THF (80.00 mL). This was followed by the addition of DIAD (1.50 g, 7.41 mmol, 1.20 equiv) dropwise with stirring at 0° C. The resulting solution was stirred for overnight at room temperature. The resulting mixture was concentrated. The residue was applied onto a silica gel column with THF/PE (30%). This resulted in 2-[[(3R)-1-(4-ethoxy-3-formylbenzoyl)piperidin-3-yl]methoxy]-6-hydroxybenzaldehyde.

Step 6:
Into a 100-mL 3-necked round-bottom flask purged and maintained with an inert atmosphere of nitrogen, was placed 2-[[(3R)-1-(4-ethoxy-3-formylbenzoyl)piperidin-3-yl]methoxy]-6-hydroxybenzaldehyde (411.00 mg, 0.99 mmol, 1.00 equiv), and DCM (20.00 mL). This was followed by the addition of BBr$_3$/DCM (9.99 mL, 9.99 mmol, 10.00 equiv) dropwise with stirring at −78° C. The resulting solution was stirred for 0.5 h at room temperature. The reaction was then quenched by the addition of 20 mL of water/ice. The resulting solution was extracted with 3×20 mL of dichloromethane, and the organic layers were combined and dried over anhydrous sodium sulfate and concentrated. The crude product (350 mg) was purified by Prep-HPLC with the following conditions: Column, XBridge Prep C18 OBD Column, 19 cm, 150 mm, 5 um; mobile phase, Water (0.1% HCOOH) and CAN (30% Phase B up to 60% in 11 min); Detector, 254. This resulted in 2-[[(3R)-1-(3-formyl-4-hydroxybenzoyl)piperidin-3-yl]methoxy]-6-hydroxybenzaldehyde. $^1$H-NMR (300 MHz, DMSO-d$_6$) δ 11.67 (s, 1H), 11.08 (s, 1H), 10.24-9.89 (m, 2H), 7.64 (s, 1H), 7.59-7.47 (m, 2H), 7.00 (d, J=8.6 Hz, 1H), 6.59-6.45 (m, 2H), 4.02-3.72 (m, 4H), 3.22-3.07 (m, 2H), 2.13-2.04 (m, 1H), 1.91-1.86 (m, 1H), 1.75-1.67 (m, 1H), 1.57-1.40 (m, 2H). LCMS (ES, m/z): [M+H]$^+$: 384.0.

Example 12. Synthesis of 2-[[(2R)-4-(2-formyl-3-hydroxybenzoyl)morpholin-2-yl]methoxy]-6-hydroxybenzaldehyde (Compound 62)

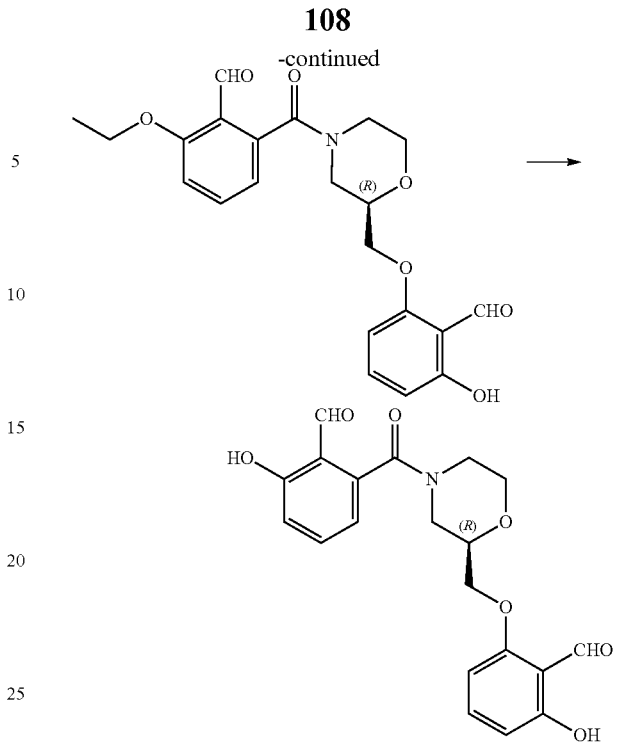

Step 1:
Into a 250-mL round-bottom flask, was placed methyl 2-formyl-3-hydroxybenzoate (8.20 g, 45.52 mmol, 1.00 equiv), DMF (200.00 mL), K$_2$CO$_3$ (12.58 g, 91.03 mmol, 2.00 equiv), and ethyl iodide (10.65 g, 68.28 mmol, 1.50 equiv). The resulting solution was stirred for overnight at room temperature. The solids were filtered out. The resulting solution was diluted with 200 mL of water and then extracted with 2×200 mL of ethyl acetate; the organic layers were combined and dried over anhydrous sodium sulfate and concentrated. This resulted in methyl 3-ethoxy-2-formylbenzoate.

Step 2:
Into a 250-mL round-bottom flask, was placed methyl 3-ethoxy-2-formylbenzoate (9.00 g, 43.23 mmol, 1.00 equiv), THF (50.00 mL), and H$_2$O (50.00 mL). This was followed by the addition of LiOH.H$_2$O (3.63 g, 86.45 mmol, 2.00 equiv), in portions at 0° C. The resulting solution was stirred for 3 h at room temperature. The resulting mixture was concentrated. The resulting solution was extracted with 100 mL of ethyl acetate and the aqueous layers combined. The pH value of the solution was adjusted to 4-5 with HCl (6 mol/L). The solids were collected by filtration, and dried under infrared light. This resulted in 3-ethoxy-2-formylbenzoic acid.

Step 3:
Into a 100-mL round-bottom flask, was placed 3-ethoxy-2-formylbenzoic acid (1.00 g, 5.15 mmol, 1.00 equiv), toluene (30.00 mL), and SOCl$_2$ (3.06 g, 25.75 mmol, 5.00 equiv). The resulting solution was stirred for overnight at 50° C. The resulting mixture was concentrated. This resulted in 3-ethoxy-2-formylbenzoyl chloride.

Step 4:
Into a 100-mL 3-necked round-bottom flask, was placed (2R)-morpholin-2-ylmethanol hydrochloride (0.70 g, 4.56 mmol, 1.00 equiv), DCM (20.00 mL), and Et$_3$N (1.84 g, 18.23 mmol, 4.00 equiv). This was followed by the addition of 3-ethoxy-2-formylbenzoyl chloride (1.07 g, 5.03 mmol, 1.10 equiv), in portions at 0° C. The resulting solution was stirred for 2 h at room temperature. The reaction was then quenched by the addition of 20 mL of water. The resulting solution was extracted with 3×20 mL of dichloromethane, and the organic layers were combined and dried over anhydrous sodium sulfate and concentrated. The residue was applied onto a silica gel column with THF/PE (50%). This resulted in 2-ethoxy-6-[(2R)-2-(hydroxymethyl)morpholine-4-carbonyl]benzaldehyde.

Step 5:

Into a 100-mL 3-necked round-bottom flask purged and maintained with an inert atmosphere of nitrogen, was placed 2,6-dihydroxybenzaldehyde (0.73 g, 5.29 mmol, 1.19 equiv), 2-ethoxy-6-[(2R)-2-(hydroxymethyl)morpholine-4-carbonyl]benzaldehyde (1.30 g, 4.43 mmol, 1.00 equiv), PPh₃ (1.39 g, 5.32 mmol, 1.20 equiv), and THF (50.00 mL). This was followed by the addition of DIAD (1.08 g, 5.32 mmol, 1.2 equiv) dropwise with stirring at 0° C. The resulting solution was stirred for overnight at room temperature. The resulting mixture was concentrated. The residue was applied onto a silica gel column with THF/PE (30%). This resulted in 2-[[(2R)-4-(3-ethoxy-2-formylbenzoyl)morpholin-2-yl]methoxy]-6-hydroxybenzaldehyde.

Step 6:

Into a 100-mL 3-necked round-bottom flask purged and maintained with an inert atmosphere of nitrogen, was placed 2-[[(2R)-4-(3-ethoxy-2-formylbenzoyl)morpholin-2-yl]methoxy]-6-hydroxybenzaldehyde (500 mg, 1.21 mmol, 1.00 equiv), and DCM (20.00 mL). This was followed by the addition of BBr₃/DCM (12.11 mL, 12.11 mmol, 10.01 equiv) dropwise with stirring at −78° C. The resulting solution was stirred for 0.5 h at 0° C. The reaction was then quenched by the addition of 20 mL of water/ice. The resulting solution was extracted with 3×20 mL of dichloromethane, and the organic layers were combined and dried over anhydrous sodium sulfate and concentrated. The crude product was purified by Prep-HPLC with the following conditions: Column, XBridge Prep C18 OBD Column, 19 cm, 150 mm, 5 um; mobile phase, Water (0.1% HCOOH) and CAN (30% Phase B up to 60% in 11 min); Detector, 254. This resulted in 2-[[(2R)-4-(2-formyl-3-hydroxybenzoyl)morpholin-2-yl]methoxy]-6-hydroxybenzaldehyde.

$^1$H-NMR (300 MHz, DMSO-$d_6$) δ 11.69 (s, 1H), 11.06 (s, 1H), 10.39-9.99 (m, 2H), 7.61-7.40 (m, 2H), 7.09-6.98 (m, 1H), 6.80-6.45 (m, 3H), 4.49-4.22 (m, 2H), 4.11-3.87 (m, 2H), 3.74-3.36 (m, 2H), 3.33-3.22 (m, 1H), 3.11-2.87 (m, 2H). LCMS (ES, m/z): [M+Na]$^+$: 408.

Example 13. Synthesis of 2-formyl-3-hydroxyphenyl (3R)-3-(2-formyl-3-hydroxyphenoxymethyl)piperidine-1-carboxylate (Compound 63)

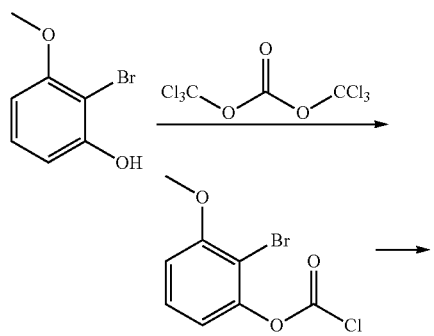

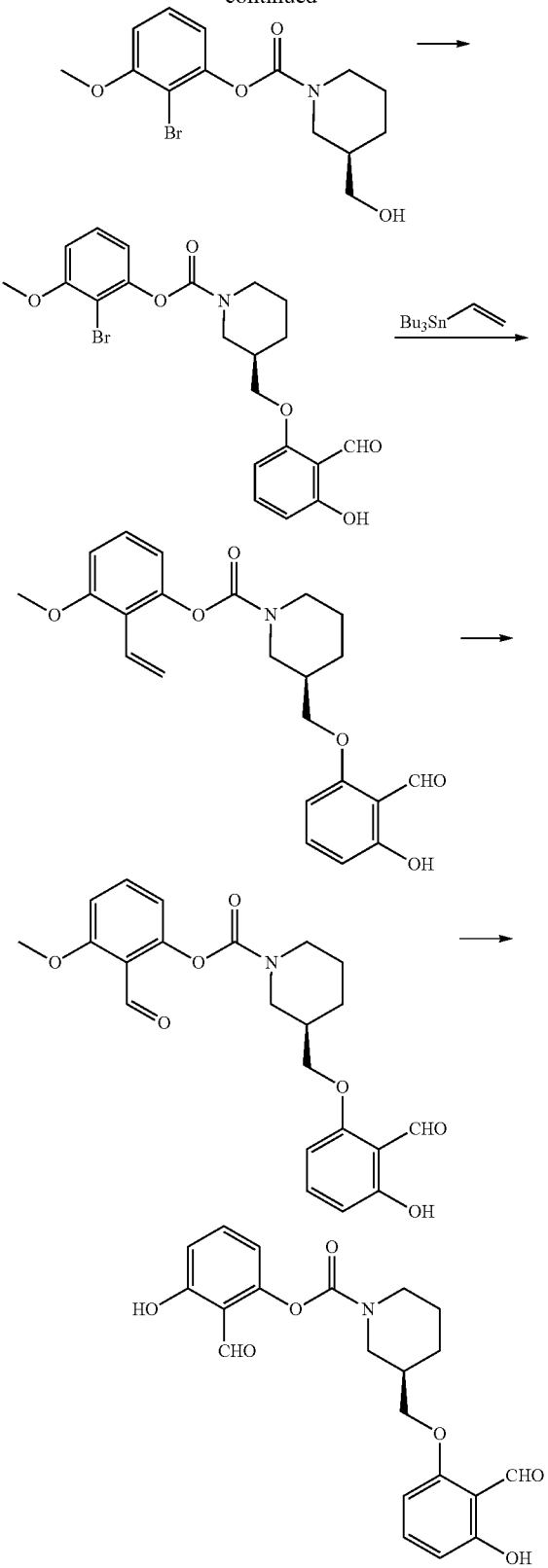

Step 1:

Into a 250-mL 3-necked round-bottom flask purged and maintained with an inert atmosphere of nitrogen, was placed triphosgene (3.65 g, 12.30 mmol, 0.50 equiv), and THF (150.00 mL). This was followed by the addition of DIEA (3.18 g, 24.63 mmol, 1.00 equiv) at 0° C. To this was added a solution of 2-bromo-3-methoxyphenol (5.00 g, 24.63 mmol, 1.00 equiv) in THF (20 mL) dropwise with stirring at 0° C. The resulting solution was stirred for overnight at room temperature. The reaction was then quenched by the addition of 100 mL of 0.1 N HCl. The resulting solution was extracted with 3×100 mL of ethyl acetate, and the organic layers were combined and dried over anhydrous sodium sulfate and concentrated. This resulted in 2-bromo-3-methoxyphenyl carbonochloridate.
Step 2:

Into a 100-mL 3-necked round-bottom flask, was placed (3R)-piperidin-3-ylmethanol (2.00 g, 17.37 mmol, 1.00 equiv), DCM (50.00 mL), and $Et_3N$ (3.51 g, 34.73 mmol, 2.00 equiv). This was followed by the addition of 2-bromo-3-methoxyphenyl carbonochloridate (5.53 g, 20.84 mmol, 1.20 equiv) dropwise with stirring at 0° C. The resulting solution was stirred for 2 h at room temperature. The reaction was then quenched by the addition of 40 mL of water. The resulting solution was extracted with 3×40 mL of dichloromethane, and the organic layers were combined and dried over anhydrous sodium sulfate and concentrated. The residue was applied onto a silica gel column with THF/PE (50%). This resulted in 2-bromo-3-methoxyphenyl (3R)-3-(hydroxymethyl)piperidine-1-carboxylate.
Step 3:

Into a 250-mL 3-necked round-bottom flask purged and maintained with an inert atmosphere of nitrogen, was placed 2,6-dihydroxybenzaldehyde (1.64 g, 11.85 mmol, 1.20 equiv), 2-bromo-3-methoxyphenyl (3R)-3-(hydroxymethyl)piperidine-1-carboxylate (3.40 g, 9.88 mmol, 1.00 equiv), THF (150.00 mL), and $PPh_3$ (3.11 g, 11.86 mmol, 1.20 equiv). This was followed by the addition of DIAD (2.40 g, 11.85 mmol, 1.20 equiv) dropwise with stirring at 0° C. The resulting solution was stirred for overnight at room temperature. The resulting mixture was concentrated. The residue was applied onto a silica gel column with THF/PE (23%). This resulted in 2-bromo-3-methoxyphenyl (3R)-3-(2-formyl-3-hydroxyphenoxymethyl)piperidine-1-carboxylate.
Step 4:

Into a 100-mL round-bottom flask purged and maintained with an inert atmosphere of nitrogen, was placed tributyl(ethenyl)stannane (3.14 g, 9.90 mmol, 2.00 equiv), 2-bromo-3-methoxyphenyl (3R)-3-(2-formyl-3-hydroxyphenoxymethyl)piperidine-1-carboxylate (2.30 g, 4.95 mmol, 1.00 equiv), dioxane (50.00 mL), and $Pd(dppf)Cl_2$ (0.36 g, 0.50 mmol, 0.10 equiv). The resulting solution was stirred for overnight at 100° C. The resulting mixture was concentrated. The residue was applied onto a silica gel column with THF/PE (20%). This resulted in 2-ethenyl-3-methoxyphenyl (3R)-3-(2-formyl-3-hydroxyphenoxymethyl)piperidine-1-carboxylate.
Step 5:

Into a 100-mL round-bottom flask, was placed 2-ethenyl-3-methoxyphenyl (3R)-3-(2-formyl-3-hydroxyphenoxymethyl)piperidine-1-carboxylate (1.70 g, 4.13 mmol, 1.00 equiv), sodium periodate (2.65 g, 12.39 mmol, 3.00 equiv), acetone (36.00 mL), $H_2O$ (6.00 mL), and $K_2OsO_4.2H_2O$ (30.45 mg, 0.08 mmol, 0.02 equiv). The resulting solution was stirred for overnight at room temperature. The resulting mixture was concentrated. The resulting solution was extracted with 3×30 mL of dichloromethane, and the organic layers were combined and dried over anhydrous sodium sulfate and concentrated. The residue was applied onto a silica gel column with THF/PE (18%). This resulted in 2-formyl-3-methoxyphenyl (3R)-3-(2-formyl-3-hydroxyphenoxymethyl)piperidine-1-carboxylate.
Step 6:

Into a 100-mL 3-necked round-bottom flask purged and maintained with an inert atmosphere of nitrogen, was placed 2-formyl-3-methoxyphenyl (3R)-3-(2-formyl-3-hydroxyphenoxymethyl)piperidine-1-carboxylate (413.00 mg, 0.99 mmol, 1.00 equiv), and DCM (20.00 mL, 314.60 mmol, 314.93 equiv). This was followed by the addition of $BBr_3$/DCM (9.99 mL, 9.99 mmol, 10.00 equiv) dropwise with stirring at −78° C. The resulting solution was stirred for 1 h at 0° C. The reaction was then quenched by the addition of 20 mL of water/ice. The resulting solution was extracted with 3×20 mL of dichloromethane, and the organic layers were combined and dried over anhydrous sodium sulfate and concentrated. The crude product (360 mg) was purified by Prep-HPLC with the following conditions: Column, XBridge Prep C18 OBD Column, 19 cm, 150 mm, 5 um; mobile phase, Water (0.1% HCOOH) and ACN (30% Phase B up to 60% in 11 min); Detector, 254. This resulted in 2-formyl-3-hydroxyphenyl (3R)-3-(2-formyl-3-hydroxyphenoxymethyl)piperidine-1-carboxylate. $^1$H-NMR: (300 MHz, DMSO-$d_6$) δ 11.74-11.66 (m, 1H), 11.09 (s, 1H), 10.31 (s, 1H), 10.20 (d, J=4.0 Hz, 1H), 7.58-7.44 (m, 2H), 6.86 (d, J=8.4 Hz, 1H), 6.65-6.62 (m, 2H), 6.51 (d, J=8.4 Hz, 1H), 4.21-3.73 (m, 4H), 3.27-3.06 (m, 2H), 2.30-2.18 (m, 1H), 1.95-1.90 (m, 1H), 1.75-1.44 (m, 3H). LCMS (ES, m/z): [M+H]$^+$: 400.

Example 14. Synthesis of 2-[[(3S)-4-(2-formyl-3-hydroxybenzoyl)-3-methylmorpholin-3-yl]methoxy]-6-hydroxybenzaldehyde (Compound 64)

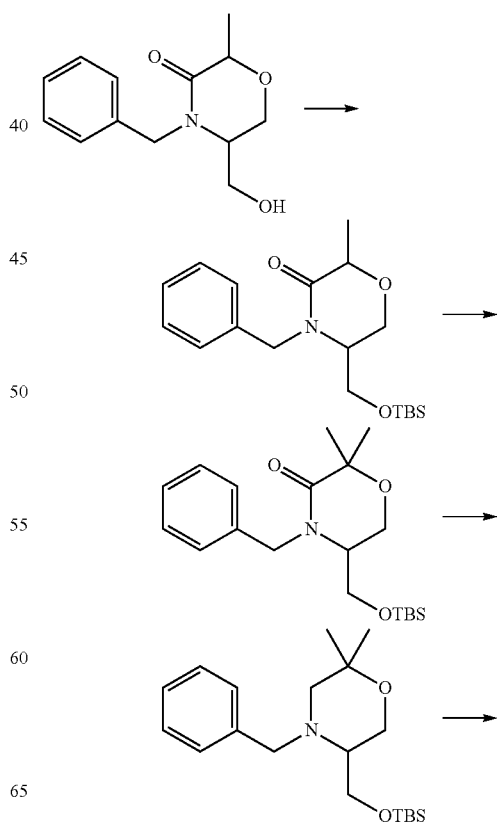

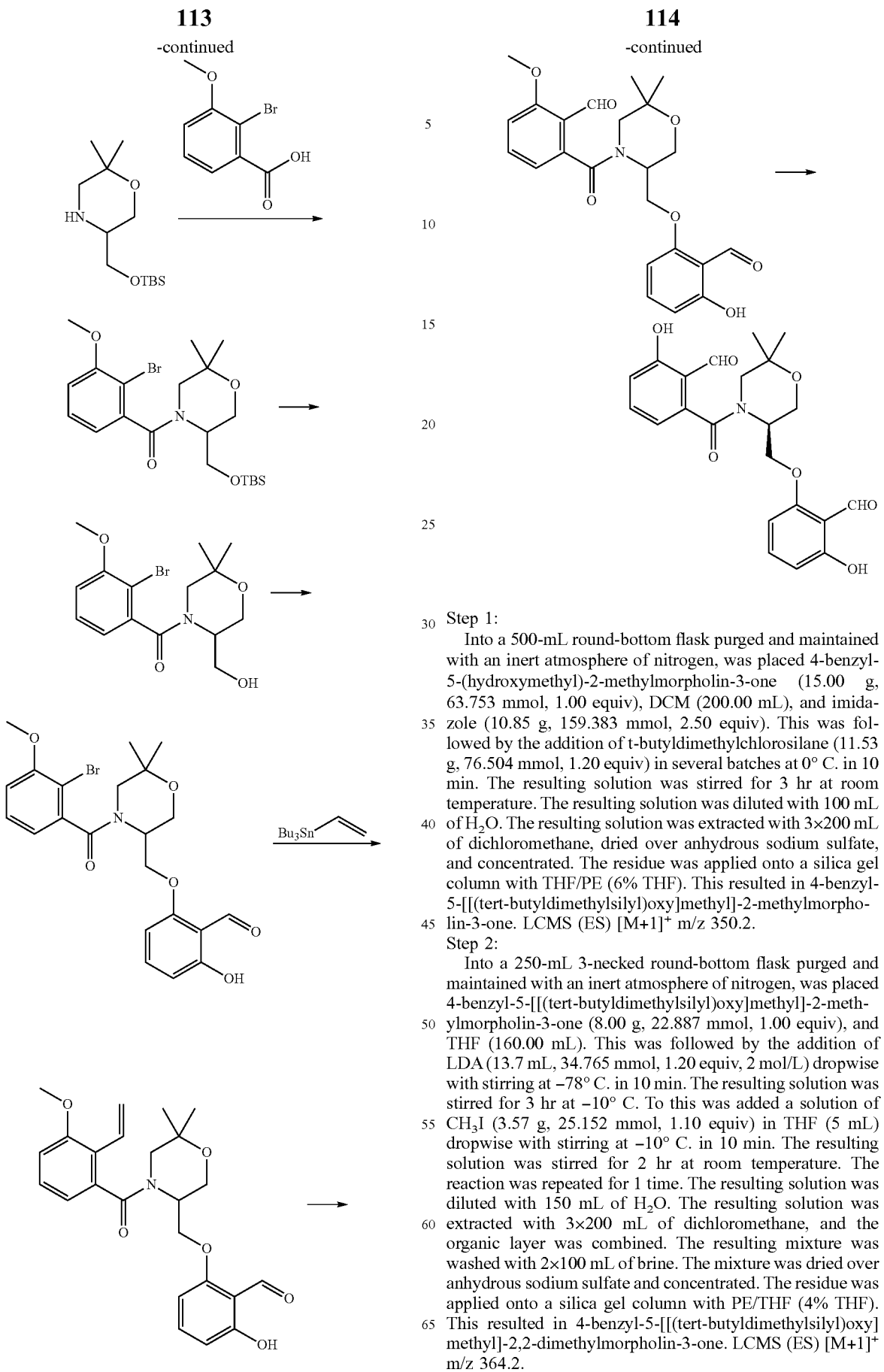

Step 1:
Into a 500-mL round-bottom flask purged and maintained with an inert atmosphere of nitrogen, was placed 4-benzyl-5-(hydroxymethyl)-2-methylmorpholin-3-one (15.00 g, 63.753 mmol, 1.00 equiv), DCM (200.00 mL), and imidazole (10.85 g, 159.383 mmol, 2.50 equiv). This was followed by the addition of t-butyldimethylchlorosilane (11.53 g, 76.504 mmol, 1.20 equiv) in several batches at 0° C. in 10 min. The resulting solution was stirred for 3 hr at room temperature. The resulting solution was diluted with 100 mL of H$_2$O. The resulting solution was extracted with 3×200 mL of dichloromethane, dried over anhydrous sodium sulfate, and concentrated. The residue was applied onto a silica gel column with THF/PE (6% THF). This resulted in 4-benzyl-5-[[(tert-butyldimethylsilyl)oxy]methyl]-2-methylmorpholin-3-one. LCMS (ES) [M+1]$^+$ m/z 350.2.

Step 2:
Into a 250-mL 3-necked round-bottom flask purged and maintained with an inert atmosphere of nitrogen, was placed 4-benzyl-5-[[(tert-butyldimethylsilyl)oxy]methyl]-2-methylmorpholin-3-one (8.00 g, 22.887 mmol, 1.00 equiv), and THF (160.00 mL). This was followed by the addition of LDA (13.7 mL, 34.765 mmol, 1.20 equiv, 2 mol/L) dropwise with stirring at −78° C. in 10 min. The resulting solution was stirred for 3 hr at −10° C. To this was added a solution of CH$_3$I (3.57 g, 25.152 mmol, 1.10 equiv) in THF (5 mL) dropwise with stirring at −10° C. in 10 min. The resulting solution was stirred for 2 hr at room temperature. The reaction was repeated for 1 time. The resulting solution was diluted with 150 mL of H$_2$O. The resulting solution was extracted with 3×200 mL of dichloromethane, and the organic layer was combined. The resulting mixture was washed with 2×100 mL of brine. The mixture was dried over anhydrous sodium sulfate and concentrated. The residue was applied onto a silica gel column with PE/THF (4% THF). This resulted in 4-benzyl-5-[[(tert-butyldimethylsilyl)oxy]methyl]-2,2-dimethylmorpholin-3-one. LCMS (ES) [M+1]$^+$ m/z 364.2.

Step 3:

Into a 500-mL 3-necked round-bottom flask purged and maintained with an inert atmosphere of nitrogen, was placed 4-benzyl-5-[[(tert-butyldimethylsilyl)oxy]methyl]-2,2-dimethylmorpholin-3-one (8.00 g, 22.004 mmol, 1.00 equiv), and THF (200 mL). This was followed by the addition of $BH_3\text{-}Me_2S$ (33 mL, 3.0 equiv, 2 M) dropwise with stirring at 0° C. in 15 min. The resulting solution was stirred for 4 hr at 80° C. in an oil bath. The reaction mixture was cooled with a water/ice bath. This was followed by the addition of MeOH (20 mL) dropwise with stirring at 0° C. in 15 min. The resulting solution was stirred for overnight at 80° C. in an oil bath. The resulting mixture was concentrated. The residue was applied onto a silica gel column with PE/THF (2% THF). This resulted in 4-benzyl-5-[[(tert-butyldimethylsilyl)oxy]methyl]-2,2-dimethylmorpholine. LCMS (ES) $[M+1]^+$ m/z 350.2.

Step 4:

Into a 250-mL round-bottom flask, was placed 4-benzyl-5-[[(tert-butyldimethylsilyl)oxy]methyl]-2,2-dimethylmorpholine (8.00 g, 22.884 mmol, 1.00 equiv), MeOH (150.00 mL), $Pd(OH)_2/C$ (2.00 g, 14.242 mmol, 0.62 equiv), and $HCO_2H$ (0.09 mL, 2.386 mmol, 0.10 equiv). To the above, $H_{2(g)}$ was introduced in. The resulting solution was stirred for 1 overnight at room temperature. The solids were filtered out. The resulting mixture was concentrated. This resulted in 5-[[(tert-butyldimethylsilyl)oxy]methyl]-2,2-dimethylmorpholine. LCMS (ES) $[M+1]^+$ m/z 260.2.

Step 5:

Into a 500-mL 3-necked round-bottom flask purged and maintained with an inert atmosphere of nitrogen, was placed 2-bromo-3-methoxybenzoic acid (3.85 g, 16.650 mmol, 1.20 equiv), toluene (100.00 mL), and $SOCl_2$ (16.51 g, 10.00 equiv). The resulting solution was stirred for overnight at 80° C. in an oil bath. The resulting mixture was concentrated to give crude acid chloride. Into a 500-mL 3-necked round-bottom flask purged and maintained with an inert atmosphere of nitrogen, was placed 5-[[(tert-butyldimethylsilyl)oxy]methyl]-2,2-dimethylmorpholine (3.60 g, 13.875 mmol, 1.00 equiv), TEA (4.21 g, 41.624 mmol, 3.00 equiv), and DCM (200.00 mL). To the mixture was added crude acid chloride solution in the first flask. The resulting solution was stirred for overnight at room temperature. The reaction was then quenched by the addition of 100 mL of water. The resulting solution was extracted with 2×200 mL of dichloromethane, and the organic layer was combined. The residue was applied onto a silica gel column with THF/PE (10% THF). This resulted in 4-(2-bromo-3-methoxybenzoyl)-5-[[(tert-butyldimethylsilyl)oxy]methyl]-2,2-dimethylmorpholine. LCMS (ES) $[M+1]^+$ m/z 472.2.

Step 6:

Into a 250-mL round-bottom flask, was placed 4-(2-bromo-3-methoxybenzoyl)-5-[[(tert-butyldimethylsilyl)oxy]methyl]-2,2-dimethylmorpholine (5.20 g, 11.005 mmol, 1.00 equiv), THF (100.00 mL), and TBAF (22 mL, 22.010 mmol, 2 equiv, 1M). The resulting solution was stirred for 2 hr at room temperature. The reaction was then quenched by the addition of 100 mL of water. The resulting solution was extracted with 3×200 mL of dichloromethane, and the organic layer was combined. The resulting mixture was washed with 2×150 ml of brine. The mixture was dried over anhydrous sodium sulfate and concentrated. The residue was applied onto a silica gel column with ethyl acetate/petroleum ether (60% EA). This resulted in [4-(2-bromo-3-methoxybenzoyl)-6,6-dimethylmorpholin-3-yl]methanol. LCMS (ES) $[M+1]^+$ m/z 358.2.

Step 7:

Into a 500-mL 3-necked round-bottom flask purged and maintained with an inert atmosphere of nitrogen, was placed [4-(2-bromo-3-methoxybenzoyl)-6,6-dimethylmorpholin-3-yl]methanol (3.70 g, 10.329 mmol, 1.00 equiv), 2,6-dihydroxybenzaldehyde (2.85 g, 20.657 mmol, 2.00 equiv), $PPh_3$ (5.42 g, 20.657 mmol, 2.00 equiv), and THF (200.00 mL). The resulting solution was stirred for 15 min at 0° C. This was followed by the addition of DIAD (4.18 g, 20.657 mmol, 2.00 equiv) dropwise with stirring at 0° C. in 10 min. The resulting solution was stirred for 4 hr at room temperature. The reaction was then quenched by the addition of 50 mL of water. The resulting solution was extracted with 200 mL of dichloromethane. The resulting mixture was washed with 1×100 mL of brine. The mixture was dried over anhydrous sodium sulfate and concentrated. The residue was applied onto a silica gel column with ethyl acetate/petroleum ether (30% EA). This resulted in 2-[[4-(2-bromo-3-methoxybenzoyl)-6,6-dimethylmorpholin-3-yl]methoxy]-6-hydroxybenzaldehyde. LCMS (ES) $[M+1]^+$ m/z 478.1.

Step 8:

Into a 250-mL round-bottom flask purged and maintained with an inert atmosphere of nitrogen, was placed 2-[[4-(2-bromo-3-methoxybenzoyl)-6,6-dimethylmorpholin-3-yl]methoxy]-6-hydroxybenzaldehyde (4.60 g, 9.617 mmol, 1.00 equiv), tributyl(ethenyl)stannane (30.49 g, 96.166 mmol, 10.00 equiv), $Pd(PPh_3)_4$ (2.22 g, 1.923 mmol, 0.20 equiv), and toluene (100 mL). The resulting solution was stirred for 24 hr at 100° C. in an oil bath. The resulting mixture was concentrated. The resulting solution was diluted with 250 mL of DCM. The mixture was dried over anhydrous sodium sulfate, filtered and concentrated. The resulting residue was applied onto a silica gel column with ethyl acetate/petroleum ether (25% EA). This resulted in 2-[[4-(2-ethenyl-3-methoxybenzoyl)-6,6-dimethylmorpholin-3-yl]methoxy]-6-hydroxybenzaldehyde. LCMS (ES) $[M+1]^+$ m/z 426.1.

Step 9:

Into a 250-mL round-bottom flask, was placed 2-[[4-(2-ethenyl-3-methoxybenzoyl)-6,6-dimethylmorpholin-3-yl]methoxy]-6-hydroxybenzaldehyde (2.00 g, 4.701 mmol, 1.00 equiv), $NaIO_4$ (3.02 g, 14.119 mmol, 3.00 equiv), $K_2OsO_4 \cdot 2H_2O$ (0.09 g, 0.235 mmol, 0.05 equiv), acetone (60.00 mL), and $H_2O$ (10.00 mL). The resulting solution was stirred for overnight at room temperature. The solids were filtered out. The resulting mixture was concentrated. The residue was applied onto a silica gel column with ethyl acetate/petroleum ether (30% EA). This resulted in 2-[[4-(2-formyl-3-methoxybenzoyl)-6,6-dimethylmorpholin-3-yl]methoxy]-6-hydroxybenzaldehyde. LCMS (ES) $[M+1]^+$ m/z 428.2.

Step 10:

Into a 100-mL round-bottom flask purged and maintained with an inert atmosphere of nitrogen, was placed 2-[[4-(2-formyl-3-methoxybenzoyl)-6,6-dimethylmorpholin-3-yl]methoxy]-6-hydroxybenzaldehyde (300.00 mg, 0.702 mmol, 1.00 equiv), and DCM (20.00 mL). This was followed by the addition of $AlCl_3$ (935.83 mg, 7.018 mmol, 10.00 equiv) in several batches at 0° C. in 2 min. The resulting solution was stirred for overnight at 50° C. The reaction was then quenched by the addition of 50 mL of 1 M HCl(ice). The resulting solution was extracted with 3×80 mL of dichloromethane and the resulting mixture was washed with 1×100 mL of brine. The mixture was dried over anhydrous sodium sulfate and concentrated. The crude product was purified by Flash-Prep-HPLC (Prep-C18, 20-45M, 120 g, Tianjin Bonna-Agela Technologies; gradient elution of 40% MeCN in water to 60% MeCN in water over a 10 min period, where both solvents contain 0.1% FA). This resulted in 2-[[(3R)-4-(2-formyl-3-hydroxybenzoyl)-6,6-dimethylmorpholin-3-yl]methoxy]-6-hydroxybenzaldehyde. LCMS (ES) [M+1]+ m/z 414.2. $^1$H NMR (300 MHz, DMSO-$d_6$) δ 11.75 (s, 1H), 11.02 (s, 1H), 10.29 (s, 1H), 10.27 (s, 1H) 7.61-7.39 (m, 2H), 7.04 (dd, J=8.3, 6.0 Hz, 1H), 6.85-6.47 (m, 3H), 4.90-4.75 (m, 1H), 4.53-4.08 (m, 2H), 4.03-3.53 (m, 2H), 3.13-2.79 (m, 2H), 1.42 (s, 1H), 1.24 (s, 1H), 1.14 (s, 2H), 1.04 (s, 2H).

Example 15. Synthesis of 2-[[(2S)-1-(2-formyl-3-hydroxybenzoyl)-4,4-dimethylpyrrolidin-2-yl]methoxy]-6-hydroxybenzaldehyde (Compound 65)

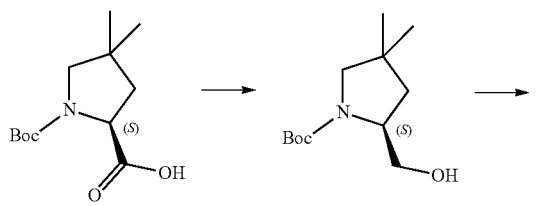

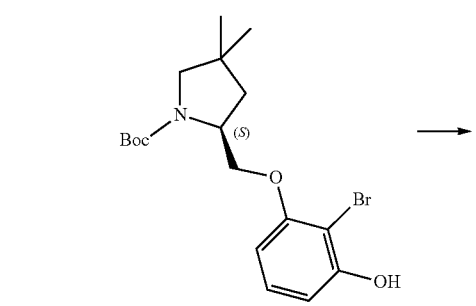

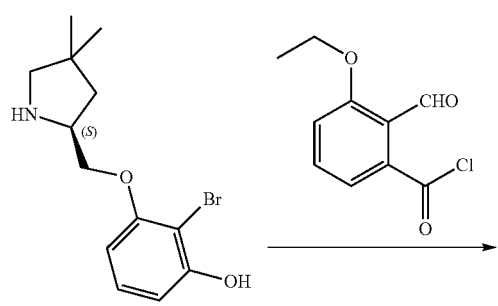

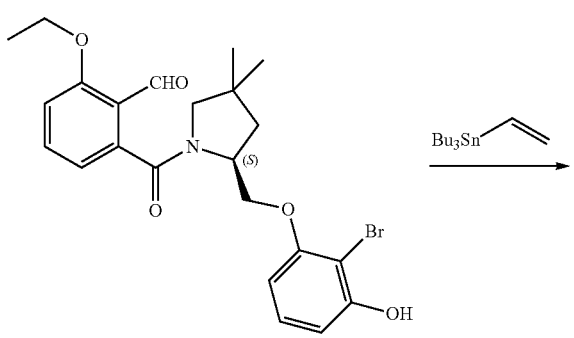

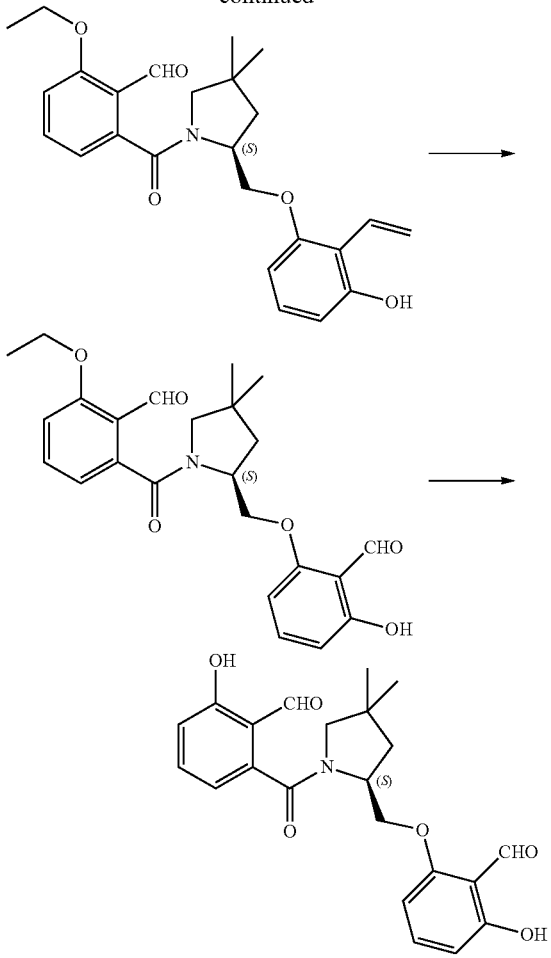

Step 1:
Into a 250-mL 3-necked round-bottom flask, was placed (2S)-1-(tert-butoxycarbonyl)-4,4-dimethylpyrrolidine-2-carboxylic acid (3.9 g, 16.03 mmol, 1.00 equiv), and THF (50.00 mL). This was followed by the addition of BH$_3$-THF (48.06 mL, 48.07 mmol, 3.00 equiv) dropwise with stirring at 0° C. The resulting solution was stirred for overnight at room temperature. The reaction was then quenched by the addition of 50 mL of MeOH. The reaction mixture was then heated to reflux for 3 h. The reaction mixture was cooled to room temperature. The resulting mixture was concentrated. The resulting solution was extracted with 3×100 mL of dichloromethane dried over anhydrous sodium sulfate and concentrated. This resulted in tert-butyl (2S)-2-(hydroxymethyl)-4,4-dimethylpyrrolidine-1-carboxylate.

Step 2:
Into a 250-mL 3-necked round-bottom flask purged and maintained with an inert atmosphere of nitrogen, was placed 2-bromobenzene-1,3-diol (3.07 g, 16.22 mmol, 1.20 equiv), tert-butyl (2S)-2-(hydroxymethyl)-4,4-dimethylpyrrolidine-1-carboxylate (3.10 g, 13.52 mmol, 1.00 equiv), PPh$_3$ (4.25 g, 16.22 mmol, 1.20 equiv), and THF (100.00 mL). This was followed by the addition of DIAD (3.28 g, 16.22 mmol, 1.20 equiv) dropwise with stirring at 0° C. The resulting solution was stirred for overnight at room temperature. The resulting mixture was concentrated. The residue was applied onto a silica gel column with THF/PE (5%). This resulted in tert-butyl (2S)-2-(2-bromo-3-hydroxyphenoxymethyl)-4,4-dimethylpyrrolidine-1-carboxylate.

Step 3:

Into a 100-mL 3-necked round-bottom flask, was placed tert-butyl (2S)-2-(2-bromo-3-hydroxyphenoxymethyl)-4,4-dimethylpyrrolidine-1-carboxylate (2.2 g, 5.49 mmol, 1.00 equiv), and EA (10.00 mL). This was followed by the addition of HCl$_{(gas)}$ in EA (5.50 mL, 10.99 mmol, 2.00 equiv) dropwise with stirring at 0° C. The resulting solution was stirred for 4 h at room temperature. The resulting mixture was concentrated. The pH value of the solution was adjusted to 8 with saturated NaHCO$_3$. The resulting solution was extracted with 3×50 mL of dichloromethane, and the organic layers were combined and dried over anhydrous sodium sulfate and concentrated. This resulted in 1 2-bromo-3-[[(2S)-4,4-dimethylpyrrolidin-2-yl]methoxy]phenol.

Step 4:

Into a 100-mL 3-necked round-bottom flask, was placed 2-bromo-3-[[(2S)-4,4-dimethylpyrrolidin-2-yl]methoxy]phenol (1.50 g, 4.99 mmol, 1.00 equiv), DCM (30.00 mL), and Et$_3$N (1.01 g, 9.99 mmol, 2.00 equiv). This was followed by the addition of 3-ethoxy-2-formylbenzoyl chloride (1.17 g, 5.50 mmol, 1.10 equiv), in portions at 0° C. The resulting solution was stirred for 2 h at room temperature. The reaction was then quenched by the addition of 20 mL of water. The resulting solution was extracted with 3×20 mL of dichloromethane, and the organic layers were combined and dried over anhydrous sodium sulfate and concentrated. The residue was applied onto a silica gel column with THF/PE (30%). This resulted in 2-[(2S)-2-(2-bromo-3-hydroxyphenoxymethyl)-4,4-dimethylpyrrolidine-1-carbonyl]-6-ethoxybenzaldehyde.

Step 5:

Into a 100-mL round-bottom flask purged and maintained with an inert atmosphere of nitrogen, was placed 2-[(2S)-2-(2-bromo-3-hydroxyphenoxymethyl)-4,4-dimethylpyrrolidine-1-carbonyl]-6-ethoxybenzaldehyde (1.50 g, 3.15 mmol, 1.00 equiv), tributyl(ethenyl)stannane (2.00 g, 6.31 mmol, 2.00 equiv), dioxane (30.00 mL), and Pd(dppf)Cl$_2$ (0.23 g, 0.32 mmol, 0.10 equiv). The resulting solution was stirred for overnight at 100° C. The reaction mixture was cooled to room temperature. The resulting mixture was concentrated. The residue was applied onto a silica gel column with THF/PE (30%). This resulted in 2-[(2S)-2-(2-ethenyl-3-hydroxyphenoxymethyl)-4,4-dimethylpyrrolidine-1-carbonyl]-6-ethoxybenzaldehyde.

Step 6:

Into a 100-mL round-bottom flask, was placed 2-[(2S)-2-(2-ethenyl-3-hydroxyphenoxymethyl)-4,4-dimethylpyrrolidine-1-carbonyl]-6-ethoxybenzaldehyde (1.00 g, 2.36 mmol, 1.00 equiv), NaIO$_4$ (1.52 g, 7.11 mmol, 3.01 equiv), acetone (24.00 mL), H$_2$O (4.00 mL), and K$_2$OsO$_4$.2H$_2$O (17.40 mg, 0.05 mmol, 0.02 equiv). The resulting solution was stirred for overnight at room temperature. The resulting mixture was concentrated. The resulting solution was extracted with 3×20 mL of dichloromethane, and the organic layers were combined and dried over anhydrous sodium sulfate and concentrated. The residue was applied onto a silica gel column with THF/PE (20%). This resulted in 2-[[(2S)-1-(3-ethoxy-2-formylbenzoyl)-4,4-dimethylpyrrolidin-2-yl]methoxy]-6-hydroxybenzaldehyde.

Step 7:

Into a 100-mL 3-necked round-bottom flask, was placed 2-[[(2S)-1-(3-ethoxy-2-formylbenzoyl)-4,4-dimethylpyrrolidin-2-yl]methoxy]-6-hydroxybenzaldehyde (425.00 mg, 0.99 mmol, 1.00 equiv), and DCM (20.00 mL). This was followed by the addition of BBr$_3$/DCM (9.99 mL, 9.99 mmol, 10.00 equiv) dropwise with stirring at –78° C. The resulting solution was stirred for 1 h at 0° C. The reaction was then quenched by the addition of 20 mL of water/ice. The resulting solution was extracted with 3×20 mL of dichloromethane, and the organic layers were combined and dried over anhydrous sodium sulfate and concentrated. The crude product (400 mg) was purified by Prep-HPLC with the following conditions: Column, XBridge Prep C18 OBD Column, 19 cm, 150 mm, 5 um; mobile phase, Water (0.1% HCOOH) and AcCN (30% up to 50% in 11 min); Detector, 254 nM. This resulted in 2-[[(2S)-1-(2-formyl-3-hydroxybenzoyl)-4,4-dimethylpyrrolidin-2-yl]methoxy]-6-hydroxybenzaldehyde. LCMS (ES, m/z): [M+H]$^+$: 398. HTEM-$^1$H NMR (300 MHz, DMSO-d$_6$) δ 11.59 (s, 1H), 10.96 (s, 1H), 10.35 (s, 1H), 10.18 (s, 1H), 7.60-7.46 (m, 2H), 7.03 (d, J=8.4 Hz, 1H), 6.80-6.67 (m, 2H), 6.53 (d, J=8.4 Hz, 1H), 4.63-4.42 (m, 3H), 3.04 (d, J=10.3 Hz, 2H), 2.87 (d, J=10.4 Hz, 1H), 2.09-1.95 (m, 1H), 1.89-1.82 (m, 1H), 1.02 (s, 3H), 0.98 (s, 3H).

Example 16. Synthesis of (±) 2-((1-(2-formyl-3-hydroxybenzyl)-6-oxopiperidin-2-yl)methoxy)-6-hydroxybenzaldehyde (Compound 66)

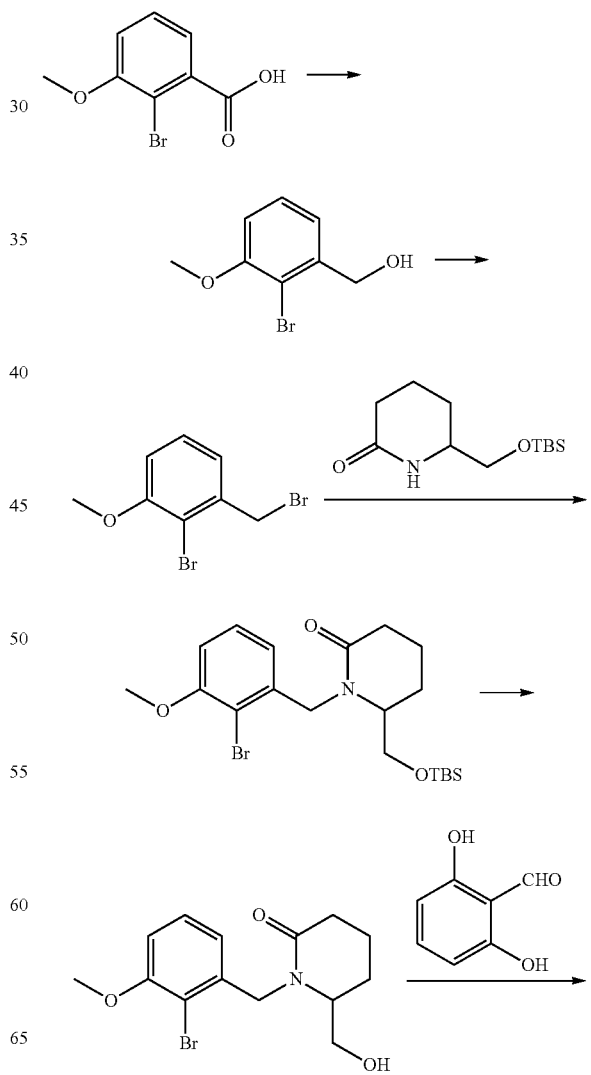

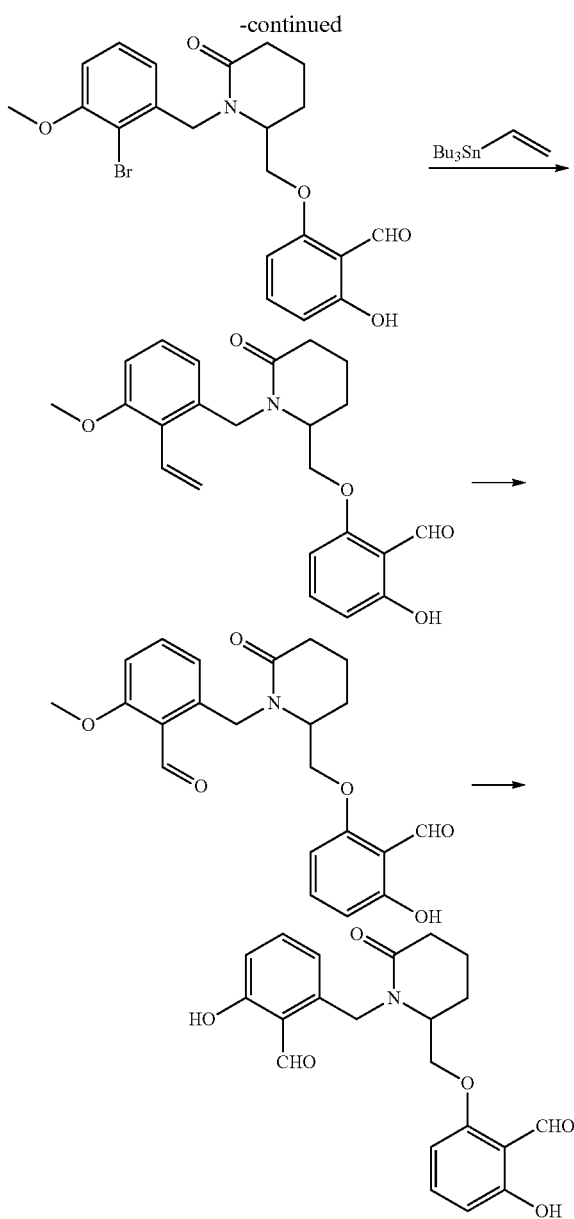

Step 1:

Into a 250-mL round-bottom flask, was placed 2-bromo-3-methoxybenzoic acid (5.00 g, 21.641 mmol, 1.00 equiv), and tetrahydrofuran (100.00 mL, 1.387 mmol, 0.06 equiv). DIBAL-H (43.3 mL, 43.282 mmol, 2.00 equiv, 1M) was added dropwise at −78° C. The resulting solution was stirred for 2 hr at 25° C. The reaction was then quenched by the addition of 100 mL of water/ice. The resulting solution was extracted with 2×200 mL of ethyl acetate. The organic layer was dried over anhydrous sodium sulfate and concentrated under vacuum. This resulted in (2-bromo-3-methoxyphenyl)methanol. LCMS (ES) [M+1]$^+$ m/z 217.0.

Step 2:

Into a 100-mL round-bottom flask, was placed (2-bromo-3-methoxyphenyl)methanol (2.00 g, 9.214 mmol, 1.00 equiv), DCM (50.00 mL, 786.502 mmol, 85.36 equiv), triphenylphosphine (4.80 g, 18.300 mmol, 1.99 equiv), and carbon tetrabromide (6.20 g, 18.696 mmol, 2.03 equiv). The resulting solution was stirred for 16 hr at 25° C. The resulting mixture was concentrated. The residue was applied onto a silica gel column with ethyl acetate/petroleum ether (1:3). The collected fractions were combined and concentrated. This resulted in 2-bromo-1-(bromomethyl)-3-methoxybenzene. LCMS (ES) [M+1]$^+$ m/z 278.9.

Step 3:

Into a 100-mL round-bottom flask, was placed (±) 6-[[(tert-butyldimethylsilyl)oxy]methyl]piperidin-2-one (1.74 g, 7 mmol, 1.00 equiv), and tetrahydrofuran (50 mL). Sodium hydride (0.57 g, 14 mmol, 2.0 equiv, 60%) was added at 0° C. The resulting solution was stirred for 0.5 hr at 0° C. Then, 2-bromo-1-(bromomethyl)-3-methoxybenzene (2.00 g, 7 mmol, 1.00 equiv) was added. The resulting solution was stirred for 3 hr at 25° C. The reaction was then quenched by the addition of 30 mL of water and extracted with 3×50 mL of ethyl acetate. The organic layer was dried over anhydrous sodium sulfate and concentrated under vacuum. The residue was applied onto a silica gel column with ethyl acetate/petroleum ether (1:2). The collected fractions were combined and concentrated. This resulted in (±) 1-[(2-bromo-3-methoxyphenyl)methyl]-6-[[(tert-butyldimethylsilyl)oxy]methyl]piperidin-2-one. LCMS (ES) [M+1]$^+$ m/z 442.1.

Step 4:

Into a 100-mL round-bottom flask, was placed (±) 1-[(2-bromo-3-methoxyphenyl)methyl]-6-[[(tert-butyldimethylsilyl)oxy]methyl]piperidin-2-one (2.80 g, 6.328 mmol, 1.00 equiv), tetrahydrofuran (30 mL), and TBAF (3.16 mL, 3.16 mmol, 0.5 equiv, 1M). The resulting solution was stirred for 2 hr at 25° C. The resulting mixture was concentrated. The residue was applied onto a silica gel column with ethyl acetate/petroleum ether (1:1). The collected fractions were combined and concentrated. This resulted in (±) 1-[(2-bromo-3-methoxyphenyl)methyl]-6-(hydroxymethyl)piperidin-2-one. LCMS (ES) [M+1]$^+$ m/z 328.1.

Step 5:

Into a 100-mL round-bottom flask, was placed (±) 1-[(2-bromo-3-methoxyphenyl)methyl]-6-(hydroxymethyl)piperidin-2-one (0.70 g, 2.133 mmol, 1.00 equiv), tetrahydrofuran (20.00 mL), 2,6-dihydroxybenzaldehyde (295 mg, 2.133 mmol, 1.00 equiv), PPh$_3$ (839 mg, 3.199 mmol, 1.50 equiv), and DIAD (647 mg, 3.199 mmol, 1.50 equiv). The resulting solution was stirred for 16 hr at 25° C. The resulting mixture was concentrated. The residue was applied onto a silica gel column with ethyl acetate/petroleum ether (1:3). The collected fractions were combined and concentrated. This resulted in (±) 2-([1-[(2-bromo-3-methoxyphenyl)methyl]-6-oxopiperidin-2-yl]methoxy)-6-hydroxybenzaldehyde. LCMS (ES) [M+1]$^+$ m/z 448.1.

Step 6:

Into a 100-mL round-bottom flask, was placed (±) 2-([1-[(2-bromo-3-methoxyphenyl)methyl]-6-oxopiperidin-2-yl]methoxy)-6-hydroxybenzaldehyde (0.68 g, 1.517 mmol, 1.00 equiv), toluene (20.00 mL), tributyl(ethenyl)stannane (962.00 mg, 3.034 mmol, 2.00 equiv), and Pd(PPh$_3$)$_4$ (175.00 mg, 0.151 mmol, 0.10 equiv). The resulting solution was stirred for 16 hr at 110° C. The resulting mixture was concentrated. The residue was applied onto a silica gel column with ethyl acetate/petroleum ether (1:3). The collected fractions were combined and concentrated. This resulted in (±) 2-([1-[(2-ethenyl-3-methoxyphenyl)methyl]-6-oxopiperidin-2-yl]methoxy)-6-hydroxybenzaldehyde. LCMS (ES) [M+1]$^+$ m/z 396.2.

Step 7:

Into a 50-mL round-bottom flask, was placed (±) 2-([1-[(2-ethenyl-3-methoxyphenyl)methyl]-6-oxopiperidin-2-yl]methoxy)-6-hydroxybenzaldehyde (100.00 mg, 0.253 mmol, 1.00 equiv), acetone (5.00 mL), water (5.00 mL), NaIO₄ (162.26 mg, 0.759 mmol, 3.00 equiv), and tetraoxodipotassioosmium (1.68 mg, 0.005 mmol, 0.02 equiv). The resulting solution was stirred for 16 hr at 25° C. The resulting mixture was concentrated. The crude reaction mixture was filtered and subjected to reverse phase preparative HPLC (Prep-C18, 5 µM XBridge column, 19 Å-150 mm, Waters; gradient elution of 30% MeCN in water to 40% MeCN in water over a 10 min period, where both solvents contain 0.1% formic acid) to provide (±) 2-((2-((2-formyl-3-hydroxyphenoxy)methyl)-6-oxopiperidin-1-yl)methyl)-6-methoxybenzaldehyde. LCMS (ES) [M+1]⁺ m/z 398.2.

Step 8:

Into a 50-mL round-bottom flask, was placed (±) 2-((2-((2-formyl-3-hydroxyphenoxy)methyl)-6-oxopiperidin-1-yl)methyl)-6-methoxybenzaldehyde (60.0 mg, 0.15 mmol, 1.00 equiv), DCM (10.00 mL), and AlCl₃ (201 mg, 1.5 mmol, 10 equiv). The resulting solution was stirred for 16 hr at 50° C. The resulting mixture was concentrated under vacuum. The crude reaction mixture was filtered and subjected to reverse phase preparative HPLC (Prep-C18, 20-45M, 120 g, Tianjin Bonna-Agela Technologies; gradient elution of 30% MeCN in water to 40% MeCN in water over a 10 min period, where both solvents contain 0.1% FA) to provide (±) 2-((1-(2-formyl-3-hydroxybenzyl)-6-oxopiperidin-2-yl)methoxy)-6-hydroxybenzaldehyde. LCMS (ES) [M+1]⁺ m/z 384.1. ¹H NMR (300 MHz, DMSO-d₆) δ 11.69 (br, 1H), 11.22 (br, 1H), 10.43 (s, 1H), 10.13 (s, 1H), 7.48 (t, J=8.4 Hz, 1H), 7.35 (t, J=8.0 Hz, 1H), 6.82 (d, J=8.3 Hz, 1H), 6.69 (d, J=7.6 Hz, 1H), 6.52 (t, J=7.6 Hz, 2H), 5.19 (d, J=17.3 Hz, 1H), 4.78 (d, J=17.4 Hz, 1H), 4.31-4.11 (m, 2H), 3.91-3.72 (m, 1H), 2.42-2.36 (m, 2H), 2.10-1.91 (m, 3H), 1.80-1.73 (m, 1H).

Example 17: Synthesis of Enantiomer 1 of 2-((4-(2-formyl-3-hydroxybenzoyl)thiomorpholin-3-yl)methoxy)-6-hydroxybenzaldehyde (Compound 67, Enantiomer 1) and Enantiomer 2 of 2-((4-(2-formyl-3-hydroxybenzoyl)thiomorpholin-3-yl)methoxy)-6-hydroxybenzaldehyde (Compound 67, Enantiomer 2)

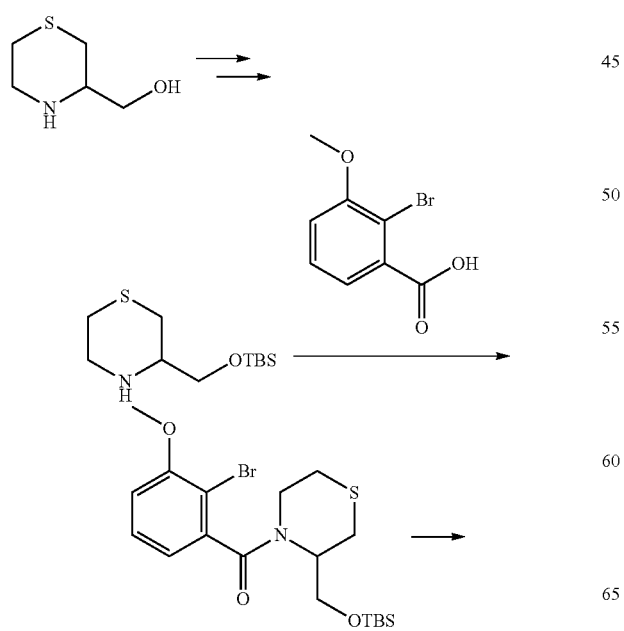

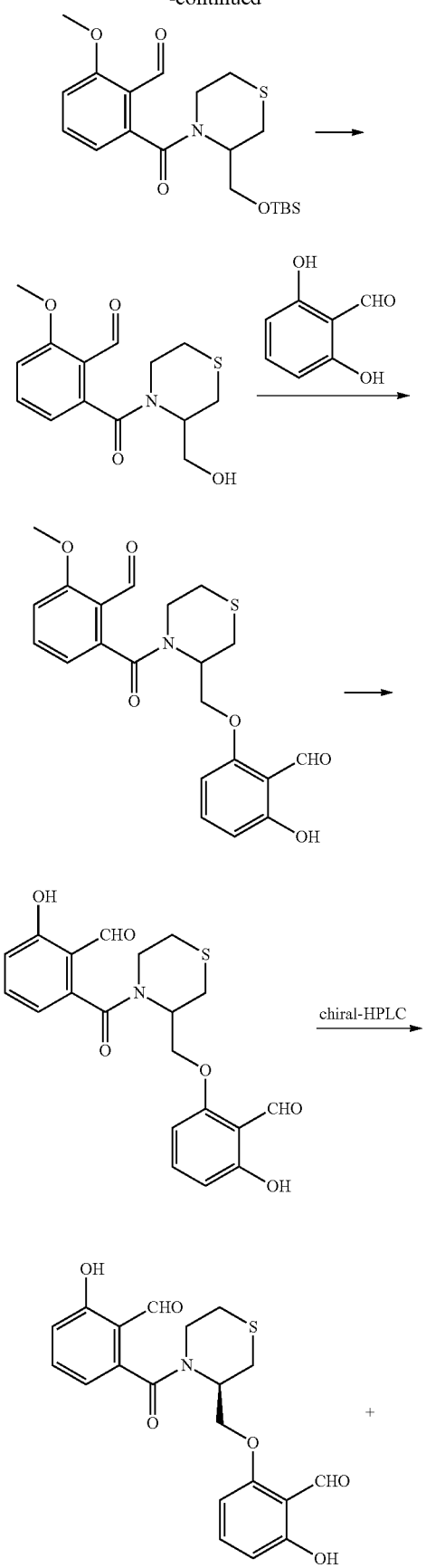

-continued

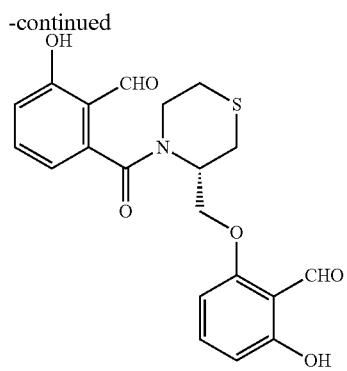

Step 1:
Into a 250-mL 3-necked round-bottom flask, was placed thiomorpholin-3-ylmethanol hydrochloride (3.00 g, 17.68 mmol, 1.00 equiv), and imidazole (3.01 g, 44.20 mmol, 2.50 equiv), DCM (30.00 mL). This was followed by the addition of TBSCl (3.20 g, 21.22 mmol, 1.20 equiv), in portions at 0° C. The resulting solution was stirred for overnight at room temperature. The reaction was then quenched by the addition of 30 mL of water. The resulting solution was extracted with 3×30 mL of dichloromethane, and the organic layers were combined and dried over anhydrous sodium sulfate and concentrated. This resulted in 3-[[(tert-butyldimethylsilyl)oxy]methyl]thiomorpholine. LCMS (ES) [M+H]$^+$ m/z: 248.

Step 2:
Into a 100-mL 3-necked round-bottom flask, was placed 2-bromo-3-methoxybenzoic acid (2.50 g, 10.8 mmol, 1.00 equiv), 3-(((tert-butyldimethylsilyl)oxy)methyl)thiomorpholine (2.95 g, 11.9 mmol, 1.10 equiv), DCM (40.00 mL), and DIEA (2.79 g, 21.64 mmol, 2.00 equiv). This was followed by the addition of HATU (6.17 g, 16.23 mmol, 1.50 equiv) in portions at 0° C. The resulting solution was stirred for overnight at room temperature. The reaction was then quenched by the addition of 50 mL of water. The resulting solution was extracted with 3×50 mL of dichloromethane, and the organic layers were combined and dried over anhydrous sodium sulfate and concentrated. The residue was applied onto a silica gel column with THF/PE (11%). This resulted in [4-(2-[2-[(tert-butyldimethylsilyl)oxy]ethyl]pyridine-3-carbonyl)thiomorpholin-3-yl]methanol. LCMS (ES) [M+H]$^+$ m/z: 460.

Step 3:
Into a 250-mL round-bottom flask, was placed bromo(isopropyl)magnesium (11 mL, 22 mmol, 2.00 equiv, 2M), and THF (20 mL). Then, butyllithium (17 mL, 43 mmol, 4.00 equiv, 2.5 M) was added dropwise at 0° C. The resulting solution was stirred for 10 min at 0° C. Then 4-(2-bromo-3-methoxybenzoyl)-3-[[(tert-butyldimethylsilyl)oxy]methyl]thiomorpholine (5.00 g, 10.858 mmol, 1.00 equiv) in THF (20 mL) was added dropwise at −78° C. The resulting solution was stirred for 1 hr at −78° C. Then dimethylformamide (3.20 g, 43.779 mmol, 4.03 equiv) was added dropwise at −78° C. The resulting solution was stirred for 2 hr at 25° C. The reaction was then quenched by the addition of 50 mL of water and extracted with 2×100 mL of ethyl acetate. The organic layer was dried over anhydrous sodium sulfate and concentrated under vacuum. The residue was applied onto a silica gel column with ethyl acetate/petroleum ether (1:3). The collected fractions were combined and concentrated. This resulted in 2-(3-[[(tert-butyldimethylsilyl)oxy]methyl]thiomorpholine-4-carbonyl)-6-methoxybenzaldehyde. LCMS (ES) [M+1]$^+$ m/z 410.2.

Step 4:
Into a 100-mL round-bottom flask, was placed 2-(3-[[(tert-butyldimethylsilyl)oxy]methyl]thiomorpholine-4-carbonyl)-6-methoxybenzaldehyde (3.00 g, 7.324 mmol, 1.00 equiv), tetrahydrofuran (20.00 mL), and TBAF (0.96 g, 3.662 mmol, 0.50 equiv). The resulting solution was stirred for 2 hr at 25° C. The resulting mixture was concentrated. The residue was applied onto a silica gel column with ethyl acetate/petroleum ether (1:2). The collected fractions were combined and concentrated. This resulted in 2-[3-(hydroxymethyl)thiomorpholine-4-carbonyl]-6-methoxybenzaldehyde. LCMS (ES) [M+1]$^+$ m/z 296.1.

Step 5:
Into a 100-mL round-bottom flask, was placed 2-[3-(hydroxymethyl)thiomorpholine-4-carbonyl]-6-methoxybenzaldehyde (2.00 g, 6.772 mmol, 1.00 equiv), tetrahydrofuran (20 mL), 2,6-dihydroxybenzaldehyde (0.94 g, 6.772 mmol, 1.00 equiv), triphenylphosphine (2.13 g, 8.126 mmol, 1.20 equiv), and DIAD (1.64 g, 8.126 mmol, 1.20 equiv). The resulting solution was stirred for 16 hr at 80° C. The resulting mixture was concentrated. The residue was applied onto a silica gel column with ethyl acetate/petroleum ether (1:3). The collected fractions were combined and concentrated. This resulted in 2-[[4-(2-formyl-3-methoxybenzoyl)thiomorpholin-3-yl]methoxy]-6-hydroxybenzaldehyde. LCMS (ES) [M+1]$^+$ m/z 416.1.

Step 4:
Into a 50-mL round-bottom flask, was placed 2-[[4-(2-formyl-3-methoxybenzoyl)thiomorpholin-3-yl]methoxy]-6-hydroxybenzaldehyde (100.00 mg, 0.241 mmol, 1 equiv), and DCM (10.00 mL). Then, boron tribromide (2.40 mL, 2.407 mmol, 10.00 equiv, 1M) was added dropwise at −78° C. The resulting solution was stirred for 4 hr at 0° C. The resulting mixture was concentrated. The crude reaction mixture was filtered and subjected to reverse phase preparative HPLC (Prep-C18, 20-45M, 120 g, Tianjin Bonna-Agela Technologies; gradient elution of 25% MeCN in water to 35% MeCN in water over a 10 min period, water contains 0.1% FA) to provide 2-((4-(2-formyl-3-hydroxybenzoyl)thiomorpholin-3-yl)methoxy)-6-hydroxybenzaldehyde. LCMS (ES) [M+1]$^+$ m/z 402.1. $^1$H NMR (300 MHz, DMSO-d$_6$) δ11.80 (br, 1H), 11.09 (br, 1H), 10.30-10.13 (m, 2H), 7.69-7.28 (m, 2H), 7.04 (dd, J=7.5, 1.5 Hz, 1H), 6.95-6.38 (m, 3H), 5.45-5.21 (m, 1H), 4.91-4.51 (m, 2H), 4.43-3.95 (m, 1H), 3.52-3.41 (m, 1H), 3.20-3.02 (m, 1H), 2.98-2.81 (m, 1H), 2.83-2.72 (m, 1H), 2.41-2.32 (m, 1H). Chiral HPLC separation of 2-((4-(2-formyl-3-hydroxybenzoyl)thiomorpholin-3-yl)methoxy)-6-hydroxybenzaldehyde 2-((4-(2-formyl-3-hydroxybenzoyl)thiomorpholin-3-yl)methoxy)-6-hydroxybenzaldehyde was separated by Chiral Prep-HPLC with the following conditions: Column: Chiralpak IA, 20*250 mm, 5 um; mobile phase: A: n-Hexane/DCM (5:1), B: Ethanol; gradient elution 50% B in 15 min; flow rate 18 mL/min. The resulting mixture was concentrated and was analyzed by analytical chiral HPLC with the following conditions: Column: Chiralpak IA-3, 4.6*50 mm, 3 um; mobile phase: A: n-Hexane/DCM (5:1), B: Ethanol. gradient elution 50% B in 5 min; flow rate: 1 mL/min. This resulted in Enantiomer 1 of 2-((4-(2-formyl-3-hydroxybenzoyl)thiomorpholin-3-yl)methoxy)-6-hydroxybenzaldehyde and Enantiomer 2 of 2-((4-(2-formyl-3-hydroxybenzoyl)thiomorpholin-3-yl)methoxy)-6-hydroxybenzaldehyde.

Compound 67, Enantiomer 1:
Analytical Chiral HPLC retention time: 3.25 min. LCMS (ES) [M+1]$^+$ m/z 402.1. $^1$H NMR (300 MHz, DMSO-d$_6$) δ11.80 (br, 1H), 11.09 (br, 1H), 10.30-10.13 (m, 2H), 7.69-7.28 (m, 2H), 7.04 (dd, J=7.5, 1.5 Hz, 1H), 6.95-6.38 (m, 3H), 5.45-5.21 (m, 1H), 4.91-4.01 (m, 3H), 3.32-2.62 (m, 4H), 2.41-2.32 (m, 1H).

Compound 67, Enantiomer 2:

Analytical Chiral HPLC retention time: 1.27 min. LCMS (ES) [M+1]$^+$ m/z 402.1. $^1$H NMR (300 MHz, DMSO-d$_6$) δ11.80 (br, 1.5H), 10.30-10.13 (m, 2H), 7.69-7.28 (m, 2H), 7.14-6.38 (m, 4H), 5.45-5.21 (m, 1H), 4.91-4.01 (m, 3H), 3.32-2.62 (m, 4H), 2.41-2.32 (m, 1H).

Compounds in Table 3 below may be made according to the methods described herein.

TABLE 3

| Compound Number | Structure | Mass Spectrometry Data |
|---|---|---|
| 1 | | 384.2 |
| 2 | | 368.1 |
| 3 | | 414 |
| 4 | | 386.1 |
| 5 | 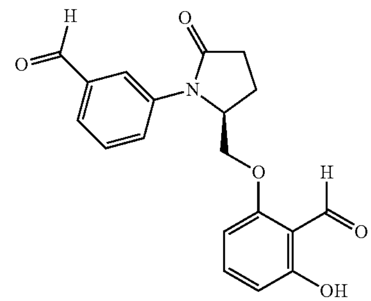 [SMILES: O=Cc1cccc(N2C(=O)CC[C@H]2COc2cccc(O)c2C=O)c1] | 340 |
| 6 | 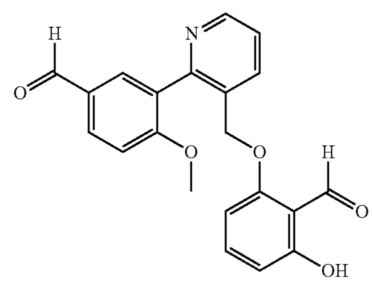 [SMILES: COc1ccc(C=O)cc1-c1ncccc1COc1cccc(O)c1C=O] | 364.1 |
| 7 | 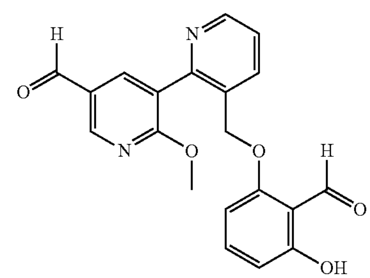 [SMILES: COc1ncc(C=O)cc1-c1ncccc1COc1cccc(O)c1C=O] | 365.2 |
| 8 | 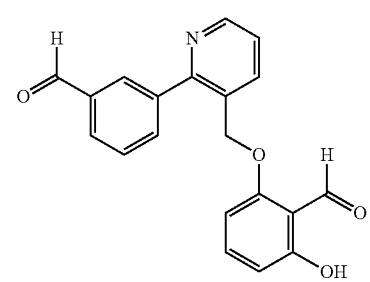 [SMILES: O=Cc1cccc(-c2ncccc2COc2cccc(O)c2C=O)c1] | 334.1 |
| 9 | 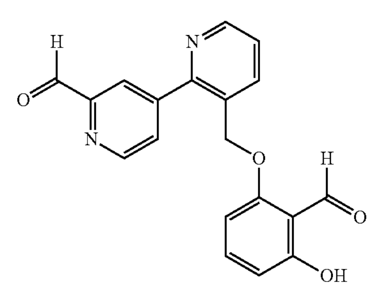 [SMILES: O=Cc1cc(-c2ncccc2COc2cccc(O)c2C=O)ccn1] | 335 |

TABLE 3-continued

| Compound Number | Structure | Mass Spectrometry Data |
|---|---|---|
| 10 | 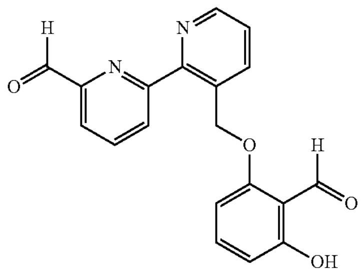 [SMILES: O=Cc1cccc(-c2ncccc2COc2cccc(O)c2C=O)n1] | 335.1 |
| 11 | 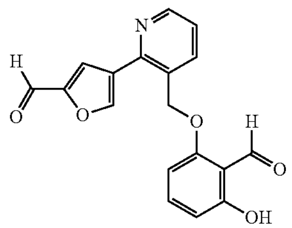 [SMILES: O=Cc1cc(-c2ncccc2COc2cccc(O)c2C=O)co1] | 324.1 |
| 12 | 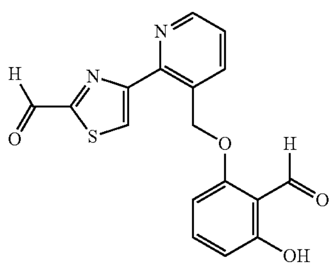 | 340.8 |
| 13 | 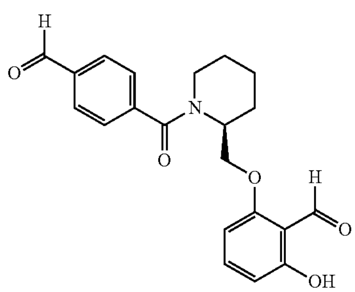 [SMILES: O=Cc1ccc(C(=O)N2CCCC[C@H]2COc2cccc(O)c2C=O)cc1] | 368.1 |
| 14 | 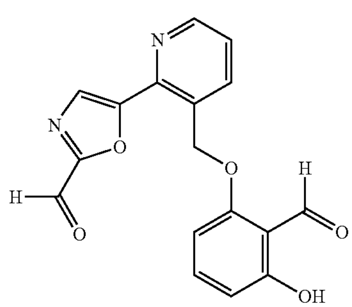 [SMILES: O=Cc1ncc(-c2ncccc2COc2cccc(O)c2C=O)o1] | 324.8 |
| 15 | | 398.2 |
| 16 | | 402 |
| 17 | | 368.2 |
| 18 | | 323.1 |
| 19 | | 372.9 (M + Na) |

TABLE 3-continued

| Compound Number | Structure | Mass Spectrometry Data |
|---|---|---|
| 20 | 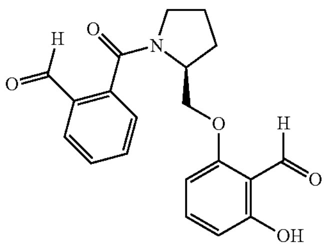 [SMILES: O=Cc1ccccc1C(=O)N1CCC[C@H]1COc1cccc(O)c1C=O] | 376.1 (M + Na) |
| 21 | 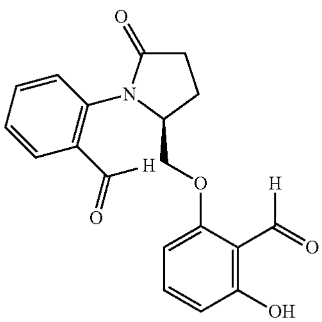 [SMILES: O=Cc1ccccc1N1C(=O)CC[C@H]1COc1cccc(O)c1C=O] | 340.1 |
| 22 | 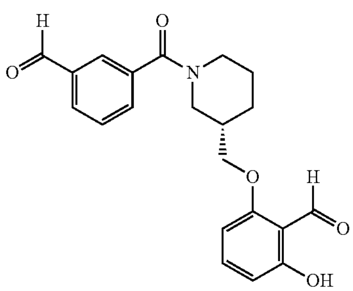 [SMILES: O=Cc1cccc(C(=O)N2CCC[C@H](COc3cccc(O)c3C=O)C2)c1] | 368.2 |
| 23 | 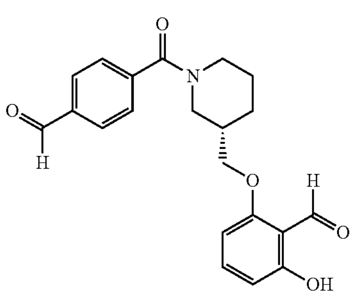 [SMILES: O=Cc1ccc(C(=O)N2CCC[C@H](COc3cccc(O)c3C=O)C2)cc1] | 368.1 |
| 24 | 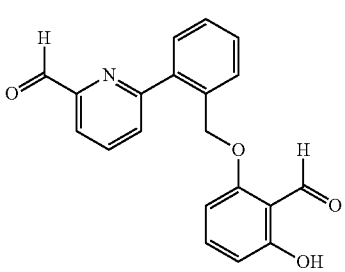 | 334 |
| 25 | | 369.2 |
| 26 | | 390.1 (M + Na) |
| 27 | | 368.2 |
| 28 | | 368.2 |

TABLE 3-continued

| Compound Number | Structure | Mass Spectrometry Data |
|---|---|---|
| 29 | 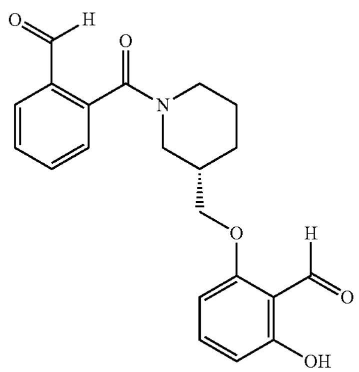 [SMILES: O=Cc1ccccc1C(=O)N1CCC[C@H](COc2cccc(O)c2C=O)C1] | 368.2 |
| 30 | 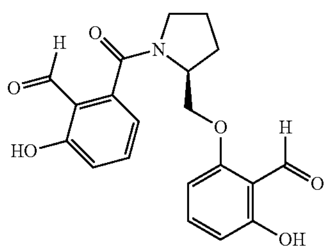 [SMILES: O=Cc1c(O)cccc1OC[C@@H]1CCCN1C(=O)c1cccc(O)c1C=O] | 370.1 |
| 31 | 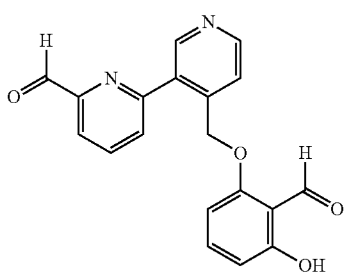 [SMILES: O=Cc1cccc(-c2cnccc2COc2cccc(O)c2C=O)n1] | 357.0 (M + Na) |
| 32 | 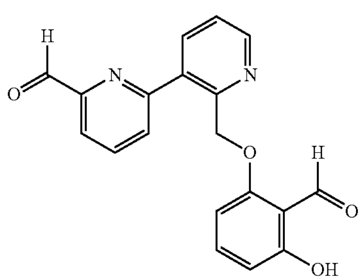 [SMILES: O=Cc1cccc(-c2cccnc2COc2cccc(O)c2C=O)n1] | 335 |
| 33 | 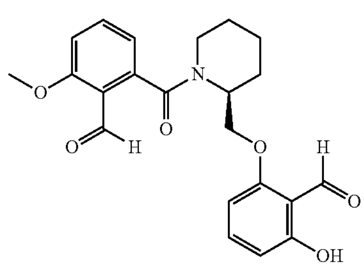 [SMILES: COc1cccc(C(=O)N2CCCC[C@H]2COc2cccc(O)c2C=O)c1C=O] | 398.2 |
| 34 | 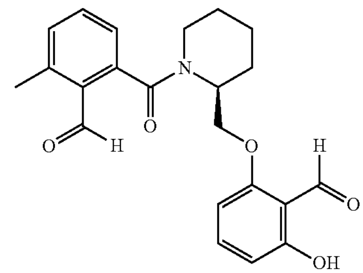 [SMILES: Cc1cccc(C(=O)N2CCCC[C@H]2COc2cccc(O)c2C=O)c1C=O] | 382.1 |
| 35 | 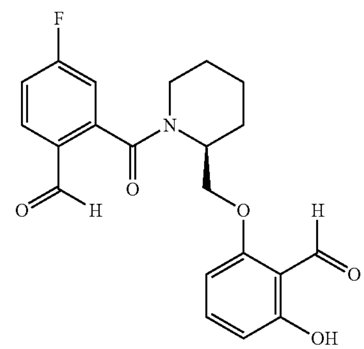 [SMILES: O=Cc1ccc(F)cc1C(=O)N1CCCC[C@H]1COc1cccc(O)c1C=O] | 408.2 (M + Na) |
| 36 | 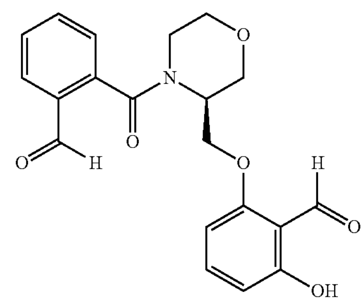 | 370.1 |
| 37 | 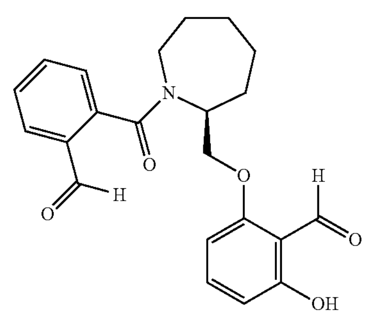 [SMILES: O=Cc1ccccc1C(=O)N1CCCCC[C@H]1COc1cccc(O)c1C=O] | 404.1 (M + Na) |
| 38 | 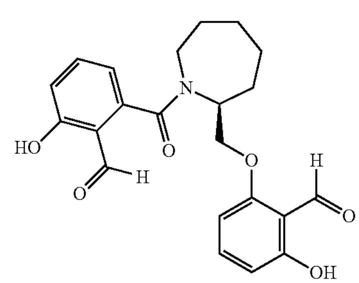 [SMILES: O=Cc1c(O)cccc1OC[C@@H]1CCCCCN1C(=O)c1cccc(O)c1C=O] | 420.2 (M + Na) |

TABLE 3-continued

| Compound Number | Structure | Mass Spectrometry Data |
|---|---|---|
| 39 | 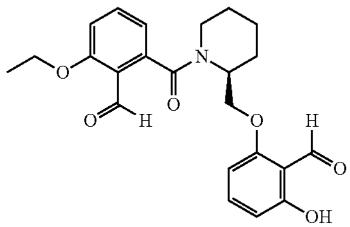 [SMILES: CCOc1cccc(C(=O)N2CCCC[C@H]2COc2cccc(O)c2C=O)c1C=O] | 412.2 |
| 40 | 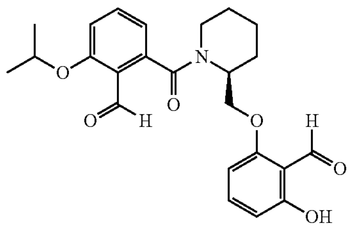 [SMILES: CC(C)Oc1cccc(C(=O)N2CCCC[C@H]2COc2cccc(O)c2C=O)c1C=O] | 426.2 |
| 41 | 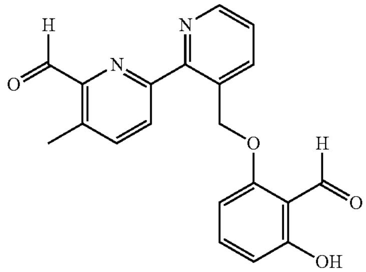 [SMILES: Cc1ccc(-c2ncccc2COc2cccc(O)c2C=O)nc1C=O] | 349.1 |
| 42 | 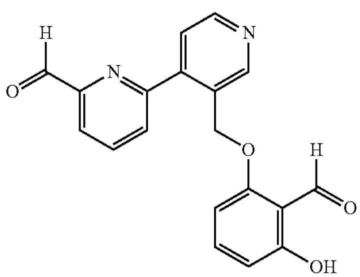 [SMILES: O=Cc1cccc(-c2ccncc2COc2cccc(O)c2C=O)n1] | 335 |
| 43 | 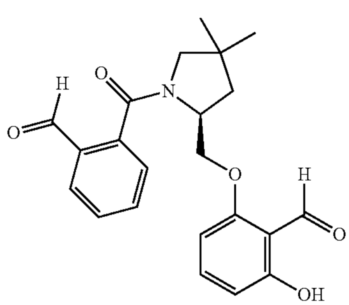 [SMILES: CC1(C)C[C@@H](COc2cccc(O)c2C=O)N(C(=O)c2ccccc2C=O)C1] | 382.1 |
| 44 | 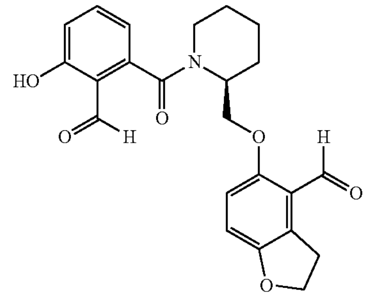 [SMILES: O=Cc1c(O)cccc1C(=O)N1CCCC[C@H]1COc1ccc2c(c1C=O)CCO2] | 410.2 |
| 45 | 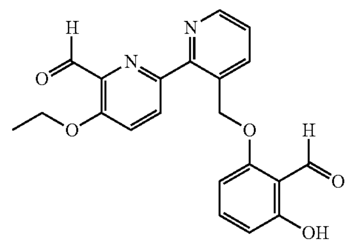 [SMILES: CCOc1ccc(-c2ncccc2COc2cccc(O)c2C=O)nc1C=O] | 379.1 |
| 46 | 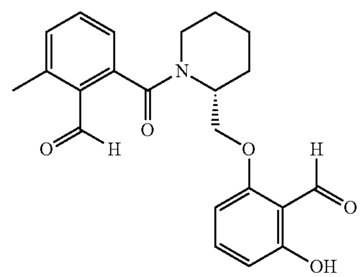 [SMILES: Cc1cccc(C(=O)N2CCCC[C@@H]2COc2cccc(O)c2C=O)c1C=O] | 382.2 |
| 47 | 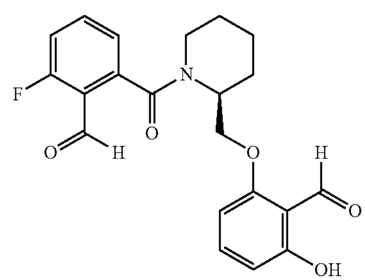 | 408.2 (M + Na) |
| 48 | 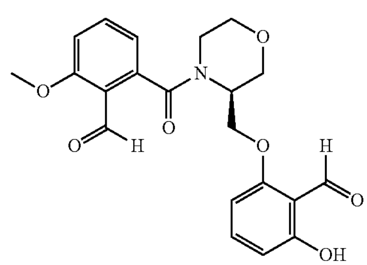 [SMILES: COc1cccc(C(=O)N2CCOC[C@H]2COc2cccc(O)c2C=O)c1C=O] | 422.1 (M + Na) |

TABLE 3-continued

| Compound Number | Structure | Mass Spectrometry Data |
|---|---|---|
| 49 | 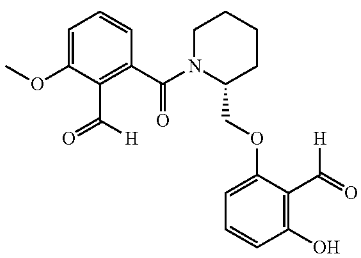 [SMILES: COc1cccc(C(=O)N2CCCC[C@@H]2COc2cccc(O)c2C=O)c1C=O] | 398.2 |
| 50 | 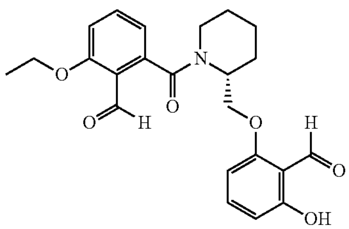 [SMILES: CCOc1cccc(C(=O)N2CCCC[C@@H]2COc2cccc(O)c2C=O)c1C=O] | 412.2 |
| 51 | 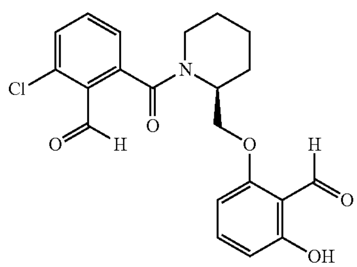 [SMILES: O=Cc1c(O)cccc1OC[C@@H]1CCCCN1C(=O)c1cccc(Cl)c1C=O] | 402.2 |
| 52 | 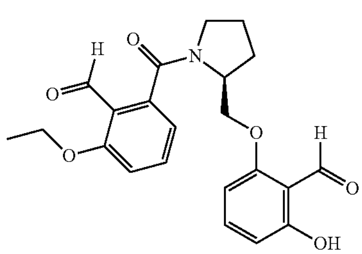 [SMILES: CCOc1cccc(C(=O)N2CCC[C@H]2COc2cccc(O)c2C=O)c1C=O] | 398.4 |
| 53 | 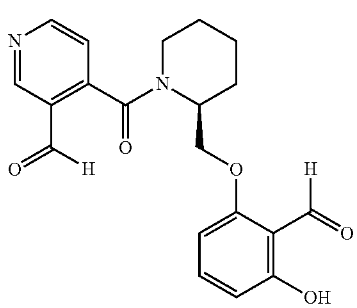 [SMILES: O=Cc1cnccc1C(=O)N1CCCC[C@H]1COc1cccc(O)c1C=O] | 369.2 |
| 54 | | 400.1 (MH+) |

Biological Assays

Example 18

Whole Blood Assay:

Oxygen equilibrium curves (OECs) were collected using a TCS Hemox Analyzer (TCS Scientific Company, New Hope, Pa., USA) to measure changes in the binding affinity of O2 to Hb. Whole blood was incubated for 1 h at 37° C. with the indicated compounds in an equimolar ratio of hemoglobin to compound and diluted into TES (2-[[1,3-dihydroxy-2-(hydroxymethyl)propan-2-yl]amino]ethane-sulfonic acid)/saline buffer prior to measurements. For example, for whole blood at 20% hematocrit [Hct], which corresponds to 1 mM Hb, a compound concentration of 1 mM was used (for example, for compounds 1-53), and the incubated sample diluted 50- to 100-fold. The concentration for compound 54 was 1.7 mM and in equimolar ratio to hemoglobin. The diluted samples were then oxygenated with compressed air within the Hemox Analyzer, and the OECs were collected during deoxygenation as previously described (Guarnone et al., *Haematologica*, 1995, 80, 426-430). p50 (partial pressure of O2 at which Hb is 50% saturated with O2) values were obtained using a non-linear regression analysis. Percentage change in p50 [Δp50(%)] was calculated as follows: Δp50(%)=[(p50 of control)−p50 with compound)/p50 control]×100. Resulting data is shown in Table 4.

TABLE 4

| Compound Number | Delta-p50 (%) |
|---|---|
| 1 | 75.8 |
| 2 | 78.3 |
| 3 | 73.6 |
| 4 | 30.9 |
| 5 | 79 |
| 6 | 16.7 |
| 7 | 32.5 |
| 8 | 44.8 |
| 9 | 36.1 |
| 10 | 0.2 |
| 11 | 17.2 |
| 12 | 2.9 |
| 13 | 45.4 |
| 14 | 17.8 |
| 15 | 19 |
| 16 | 39 |
| 17 | 67 |
| 18 | 17 |
| 19 | 11 |
| 20 | 32 |

TABLE 4-continued

| Compound Number | Delta-p50 (%) |
| --- | --- |
| 21 | 23 |
| 22 | 68.5 |
| 23 | 20 |
| 24 | 11 |
| 25 | 4 |
| 26 | 56 |
| 27 | 74 |
| 28 | 45 |
| 29 | 82 |
| 30 | 45 |
| 31 | 3.5 |
| 32 | 50 |
| 33 | 84 |
| 34 | 78 |
| 35 | 70 |
| 36 | 77 |
| 37 | 31.5 |
| 38 | 33.8 |
| 39 | 79.5 |
| 40 | 72.5 |
| 41 | 29.1 |
| 42 | 17.4 |
| 43 | 70 |
| 44 | 34.2 |
| 45 | 55.7 |
| 46 | 69 |
| 47 | 70 |
| 48 | 70.3 |
| 49 | 59 |
| 50 | 45.3 |
| 51 | 65.5 |
| 52 | 75.5 |
| 53 | 71.9 |
| 54 | 72.6 |

Example 19

Hemoglobin assay: Oxygen equilibrium curves (OECs) were collected as described above. Purified hemoglobin (25 µM) was incubated for 1 h at 37° C. with the indicated compounds (30 µM for compounds 6, 7, 8, and 11; 25 µM for compounds 55 to 67 (Enantiomer 1 and Enantiomer 2)) in 5 ml of TES (2-[[1,3-dihydroxy-2-(hydroxymethyl)propan-2-yl]amino]ethanesulfonic acid)/saline buffer prior to measurements. The samples were then oxygenated with compressed air within the Hemox Analyzer and the OECs were collected during deoxygenation as previously described. p50 values were obtained using a non-linear regression analysis, and Δp50(%) was calculated as described above. Resulting data is shown in Table 5.

TABLE 5

| Compound Number | Delta-p50 (%) |
| --- | --- |
| 6 | 60.66 |
| 7 | 58.29 |
| 8 | 57.3 |
| 11 | 14.12 |
| 55 | 71 |
| 56 | 70 |
| 57 | 71 |
| 58 | 71 |
| 59 | 71 |
| 60 | 67 |
| 61 | 71 |
| 62 | 69 |
| 63 | 70 |
| 64 | 67 |
| 65 | 69 |

TABLE 5-continued

| Compound Number | Delta-p50 (%) |
| --- | --- |
| 66 | 71 |
| 67 (Enantiomer 1) | 67.2 |
| 67 (Enantiomer 2) | 69.3 |

Example 20

Pharmacokinetics Measurements in Rats Following 10 mg/kg Oral Administration of Bis-Aldehydes:

The pharmacokinetic (PK) profile of Compound 2 was characterized in Sprague-Dawley rats following oral administration of 10 mg/kg. Blood and plasma samples were serially collected from each animal up to 240 h post-dose and analyzed for their concentrations using LC/MS. The analytical range was 100 to 100,000 ng/ml for both plasma and blood samples. Blood and plasma concentrations of Compound 2 were analyzed by non-compartmental analysis using Phoenix WinNonlin software (version 6-4; Pharsight Inc., Cary, N.C., USA) to obtain pharmacokinetic parameters, including half-life (T½) and area under the curve (AUC). $AUC_{last}$ refers to the area under the curve calculated from t=0 to the last detectable time-point. Blood to plasma concentration ratio was calculated from a ratio of $AUC_{last}$ in blood divided by $AUC_{last}$ in plasma.

Blood pharmacokinetic parameters in rat were determined in individual animals and reported as mean.

TABLE 6

Summary of pharmacokinetics parameters in rat

| Parameter | Compound 2 |
| --- | --- |
| Dose (PO, mg/kg) | 10 |
| Vehicle | 0.5% MC |
| N | 3 |
| $AUC_{last}$ (µg * h/ml) | 239 |
| T½ (h) | 187 |
| Blood/Plasma Ratio ($AUC_{last}/AUC_{last}$) | 937 |

MC = Methylcellulose suspension
PO, oral; T½, half-life; N, number; AUC, area under the curve.

Example 21

Preparation of HbS for Crystallography:

Purified HbS was prepared from blood using a combination of gel filtration and anion exchange chromatography. Following preparation, the purified HbS solution was concentrated to 1 mM in a volume of 1 mL using a Vivaspin 20 concentrator (GE healthcare) via centrifugation at room temperature in an Eppendorf 5810 R centrifuge. The concentrated HbS solution was then buffer exchanged into potassium phosphate buffer by mixing 1 mL of concentrated HbS solution with 20 mL of 1.8 M potassium phosphate buffer, pH 7.4 and re-concentrating back to 1 mL using a Vivaspin 20. This process was repeated twice and aliquots of the resulting HbS solution were flash frozen using liquid nitrogen and stored at −80° C. To prepare HbS-CO, purified HbS was first saturated with CO for five hours before it was buffer exchanged into 20 mM Hepes buffer, pH 7.4, and concentrated to 3 mM.

Crystallization of Human CO-Liganded HbS:

Human CO-HbS was crystallized using sitting drop vapor diffusion method. Freshly prepared CO-HbS at 0.8 mM and buffered with 20 mM HEPES pH 7.4 was mixed with compounds (specifically, Compound 1 and Compound 2) at a final concentration of 1 mM. For crystallization, an equal volume of a precipitant solution containing 100 mM HEPES pH 7.4, 28-33% (v/v) PEG 3350 and 20 mM of sodium chloride in 24-well VDX plate (Hampton Research, Aliso Viejo, Calif., USA) and equilibrated against 0.5 mL of precipitant solution at room temperature (294° K) for 1-7 days using the hanging drop method. The appearance of hemoglobin crystals was monitored visually and microscopically every 48-72 hours after beginning of the experiments. In most cases, CO-HbS crystal clusters were carefully "broken" and separated into individual crystals either manually or by soaking them into a precipitant solution supplemented with 10-20% of glycerol before flash freezing in liquid nitrogen.

Structure Determination:

Crystal screening and final X-ray diffraction data collection was carried out at beamline 8.3.1 at the Advanced Light Source in Berkeley, Calif. Data reduction was carried out using iMOSFLM and the CCP4 software suite. The crystal structure of human HbS protein (PDB code 5E83) was used as a molecular replacement model. All models were built using COOT and refinement was carried out using the PHENIX suit. Figures were made using PyMOL.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound of formula (I):

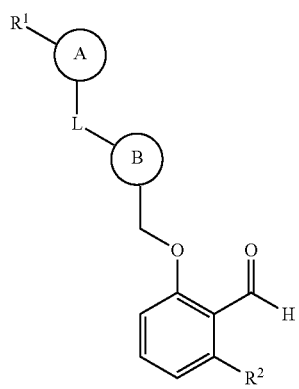

(I)

or an isotopically enriched analog, stereoisomer, or mixture of stereoisomers thereof, or a pharmaceutically acceptable salt of each thereof, wherein:
ring A is aryl or heteroaryl, wherein ring A is optionally substituted with 1-3 $R^3$;
ring B is aryl, nitrogen-containing heteroaryl, or nitrogen-containing heterocyclyl, wherein ring B is optionally substituted with 1-3 $R^4$;
L is absent, —C(O)—, —C(O)O—, or —CH$_2$—;
$R^1$ is —C(O)H;
$R^2$ is H or OH;
each $R^3$ is independently halo, hydroxy, $C_{1-3}$ alkyl, $C_{2-3}$ alkenyl, $C_{1-3}$ alkoxy, $C_{1-3}$ haloalkyl, or $C_{1-3}$ haloalkoxy; and
each $R^4$ is independently oxo, $C_{1-3}$ alkyl, $C_{1-3}$ alkoxy, $C_{1-3}$ haloalkyl, $C_{1-3}$ haloalkoxy, or $C_{3-5}$ cycloalkyl.

2. The compound of claim 1, wherein L is absent, and ring B is aryl or nitrogen-containing heteroaryl, wherein ring B is optionally substituted with 1-3 $R^4$.

3. The compound of claim 1, wherein L is absent, and ring B is $C_6$ or $C_{10}$ aryl optionally substituted with 1-3 $R^4$.

4. The compound of claim 3, wherein ring B is phenyl optionally substituted with 1-3 $R^4$.

5. The compound of claim 4, wherein ring B is phenyl.

6. The compound of claim 1, wherein L is absent, and ring B is a 5-membered or 6-membered nitrogen-containing heteroaryl optionally substituted with 1-3 $R^4$.

7. The compound of claim 6, wherein ring B is a pyridyl ring or pyrazinyl ring, each of which is optionally substituted with 1-3 $R^4$.

8. The compound of claim 7, wherein

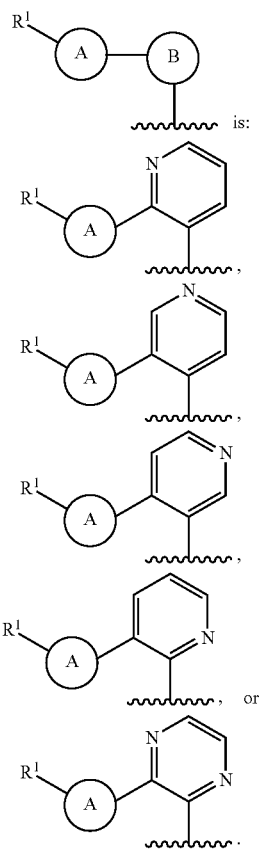

9. The compound of claim 8, wherein

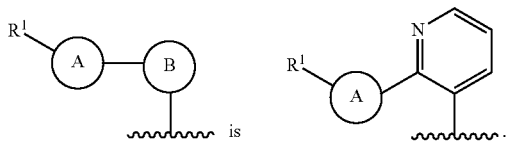 is 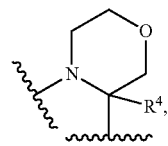.

10. The compound of claim 1, wherein L is —C(O)—, and ring B is a nitrogen-containing heterocyclyl optionally substituted with 1-3 $R^4$.

11. The compound of claim 10, wherein ring B is a 5-membered or 6-membered nitrogen-containing heterocyclyl optionally substituted with 1-3 $R^4$.

12. The compound of claim 11, wherein ring B is a 5-membered or 6-membered nitrogen-containing heterocyclyl.

13. The compound of claim 10, wherein ring B is

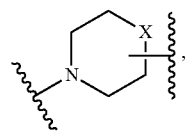

and X is absent, —CH$_2$—, —N(R$^5$)—, —O—, —S(O)$_{0-2}$—, —CH$_2$CH$_2$—, —CH$_2$—O—, or —O—CH$_2$—; wherein $R^5$ is H, $C_{1-3}$ alkyl, or $C_{3-5}$ cycloalkyl.

14. The compound of claim 13, wherein ring B is

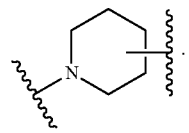

15. The compound of claim 13, wherein ring B is

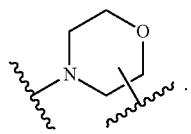

16. The compound of claim 11, wherein ring B is a 5-membered or 6-membered nitrogen-containing heterocyclyl substituted with one $R^4$, wherein $R^4$ is $C_{1-3}$ alkyl.

17. The compound of claim 10, wherein ring B is

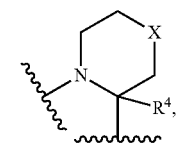

and X is absent, —CH$_2$—, —N(R$^5$)—, —O—, —S(O)$_{0-2}$—, —CH$_2$CH$_2$—, —CH$_2$—O—, or —O—CH$_2$—; wherein $R^5$ is H, $C_{1-3}$ alkyl, or $C_{3-5}$ cycloalkyl.

18. The compound of claim 17, wherein ring B is

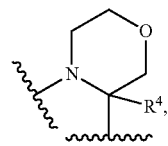

wherein $R^4$ is $C_{1-3}$ alkyl.

19. The compound of claim 1, wherein

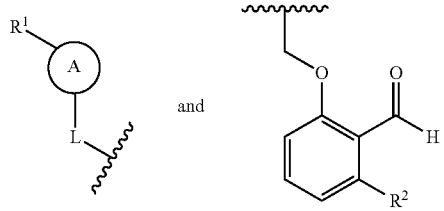

are attached in a 1,2-position relative to each other on ring B.

20. The compound of claim 1, wherein

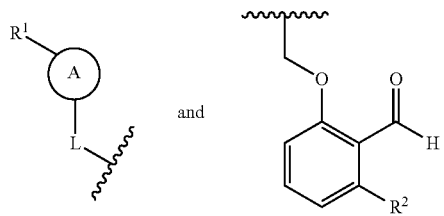

are attached in a 1,3-position relative to each other on ring B.

21. The compound of claim 1, wherein

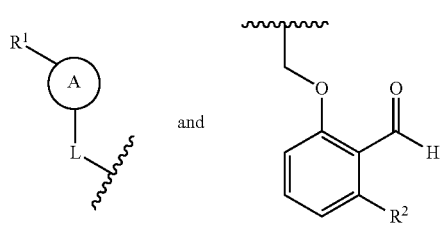

are attached in a 1,4-position relative to each other on ring B.

22. The compound of claim 1, wherein ring A is a $C_6$ or $C_{10}$ aryl optionally substituted with 1-3 $R^3$.

23. The compound of claim 22, wherein ring A is a phenyl optionally substituted with 1-3 $R^3$.

24. The compound of claim 23, wherein ring A is a phenyl substituted with 1-3 $R^3$.

25. The compound of claim 1, wherein ring A is a 5-membered or 6-membered heteroaryl optionally substituted with 1-3 $R^3$.

26. The compound of claim 25, wherein ring A is a 5-membered heteroaryl substituted with 1-3 $R^3$.

27. The compound of claim 25, wherein ring A is a 6-membered heteroaryl substituted with 1-3 $R^3$.

28. The compound of claim 25, wherein ring A is a pyridinyl, pyrimidinyl, pyrazolyl, furanyl, oxazolyl, or thiazolyl, each of which is substituted with 1-3 $R^3$.

29. The compound of claim 1, wherein $R^1$ and L are attached in a 1,3-position relative to each other on ring A.

30. The compound of claim 1, wherein $R^1$ and L are attached in a 1,2-position relative to each other on ring A.

31. The compound of claim 1, wherein $R^1$ and L are attached in a 1,4-position relative to each other on ring A.

32. The compound of claim 1, wherein each $R^3$ is independently halo, hydroxy, $C_{1-3}$ alkyl, or $C_{1-3}$ alkoxy.

33. The compound of claim 1, of formula (IIa):

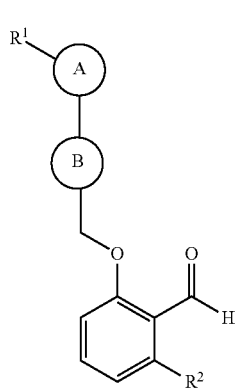

(IIa)

wherein:
    ring B is aryl or nitrogen-containing heteroaryl, wherein ring B is optionally substituted with 1-3 $R^4$; and
    $R^1$ and ring B are attached in a 1,3-position relative to each other on ring A.

34. The compound of claim 1, of formula (IIIa):

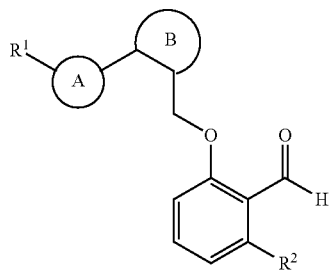

(IIIa)

wherein:
ring B is phenyl or 6-membered nitrogen-containing heteroaryl; and ring A and

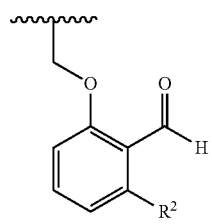

are attached on adjacent ring carbon atoms of ring B.

35. The compound of claim 34, of formula (IIIa(i)):

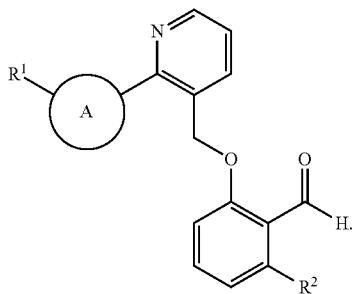

(IIIa(i))

36. The compound of claim 35, wherein $R^1$ and

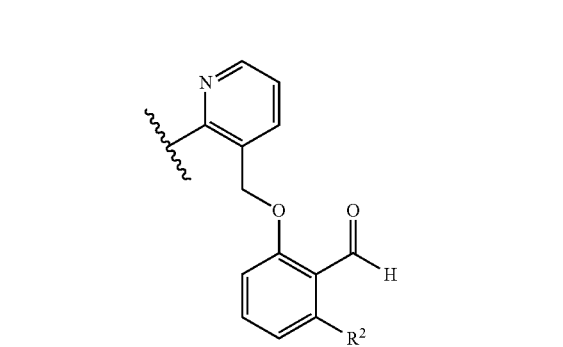

are attached in a 1,3-position relative to each other on ring A.

37. The compound of claim 34, wherein ring A is phenyl, 5-membered heteroaryl, or 6-membered heteroaryl, each of which is optionally substituted with 1-3 $R^3$;
    wherein each $R^3$ is independently halo, hydroxy, $C_{1-3}$ alkyl, or $C_{1-3}$ alkoxy.

38. The compound of claim 1, of formula (IVa):

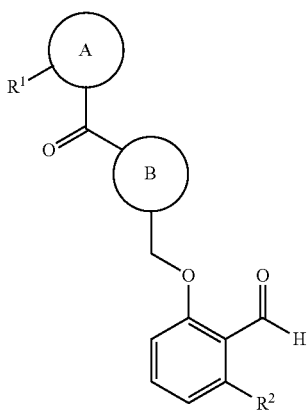

(IVa)

wherein:
ring B is a nitrogen-containing heterocyclyl optionally substituted with 1-3 $R^4$; and
$R^1$ and —C(O)— of the moiety

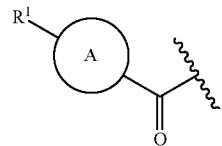

are attached on adjacent ring atoms of ring A.

39. The compound of claim 1, of formula (IVb):

(IVb)

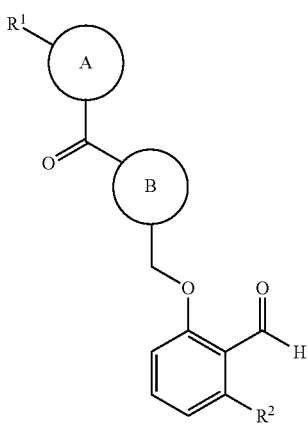

wherein:
ring B is a nitrogen-containing heterocyclyl optionally substituted with 1-3 $R^4$; and
$R^1$ and —C(O)— of the moiety

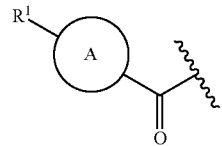

are attached in a 1,3-position relative to each other on ring A.

40. The compound of claim 1, of formula (IVc):

(IVc)

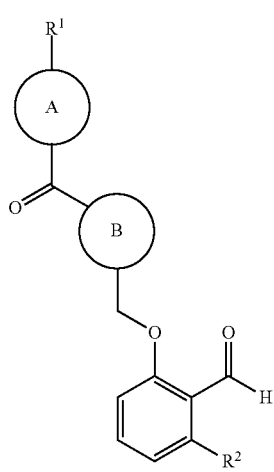

wherein:
ring B is a nitrogen-containing heterocyclyl optionally substituted with 1-3 $R^4$; and
$R^1$ and —C(O)— of the moiety

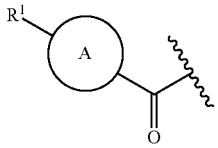

are attached in a 1,4-position relative to each other on ring A.

41. The compound of claim 1, of formula (Va(1)):

(Va(1))

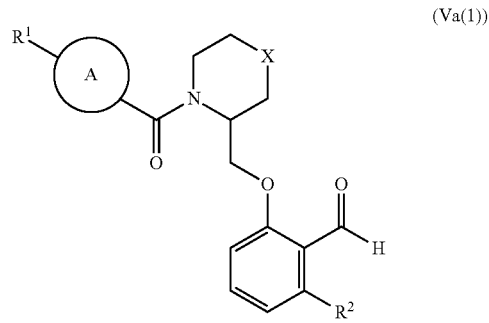

wherein X is absent, —$CH_2$—, —$CH_2CH_2$—, —O—, or —S—.

42. The compound of claim 41, wherein $R^1$ and —C(O)— of the moiety

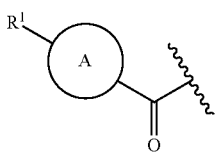

are attached on adjacent ring atoms of ring A.

43. The compound of claim 41, wherein ring A is phenyl or pyridinyl, each of which is optionally substituted with 1-3 $R^3$; wherein each $R^3$ is independently halo, hydroxy, $C_{1-3}$ alkyl, or $C_{1-3}$ alkoxy.

44. The compound of claim 1, of formula (Vb):

(Vb)

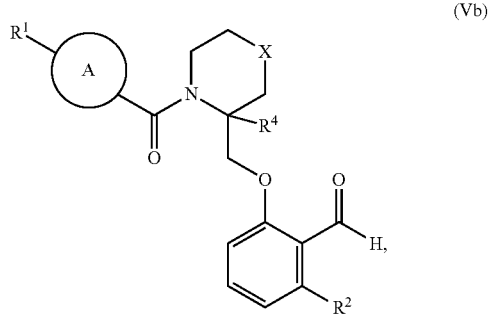

wherein X is absent, —$CH_2$—, —$N(R^5)$—, —O—, —$S(O)_{0-2}$—, —$CH_2CH_2$—, —$CH_2$—O—, or —O—$CH_2$—; and
$R^5$ is H, $C_{1-3}$ alkyl, or $C_{3-5}$ cycloalkyl.

45. The compound of claim 44, wherein R¹ and —C(O)— of the moiety

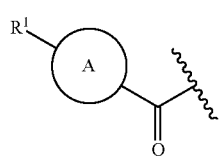

are attached on adjacent ring atoms of ring A.

46. The compound of claim 44, wherein ring A is phenyl or pyridinyl, each of which is optionally substituted with 1-3 R³; wherein each R³ is independently halo, hydroxy, $C_{1-3}$ alkyl, or $C_{1-3}$ alkoxy.

47. The compound of claim 44, wherein ring A is phenyl optionally substituted with 1-3 R³; wherein each R³ is independently halo, hydroxy, $C_{1-3}$ alkyl, or $C_{1-3}$ alkoxy.

48. The compound of claim 44, wherein R⁴ is $C_{1-3}$ alkyl.

49. The compound of claim 1, of formula (VIa):

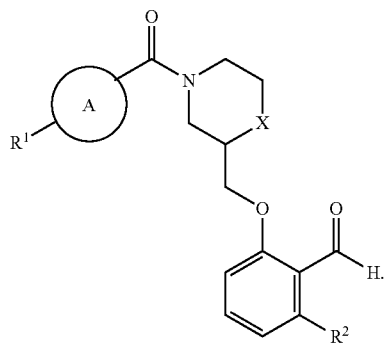

(VIa)

wherein X is absent, —CH₂—, —CH₂CH₂—, —O—, or —S—.

50. The compound of claim 49, wherein R¹ and —C(O)— of the moiety

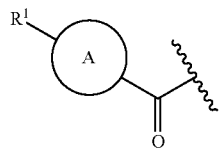

are attached in a 1,2-position or a 1,3-position relative to each other on ring A.

51. The compound of claim 49, wherein ring A is phenyl optionally substituted with 1-3 R³; wherein each R³ is independently halo, hydroxy, $C_{1-3}$ alkyl, or $C_{1-3}$ alkoxy.

52. The compound of claim 1, wherein R² is OH.

53. The compound of claim 1, wherein R² is H.

54. A compound of formula:

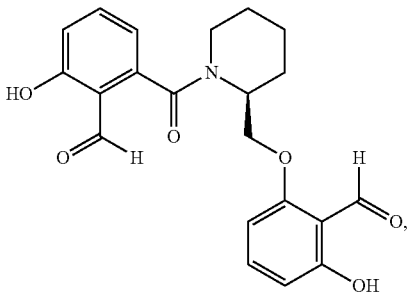

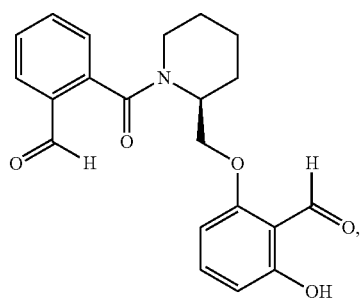

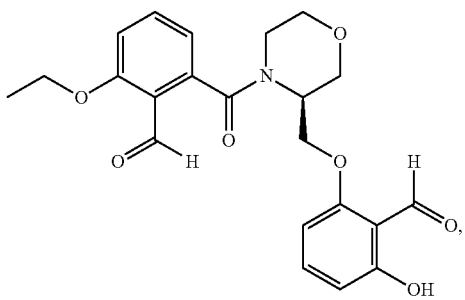

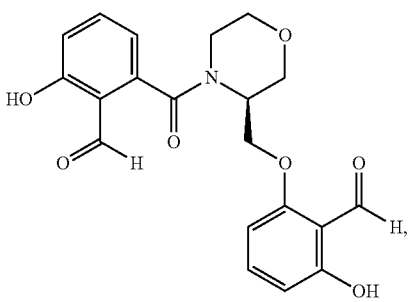

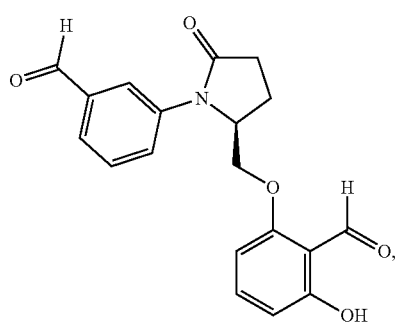

151
-continued
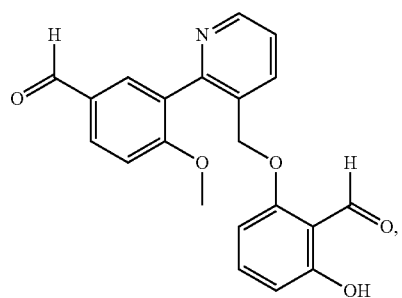
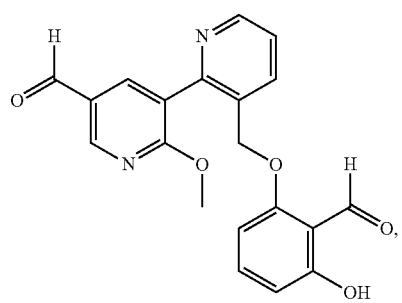
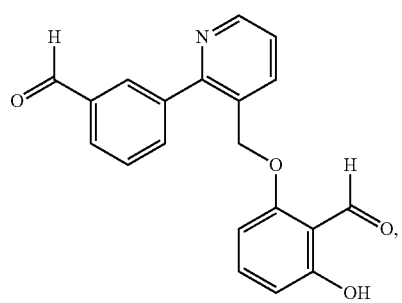
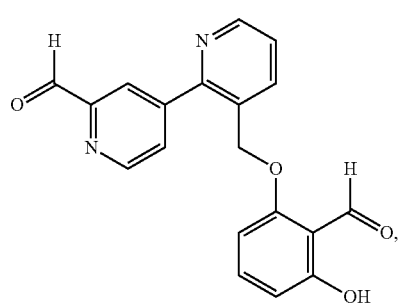
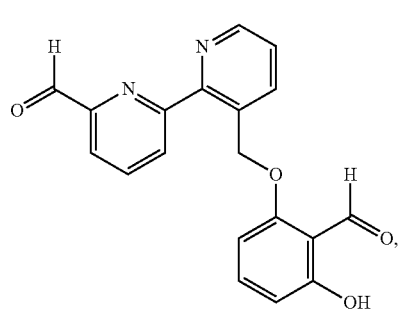
152
-continued
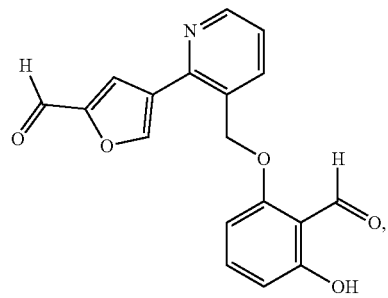
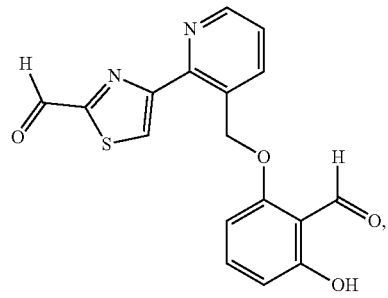
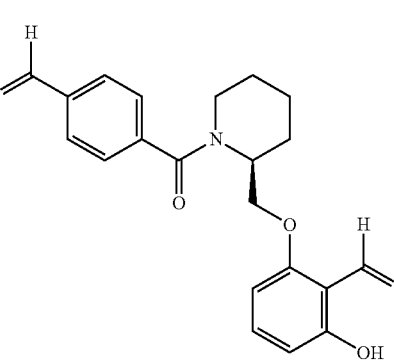
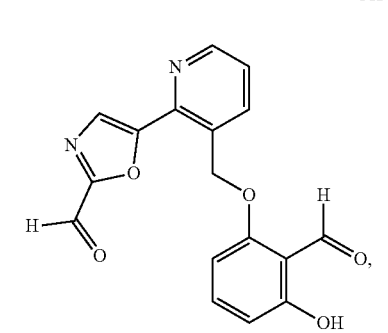
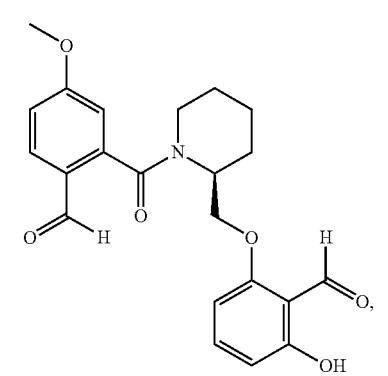

153
-continued
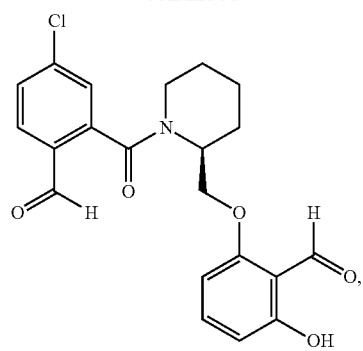
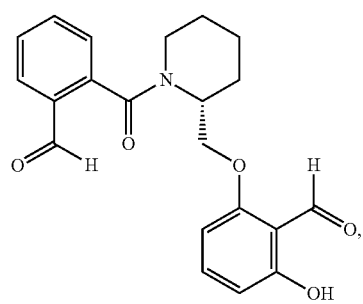
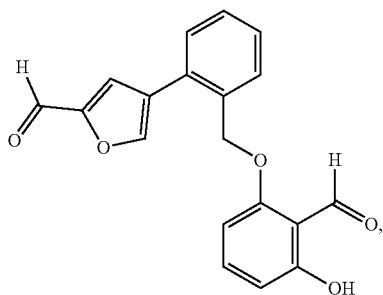
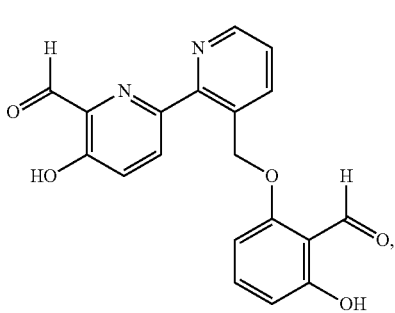
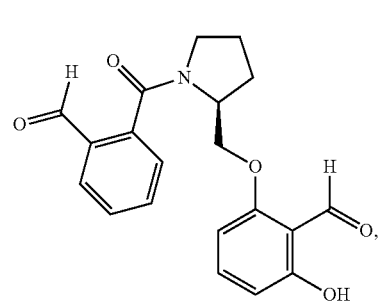
154
-continued
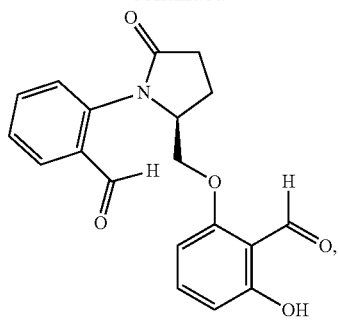
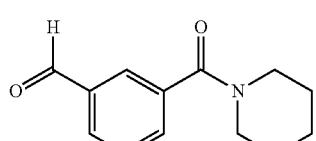
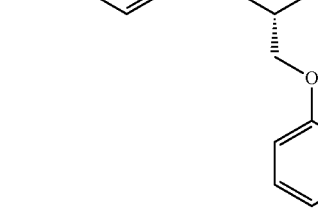
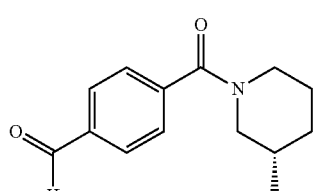
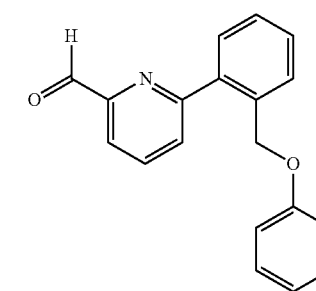
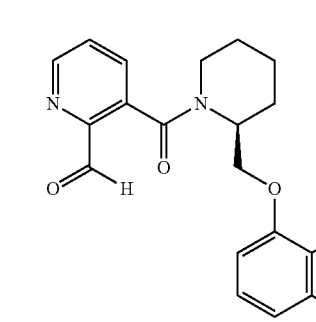

155
-continued
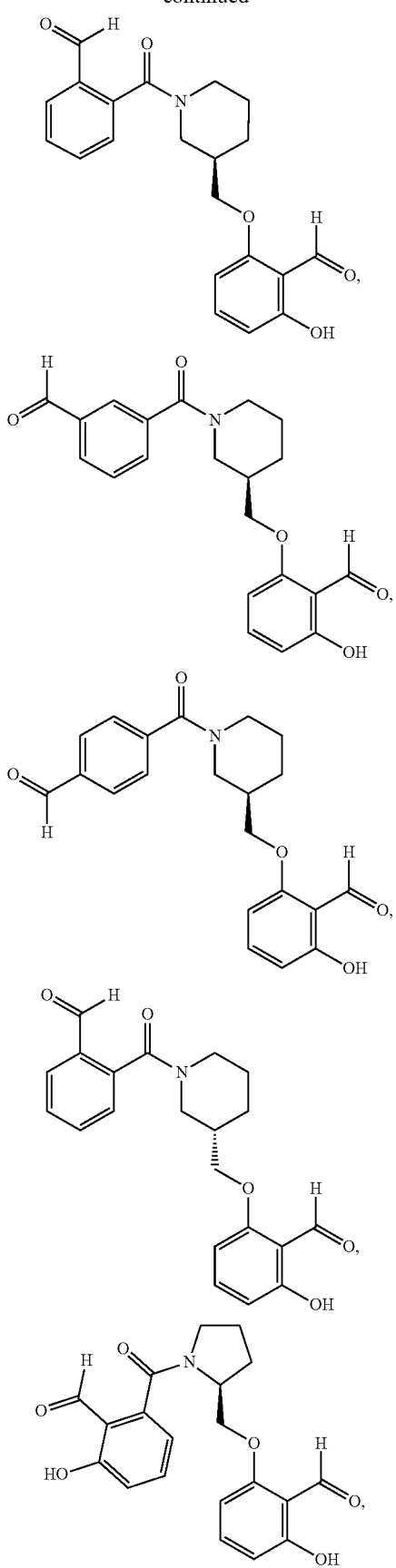
156
-continued
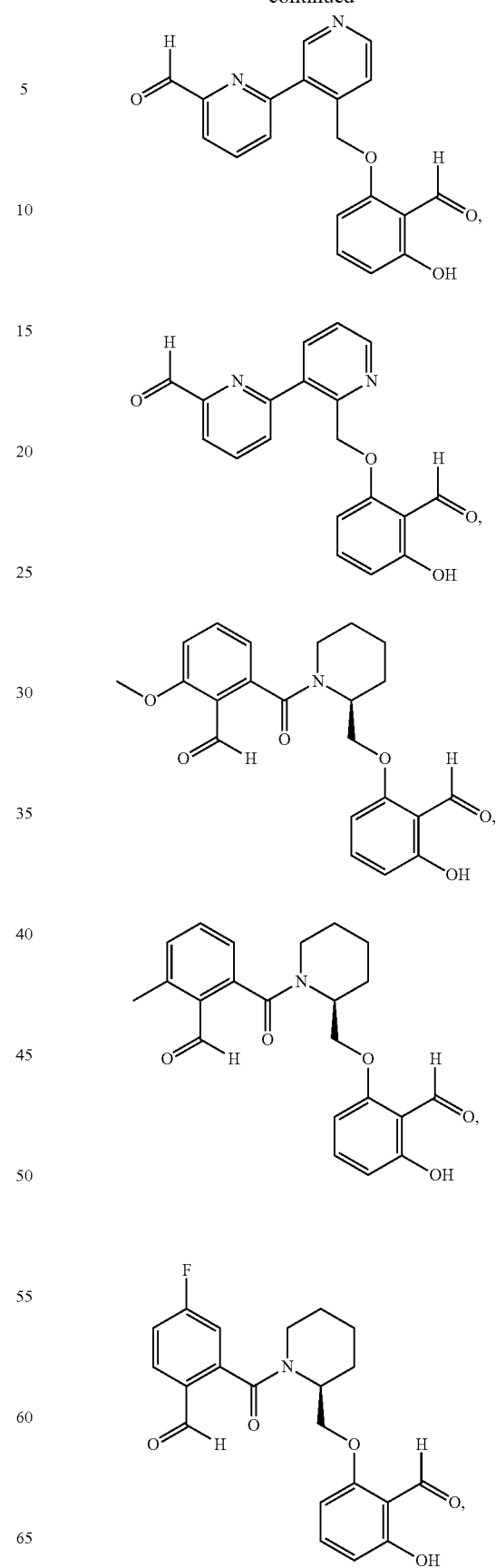

157
-continued
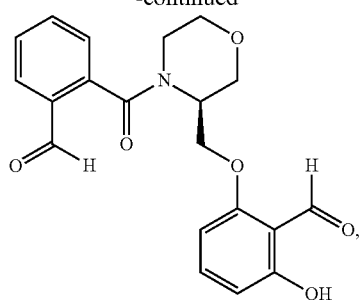
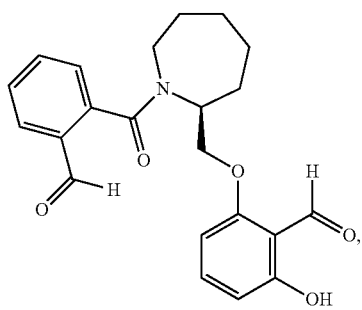
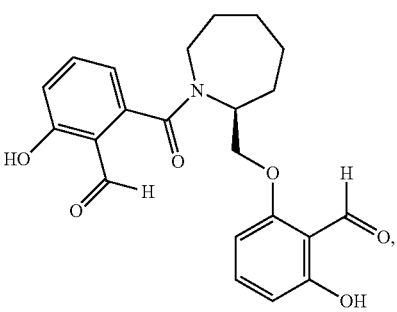
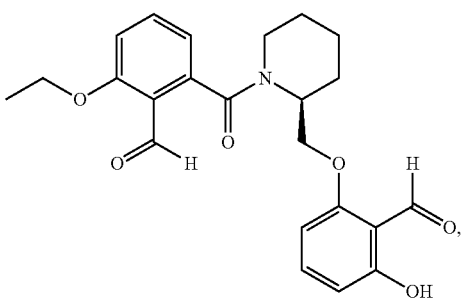
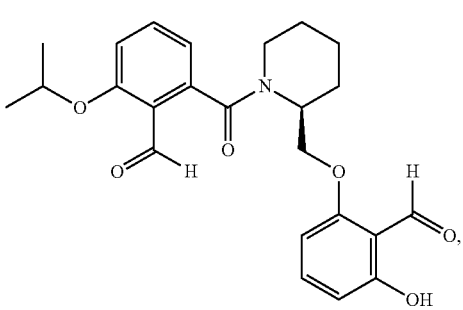
158
-continued
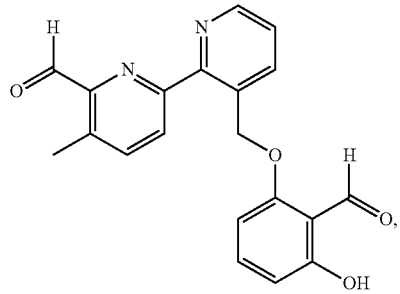
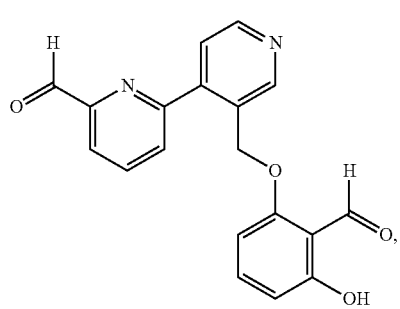
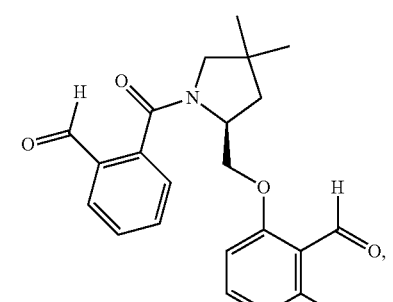
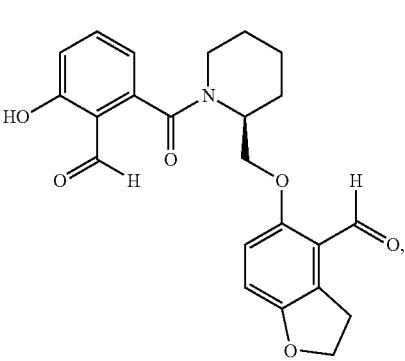
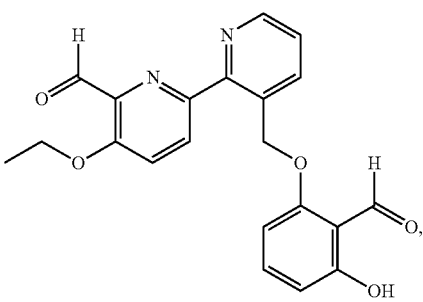

159
-continued
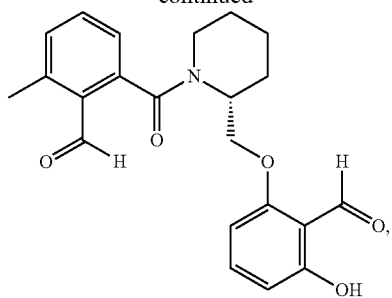
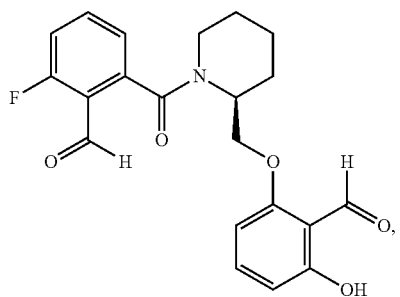
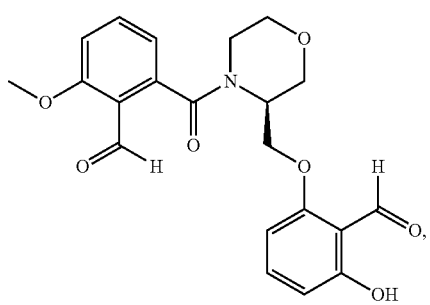
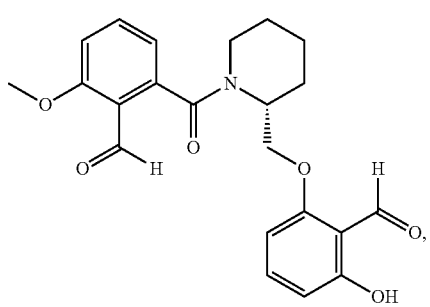
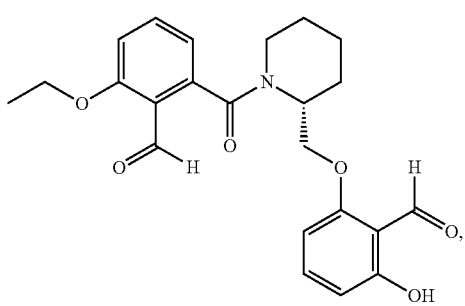
160
-continued
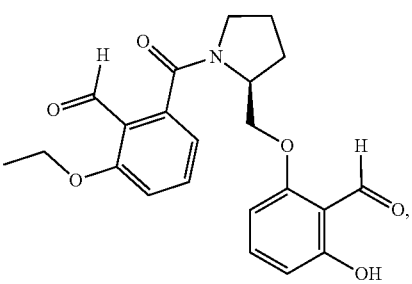
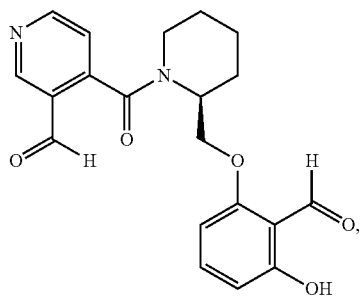
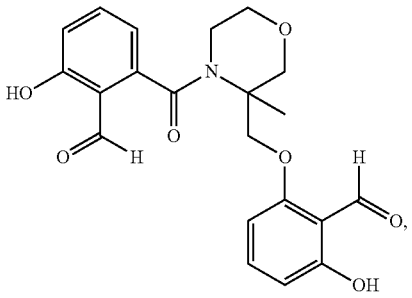
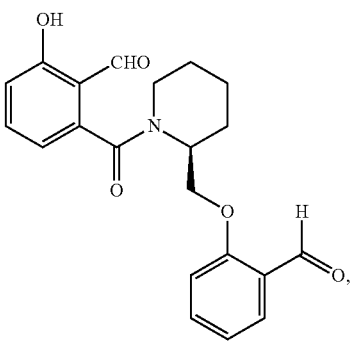

161
-continued
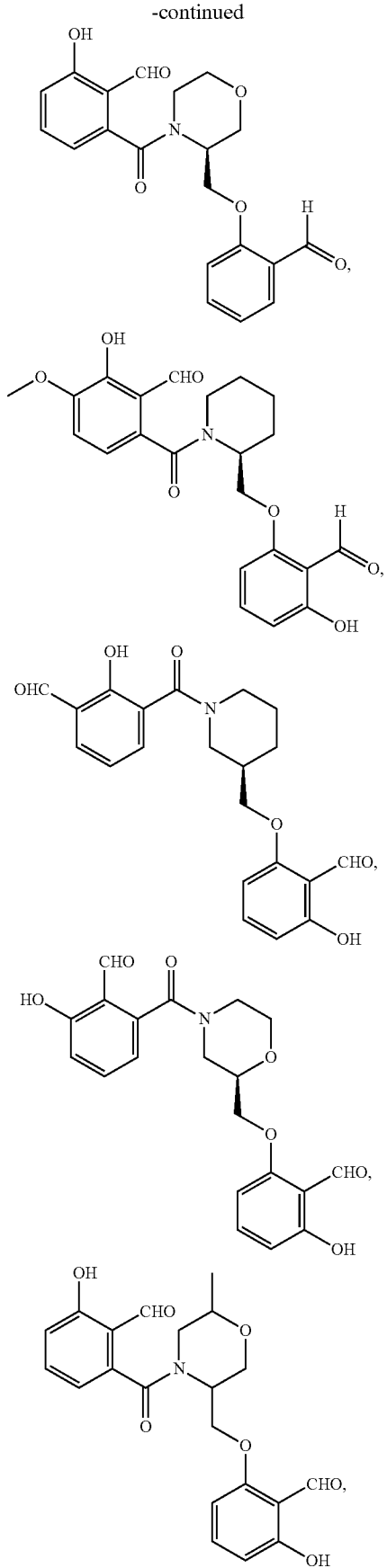
162
-continued
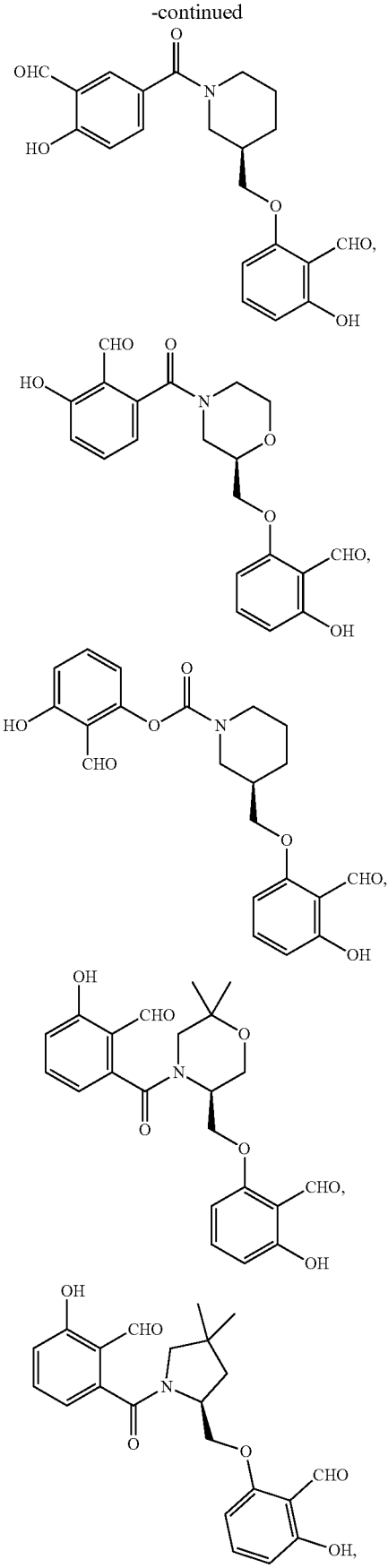

-continued

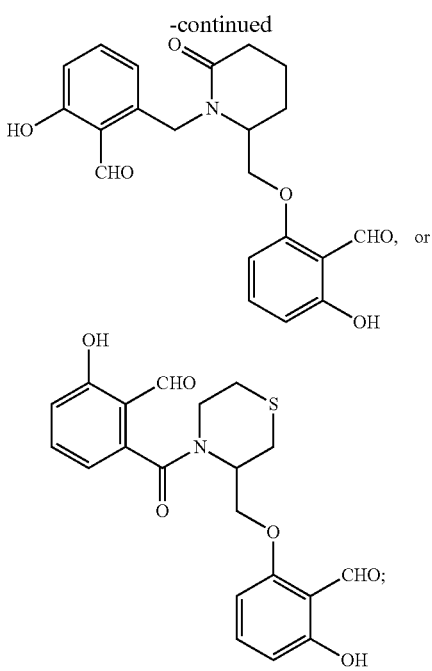

or a pharmaceutically acceptable salt thereof.

55. A compound of formula:

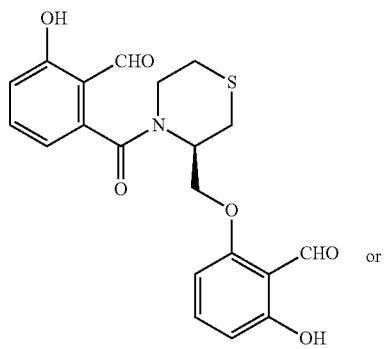

-continued

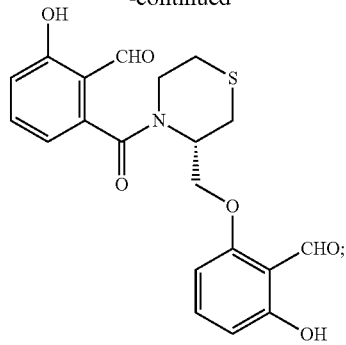

or a pharmaceutically acceptable salt thereof.

56. A pharmaceutical composition comprising a compound according to claim 1, or an isotopically enriched analog, stereoisomer, or mixture of stereoisomers thereof, or a pharmaceutically acceptable salt of each thereof, and a pharmaceutically acceptable excipient.

57. A method for increasing oxygen affinity of hemoglobin S in a subject in need thereof, comprising administering to the subject a compound according to claim 1, or an isotopically enriched analog, stereoisomer, or mixture of stereoisomers thereof, or a pharmaceutically acceptable salt of each thereof.

58. A method for treating a disorder mediated by hemoglobin in a subject in need thereof, comprising administering to the subject a compound according to claim 1, or an isotopically enriched analog, stereoisomer, or mixture of stereoisomers thereof, or a pharmaceutically acceptable salt of each thereof.

59. The method of claim 58, wherein the hemoglobin is sickle hemoglobin.

60. A method for treating sickle cell disease in a subject in need thereof, comprising administering to the subject a compound according to claim 1, or an isotopically enriched analog, stereoisomer, or mixture of stereoisomers thereof, or a pharmaceutically acceptable salt of each thereof.

* * * * *